US006171846B1

(12) United States Patent
Blanc et al.

(10) Patent No.: US 6,171,846 B1
(45) Date of Patent: Jan. 9, 2001

(54) POLYPEPTIDES INVOLVED IN THE BIOSYNTHESIS OF STREPTOGRAMINS, NUCLEOTIDE SEQUENCES CODING FOR THESE POLYPEPTIDES AND THEIR USE

(75) Inventors: Veronique Blanc; Francis Blanche; Joel Crouzet; Nathalie Jacques, all of Paris; Patricia LaCroix, Bry-sur-Marne; Denis Thibaut; Monique Zagorec, both of Paris; Laurent DeBussche, Athis Mons; Valerie De Crecy-Lagard, Grosrouvre, all of (FR)

(73) Assignee: Aventis Pharma S.A., Antony (FR)

(*) Notice: Under 35 U.S.C. 154(b), the term of this patent shall be extended for 0 days.

(21) Appl. No.: 09/231,818

(22) Filed: Jan. 15, 1999

Related U.S. Application Data

(62) Division of application No. 08/403,852, filed as application No. PCT/FR93/00923 on Sep. 25, 1993, now Pat. No. 5,891,695.

(30) Foreign Application Priority Data

Sep. 25, 1992 (FR) .................................................. 92 11441

(51) Int. Cl.⁷ .............................. C12N 1/20; C12N 15/74; C12N 15/76
(52) U.S. Cl. ............................... 435/252.35; 435/252.33; 435/471; 435/486; 435/488; 435/320.1; 536/23.1; 536/23.2; 536/23.7
(58) Field of Search ....................... 435/252.33, 252.35, 435/471, 486, 488, 183, 320.1; 536/23.2, 23.1, 23.7

(56) References Cited

U.S. PATENT DOCUMENTS

| 5,252,474 | 10/1993 | Gewain et al. | 435/172.3 |
| 5,591,614 | 1/1997 | Blanche et al. | 435/120 |

OTHER PUBLICATIONS

Chater et al., "The improving prospects for yield increase by genetic engineering . . . ", *Biotechnology*, vol. 8, NY, US, pp. 115–121, Feb. 1990.

Hallam et al., "Nucleotide sequence transcription and deduced function of a gene . . . ", *Gene*, vol. 74, Amsterdam, NL, pp. 305–320, 1988.

Funane, Kazume et al., "Isolation and properties of IM factor . . . ", *Chemical Abstracts*, vol. 115, No. 23, Abstract No. 251978n, Dec. 1991.

Biot, "Virginiamycin: properties, biosynthesis and fermentation", Drugs and the Pharmaceutical Sciences, vol. 22, pp. 695–720, 1984.

Paquet, et al., "Induction of pristinamycins production in Streptomyces", *Biotechnology Letters*, vol. 14, No. 11, pp. 1065–1070, Nov. 1992.

"Selective production of neoviridogrisein . . . ", Database WPI, Sec. CH, Week 8420, Derwent Publ., London GB, Class B02, AN 84–123313, Apr. 1984.

Blumauerova, M., "Abstract", "Physiological and genetic aspects of Virginiamycin . . . ", *Folia Microbiologica*, vol. 35, No. 6, Prague, p. 494, 1990.

Prykrylova V, "Strain development in *Streptomyces virginiae*, a producer of . . . ", *Biotechnology and Bioindustry*, vol. 2, pp. 20–21, 1988.

Spyrou et al., "Characterization of the flavin reductase gene (fre) of *Escherichia coli* and construction of a plasmid for over production of the enzyme", *J. Bacteriol.*, 173, 3673–3679, Jun. 1991.

Francis, et al., "Biosynthesis of chloramphenicol in streptomyces species 3022a: the nature of arylamine synthetase system", *Can., J. Microbiol.*, 25, 1408–1515, 1979.

*Primary Examiner*—Nashaat T. Nashed
(74) *Attorney, Agent, or Firm*—Finnegan, Henderson, Farabow, Garrett & Dunner, L.L.P.

(57) ABSTRACT

The invention concerns mutant microorganisms blocked in a step of Streptogramin biosynthesis and methods for preparing cells blocked in a step of Streptogramin biosynthesis.

20 Claims, 31 Drawing Sheets

| FORMULA 1 | FORMULA 2 |
|---|---|
| PRISTINAMYCIN IIA<br>MIKAMYCIN A<br>OSTREOGRYCIN A<br>STREPTOGRAMIN A<br>SYNERGISTIN A-I<br>VERNAMYCIN A<br>VIRGINIAMYCIN M$_1$ | PRISTINAMYCIN IIB<br>OSTREOGRYCIN G<br>VIRGINIAMYCIN M$_2$ |

A

GRISEOVIRIDIN  MADUMYCIN I

B

VIRGINIAMYCIN S₁  VERNAMYCIN C

ETAMYCIN pIBV3

B: BamHI
Sp: SphI
P: PstI
X: XhoI
Pv: PvuII

Phe(pNH₂) : PARA-AMINOPHENYLALANINE
Phe(pNHMe) : PARA-METHYLAMINOPHENYLALANINE
Phe(pNMe₂) : PARA-DIMETHYLAMINOPHENYLALANINE

POLYPEPTIDES INVOLVED IN THE BIOSYNTHESIS OF STREPTOGRAMINS, NUCLEOTIDE SEQUENCES CODING FOR THESE POLYPEPTIDES AND THEIR USE

This is a division of application Ser. No. 08/403,852, filed May 10, 1995, now U.S. Pat. No. 5,891,695 which was the National Stage of International Application No. PCT/FR/93/00923, filed Sep. 25, 1993, both of which are incorporated herein by reference.

The present invention relates to novel polypeptides involved in the biosynthesis of streptogramins, and also comprises the isolation and identification of genes for the biosynthesis of the A and B components of streptogramins, the expression of these genes with the object of increasing the levels of production and their use for the construction of blocked mutants capable of leading to the synthesis of novel antibiotics or to derived forms of streptogramins.

Figure 1:
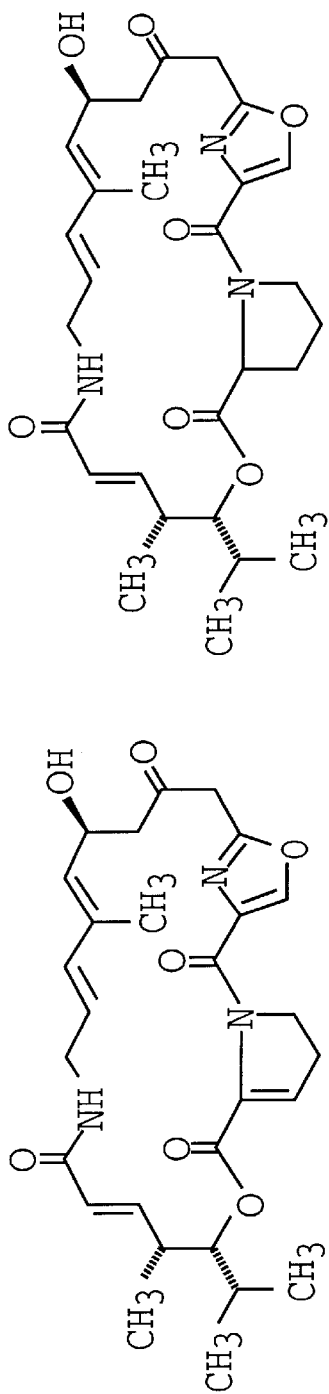
Figure 2:
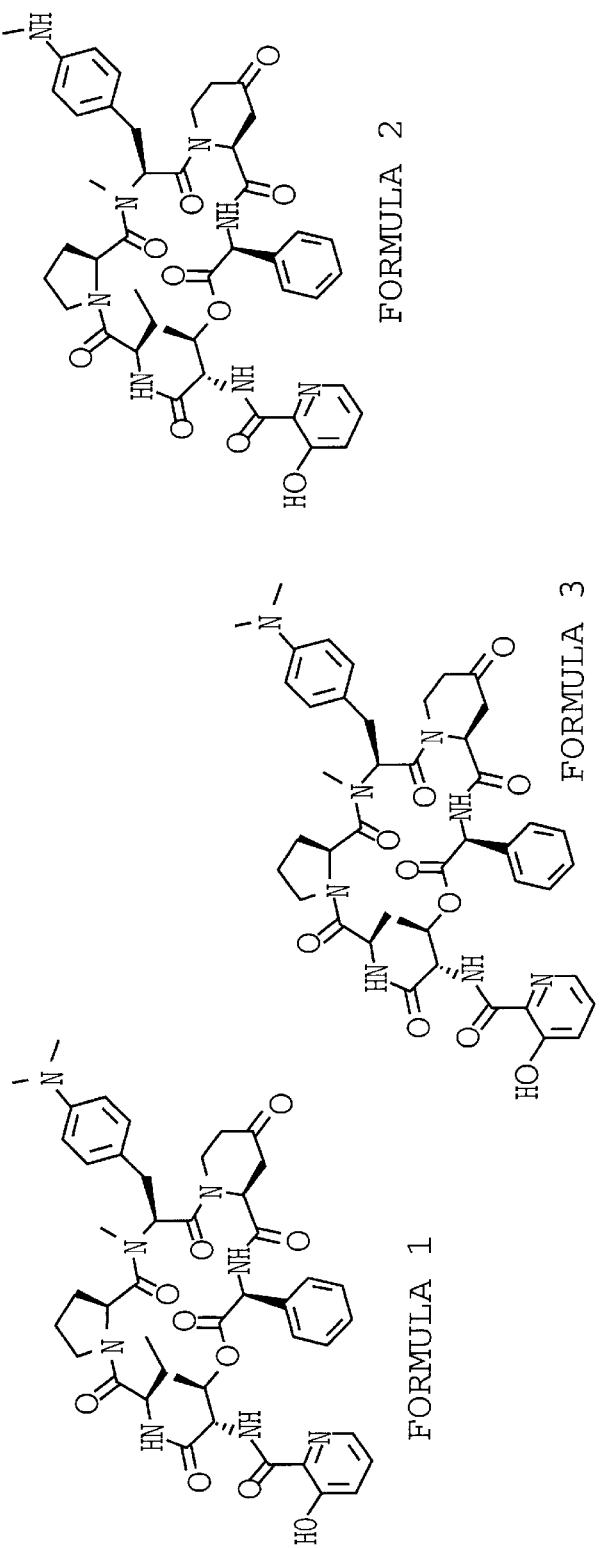

Streptogramins form a homogeneous group of antibiotics, consisting of a combination of two types of molecules which are chemically different; on the one hand polyunsaturated macrolactones (A-group components, two examples of structures of which are presented in FIG. 1), and on the other hand depsipeptides (B-group components, three examples of the structure of which are presented in FIG. 2). This group comprises many antibiotics (see Table 1 and FIG. 3), which are known by different names in accordance with their origin, including pristinamycins, mikamycins and virginiamycins (for a review, see Cocito 1979, 1983).

The A and B components have a synergistic antibacterial activity which can reach 100 times that of the separate components and which, in contrast to that of each component, is bactericidal (Cocito 1979). This activity is more especially effective against Gram-positive bacteria such as staphylococci and streptococci (Cocito 1979, Videau 1982). The A and B components inhibit protein synthesis by binding to the 50S subunit of the ribosome (Cocito 1979; for a review, see Di Giambattista et al. 1989).

Streptogramins are chiefly produced by actinomycetes, including many streptomycetes, presented in Table 1. In addition, streptogramins are also synthesized by eukaryotes ouch as Micromonospora which synthesizes vernamycins. Actinomycetes constitute a very important group of microorganisms on account of the large amount of secondary metabolites they produce, including many antibiotics (beta-lactams, tetracyclines, macrolides, aminoglycosides, polyacetates and the like), herbicides, anticancer agents, antifungal agents, immunomodulators and enzyme inhibitors. Many biosynthesis pathways relating to antibiotics belonging to miscellaneous classes as well as other secondary metabolites such as pigments (for a review, Chater 1990) have already been studied at the present time in actinomycetes. An important aspect of this group of bacteria is that the genes involved in the same biosynthesis pathway, structural genes and also resistance gene(s) and regulatory gene(s), are grouped together physically on the chromosome, constituting clusters which can reach more than 100 kb (Hopwood et al. 1986a, Hopwood et al. 1986b, Hallam et al. 1988, Anzai et al. 1987, Ohnuki et al. 1985). To date, no example has been found to contradict this observation. Such a structural organization is of great interest in the development of strategies for cloning biosynthesis genes. In effect, it is possible, starting from a single gene previously cloned by various techniques, a biosynthesis, resistance or regulatory gene, to walk along the chromosome and thus to isolate the set of genes of the biosynthesis cluster.

Our knowledge of the biosynthesis pathways of each of the components of streptogramins is still very incomplete, but the origin of the different parts of each molecule has been identified by radioactive labelling (Kingston et al. 1983). Thus, the A-type components are made up of two regions originating from the condensation of acetates and several amino acids such as serine and glycine, for example. As regards the B-type components, studies have shown that all the amino acids present in the peptide chain are derived from natural amino acids (Hook and Vining 1973). However, no polypeptide involved in these pathways has, to date, been purified in sufficient amounts to permit its molecular characterization, and no biosynthesis gene has been described. In the process of biosynthesis of the B-type components, two parts may be distinguished:

1) Synthesis of the precursors, or of their analogues, of the macrocycle: 3-hydroxypicolinic acid, L-2-aminobutyric acid, p-dimethylamino-L-phenylalanine, 4-oxo-L-pipecolic acid, L-phenylglycine.

2) Formation of the macrocycle from the precursors mentioned above, L-threonine and L-proline, or their analogues, with possible modification of these precursors or peptide N-methylation.

To date, only the probable metabolic origin of the precursors of the macrocycle of the B-type components has been determined by studies using labelled isotopes (Reed et al., 1986, Molinero et al., 1989, Reed et al., 1989).

The present invention results from the purification of polypeptides participating in the biosynthesis of streptogramins, as well as from the cloning of genes whose product participates in the biosynthesis of streptogramins. The term biosynthesis of streptogramins is understood to comprise the regulatory genes and the genes conferring resistance on the producing microorganisms. Thus, the present invention makes it possible to increase the levels of production of these metabolites by means of recombinant DNA techniques. Another benefit of the present invention lies in the possibility, by construction of mutants blocked in the different steps of this biosynthesis, of producing synthesis intermediates for each of the two components. These intermediates may serve as substrates for further modification for chemical, biochemical, enzymatic or microbiological means. Similarly, isolation of the biosynthesis genes makes it possible, by gene transfer between producing strains, to manufacture hybrid antibiotics having pharmacologically advantageous properties (Hopwood et al., 1985a, Hopwood et al., 1985b, Hutchinson et al. 1989). Another benefit of the present invention lies in the fact that it provides a better knowledge of the biosynthesis pathways of the metabolites classed as streptogramins. In effect, the invention enables bacterial or fungal strains to be constructed in which one or more proteins participating in the biosynthesis of streptogramins is/are expressed under the control of suitable expression signals. Such strains may then be used to carry out bioconversions. These bioconversions may be carried out either using whole cells, or using acellular extracts of the said cells. These bioconversions may enable a streptogramin to be converted to a derived form with an enzyme of a biosynthesis pathway. For example, pristinamycin IIB may be converted in this manner to pristinamycin IIA. The same reasoning may be applied to any biosynthesis intermediate.

A first subject of the invention hence relates to a nucleotide sequence coding for a polypeptide involved in the biosynthesis of streptogramins.

More especially, several genes whose product participates in the biosynthesis of streptogramins have been isolated from *Streptomyces pristinaespiralis*. Since the streptogramins produced by this strain are more commonly designated by the term pristinamycins (see Table 1), in what follows, reference will be made in some cases to genes for the biosynthesis of pristinamycins. However, it is clear that the results obtained apply to all the streptogramins. Pristinamycins I and II correspond, respectively, to the B and A components of streptogramins. Molecules of the pristinamycin II family and of the pristinamycin I family hence designate in what follows the A and B components of streptogramins, respectively.

The present invention describes in particular the isolation and characterization of the snaA, snaB, snaC, snaD, papA, papM, samS, snbA, snbC, snbD, snbE and snbR genes. These genes were isolated from a library of genomic DNA of S.pristinaespiralis. This library was obtained by partial digestion of genomic DNA S.pristinaespiralis with the restriction enzyme Sau3A. Large DNA fragments, from 40 to 50 kb on average, were cloned into cosmid pHC79 (Hohn, B., and Collins, J. F., 1980). After in vitro encapsidation, E.coli strains HB101 (Boyer et Roulland-Dussoix, 1969) and DH1 (Low, 1968) were transfected. The DNA library of S.pristinaespiralis thus occurs in two different strains of E.coli.

Figure 4:
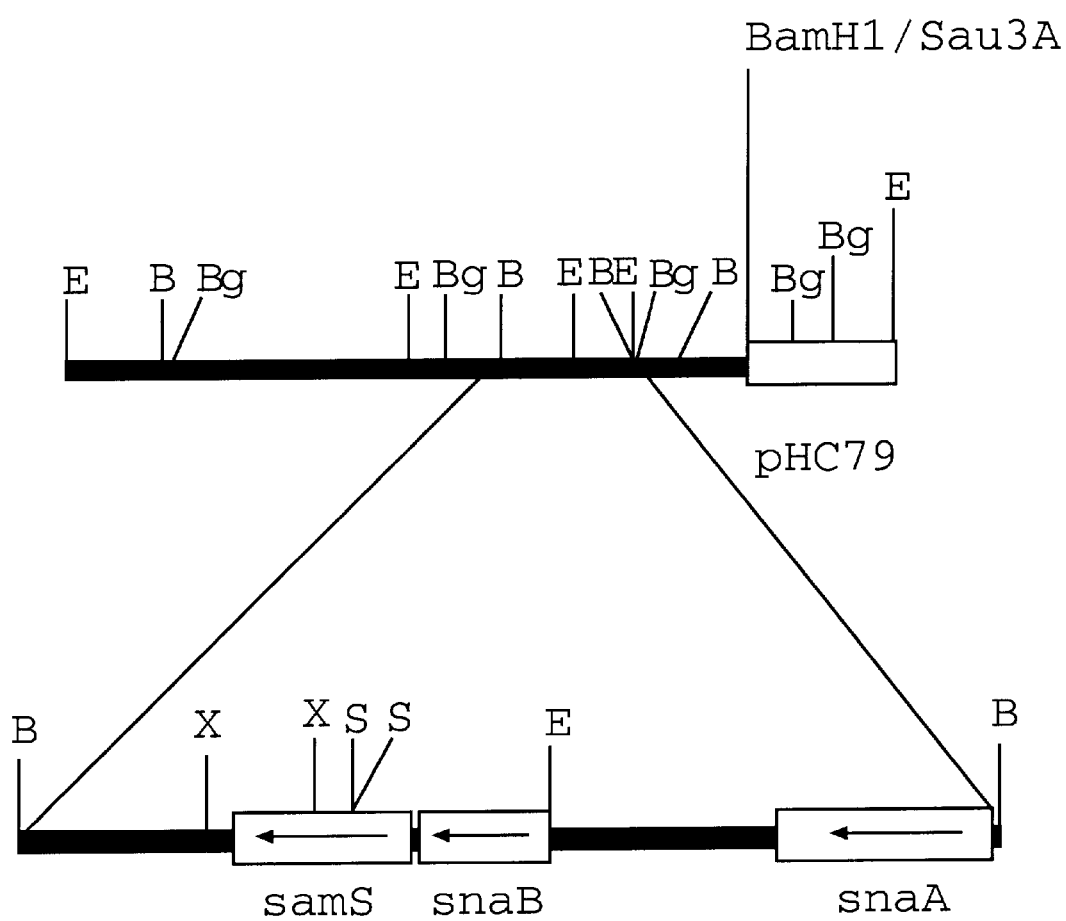

The snaA, snaB and samS (initially designated SnaC genes are present on cosmid pIBV1 (FIG. 4). The product of the snaA and snaB genes, corresponding to the polypeptides SnaA and SnaB, participates in the final step of biosynthesis of the II component of pristinamycins (conversion of pristinamycin IIB to pristinamycin IIA), corresponding to the oxidation of the 2,3 bond of D-proline. These two polypeptides constitute the two subunits of pristinamycin IIA synthase, the purification of which is described in the present invention. The product of the samS gene is considered to participate in the synthesis of SAM (methyl group donor) from ATP and methionine. The A component of most streptogramins is, in effect, methylated at C-4 (FIG. 1), and this methyl has been described (Kingston et al., 1983) as being derived from the methyl of methionine, very probably via a methylation reaction with SAM. The samS gene is hence considered to code for a SAM synthase (SamS; EC. 2.5.1.6) which is specific to the biosynthesis pathway of pristinamycins.

Figure 5:
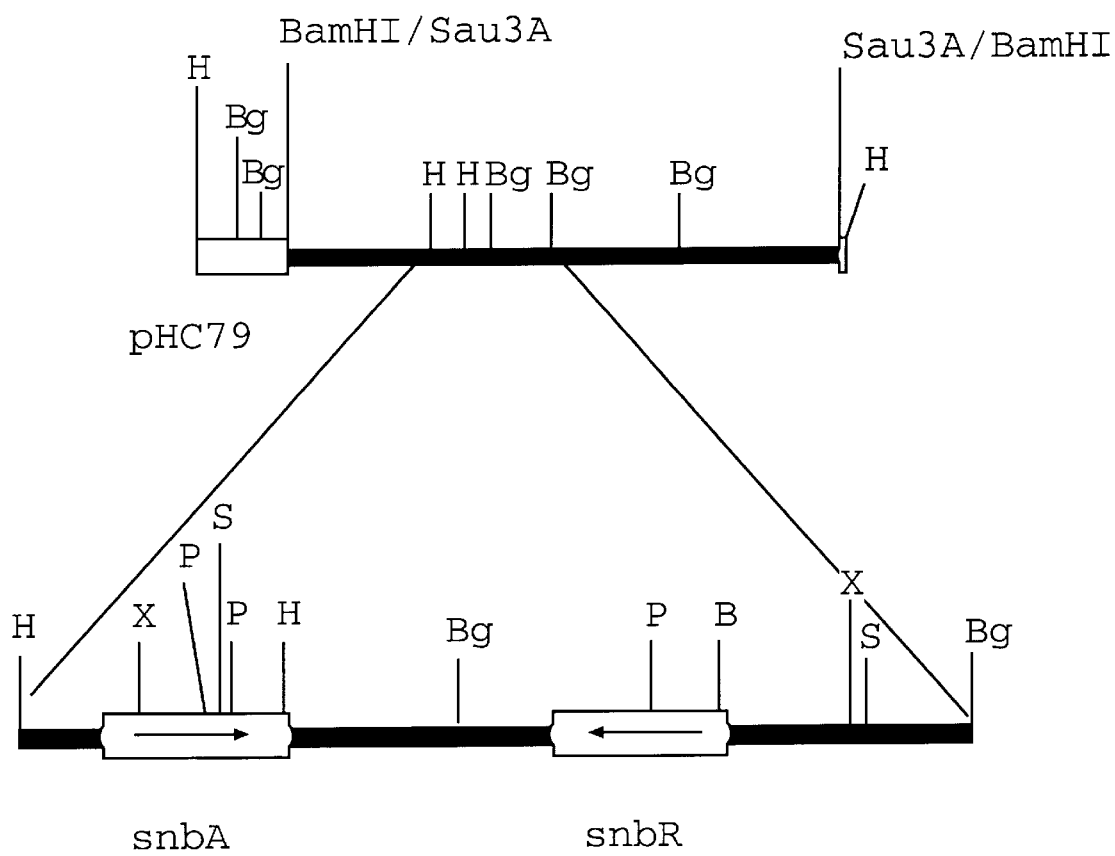

The snbA, snbR, papA and papM genes are present on cosmid pIBV2 (FIG. 5). The snbA gene corresponds, on the basis of the biochemical studies presented in Example 5, to the first step for synthesis of pristinamycins I. This comprises activation of the first acid of the chain, 3-hydroxypicolinic acid, by adenylation. The snbR gene might participate in the transport of molecules of the pristinamycin I (or possibly pristinamycin II) family out of the cell after synthesis, thereby conferring a resistance to this component on the producing strain. The papA gene corresponds, on the basis of sequence analyses (Example 8.8) and the study of a mutant disrupted in this gene (Example 9.3), to a gene for the biosynthesis of para-aminophenylalanine from chorismate. para-Aminophenylalanine is then dimethylated by the product of the papM gene, an N-methyltransferase described in the present invention, to form para-dimethylaminophenylalanine, which is then incorporated in pristinamycin IA. The papA and papM genes hence participate in the synthesis of one of the precursors of pristinamycin IA.

The snaA, snaD, snbC, snbD and snbE genes are present on cosmid pIBV3 (FIG. 6), which hence adjoins cosmid pIBV1 on which the snaA gene is already present. The snaD gene codes, on the basis of analysis of its sequence (Example 8.9) and the study of a mutant disrupted in this gene (Example 9.5), for a peptide synthase involved in the biosynthesis of pristinamycin II. The snbC gene, whose product is described in the present invention, participates in the incorporation of threonine and aminobutyric acid residues in the peptide chain of pristinamycin IA. The snbD gene, whose product is also described in the present invention, is involved in the incorporation of proline and para-dimethylaminophenylalanine residues in the peptide chain of pristinamycin IA. It also governs the N-methylation of the peptide bond between these 2 residues. Lastly, the snbE gene, whose product is also described in the present invention, participates in the incorporation of the last two residues of pristinamycin IA, namely phenylglycine and 4-oxopipecolic acid.

Figure 7:
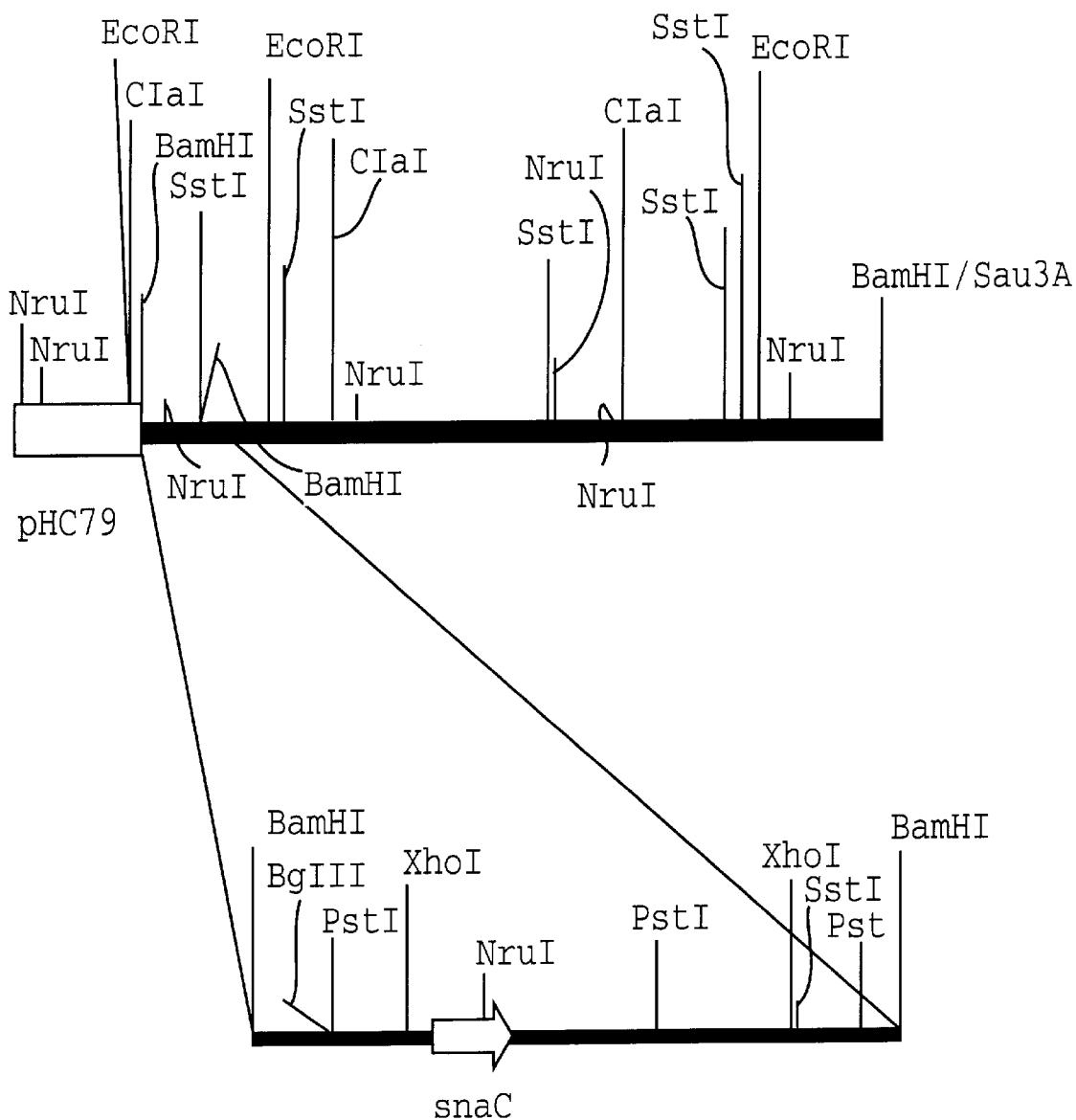

The snaC gene is present on cosmid pIBV4 (FIG. 7). It codes for an FMN:NADH oxidoreductase, also designated FMN reductase, described in the present invention and which supplies pristinamycin IIA synthase with $FMNH_2$ from FMN and NADH. The snaC gene hence participates in the final step of the biosynthesis of pristinamycin IIA.

These different genes were subcloned from their cosmid of origin and their nucleic acid sequences were determined. The snaA, snaB and samS genes were subcloned on a 6-kb BamHI-BamHI fragment, a portion of which was sequenced (SEQ ID no. 1). The snbA gene was subcloned in a 5.5-kb EcoRI-BglII fragment, a portion of which was sequenced (SEQ ID no. 5). The snbR gene was subcloned in a 4.6-kb BglII-BglII fragment, a portion of which was sequenced (SEQ ID no. 6). A portion of the papA gene was subcloned in a 3.4-kb XhoI-XhoI fragment, a portion of which was sequenced (SEQ ID no. 9). The papM gene was subcloned in a 4.1-kb PstI-PstI fragment, a portion of which was sequenced (SEQ ID no. 10). A portion of the snaD gene was subcloned in a 1.5-kb BamHI-SstI fragment, a portion of which was sequenced (SEQ ID no. 8). A portion of the snbC gene was subcloned on a 6.2-kb SphI-SphI fragment, 2 regions of which were sequences (SEQ ID nos. 11 and 12). A portion of the snbD gene was subcloned on an 8.4-kb SphI-SphI fragment, 2 regions of which were sequenced (SEQ ID Nos. 13 and 14). A portion of the snbE gene was subcloned on a 6.6-kb SphI-SphI fragment, 2 regions of which were sequenced (SEQ ID Nos. 15 and 16). The snaC gene was subcloned in a 4-kb BamHI-BamHI fragment, a portion of which was sequenced (SEQ ID no. 7).

The proximity of the snaA, snaB, snaD, samS, snbC, snbD and snbE genes on the one hand, as well as the snbA, snbR, papA and papM genes, confirms the cluster localization of the genes for biosynthesis of the A and B components of streptogramins. Furthermore, the 4 cosmids described in the present invention are grouped together in a region of the chromosome whose size is estimated at 200 kb by pulsed-field electrophoresis, equivalent to 3% of the total genome (7500 kb) of *Streptomyces pristinaespiralis* (Example 13). It is hence obvious that the regions surrounding the genes identified in the present invention (snaA, snaB, snaD, samS, snbC, snbD and snbE; snbA, snbR, papA and papM, snaC) contain the other genes of the pristinamycin biosynthesis cluster, and that these genes may be used to localize the other genes for the biosynthesis of streptogramins.

Preferably, the subject of the invention is a nucleotide sequence chosen from:

(a) all or part of the snaA (SEQ ID no. 2), snaB (SEQ ID no. 3), snaC (SEQ ID no. 7), snaD (SEQ ID no. 8), papA (SEQ ID no. 9), papM (SEQ ID no. 10), samS (SEQ ID no. 4), snbA (SEQ ID no. 5), snbC (SEQ ID nos. 11 and 12), snbD (SEQ ID nos. 13 and 14), snbE (SEQ ID nos. 15 and 16) and snbR (SEQ ID no. 6) genes, (b) the sequences adjacent to the genes (a) constituting the biosynthesis clusters and coding for the polypeptides involved in the biosynthesis of streptogramins, (c) the sequences which hybridize with all or part of the genes (a) or (b) and which code for a polypeptide involved in the biosynthesis of streptogramins, and (d) the sequences derived from the sequences (a), (b) and (c) owing to the degeneracy of the genetic code.

Still more preferably, the subject of the invention is the nucleotide sequences represented by the snaA (SEQ ID no. 2), snaB (SEQ ID no. 3), snaC (SEQ ID no. 7), snaD (SEQ ID no. 8), papA (SEQ ID no. 9), papM (SEQ no. 10), samS (SEQ ID no. 4), snbA (SEQ ID no. 5), snbC (SEQ ID nos. 11 and 12), snbD (SEQ ID nos. 13 and 14), snbE (SEQ ID nos. 15 and 16) and snbR (SEQ ID no. 6) genes.

Another subject of the invention relates to any recombinant DNA comprising a gene for the biosynthesis of streptogramins. More preferably, this is a recombinant DNA comprising all or part of cosmids pIBV1, pIBV2, pIBV3 or pIBV4 as shown in FIGS. 4 to 7, or all or part of sequences which hybridize with cosmids pIBV1 to pIBV4 or with fragments of these latter.

In a preferred embodiment of the invention, the nucleotide sequences defined above form part of an expression vector, which can he autonomously replicating or integrative.

As stated above, although the invention is more especially illustrated with the genes for the biosynthesis of pristinamycin, it is clear that the results obtained apply to all streptogramins.

More especially, the techniques developed in the present invention for purifying proteins or cloning genes for the biosynthesis of streptogramins from *S. pristinaespiralis* may be applied to other microorganisms producing streptogramins (see Table 1).

Thus, the purification of an enzymatic activity from *S. pristinaespiralis* makes it possible to purify the same activity from another strain producing streptogramin. The present invention may hence by applied to the cloning of genes for the biosynthesis of streptogramins from any producing microorganism, by purification of a protein participating in the biosynthesis and then, using the $NH_2$-terminal sequence thereof, synthesis of an oligonucleotide probe which enables the corresponding gene to be cloned. Chromosome walking then enables whole biosynthesis cluster to be identified.

Furthermore, from the genes identified in the present application, it is possible, by hybridization, to clone the genes for the biosynthesis of streptogramins directly from the DNA of another producing microorganism. In effect, the genes for the biosynthesis of pristinamycins hybridize strongly with those for the other streptogramins. It is thus possible to clone, by hybridization, the genes for the biosynthesis of streptogramins using as a probe the sna, snb or pap genes, or fragments of the latter, or fragments adjacent to these containing, as is shown in the present invention, other sna and snb genes. This is due to the fact that: 1) the streptogramins produced by the different microorganisms have identical or similar structures (see FIG. 3), 2) the genes for the biosynthesis of streptogramins are organized in clusters, and 3) the enzyme systems responsible for this biosynthesis do not have an absolute specificity for their substrate.

Moreover, the cloning of genes involved in the biosynthesis of streptogramins may also he carried out using degenerate oligonucleotides, prepared from the sequences of the sna or snb genes mentioned above, or fragments of these genes, or fragments adjacent to these genes. It is thus possible to take one's pick of the genes for the biosynthesis of the A and B components of the different strains producing streptogramins. These strains can belong to the genus Streptomyces, and also to other genera (see Table 1). In addition, if the genomic DNA of the starting strains used has a G+C composition different from that observed in Streptomyces, the probes used may be synthesized with a codon bias specific to the genus or species from which it is desired to isolate the DNA.

Another subject of the present invention relates to the polypeptides resulting from the expression of the nucleotide sequences defined above. More especially, the present invention relates to polypeptides comprising all or part of the polypeptides SnaA (SEQ ID no. 17), SnaB (SEQ ID no. 18), SnaC (SEQ ID no. 22), SnaD (SEQ ID no. 23), PapA (SEQ ID no. 24), PapM (SEQ ID no. 25), SamS (SEQ ID no. 19), SnaA (SEQ ID no. 20), SnaC (SEQ ID nos. 26 and 27), SnbD (SEQ ID nos. 28 and 29), SnbE (SEQ ID no. 30 and 31) and SnbR (SEQ ID no. 21) or of derivatives of these. Within the meaning used in the present invention, the term derivative denotes any molecule obtained by modification of a genetic and/or chemical nature of the peptide sequence. Modification of a genetic and/or chemical nature is understood to mean any mutation, substitution, deletion, addition and/or modification of one or more residues. Such derivatives may be generated for different purposes, such as, in particular, that of increasing the affinity of the peptide for its substrate(s), that of improving its levels of production, that of increasing its resistance to proteases, that of increasing and/or modifying its activity, or that of endowing it with novel biological properties. Among derivatives resulting from an addition, there may be mentioned, for example, chimeric polypeptides containing an additional heterologous portion attached to one end. The term derivative also comprises polypeptides homologous to the polypeptides described in the present invention and originating from other call sources, and in particular from strains producing streptogramins.

The subject of the invention is also any recombinant cell containing a nucleotide sequence or a vector as defined above. The recombinant cells according to the invention can equally well be eukaryotic cells or prokaryotic cells. Among eukaryotic cells which are suitable, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127 cells, Xenopus eggs, and the like, may be mentioned. Among fungi, special mention may be made of Micromonospora, Aspergillus ssp. or Trichoderma ssp. As prokaryotic cells, it is preferable to use the following bacteria: Actinomycetes, and Streptomyces in particular, *E. coli* (Example 11), Bacillus. Preferably, the recombinant cells of the invention are chosen from cells producing streptogramins (see Table 1). The recombinant cells of the invention may be obtained by any method which enables a foreign nucleotide sequence to be introduced into a cell. It can be, in particular, transformation, electroporation, conjugation, protoplast fusion or any other technique known to a person skilled in the art.

A further subject of the invention is a method for producing a polypeptide involved in the biosynthesis of streptogramins, according to which a recombinant cell as defined above is cultured and the polypeptide produced is recovered.

The subject of the invention is also the use of a recombinant cell as defined above, expressing at least one polypeptide involved in the biosynthesis of streptogramins, in a bioconversion reaction. In particular, these cells can enable a streptogramin to be converted into a derived form. For example, pristinamycin IIB can be converted in this manner to pristinamycin IIA. The same reasoning may be applied to any biosynthesis intermediate. These cells can also enable hybrid antibiotics having advantageous pharmacological properties to be manufactured (Hopwood et al. 1985a, Hopwood et al. 1985b, Hutchinson et al. 1984). These bioconversions may be carried out either using whole cells, or using acellular extracts of the said cells.

Another subject of the invention relates to the use of a nucleotide sequence as defined above for amplifying streptogramin production. The invention also relates to a method for producing streptogramins, according to which one or more nucleotide sequences according to the invention is/are introduced and/or amplified in a cell producing streptogramins or which is potentially a producer of streptogramins, the said cell is cultured under conditions of streptogramin production, and the streptogramins produced are recovered.

The overexpression of certain genes involved in the biosynthesis can enable the streptogramin A and/or B production of the producing strains to be increased. This overproduction may be carried out in several strains: either strains which produce only molecules of the streptogramin A family, or strains which produce only molecules of the streptogramin B family, or strains which produce both the A and B components. These overexpressions can result from an increase in the level of synthesis, and hence in the productivity, of the A and/or B components, either in an Erlenmeyer, or in small fermenters, or in large industrial fermenters. Moreover, the specific overexpression of a gene involved in the biosynthesis of an A or B component also makes it possible to vary the % of A and B components produced by the strain, and thus to obtain a better synergy between these molecules. In addition, the biosynthesis genes isolated from a microorganism producing streptogramins may be used to amplify production in another producing microorganism.

Another subject of the invention relates to a method for preparing cells blocked in a step of the pathway of biosynthesis of streptogramins, according to which a mutagenesis is performed on at least one gene of the biosynthesis pathway, on a cell producing streptogramins.

Preferably, the mutagenesis is performed in vitro or in situ, by suppression, substitution, deletion and/or addition of one or more bases in the gene in question, or by gene disruption.

Another aspect of the present invention lies, in effect, in the construction of mutants blocked in certain steps of biosynthesis of streptogramins. The value lies, on the one hand in the study of the functionality of the mutated proteins, and on the other hand in the production of strains producing biosynthesis intermediates. These intermediates may be modified, where appropriate after separation, either by adding particular components to the production media, or by introducing into the strains thus mutated other genes capable of modifying the intermediate by acting as a substrate for them. These intermediates may thus be modified by chemical, biochemical, enzymatic and/or microbiological means. In this context, the mutant SP92::pVRC505 of *S. pristinaespiralis* strain SP92 was constructed: *S. pristinaespiralis* SP92::pVRC505 was isolated by homologous integration in the snaA gene of a suicide plasmid pVRC505, constructed from the vector pDH5 and a fragment internal to the snaA gene. The following mutants were also constructed: SP92 samS::QamR; SP92::pVRC508; SP92::pVRC404 and SP92::pVRC1000 (Example 9).

The invention hence also relates to a method for preparing an intermediate of the biosynthesis of streptogramins, according to which:
- a cell blocked in a step of the pathway of biosynthesis of streptogramins is prepared as described above,
- the said cell is cultured, and
- the accumulated intermediate is recovered.

The invention also relates to a method for preparing a molecule derived from streptogramins, according to which:
- a cell blocked in a step of the pathway of biosynthesis of streptogramins is prepared as described above,
- the said cell is cultured, and
- the intermediate accumulated by this cell is modified, where appropriate after separation of the culture medium.

The present invention is illustrated by means of the examples which follow, which are to be considered as illustrative and non-limiting.

LIST OF FIGURES

FIG. 1: Example of structure of the A components of streptogramins.

FIG. 2: Example of structure of the B components of streptogramins.

Figure 3:
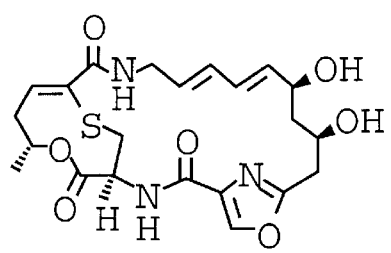
Figure 3:
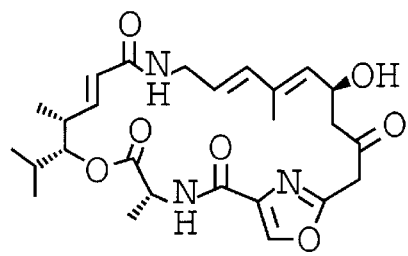
Figure 3:
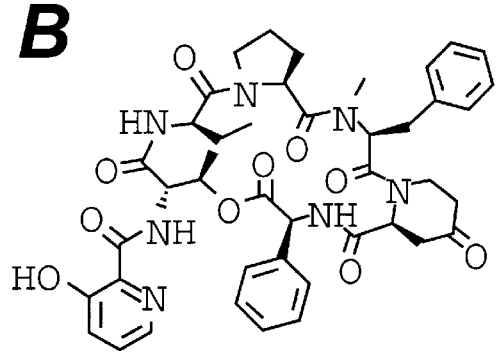
Figure 3:
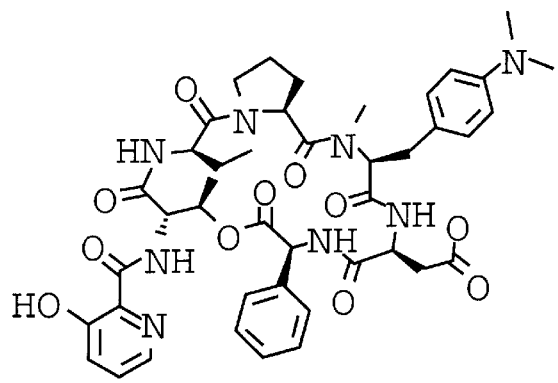
Figure 3:
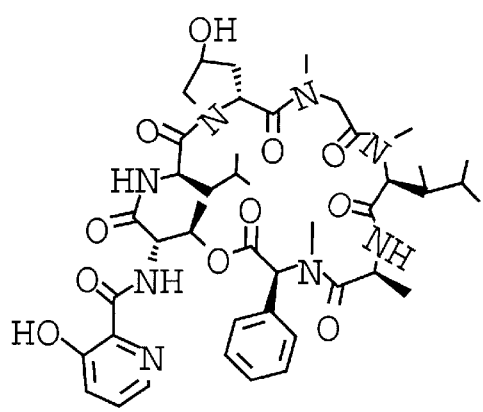

FIG. 3: Other examples of structures of streptogramins.

FIG. 4: Diagram of cosmid pIBV1.

FIG. 5: Diagram of cosmid pIBV2.

Figure 6:
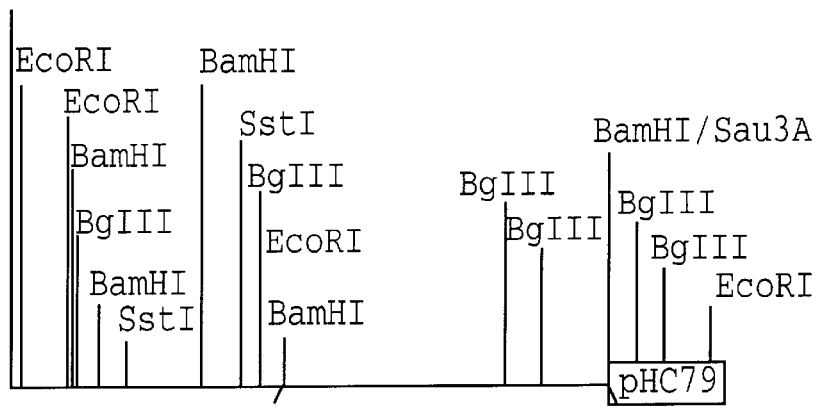
Figure 6:
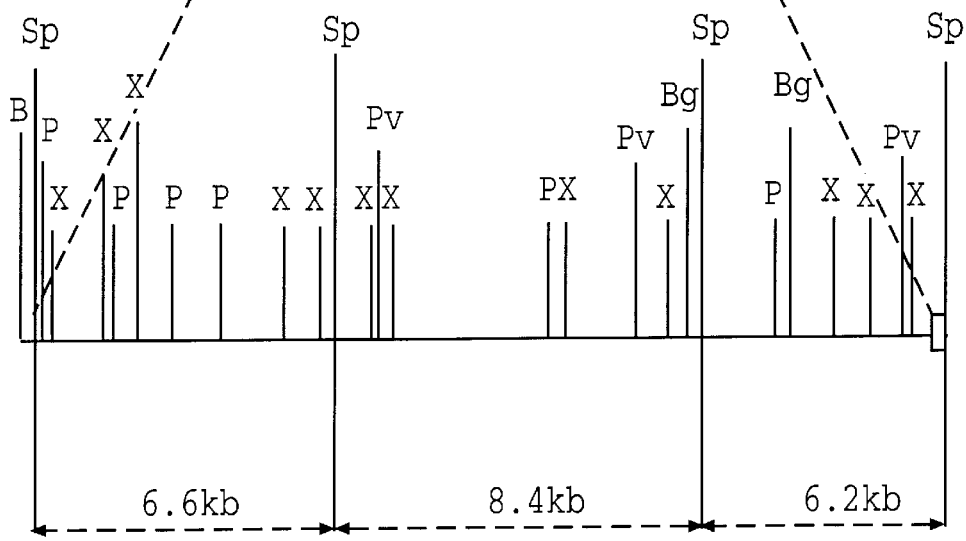

FIG. 6: Diagram of cosmid pIBV3.

FIG. 7: Diagram of cosmid pIBV4.

Figure 8:
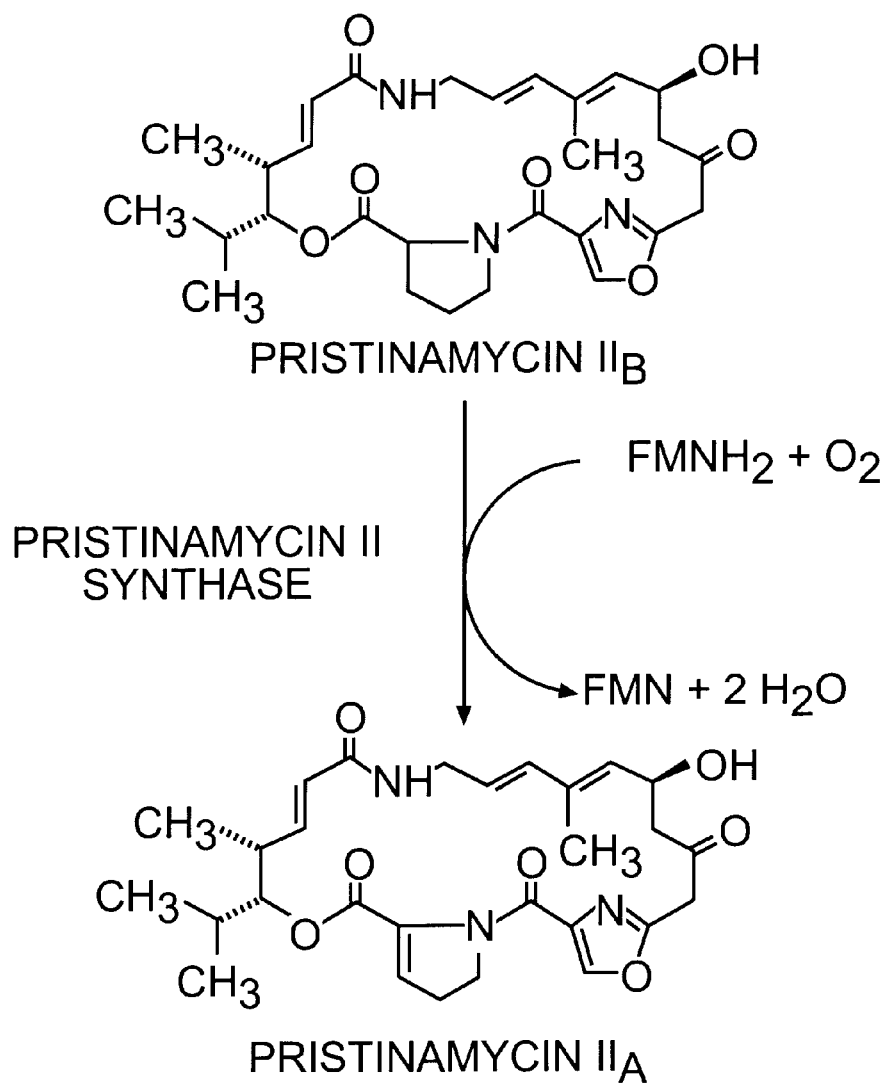

FIG. 8: Reaction catalysed by pristinamycin IIA synthase.

Figure 9:
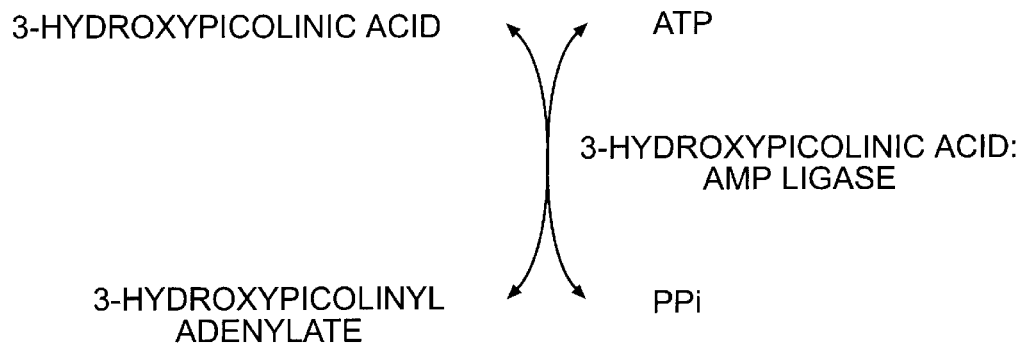

FIG. 9: Reaction catalysed by 3-hydroxypicolinic acid:AMP ligase.

Figure 10:
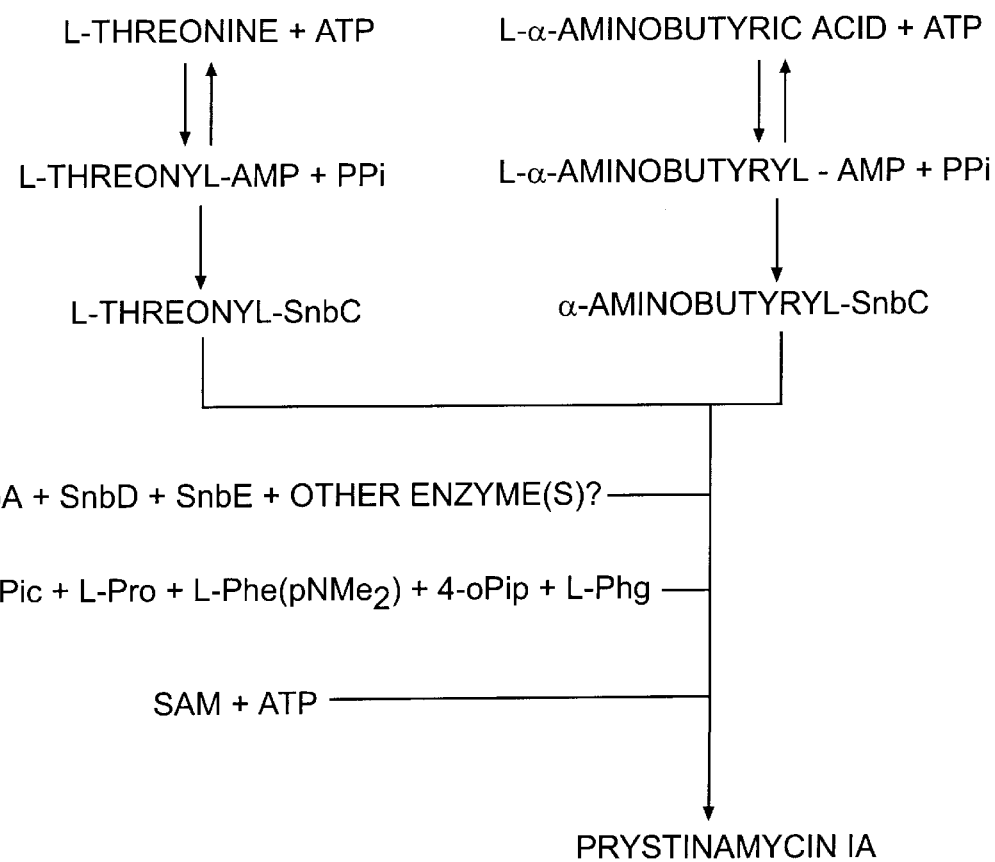

FIG. 10: Reaction catalysed by SnbC.

Figure 11:
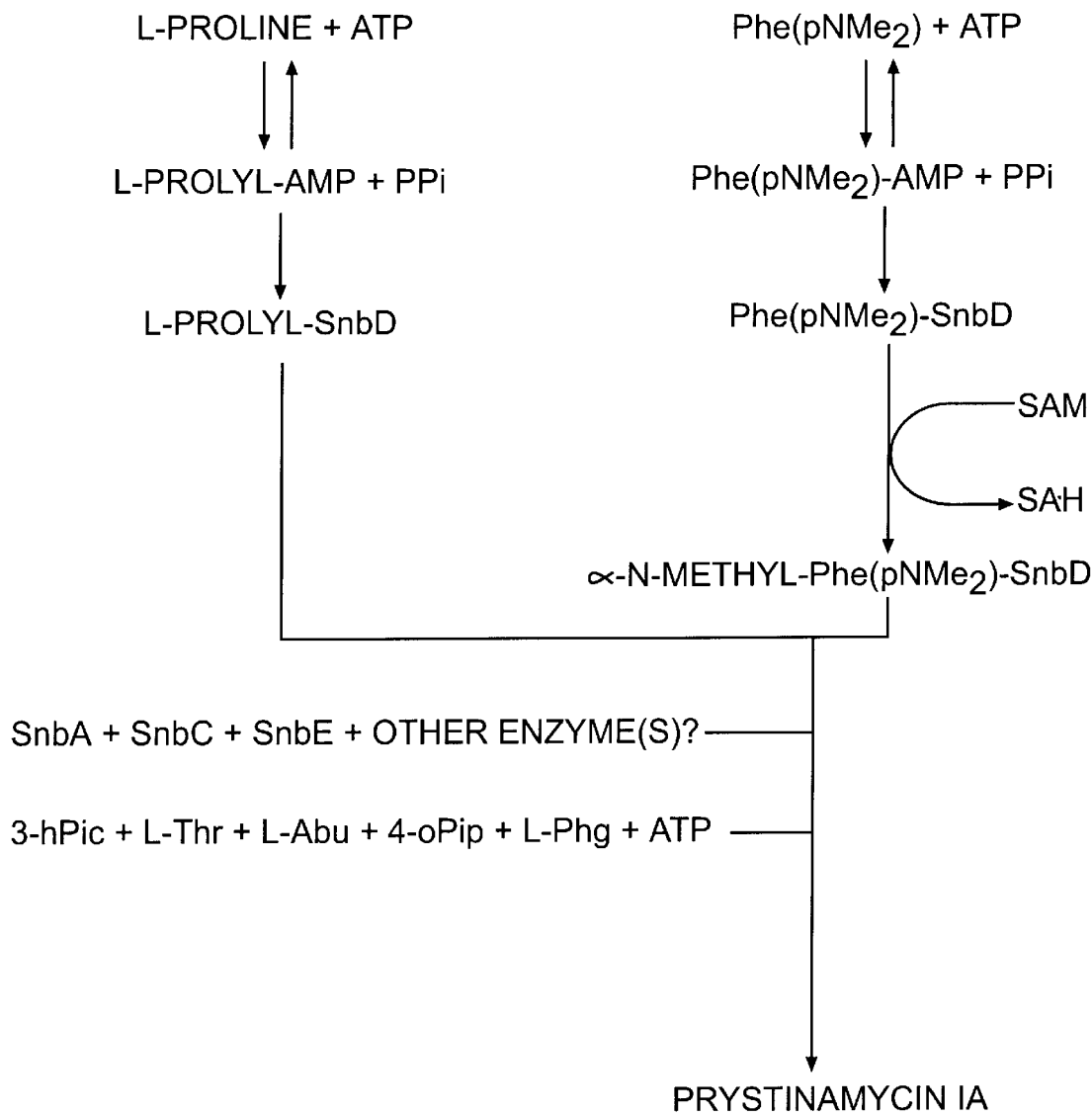

FIG. 11: Reaction catalysed by SnbD.

Figure 12:
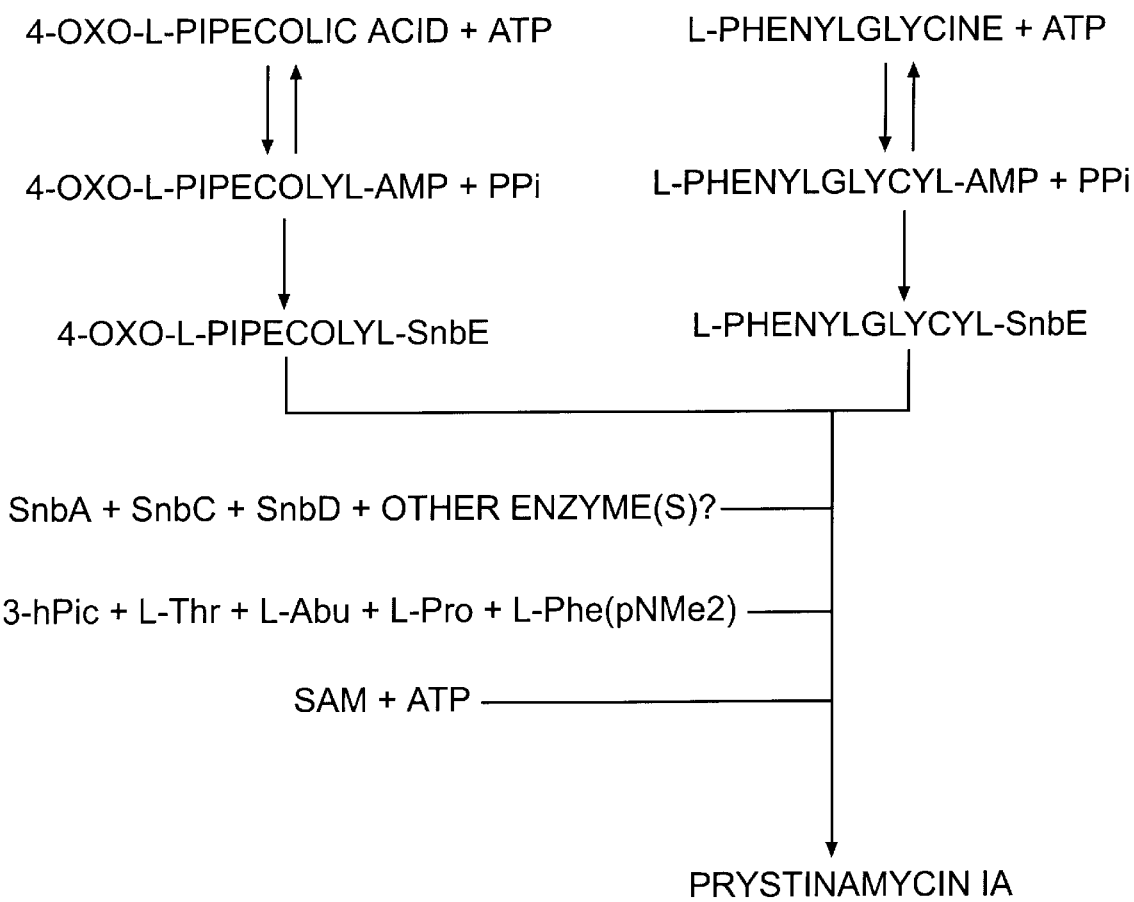

FIG. 12: Reaction catalysed by SnbE.

Figure 13:
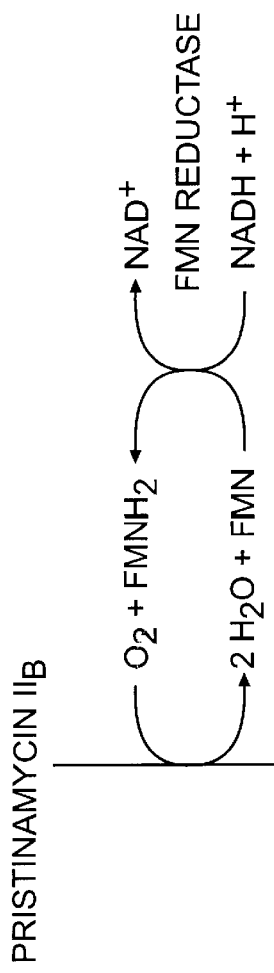

FIG. 13: Reaction catalysed by SnaC.

Figure 14:
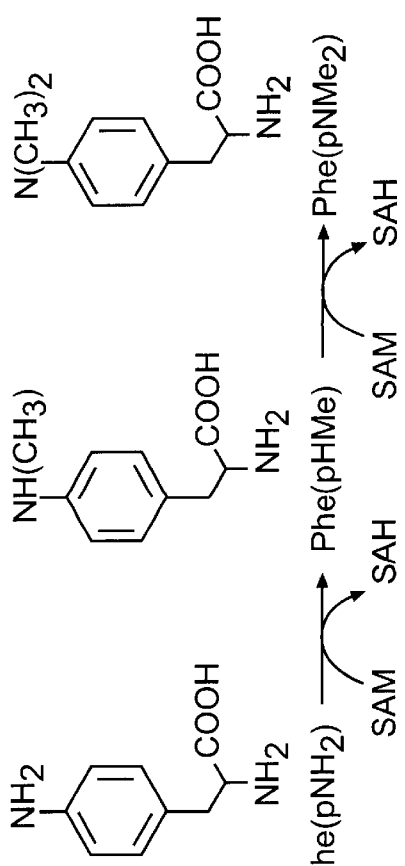

FIG. 14: Reaction catalysed by PapM.

FIG. 15: Diagram of plasmids pVRC402 (A) and pVRC501 (B).

Figure 16:
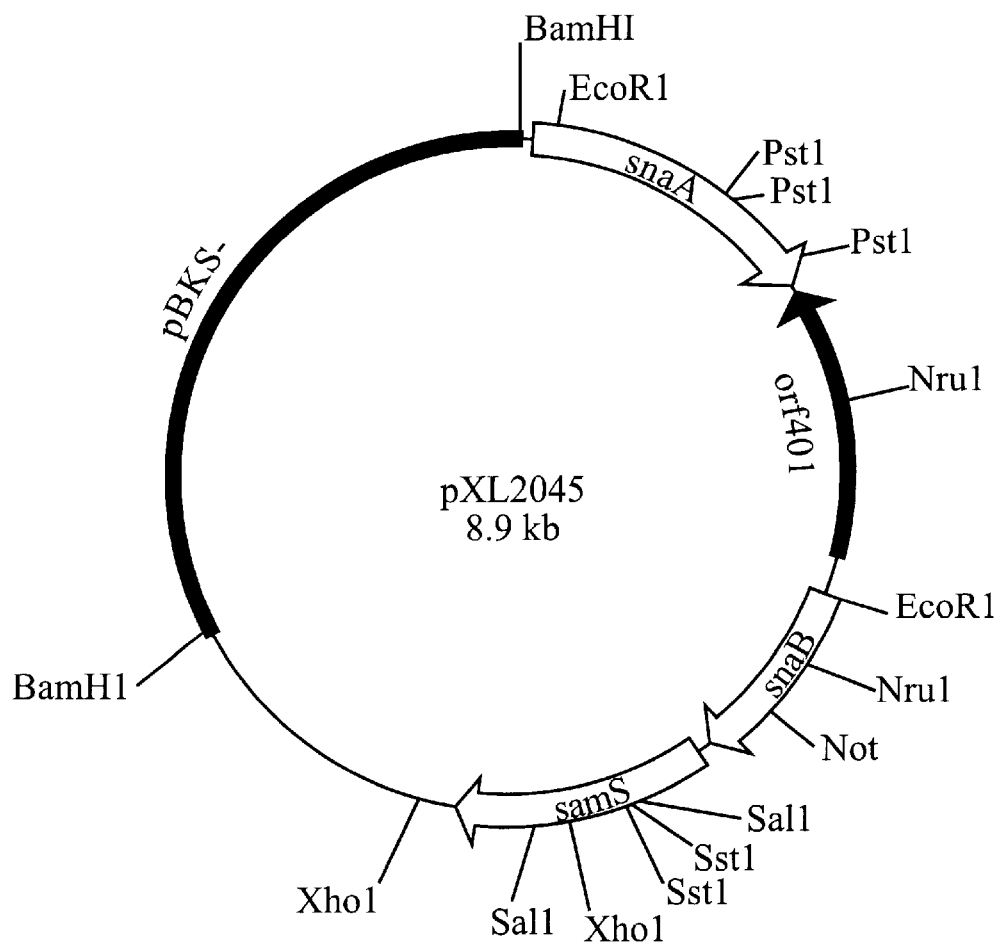

FIG. 16: Diagram of plasmid pXL2045.

Figure 17:
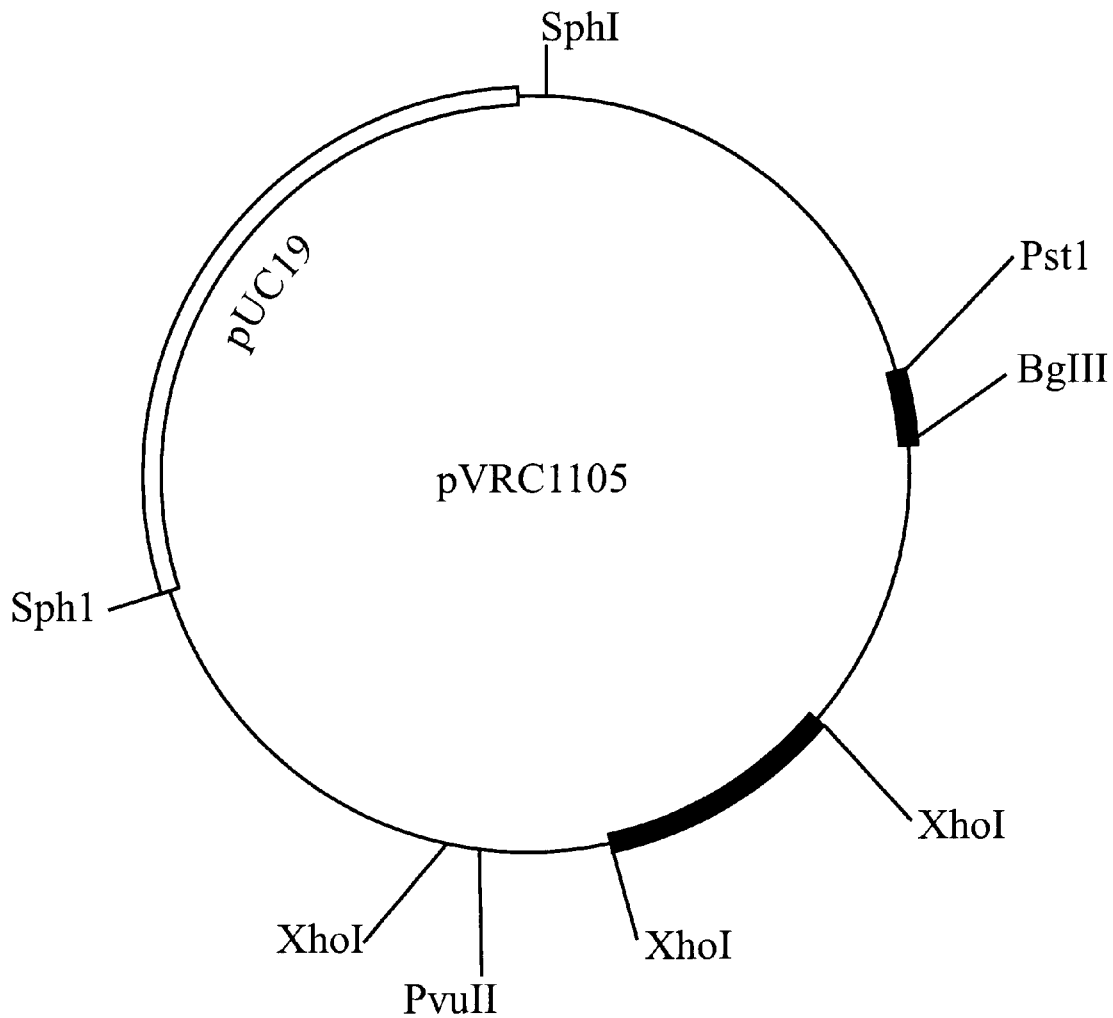

FIG. 17: Diagram of plasmid pVRC1105.

Figure 18:
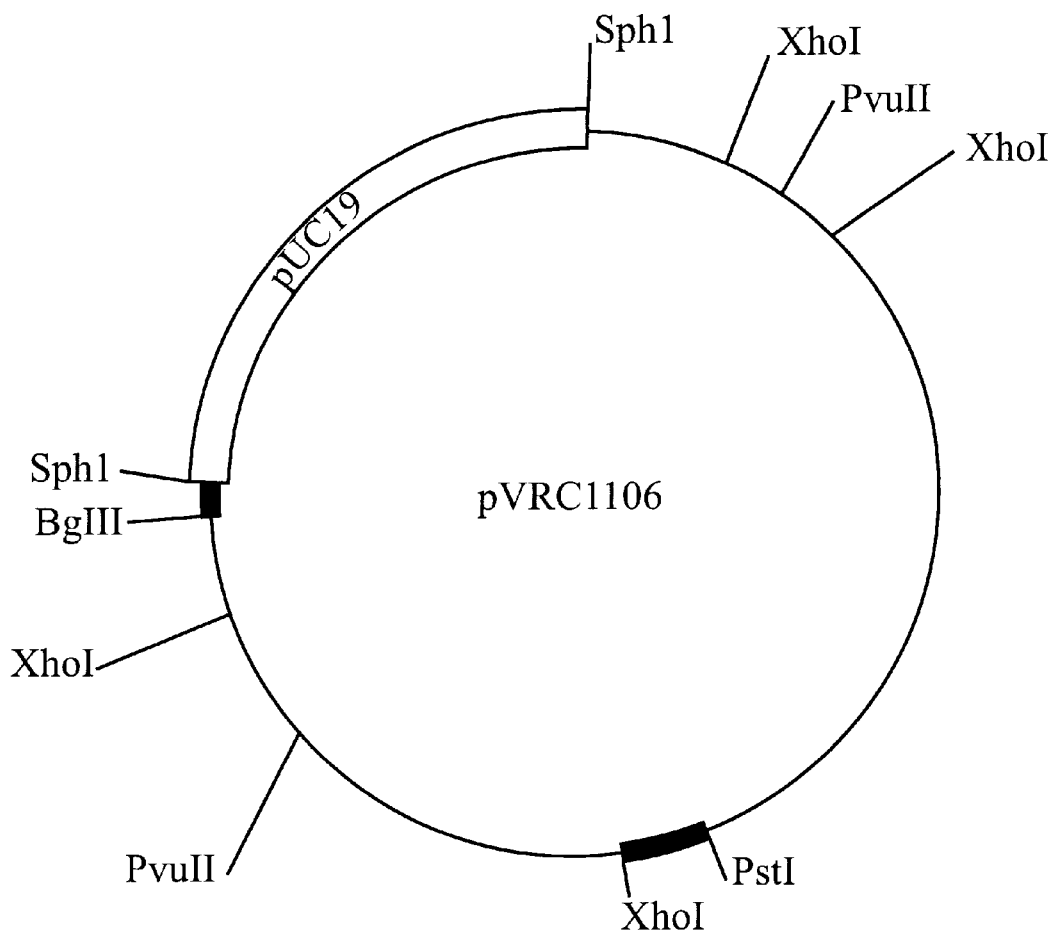

FIG. 18: Diagram of plasmid pVRC1106.

Figure 19:
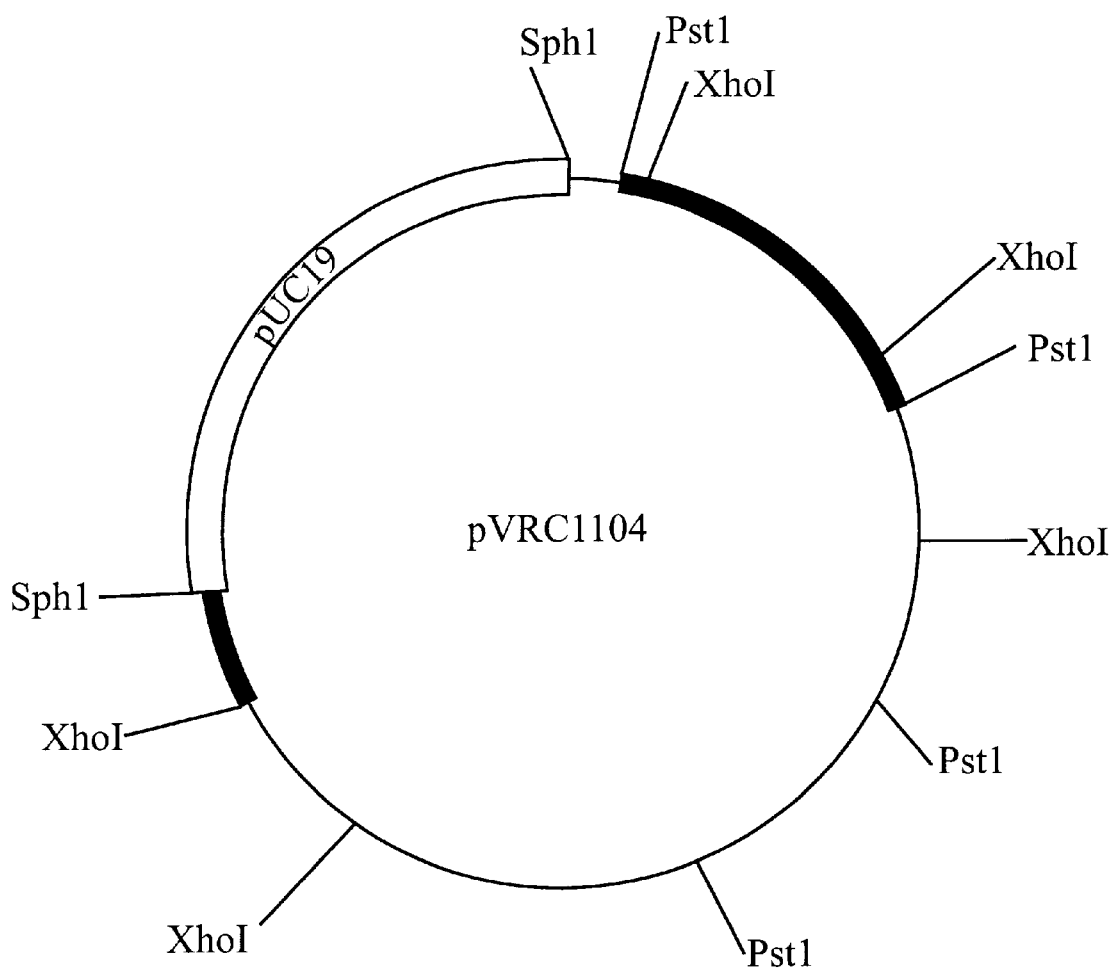

FIG. 19: Diagram of plasmid pVRC1104.

Figure 20:
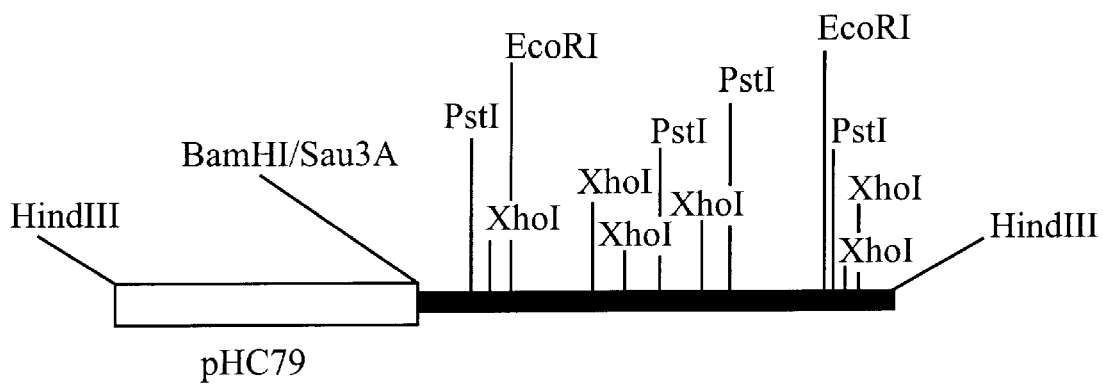

FIG. 20: Diagram of plasmid pVRC900.

Figure 21:
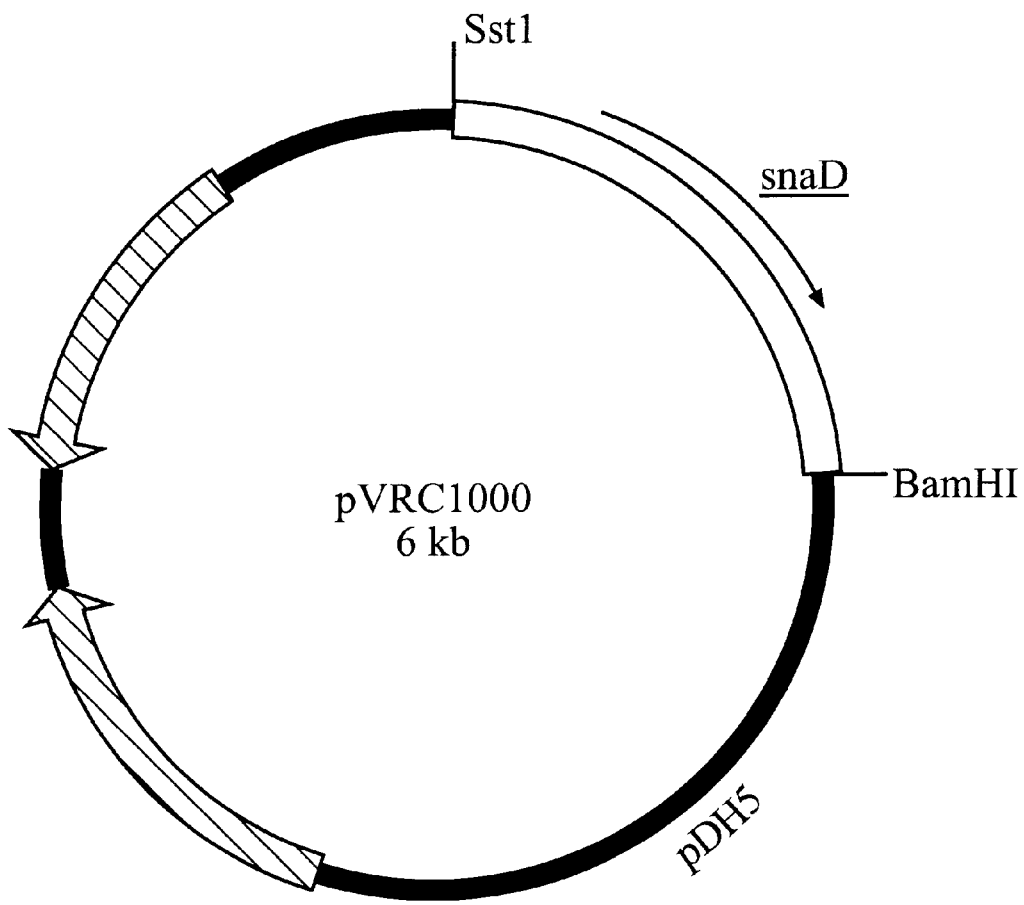

FIG. 21: Diagram of plasmid pVRC1000.

Figure 22:
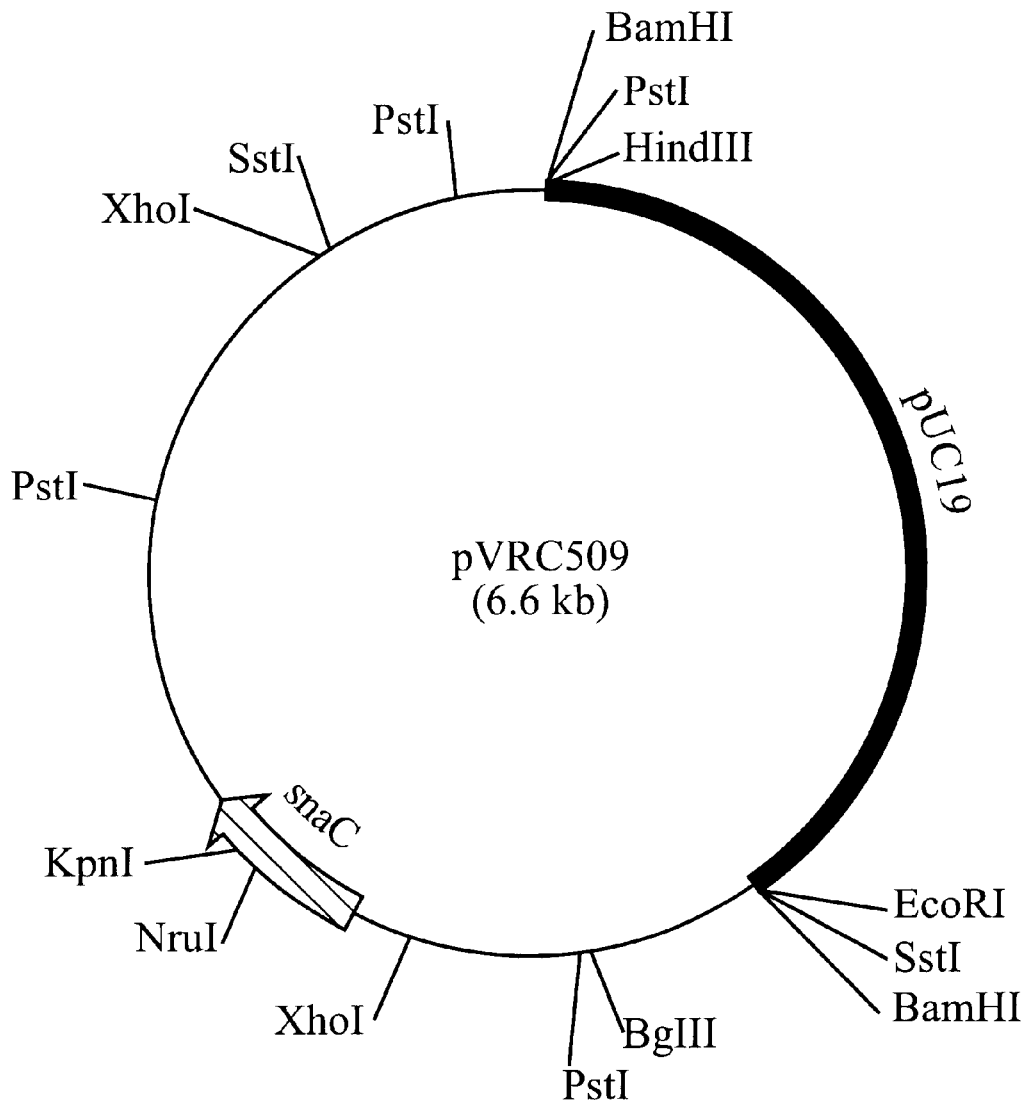

FIG. 22: Diagram of plasmid pVRC509.

Figure 23:
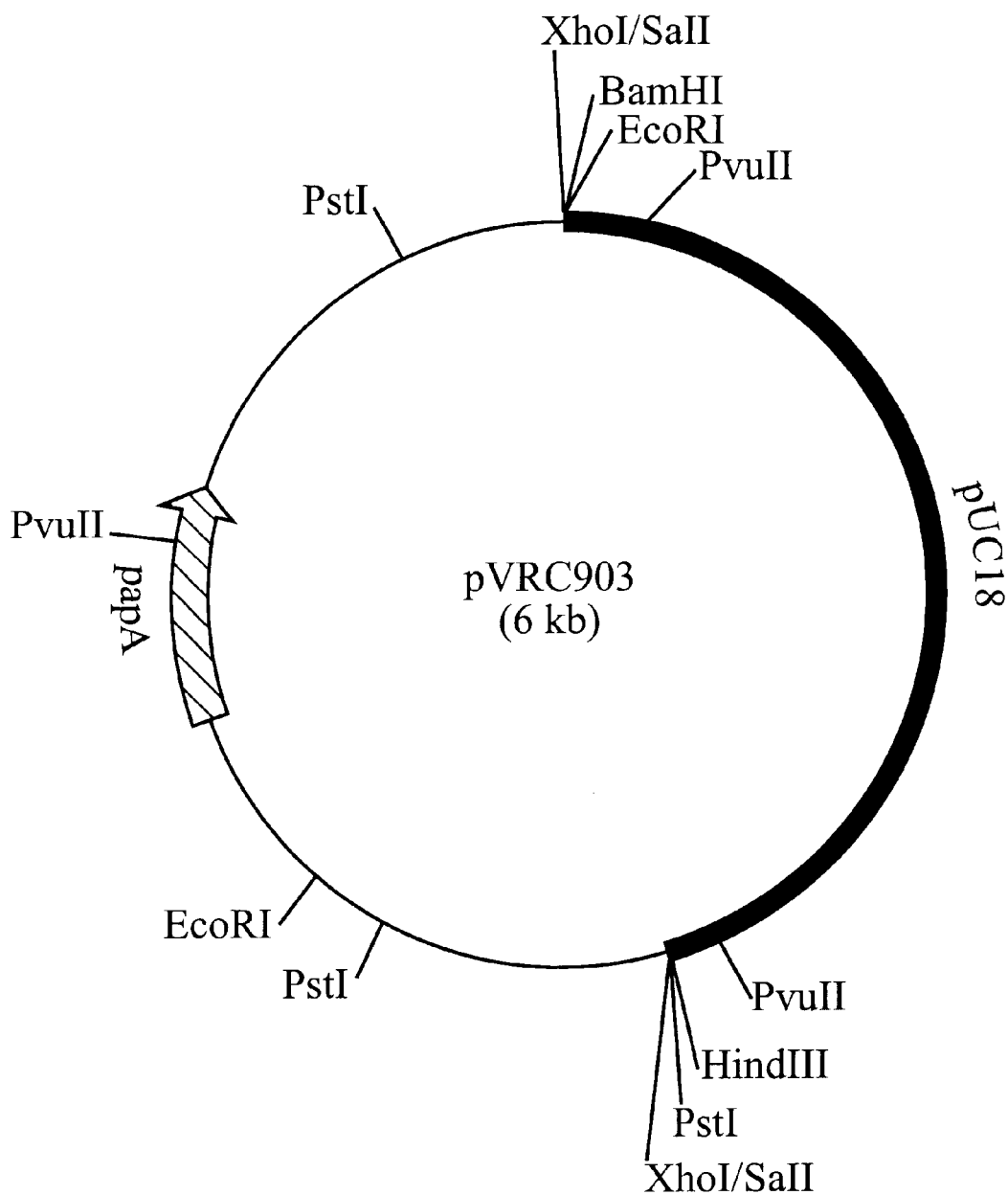

FIG. 23: Diagram of plasmid pVRC903.

Figure 24:
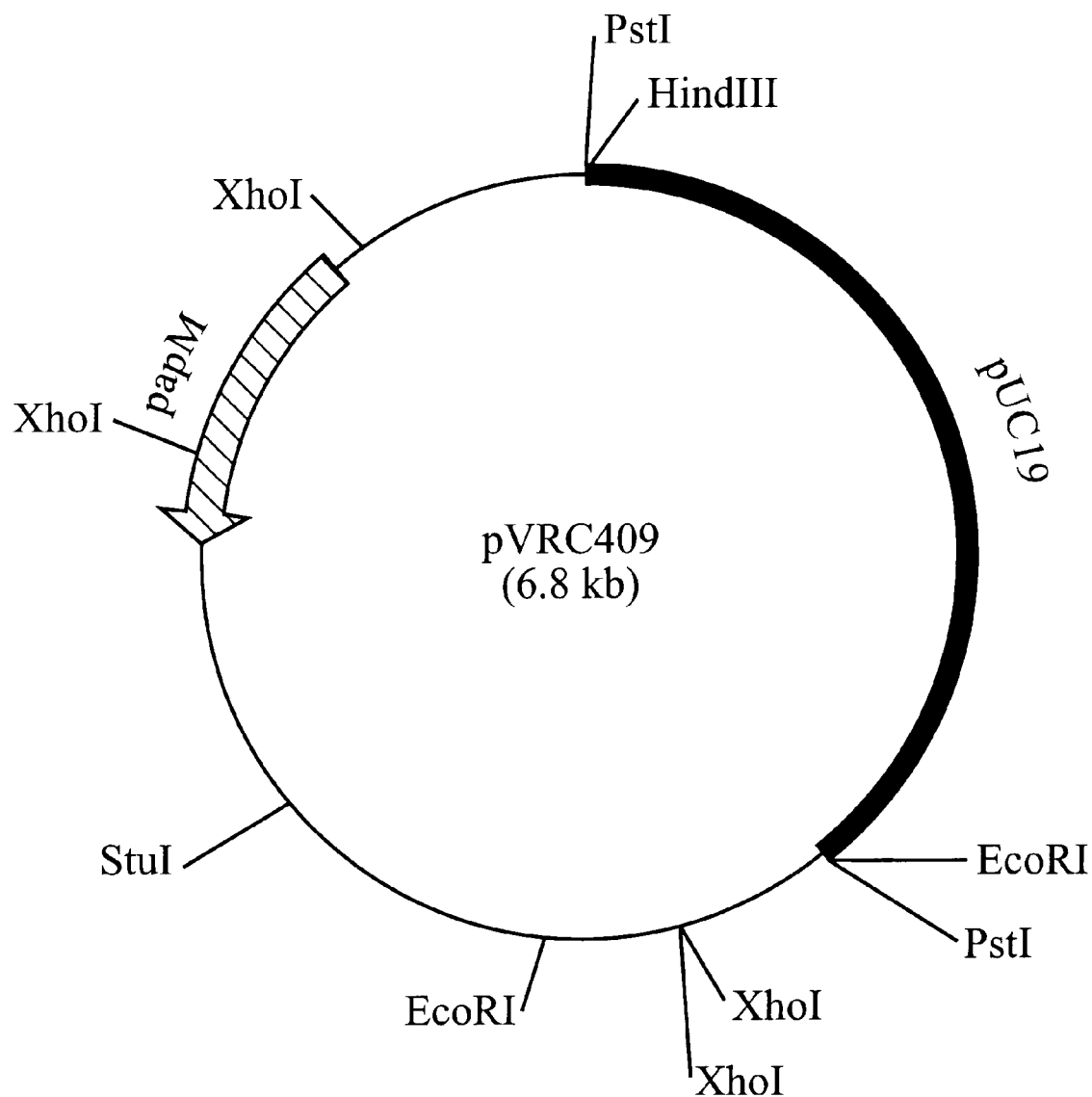

FIG. 24: Diagram of plasmid pVRC409.

Figure 25:
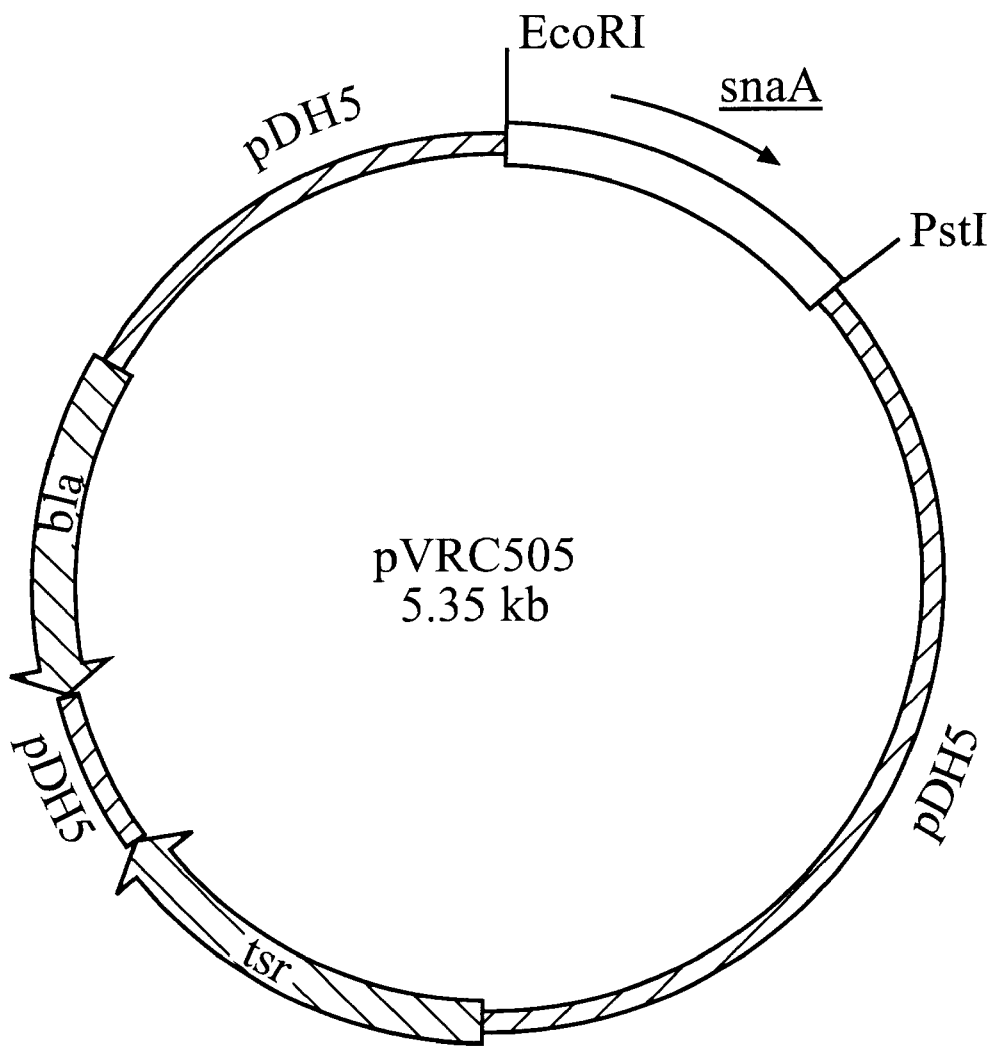

FIG. 25: Diagram of plasmid pVRC505.

Figure 26:
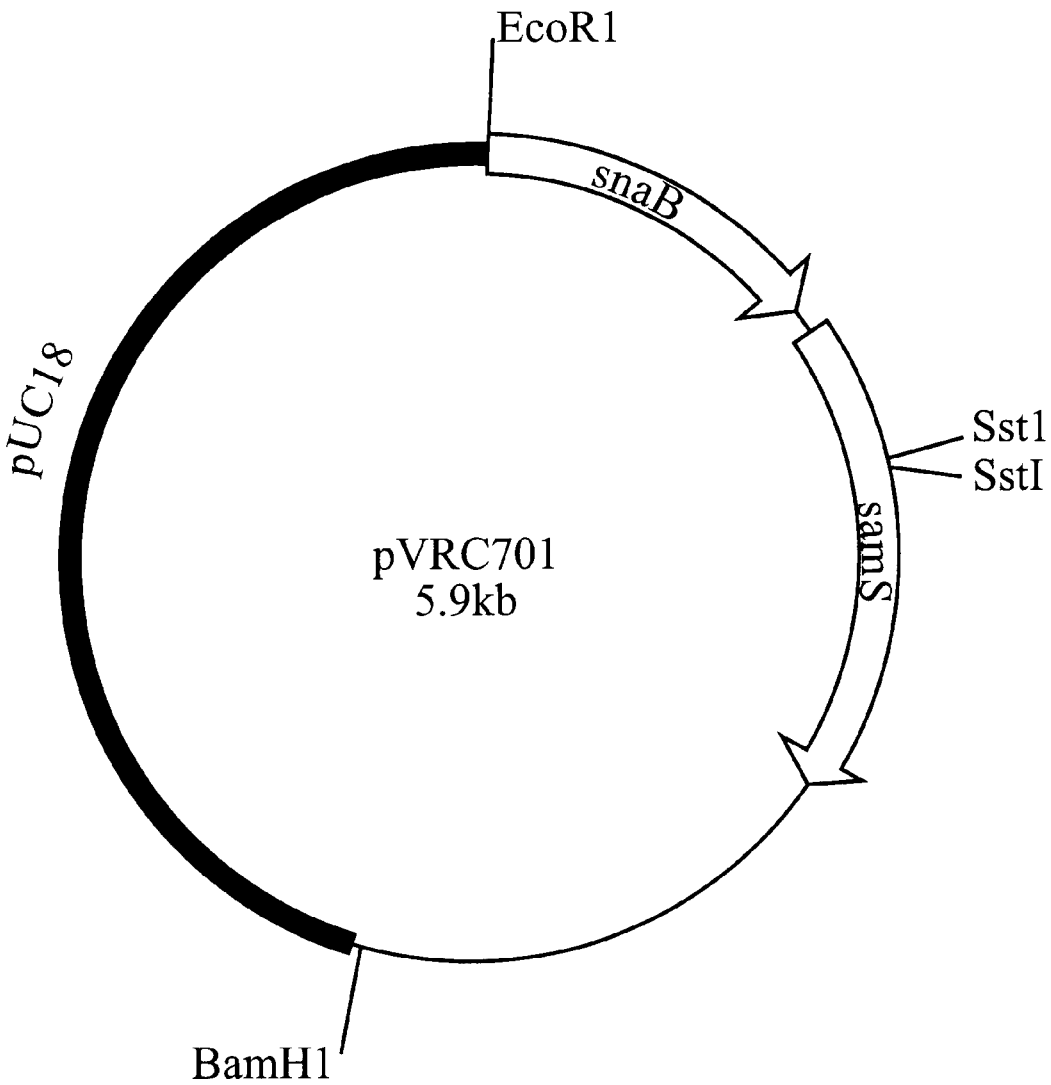

FIG. 26: Diagram of plasmid pVRC701.

Figure 27:
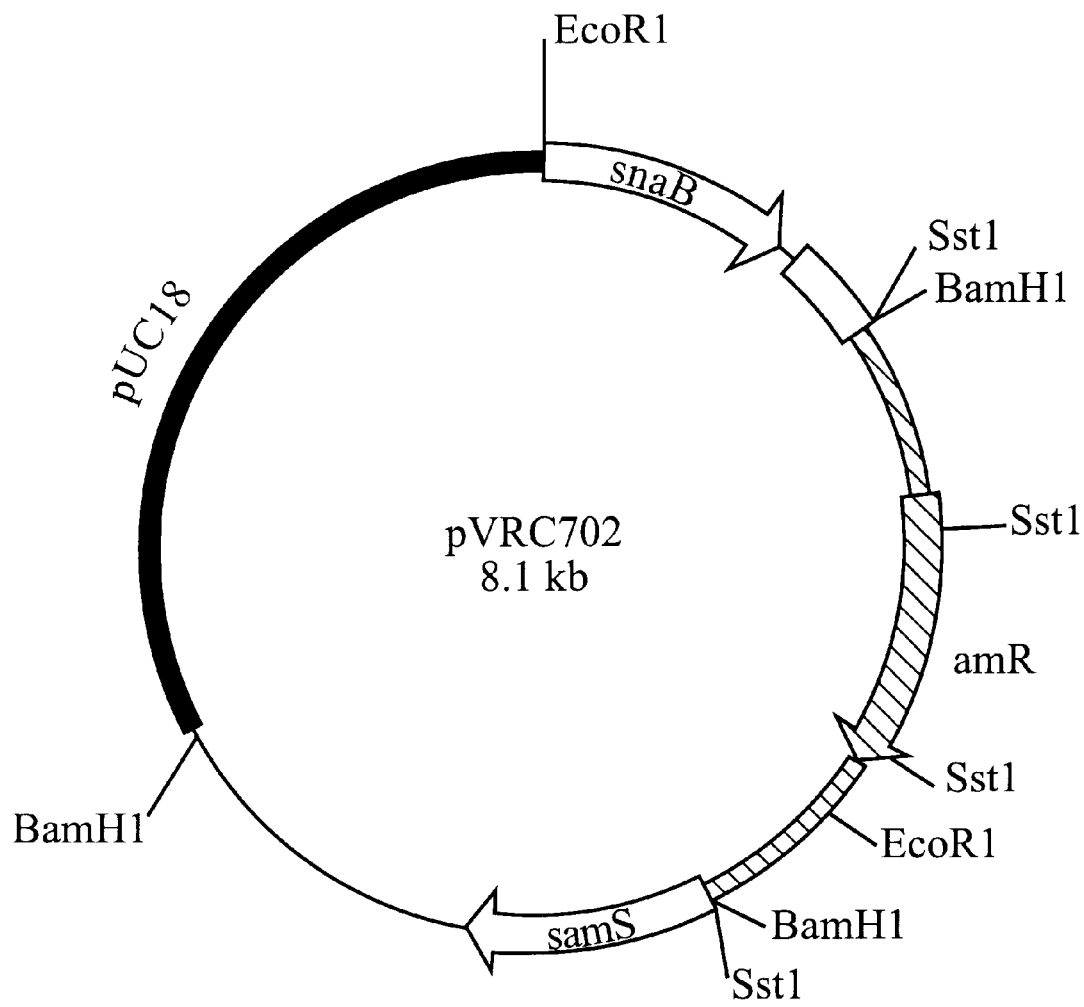

FIG. 27: Diagram of plasmid pVRC702.

Figure 28:
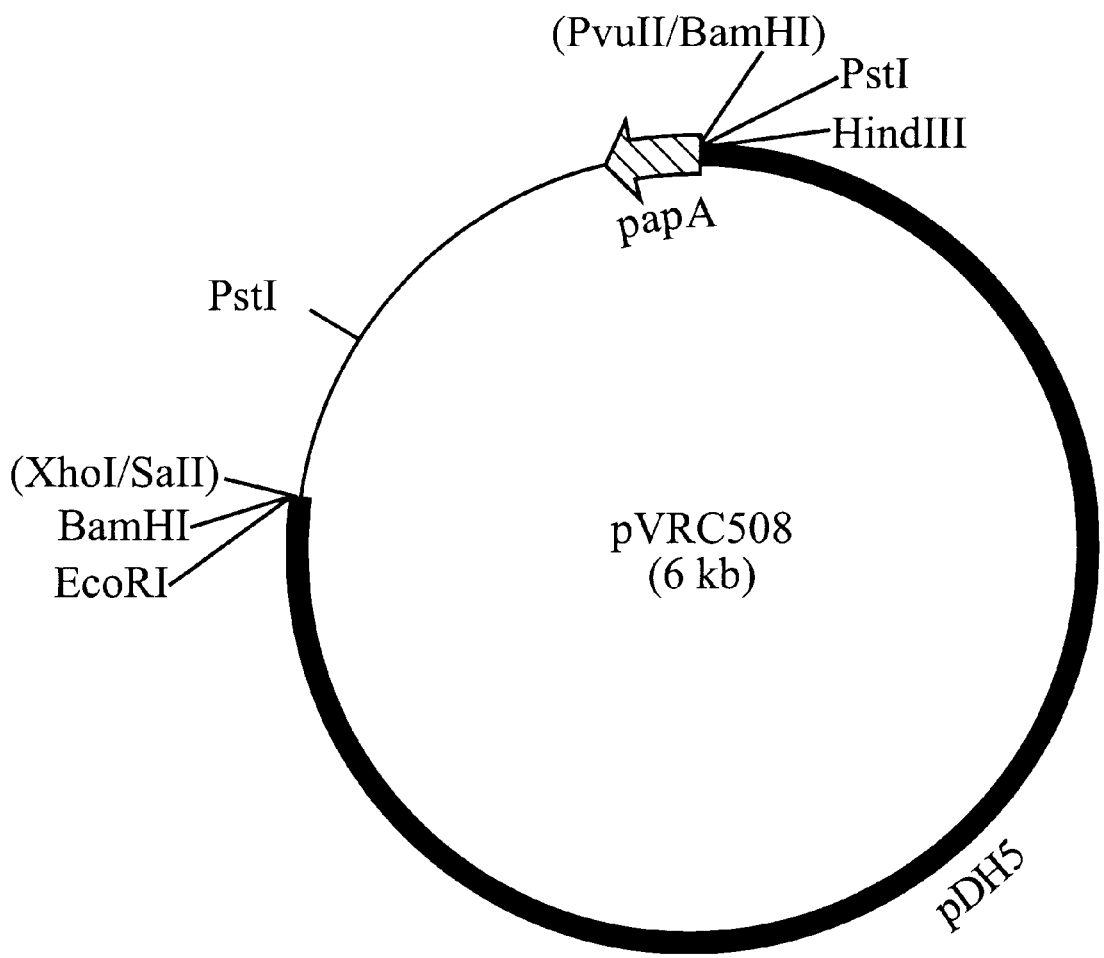

FIG. 28: Diagram of plasmid pVRC508.

Figure 29:
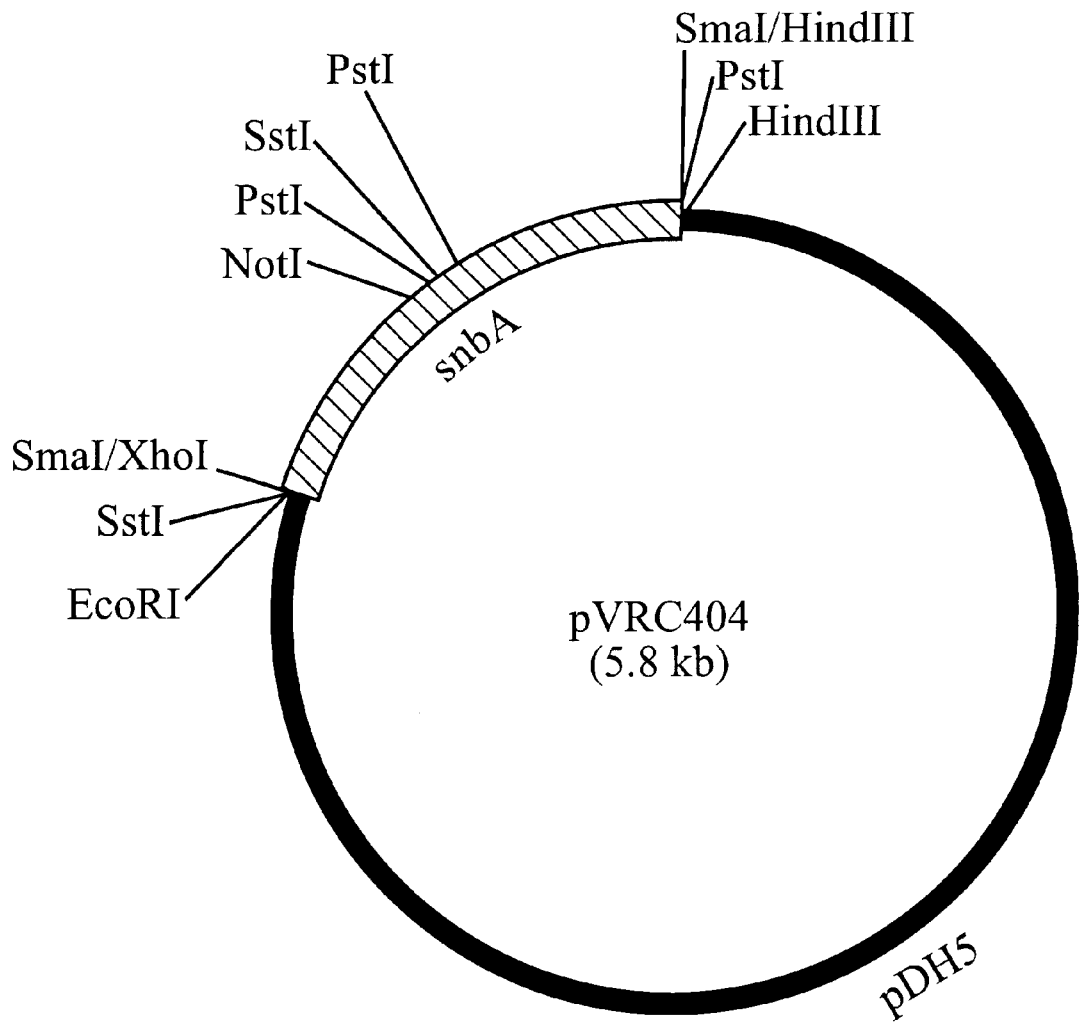

FIG. 29: Diagram of plasmid pVRC404.

Figure 30:
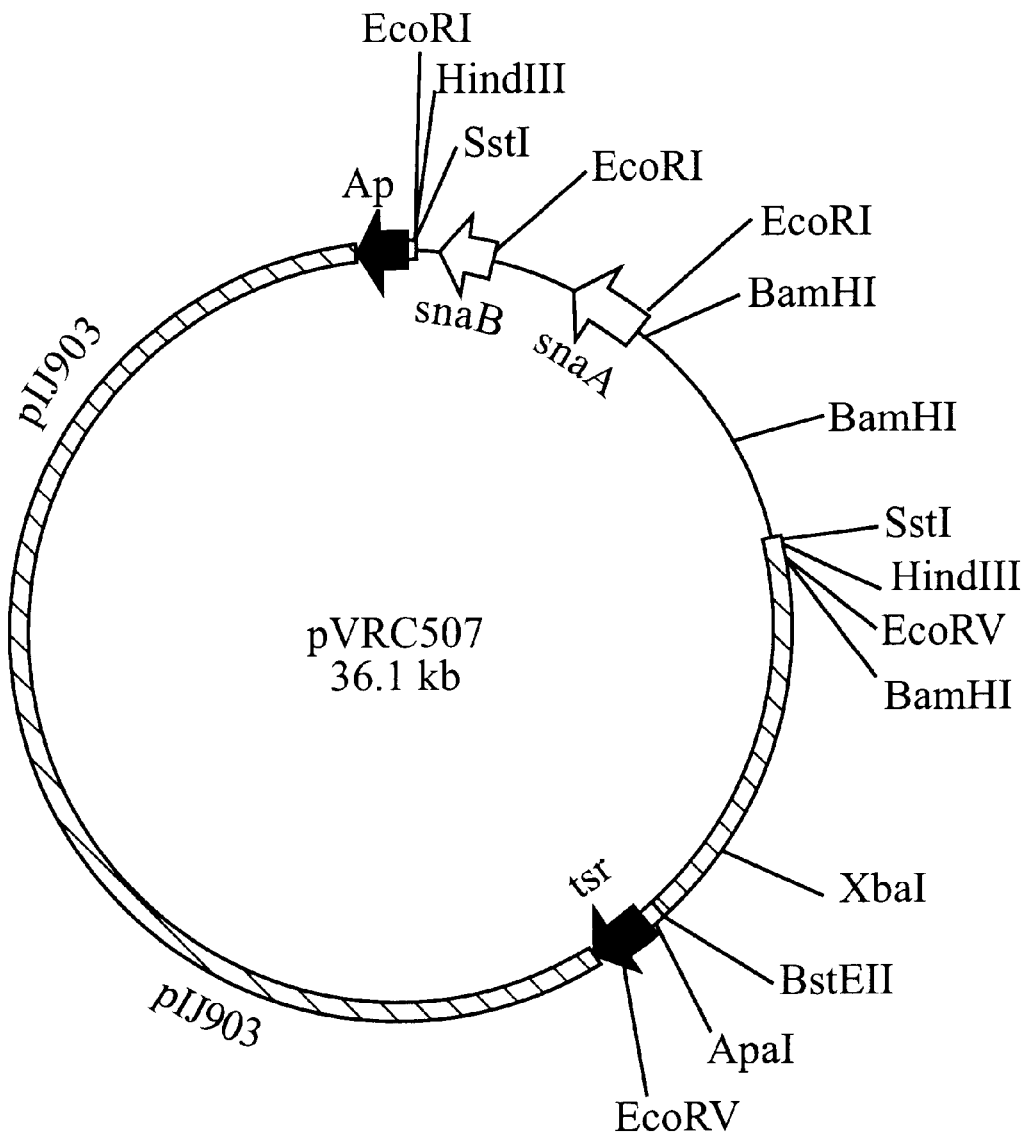

FIG. 30: Diagram of plasmid pVRC507.

Figure 31:
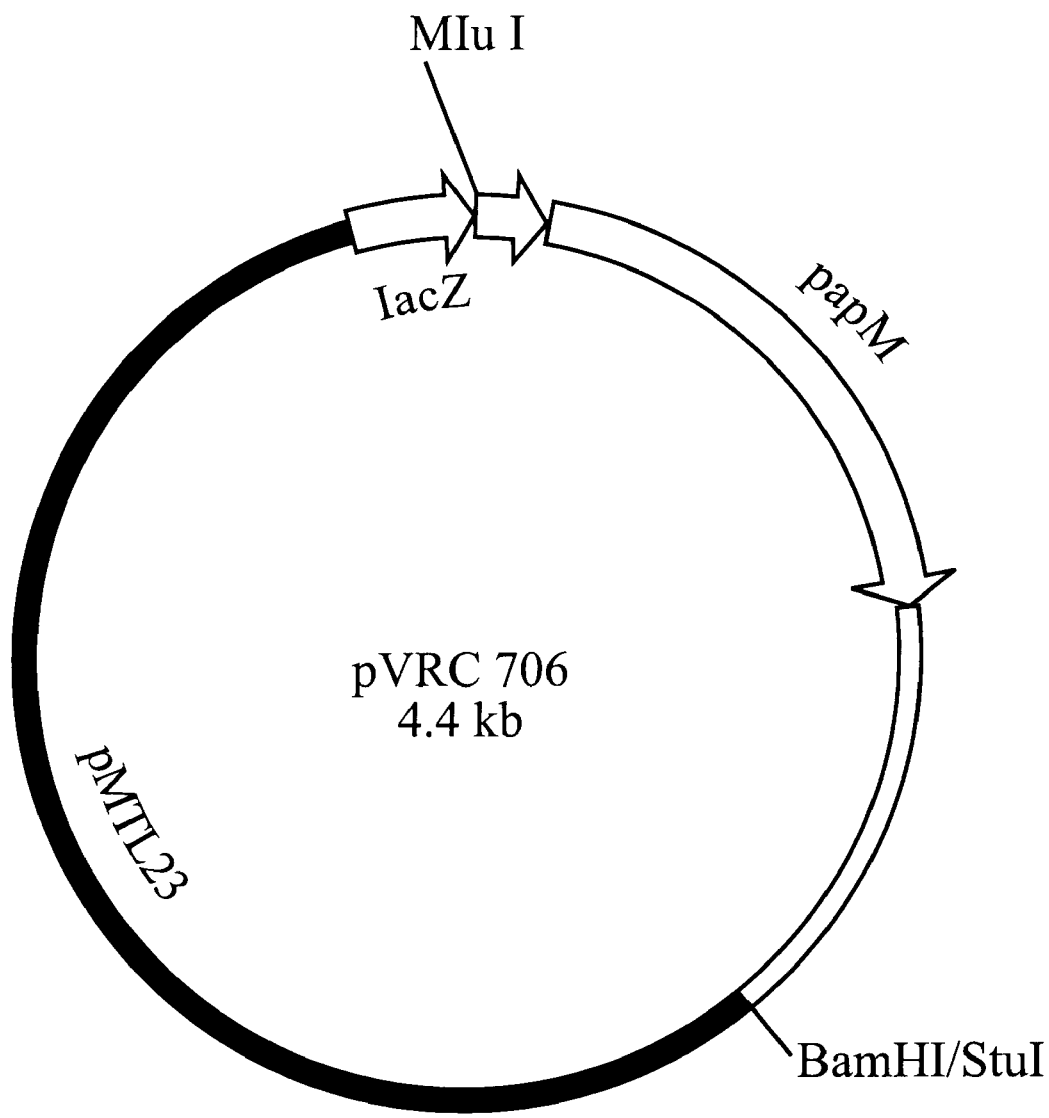

FIG. 31: Diagram of plasmid pVRC706.

Figure 32:
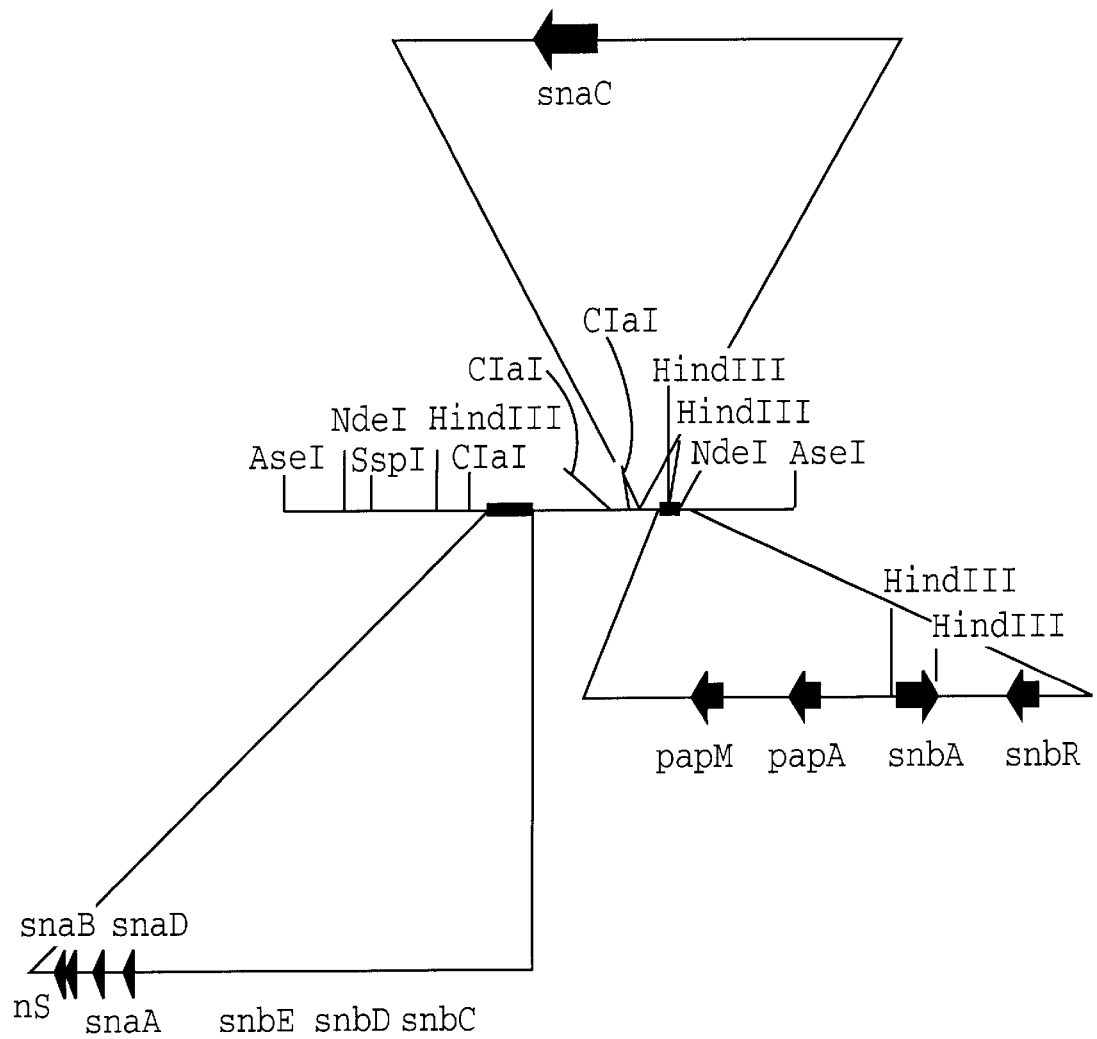

FIG. 32: General map.

MATERIALS

Bio-Sil SEC 125 and 250 columns (Bio-Rad)
MonoQ HR 5/5, 10/10 and 16/10 columns (Pharmacia)

PD-10 column (Pharmacia)
Superose 6 HR 10/30 column (Pharmacia)
Superdex 200 Hi-Load 16/60 and 75 HR 10/30 column (Pharmacia)
Superose 12 prep grade column (Pharmacia)
Vydac C4 and C18 columns (The Separations Group)
Nucleosil 5-C18 column (Macherey-Nagel)
Phenyl Superose HR 10/10 column (Pharmacia)
TSK G2000 SW column (Tosoh, Japan)
Phenyl Sepharose (Pharmacia)
FMN-agarose (Sigma)
Q Sepharose Fast Flow (Pharmacia)
Sephadex G-25 Fine (Pharmacia)
Centricon 10 or 30 (Amicon)
Centriprep 10 or 30 (Amicon)
Centrilutor (Amicon)

EXAMPLE 1

Isolation of Total DNA of *Streptomyces pristinaespiralis* Strain SP92

This example illustrates how *S. pristinaespiralis* SP92 DNA may be purified.

*S. pristinaespiralis* strain SP92 is derived from *S. pristinaespiralis* strain DS5647 (ATCC25486).

50 ml of YEME medium (34% sucrose, 5 mM $MgCl_2$, 0.25% glycine (D. Hopwood et al. 1985)) are inoculated with $10^8$ *S.pristinaespiralis* SP92 spores, and the culture is incubated for 40 hours at 30° C. with stirring at 280 rpm.

The mycelium is harvested and washed with 15 ml of 10.3% sucrose. Approximately 1 g of the mycelium pellet is taken up with 5 ml of TE supplemented with 34% of sucrose, to which are added 1 ml of lysozyme at a concentration of 50 mg/ml in 10 mM Tris-HCl solution pH 8.0 and 1 ml of 0.25 M EDTA pH 8.0. After incubation at 30° C. for a period of 30 to 60 min, the mixture is clarified by adding 0.8 ml of 10% sarkosyl. 2 ml of 0.25 M EDTA pH 8.0, 10 ml of TE, 18 g of CsCl and 1.2 ml of ETB at a concentration 10 mg/ml are then added. The preparation is ultracentrifuged overnight at 55,000 rpm at 20° C.

The chromosomal DNA, present in the CsCl gradient in the form of a band, is recovered using a Pasteur pipette. The ETB is removed by several washes with a solution of isopropanol saturated with TE buffer, 5 M NaCl. The DNA is precipitated by adding 3 volumes of TE and 4 volumes of isopropanol. After washing with 70% ethanol, the DNA is taken up in a suitable volume of TE. The total amount of DNA obtained varies between 250 and 500 μg per g of mycelium.

EXAMPLE 2

Isolation of *E. coli* Plasmid DNA

This example illustrates how *E. coli* plasmid DNA is prepared from recombinant strains of *E. coli*.

2.1 Preparation of *E. coli* Plasmid DNA in Large Amounts

This example illustrates how maxi preparations of plasmid DNA are produced in *E. coli*.

This preparation is performed using a 500 ml culture in LB medium containing 150 μg/ml of ampicillin. The extraction protocol is derived from the methods described by Birnboim and poly (1979) and Ish-Horowicz and Burke (1981), and is described in Maniatis et al. (1989).

After this extraction, the plasmid DNA is purified using a CsCl gradient as described by Maniatis et al. (1989). The plasmid DNA is then precipitated by adding 3 volumes of TE and 4 volumes of isopropanol. After centrifugation, the pellet is taken up in 0.5 to 1 ml of TE.

2.2. Preparation of *E. coli* Plasmid DNA in Small Amounts

This example illustrates how minipreparations of plasmid DNA are produced in *E. coli*.

This preparation is carried out using 1.5 ml of culture in LB medium containing 150 μg/ml of ampicillin. The procedure is that described by Birnboim and Doly (1979).

EXAMPLE 3

Construction of the Genomic DNA Library of *S. pristinaespiralis* SP92 in *E. coli* and Preparation of Hybridization Membranes This example illustrates how a genomic DNA library of *S. pristinaespiralis* SP92 is produced in *E. coli*.

3.1. Preparation of Genomic DNA Fragments

This example illustrates how high molecular weight genomic DNA fragments may be prepared.

Total DNA of the strain SP92, prepared as described in Example 1, is partially digested with Sau3A (New England Biolabs, Beverly, Mass. 01915-5510 USA) in the buffer recommended by the supplier: 100 mM NaCl, 10 mM Tris-HCl (pH7.5), 10 mM $MgCl_2$, 100 μg/ml BSA. The amount of enzyme used to obtain high molecular weight DNA fragments was determined empirically. Approximately 0.025 enzyme units are used to digest 1 μg of total DNA for 20 min at 37° C. The reaction is then stopped by incubation for 15 min at 65° C., and the enzyme is removed by adding an equal volume of phenol/chloroform. After centrifugation, the supernatant containing the partially digested total DNA is precipitated by adding 0.3 M final sodium acetate and 2.5 volumes of ethanol.

Approximately 100 μg of total DNA are digested in this way, and DNA fragments between 30 and 50 kb in size are isolated with a 10–40% sucrose gradient. Their size is verified by electrophoresis on 0.4% agarose gel.

3.2. Preparation of cosmid pHC79

This example illustrates how cosmid pHC79 is prepared from *E. coli*.

Cosmid pHC79 (Hohn, B. and Collins, 1980) comprises a portion of pBR322 (Bolivar, F. et al., 1977), the cro-cII region of λ and the region containing the cos sequence of Charon 4A (Blattner, F. R. et al., 1977).

Extraction of the cosmid was carried out as described on Example 2.1., from an *E. coli* strain TG1 (K12, Δ(lac-pro) supE thi hsd DS F' traD36 $proA^+B^+$ lacIq LacZ ΔM15, Gibson, 1984).

500 ng of cosmid pHC79 are digested with BamHI (New England Biolabs, Beverly, Mass. 01915-5520 USA) in 20 μl of buffer comprising 150 mM NaCl, 6 mM Tris-HCl pH 7.9, 6 mM $MgCl_2$, 6 mM 2-mercaptoethanol, 100 μg/ml BSA.

3.3. Ligation of the DNA fragments and the cosmid

This example illustrates how the fragments of the *S. pristinaespiralis* SP92 genome originating from an Sau3A digestion may be ligated with the BamHI-linearized vector pHC79.

Approximately 150 ng of cosmid linearized as described above were precipitated by means of ethanol with 350 ng of fragments of total DNA of *S. pristinaespiralis* SP92 prepared as described in Example 3.2. The pellet was taken up in 10 μl of ligation buffer: 50 mM Tris-HCl pH7.8, 10 mM MgCl$_2$, 20 mM DTT, 1 Mm ATP, 50 μg/ml of BSA, and 0.5 μl of T4 DNA ligase at a concentration of 400,000 units per ml (New England Biolabs, Beverly, Mass. 01915-5510 USA) were added. Incubation was carried out overnight at 15° C.

3.4. Carrying out encapsidation in vitro

This example illustrates how the cosmids constructed in 3.3 are encapsidated in vitro.

Encapsidation of the hybrid cosmids after ligation was carried out using the Gigapack II Gold kit developed by Stratagene (Stratagene Cloning Systems, La Jolla, Calif. 92037, USA).

2×4 μl of ligation mixture, equivalent to 2×70 ng of hybrid cosmids, were encapsidated in vitro according to the procedure described by the supplier.

3.5. Transfection of *E. coli* strains DH1 and HB101

This example illustrates how the cosmids are introduced into *E. coli*.

Two transfections were carried out in parallel with *E. coli* strains DH1 (F$^-$ gyrA96 recA1 relA1 endA1 thi-1 hsdR17 supE44L-, Low 1968) and HB101 (F$^-$ supE44 hsdS20(rB$^-$ mB$^-$) recA13 ara-14 proA2 lacY1 galK2 rpsL20 xyl-5 mtl-1, Boyer and Roulland-Dussoix 1969).

The cells were prepared according to the following protocol: a 100-ml preculture is produced in LB medium supplemented with 0.2% maltose and 10 mM MgSO$_4$ for 4 to 5 hours until the OD$_{600}$ reaches a value of 0.8. The culture is then centrifuged, and the pellet is taken up in 40 ml of 10 mM MgSO$_4$ and diluted to OD$_{600}$=0.5 in the same solution. 200 μl of the cell suspension thus prepared are mixed with 100 μl of encapsidation mixture. After 20 min of contact at 37° C., 1 ml of LB is added and the whole is incubated for 1 hour at 37° C. The transfectants are then selected on solid LB medium containing 150 μg/ml of ampicillin. The number of transfectants obtained is approximately 10$^4$ per μg of recombinant cosmid.

3.6. Storage of genomic DNA libraries of *S. pristinaespiralis* SP92

This example illustrates how the genomic DNA libraries of *S. pristinaespiralis* SP92 are stored.

After verification of the average size of the fragments inserted into cosmid pHC79, approximately 1500 colonies originating from each of the transfections carried out with the strains HB101 and DH1 are subcultured in 96-well microtitration plates containing 200 μl of Hogness medium (LB medium supplemented with 8.8% glycerol, 3 mM sodium acetate, 55 mM K$_2$HPO$_4$, 26 mM KH$_2$PO$_4$, 1 mM MgSO$_4$, 15 mM (NH$_4$)$_2$SO$_4$, 150 μg/ml ampicillin). These plates are incubated overnight at 37° C. and then stored at −80° C.

3.7. Preparation of hybridization membranes from genomic libraries of *S. pristinaespiralis* SP92

This example illustrates how the DNA of the colonies constituting the genomic libraries of *S. pristinaespiralis* SP92 is transferred onto a hybridization membrane.

These hybridization membranes were produced in duplicate for each of the 2 libraries according to the following protocol:

The 15 microtitration plates of each library are replicated using a replica plater on LB agar medium containing 150 μg/ml of ampicillin. After growth overnight at 37° C., colony transfer is performed onto a Biohylon Z$^+$ membrane (Bioprope System) according to the following protocol: the membrane is cut to the appropriate size and left in contact with the colonies for 1 min. Denaturation is then performed by soaking the membrane with 0.5 M NaOH, 1.5 M NaCl solution for 5 min, followed by neutralization by soaking the membrane in 3 M sodium acetate solution for 5 min. The DNA is fixed to the membrane by exposure under a UV lamp for 5 min.

EXAMPLE 4

4.1. Preparation of chromosomal DNA of *S. pristinaesprialis* strain SP92 and strains derived from SP92 in the form of inserts for pulsed-field electrophoresis This example illustrates how DNA of *S. pristinaespiralis* strain SP92 and strains derived from SP92 is prepared in the form of inserts for pulsed-field electrophoresis.

This preparation is made from a mycelium culture obtained in the following manner: 30 ml of YEME medium containing 0.25% of glycine are inoculated with 10$^8$ spores of the strain under study, and the culture is incubated for 48 hours at 30° C. and stirred at 280 rpm in 250-ml Erlenmeyers. The mycelium is then harvested by centrifugation for 10 min at 3800 rpm and washed twice with 10% sucrose. The mycelium pellet is then resuspended in 5 ml of solution I (250 mM EDTA pH 8.0, 20.6% sucrose). To 200 Ml of mycelium thereby obtained, 400 Ml of a lysozyme solution at a concentration of 50 mg/ml in solution I together with 800 Ml of 1% LMP agarose in 25 mM EDTA pH 8 and 10.3% sucrose, maintained at 42° C., are added. The mixture maintained at 42° C. is then poured into the wells of special combs, which are closed with adhesive tape and kept for 30 min at 4° C. The mixture solidifies, and the 30 to 40 inserts thereby obtained and contained in the wells are carefully removed from the moulds.

The inserts are first rinsed for 30 min at 4° C. in a solution containing 25 mM EDTA and 10.3% sucrose. They are then soaked in a solution of 500 mM EDTA, 1% lauryl sarcosyl and 1 mg/ml of proteinase K for twice 24 hours at 50° C., stirring from time to time. The inserts are then washed for 3 times one hour in TE containing 1 mM PMSF, changing the solution after each wash. The inserts thereby obtained are stored at 4° C. for not more than 4 months in 0.5 M EDTA pH 8.0.

4.2. Digestion of inserts of DNA of *S. pristinaespiralis* strain SP92 and strains derived from SP92 and analysis by pulsed-field electrophoresis This example illustrates how chromosomal DNA of *S. pristinaespiralis* strain SP92 and strains derived from SP92, prepared in the form of inserts as described in Example 4.1., is cut with different restriction enzymes for pulsed-field electrophoresis.

4.2.1. Digestion of chromosomal DNA in the form of inserts:

The inserts are first washed six times in TE, and then incubated twice for one hour in the buffer of the chosen restriction enzyme, Each insert is then placed in the lid of an Eppendorf tube containing 160 Ml of buffer of the restriction enzyme and 40 units of enzyme. The whole is covered with Parafilm, and the Eppendorf is closed to hold in place the Parafilm which enables any evaporation of the buffer to be avoided. The tubes are incubated at the desired temperature in an incubator overnight.

4.2.2. Analysis of digested DNA by pulsed-field electrophoresis:

The pulsed-field electrophoresis technique chosen for this study is that of the CHEF (Clamped Homogenous Electric Field) system developed by Chu et al. (1986), which makes it possible to obtain two homogeneous alternating fields oriented at 120° C. with respect to one another and linear trajectories for the DNA molecules. The apparatus used is the "Pulsafor System" marketed by Pharmacia-LKB.

The electrophoresis migration paratmeters, such as the pulse time and the migration period, were varied so as to obtain an optimal separation of DNA fragments ranging in size between 10 and 2500 kb. The three migration conditions used are as follows: to separate large fragments from 200 to 1700 kb in size, the chosen migration is 40 hours with a pulse time of 90 seconds; to separate fragments from 50 to 400 kb in size, the chosen migration is 20 hours with a pulse time of 10 seconds followed by 20 hours with a pulse time of 30 seconds; lastly, to separate smaller fragments from 10 kb to 200 kb in size, the chosen migration is 24 hours with a pulse time of 10 seconds. For these three migration conditions, the voltage is set at a constant 150 volts, the temperature is maintained at 13° C. and the electrophoresis gels contain 1.3% of agarose.

The inserts containing chromosomal DNA of *S. pristinaespiralis* strain SP92 and strains derived from SP92 are digested with the restriction enzymes as described above and are placed in the wells of the electrophoresis gel using two scalpel blades. The molecular weight markers used are "Yeast chromosome PFG marker" and "Lambda Ladder PFG marker" marketed by the company New England Biolabs. Migration is performed under one of the conditions described above and the gel is then stained in a bath of ETB (ethidium bromide) at a concentration of 4 Mg/ml for 20 min and thereafter decolorized in water for 20 min. After the gel is photographed, the DNA fragments are transferred onto a nylon membrane and then hybridized with $[\alpha^{-32}P]$dCTP-labelled probes as described in Example 9.1.

EXAMPLE 5

Isolation of cosmids carrying the genes coding for purified proteins involved in the biosynthesis of streptogramins This example describes how, starting from a purified protein participating in biosynthesis of pristinamycins and whose $NH_2$-terminal sequence or an internal sequence has been established, it is possible to isolate a cosmid carrying the structural gene for this same protein from the genomic libraries produced above, or alternatively to identify the corresponding structural gene from among the genes carried by the cosmids and which have already been sequenced.

5.1. Isolation of cosmids pIBV1 and pIBV3 carrying one or both structural genes for the two subunits of pristinamycin IIA synthase 5.1.1. Identification and purification of one of the proteins involved in the final step of the synthesis of pristinamycins II: pristinamycin IIA synthase As stated in the introduction, the final step of synthesis of pristinamycin IIA corresponds to an oxidation of the 2,3 bond of D-proline to dehydroproline. The protein responsible for this activity has been purified to homogeneity, as illustrated by this example.

5.1.1.A. Assay of pristinamycin IIA synthase activity

This example illustrates the assay of an activity of the biosynthesis pathway of pristinamycin IIA which has never before been described and which possesses the noteworthy property of being expressed only during the period of production of pristinamycins. The enzyme in question is pristinamycin IIA synthase, which catalyses the conversion of pristinamycin IIB to pristinamycin IIA by oxidation of the D-proline residue of pristinamycin IIB to a 2,3-dehydroproline residue (FIG. 8) in the presence of molecular oxygen and $FMNH_2$. The enzyme fractions to be assayed (0.002 to 0.005 units) are incubated for 1 h at 27° C. in a total volume of 500 ml of 50 mM bis-tris propane buffer pH 6.8 containing NADH (500 $\mu$M), FMN (5 $\mu$M), pristinamycin IIB (20 $\mu$M) and 0.02 units of FMN reductase (Boehringer Mannheim).

The pristinamycin IIA formed is assayed by HPLC after incubation is stopped by adding 500 $\mu$l of 0.1 N hydrochloric acid and 500 $\mu$l of acetonitrile and centrifugation of the sample for 5 min at 5000 g. 150 $\mu$l of the centrifugation supernatant are injected onto a 15-cm Nucleosil 5-C8 column eluted with a mixture of 34% of acetonitrile and 66% of 0.1 M phosphate buffer pH 2.9. Pristinamycins IIA and IIB are detected by means of their UV absorbance at 206 nm.

The unit of enzymatic activity is defined as the amount of enzyme needed to synthesize 1 $\mu$mol of pristinamycin IIA per hour under the conditions described.

5.1.1.B. Purification of *S. pristinaespiralis* SP92 pristinamycin IIA synthase

This experiment illustrates how an enzyme of *S. pristinaespiralis* SP92 participating in the biosynthesis pathway of pristinamycin IIA may be purified.

Using the assay described above in Example 5.1.1.A, the purification of pristinamycin IIA synthase is carried out as described below taking care to freeze and store the active fractions at −30° C. between successive steps if necessary.

150 g of a centrifugation pellet, washed with 0.1 M phosphate buffer pH 7.2 containing 10% v/v of glycerol, of an *S. pristinaespiralis* SP92 culture harvested at the beginning of the pristinamycin production phase are taken up with 450 ml of 50 mM bis-tris propane buffer pH 6.8 containing 5 mM DTT and 0.2 mg/ml of lysozyme. The suspension thereby obtained is incubated for 45 minutes at 27° C. and then centrifuged at 50,000 g for 1 hour. The crude extract thereby collected is fractionated by ammonium sulphate precipitation. The protein fraction precipitating at between 40 and 55% saturation is desalted on a column of Sephadex G-25 Fine, and then injected (100 mg per injection) in pH 6.8 50 mM bis-tris propane buffer, 1 mM DTT onto a monoQ HR 10/10 column. The proteins are eluted with a linear KCl gradient (0 to 0.5 M). The fractions containing the enzymatic activity (detected by means of the test described in Example 5.1.1.A) are pooled and concentrated to 20 ml on Centriprep 10. After dilution with one volume of pH 6.8 50 mM bis-tris propane buffer, 1 mM DTT containing 2 M ammonium sulphate, the proteins are chromatographed (22.5 mg per injection) on a Phenyl Superose HR 10/10 column with a decreasing ammonium sulphate gradient (1.0 M to 0 M). The best fractions containing the desired activity are pooled, reconcentrated to 1 ml on Centriprep 10 and then applied (200 $\mu$l per injection) to a Bio-Sil SEC 250 column. The activity peak is detected in this technique at a molecular weight centred at 77,000. The fraction containing the activity is injected onto a MonoQ HR 5/5 column in pH 6.8 50 mM bis-tris propane buffer, DTT 1 mM eluted with a linear KCl gradient (0 to 0.5 M).

After this step, the enzyme is pure and, in SDS-PAGE electrophoresis, two subunits of molecular weight estimated at 35,000 and 50,000 are detected. They are separated on a 25-cm Vydac C4 column eluted with a linear gradient of from 30 to 50% of acetonitrile in water containing 0.07% of trifluoroacetic acid.

TABLE

Purification of pristinamycin IIA synthase

| Purification step | Vol. (ml) | Protein (mg) | Sp.Act. μmol/h/mg | Yield (%) | Purification factor |
|---|---|---|---|---|---|
| Crude extract | 490 | 1690 | 0.14 | 100 | 1 |
| 40–45% A.S. | 60 | 1050 | 0.19 | 65 | 1.4 |
| MonoQ 10/10 | 95 | 45 | 3.0 | 58 | 21 |
| Phenyl Superose | 8 | 2.8 | 12 | 14 | 86 |
| Bio-Sil SEC | 5 | 1.3 | 18 | 14 | 130 |
| MonoQ 5/5 | 10 | 0.7 | 23 | 10 | 160 |

The purification factor is calculated from the increase in specific activity of the fractions during the purification.

5.1.2. Production of oligonucleotides from the protein sequences:

This example describes how, starting from the NH$_2$-terminal sequences of the two subunits of pristinamycin IIA synthase purified as described in Example 5.1.1.B., it is possible to synthesize oligonucleotides. The two subunits of pristinamycin IIA synthase are referred to as SnaA and SnaB, and correspond to polypeptides of molecular weights 50,000 and 35,000, respectively, as described in Example 5.1.1.B.

The NH$_2$-terminal sequences of the proteins SnaA and SnaB, corresponding to the subunits of pristinamycin IIA synthase, were deducted by microsequencing. This is carried out by the Edman degradation technique, using an automated sequencer (Applied Biosystems model 407A) coupled to an HPLC apparatus for identification of the phenylthiohydantoin derivatives. About thirty residues were determined for each of them.
Protein SnaA: (see residues 2 to 29 on SEQ ID No. 17) T A P(R) (R,W)R I T L A G I I D G P G G H V A A (W)R H P (A) T
Protein SnaB: (see residues 2 to 31 on SEQ ID No. 18) T A P I L V A T L D T R G P A A T L G T I T(R)A V(R)A A E A Moreover, sequences internal to these two polypeptides were determined after trypsin digestion of SnaA and SnaB and purification of the fragments obtained on a Vydac C18 HPLC column. The following internal sequences were found:
Protein SnaA: (see residues 365 to 384 on SEQ ID No. 17) G A D G F N I D F P Y L P G S A D D F V
Protein SnaB: (see residues 122 to 136 on SEQ ID No. 18) G L(–)D S F D D D A F V H D R From the underlined regions in each of the sequences of the fragments internal to the proteins SnaA and SnaB, and in accordance with the degeneracy of the genetic code specific to Streptomyces (see Example 8), the following mixtures of oligonucleotides were synthesized with a Biosearch 8600 automated synthesizer. They were then purified by the technique already described (Sawadogo M. and Von Dyke M. W., 1991). The snaA and snaB genes denote the structural genes for the proteins SnaA and SnaB, respectively.

Mixture corresponding to the underlined portion of the internal sequence of SnaA:

```
ATC GAC TTC CCC TAC CTC CCC GG   (SEQ ID NO:32)
    T   T   G   T   G   G
                A
                T
```

Mixture corresponding to underlined portion of the internal sequence of SnaB:

```
TTC GAC GAT GAT GCA TTC GTC CAT GAC   (SEQ ID NO:32)
    C   C   T           G   C
            C
            G
```

5.1.3. Labelling of the mixtures of synthetic oligonucleotides and hybridization with the genomic DNA libraries of the strain SP92

This example described how oligonucleotides specific for a gene for the biosynthesis of pristinamycins may be radioactively labelled and then hybridized with membranes onto which DNA of genomic libraries of *S. pristinaespiralis* SP92 has been transferred.

Labelling of the oligonucleotides is carried out by transfer at the 5'-terminal position of the [γ-$^{32}$P]phosphate group of ATP with T4 polynucleotide kinase. This labelling is carried out as described in Maniatis et al. (1989). After labelling, the oligonucleotides are used without purification.

Approximately 2×500 ng of each mixture of oligonucleotides were labelled in this way with $^{32}$P and were used to hybridize each of the two libraries.

Hybridization of the membranes of each library is carried out according to a protocol derived from those developed by Meinkoth, J. and Wahl, G. (1984) and Hames, B. D. and Higgins, S. J. (1985): the 15 membranes are prehybridized for 3 hours at 50° C. in 40 ml of a solution containing: Denhardt (×5) [Denhardt (×100): 2% (w/v) Ficoll, 2% (w/v) polyvinylpyrrolidone, 2% (w/v) BSA)], SSC (×5) [SCC (×20): 3 M NaCl, 0.3 M sodium citrate), 50 mM NaPO$_4$ pH6.5, 0.1% SDS, 250 μg/ml salmon sperm DNA].

Hybridization is then carried out overnight at 50° C. in 20 ml of the same solution to which the 500 ng of labelled oligonucleotides are added.

The filters are then washed in a solution of SSC (×6) and 0.5% SDS, twice for 30 min at room temperature and then empirically at gradually higher temperatures (50 to 65° C.). The temperature of these latter washes is gradually increased after successive autoradiographic exposures in order to determine the specificity of the hybridizing clones with the mixtures of oligonucleotides.

5.1.4. Isolation of cosmids pIBV1 and pIBV3 and determination of the regions containing the snaA and snaB genes This example illustrates how it is possible to isolate cosmids constructed as described in Example 3 containing genes for the biosynthesis of pristinamycins.

Cosmids pIBV1 and pIBV3 were isolated from two clones originating, respectively, from the library produced in the strain HB101 and from the library produced in the strain DH1 which hybridized with both mixtures of oligonucleotides simultaneously for pIBV1 and with the mixture of oligonucleotides originating from the internal sequence of the protein SnaA for pIBV3.

These cosmids were purified as described in Example 2. Cosmids pIBV1 and pIBV3 contain, respectively, a genomic DNA insert of *S. pristinaespiralis* SP92 whose sizes were estimated, respectively, at 30 kb and 34 kb. Maps (FIGS. 4 and 6) were established from digestions with different restriction enzymes, according to the protocols of the supplier (New England Biolabs, Beverly, Mass. 01915-5510 USA).

Southern hybridizations of pIBV1 and pIBV3 DNA, digested by means of different enzymes, with the mixtures of oligonucleotides enabled the region of this cosmid containing the snaA and/or snaB genes to be identified.

Southern hybridization was carried out as described in Maniatis et al. (1989). After separation of the restriction fragments by electrophoresis on 0.8% agarose gel, the DNA is transferred onto a Biohylon $Z^+$ membrane (Bioprope System). Hybridization of the DNA thus transferred onto the membranes with the mixtures of oligonucleotides was carried out as described in Example 5.1.3.

These Southern hybridizations enabled it to be shown that cosmid pIBV1 possessed a 6-kb BamHI fragment containing the sequences homologous to the probes synthesized in Example 5.1.2 (originating from the proteins SnaA and SnaB), as well as a 2.5-kb EcoRI fragment internal to the BamHI fragment containing the sequences homologous to the probes originating exclusively from the protein SnaA. Furthermore, the hybridization signals obtained with cosmid pIBV3 showed that it possessed only the 2.5-kb EcorRI fragment containing the sequences homologous to probes originating exclusively from the protein SnaA.

5.2. Isolation of cosmid pIBV2 containing the structural gene for 3-hydroxypicolinic acid:AMP ligase (snbA)

This example illustrates how it is possible to obtain a cosmid as constructed in Example 3 containing at least one gene for the biosynthesis of pristinamycins I.

5.2.1. Identification and purification of the protein involved in the activation of 3-hydroxypicolinic acid.

This example illustrates how the protein responsible for the activation of 3-hydroxypicolinic acid may be purified to homogeneity from *S. pristinaespiralis* SP92.

5.2.1.A. Assay of 3-hydroxypicolinic acid:AMP ligase

This example illustrates the assay of an activity of the biosynthesis pathway of pristinamycin IA which has never before been described and which possesses the noteworthy property of being expressed only during the period of production of pristinamycins. The enzyme in question is 3-hydroxypicolinic acid:AMP ligase, which catalyses the formation of the adenylate of 3-hydroxypicolinic acid (FIG. 9) from this free acid and ATP in the presence of $MgCl_2$.

The enzyme fractions to be assayed (0.002 to 0.020 units) are incubated for 15 min at 27° C. in a total volume of 250 $\mu$l of pH 6.8 50 mM bis-tris propane buffer, 1 mM DTT, 10% v/v glycerol, in the presence of 3-hydroxypicolinic acid (1 mM), ATP (2 mM), $MgCl_2$ (5 mM) and tetrasodium pyrophosphate labelled with the radioactive isotope 32 of the phosphorus atom (200 $\mu$M).

The reaction is stopped by adding 1 ml of a suspension of activated charcoal at a concentration of 10 g/l in a mixture of 75% of 0.1 M tetrasodium pyrophosphate and 25% of 14% perchloric acid. After stirring, the charcoal is collected and washed with twice 1 ml of the pyrophosphate/perchloric acid mixture. The radioactive organic molecules are then eluted with three times 1 ml of a mixture of 50% of methanol and 50% of N ammonia solution into a counting vial containing 12 ml of water. The radioactivity is measured by the Cerenkov effect with a scintillation counter (PACKARD Minaxi TriCarb 4000).

The unit of enzymatic activity is defined as the amount of enzyme needed to incorporate 1 $\mu$mol of pyrophosphate into ATP in the course of 1 hour under the conditions described above.

5.2.1.B. Purification of *S. pristinaespiralis* SP92 3-hydroxypicolinic acid:AMP ligase This example illustrates how an enzyme of *S. pristinaespiralis* SP92 participating in the biosynthesis pathway of pristinamycin IA may be purified.

Using the assay described in Example 5.2.1.A, the purification of 3-hydroxypicolinic acid:AMP ligase is carried out as described below, taking care to freeze the active fractions at −70° C. and store them at −30° C. between successive steps if necessary.

234 g of a centrifugation pellet, washed with 0.1 M phosphate buffer pH 7.2 containing 10% v/v of glycerol, of an *S. pristinaespiralis* SP92 culture harvested at the beginning of the pristinamycin production phase are taken up with 234 ml of pH 8.0 100 mM Tris-HCl buffer containing 4 mM DTE, 1 mM benzamidine, 1 mM PMSF, 15% v/v glycerol and 0.6 mg/ml of lysozyme. The suspension thereby obtained is incubated for 30 minutes at 27° C. and the centrifuged at 50,000 g for 1 hour. The crude extract thereby collected is injected in pH 8.0 100 mM Tris-HCl buffer, 4 mM DTE, 1 mM benzamidine, 1 mM PMSF, 15% v/v glycerol onto a column (80 ml) of Q Sepharose Fast Flow. The proteins are eluted with a linear KCl gradient (0 to 0.4 M). The fractions containing the enzymatic activity (detected by means of the test described in Example 5.2.1.A) are pooled and diluted with one volume of pH 8.0 100 mM Tris-HCl buffer, 1 mM benzamidine, 1 mM PMSF, 15% v/v glycerol containing 2 M ammonium sulphate. The proteins are then chromatographed on a column (50 ml) of Phenyl Sepharose with a decreasing ammonium sulphate gradient (1.0 M to 0 M) in pH 8.0 100 mM Tris-HCl buffer, 1 mM benzamidine, 1 mM PMSF, 15% v/v glycerol. After the addition of 4 mM DTE, the active fractions are pooled, concentrated to 5 ml on Centriprep 10 and then applied to a column (100 ml) of Superose 12 prep grade. The fractions containing the desired activity are pooled and injected in pH 8.0 100 mM Tris-HCl buffer, 4 mM DTE, 1 mM benzamidine, 1 mM PMSF, 15% v/v glycerol (approximately 6 mg per injection) onto a column of MonoQ HR 5/5 eluted with a linear KCl gradient (0 to 0.4 M). The active fractions are pooled, concentrated to 1 ml on Centricon 10, diluted with 3 volumes of pH 6.8 50 mM bis-tris propane buffer, 4 mM DTE, 1 mM benzamidine, 1 mM PMSF, 15% v/v glycerol, and then injected (2 mg per injection) in the latter buffer onto a column of MonoQ HR 5/5 eluted with a linear KCl gradient (0 to 0.3 M). The best fractions containing the desired ligase are pooled and then applied in pH 6.8 20 mM sodium phosphate buffer, 50 mM sodium sulphate to a Bio-Sil SEC 250 column. The activity peak is detected in this technique at a molecular weight centred at 60,000.

The protein possessing the activity of activation of 3-hydroxypicolinic acid is hereinafter designated SnbA.

After this step, the enzyme is pure and, in SDS-PAGE electrophoresis, its molecular weight is estimated at approximately 67,000.

TABLE

Purification of 3-hydroxypicolinic acid:AMP ligase

| Purification step | Vol. (ml) | Protein (mg) | Sp.Act. $\mu$mol/h/mg[a] | Yield (%) | Purification factor |
|---|---|---|---|---|---|
| Crude extract | 246 | 2050 | (0.06) | | |
| Q Sepharos | 40 | 188 | 0.47 | 100 | 1 |
| Phenyl Sepharose | 70 | 35 | 2.21 | 88 | 4.7 |
| Superose 12 | 16 | 17 | 2.03 | 39 | 4.3 |

TABLE-continued

Purification of 3-hydroxypicolinic acid:AMP ligase

| Purification step | Vol. (ml) | Protein (mg) | Sp.Act. μmol/h/mg[a] | Yield (%) | Purification factor |
|---|---|---|---|---|---|
| MonoQ pH 8.0 | 4.5 | 9.0 | 2.09 | 21 | 4.5 |
| MonoQ pH 6.8 | 1.0 | 2.0 | 2.9 | 6.6 | 6.2 |
| Bio-Sil 250 | 2.5 | 0.23 | 12.4 | 3.2 | 26 |

[a]The activity in the crude extract cannot be measured accurately owing to exchanges between pyro-phosphate and ATP which are not specific to 3-hydroxy-picolinic acid.

The purification factor is calculated from the increase in specific activity of the fractions during the purification.

5.2.2. Production of oligonucleotides from the protein sequence:

This example describes how, starting from the $NH_2$-terminal and internal sequences of the protein 3-hydroxypicolinic:AMP ligase, it is possible to synthesize oligonucleotides.

The $NH_2$-terminal sequence of the protein SnbA was deduced by microsequencing as described in Example 5.1.2. About twenty residues were identified in this way.

A sequence of approximately 20 amino acids internal to the protein SnbA was also identified after trypsin hydrolysis and purification of the fragments obtained on a Vydac C18 HPLC column.

$NH_2$-terminal sequence of the protein 3-hydroxypicolinic:AMP ligase:

(See residues 1 to 21 on SEQ ID No. 20)

M L D G S V P W P E D V A A K Y R A A G Y

Internal sequence of the protein 3-hydroxypicolinic:AMP ligase (See residues 448 to 467 on SEQ ID No. 20)

V S A (-) E V E G H L G A H P D V Q Q A A

From the underlined regions in each of the sequences, and in accordance with the degeneracy of the genetic code specific to Streptomyces (see Example 8), the following mixtures of oligonucleotides were synthesized:

Mixture corresponding to the underlined portion of the $NH_2$-terminal sequence of the protein 3-hydroxypicolinic:AMP ligase:

```
'                                       3'  (SEQ ID NO:34)
 GTC CCC TGG CCC GAG GAC GTC GCC GCC AAG TAC
  G   G       G           G   G   G
```

Mixture corresponding to the underlined portion of the internal sequence of the protein 3-hydroxypicolinic:AMP ligase:

```
5'                                                   3' (SEQ ID NO:35)
GAG GTC GAG GGC CAC CTC GGC GCC CAC CCC GAC GTC CAG CAG GC
     G       G   G   G       G   G           G
```

5.2.3. Labelling of the mixtures of synthetic oligonucleotides and hybridization of the genomic DNA libraries of *S. pristinaespiralis* SP92.

This example describes how oligonucleotides specific for a gene for the biosynthesis of pristinamycins may be radioactively labelled and then hybridized with membranes onto which DNA of genomic libraries of *S. pristinaespiralis* has been transferred.

Labelling the oligonucleotides is carried out by transfer at the 5'-terminal position of the $[\gamma-^{32}P]$phosphate group of ATP with T4 polynucleotide kinase, as described in Example 5.1.3.

Approximately 2×500 ng of each mixture of oligonucleotides were labelled in this way with $^{32}P$ and were used to hybridize each of the two libraries.

Hybridization of the membranes of each library was carried out as described in Example 5.1.3.

5.2.4. Isolation of cosmid pIBV2 and determination of the region containing the structural gene for 3-hydroxypicolinic acid:AMP ligase This example illustrates how it is possible to obtain a cosmid as constructed in Example 3 containing at least the structural gene for 3-hydroxypicolinic acid:AMP ligase.

Cosmid pIBV2 was isolated from a clone of the library produce in *E. coli* strain DH1 which hybridized with both mixtures of oligonucleotides simultaneously.

This cosmid was purified as described in Example 2. It contains a genomic DNA insert of *S. pristinaespiralis* SP92 whose size was estimated at 47 kb. A map (FIG. 5) was established from digestions with different restriction enzymes, as described in Example 5.1.4.

Southern hybridizations of pIBV2DNA, digested by means of different enzymes, with the mixtures of oligonucleotides enabled the region containing the structural gene for 3-hydroxypicolinic acid:AMP ligase to be identified. Southern blotting and hybridization were carried out as described in Example 5.1.4.

The hybridization results enabled it to be shown that cosmid pIBV2 possessed a 5.5-kb EcoRI-BglII fragment containing the sequence homologous to the probes synthesized in Example 5.2.2.

5.3. Demonstration of the presence of a portion of the structural gene for pristinamycin I synthase II (SnbC) on cosmid pIBV3

This example illustrates how it is possible to identify the presence of genes for the biosynthesis of pristinamycins I on a cosmid which has already been isolated (Example 5.1).

5.3.1. Identification of pristinamycin I synthase II involved in the incorporation of threonine and aminobutyric acid residues into the peptide chain pristinamycin IA This example illustrates how the protein responsible for the incorporation of threonine and aminobutyric acid residues into the peptide chain of pristinamycin IA may be purified to homogeneity from *S. pristinaespiralis* SP92.

5.3.1.A. Assay of the partial activities of pristinamycin I synthase II

This example illustrates the assay of activities of the biosynthesis pathway of pristinamycin IA which have never before been described and which possess the noteworth property of being expressed only during the period of production of pristinamycins. The activities in question are the partial activities of the peptide synthase responsible for the incorporation of threonine and aminobutyric acid residues into the peptide chain of pristinamycin IA (FIG. 10) in the presence of ATP and $MgCl_2$.

The threonine:AMP ligase and aminobutyric acid:AMP ligase activities are measured in an enzymatic test of ATP-pyrophosphate exchange similar to that described in 5.2.1.A for 3-hydroxypicolinic acid:AMP ligase.

The aminoacylation reactions of the enzyme with threonine or alanine (an analogue of aminobutyric acid which is found in pristinamycin IC) enable the peptide synthase to be differentiated from other enzymes which may effect an ATP-pyrophosphate exchange, and in particular aminoacyl-tRNA synthetases. The test of aminoacylation of the enzyme with tritium-labelled threonine described below is hence the one which was used in this example.

The enzyme fractions to be assayed (0.2 to 2 units) are incubated for 15 min at 27° C. in a total volume of 250 μl of pH 6.8 50 mM bis-tris propane buffer, 1 mM DTT, 10% v/v glycerol in the presence of 1 μCi of [3-$^3$H]-L-threonine (15 Ci/mmol), ATP (2 mM) and $MgCl_2$ (5 mM).

The reaction is stopped by adding 150 μl of 25% trichloroacetic acid solution. The precipitated proteins are collected on a microfilter and washed with 3 times 400 μl of 7% trichloroacetic acid, before being eluted with twice 400 μl of N sodium hydroxide into a counting vial containing 1 ml of N HCl and 12 ml of scintillation cocktail (Beckmann Readygel). The amount of radioactivity contained in this vial is measured with a scintillation counter (PACKARD Minaxi TriCarb 4000). It represents the amount of threonine bound covalently to the desired peptide synthase.

The unit of enzymatic activity is defined as the amount of enzyme needed to bind 1 picomole of threonine covalently in 15 min under the conditions described above.

5.3.1.B. Purification of pristinamycin I synthase II

This experiment illustrates how an enzyme of *S. pristinaespiralis* SP92 participating in the biosynthesis pathway of pristinamycin IA may be purified.

Using the acid described above in Example 5.3.1.A., purification of the peptide synthase responsible for the incorporation of threonine and aminobutyric acid residues into the peptide chain of pristinamycin IA is carried out as described below, taking care to work at 4° C. and to store the active fractions at −70° C.

150 g of centrifugation pellet, washed with 0.1M phosphate buffer pH 7.2 containing 10% v/v of glycerol, of an *S. pristinaespiralis* SP92 culture harvested at the beginning of the pristinamycin production phase area taken up with 450 ml of pH 8.0 100 mM Tris-HCl buffer containing 4 mM DTE, 1 mM benzamidine, 1 mM PMSF, 1 mM EDTA, 1 mM EGTA, 15% v/v glycerol. The suspension thereby obtained is ground using a French Press adjusted to a pressure of 5000 psi, and then centrifuged at 50,000 g for 1 hours. The crude extract thereby collected is injected in pH 8 100 mM Tris-HCl buffer, 4 mM DTE, 2 mM benzamidine, 2 mg/l leupeptin, 1 mg/l E-64, 15% v/v glycerol onto a column (200 ml) of Q Sepharose Fast Flow. The proteins are eluted with a linear KCl gradient (0 to 0.6M). At outflow from the column, each fraction is treated with one-tenth of its volume of a solution of 1 mM PMSF, 5 mM EDTA, 5 mM EGTA. The fractions containing the enzymatic activity (detected by means of the test described in Example 5.3.1.A) are pooled and reconcentrated by ultrafiltration on Centriprep 30 to a final volume of 28 ml. This concentrate is injected in 4-ml aliquots onto a Superdex 200 Hi-Load 16/60 permeation column equilibrated in pH 6.8 50 mM bis-tris propane buffer, 1 mM benzamidine, 4 mM DTE, 0.2 mM Pefabloc, 1 mM EDTA, 0.1M KCl, 20% v/v glycerol. After assaying, the active fractions are pooled and reconcentrated to 15 ml on Centriprep 30, then desalted on PD-10 in pH 8.0 100 mM Tris-HCl buffer, 4 mM DTE, 2 mM benzamidine, 2 mg/l leupeptin, 1 mg/l E-64, 20% v/v glycerol and applied in two portions to a MonoQ HR 10/10 column equilibrated and eluted with a linear gradient of from 0.4M KCl in this same buffer. The fractions containing the desired activity are pooled, reconcentrated on Centriprep 30 and then Centricon 30 to a final volume of 1 ml and injected in five portions onto a column of Superose 6 HR 10/30 in pH 6.8 50 mM bis-tris propane buffer, 1 mM benzamidine, 4 mM DTE, 0.2 mM Pefabloc, 1 mM EDTA, 0.1M KCl, 20% v/v glycerol. The activity peak is detected in this technique at a molecular weight centered at 450,000.

After this step the enzyme is pure and, in SDS-PAGE electophoresis, its molecular weight is estimated at approximately 240,000. This band also contains all radioactivity of the protein labelled by aminoacylation with tritiated threonine.

At this stage, the maximal activity of the enzyme using a concentration of 100 μCi/ml of threonine (15 ci/mmol) amounts to 3670 units/mg; the enzyme is also capable of forming adenylates with L-aminobutyric acid or L-alanine; an aminoacylation reaction of the enzyme with tritiated alanine is detected, and the maximal activity in the presence of 200 μCi/ml of [2,3-$^3$H]-L-alanine (15 Ci/mmol) is 2290 pmol/mg in 15 min.

TABLE

Purification of pristinamycin I synthase II

| Purification step | Vol. (ml) | Protein (mg) | Sp.Act.[a] (units/mg) | Yield (%) | Purification factor |
|---|---|---|---|---|---|
| Crude extract | 445 | 4700 | (1) | — | — |
| Q Sepharose | 308 | 834 | 7 | 100 | 1 |
| Superdex 200 | 120 | 105 | 22 | 40 | 3.1 |
| MonoQ HR | 15 | 11.5 | 96 | 19 | 14 |
| Superose 6 | 7.5 | 2.8 | 122 | 6 | 17 |

[a]:The activity in the crude extract cannot be measured accurately.

The purification factor is calculated from the increase in specific activity of the fractions during the purification.

5.3.2. Production of oligonucleotides from the protein sequence

This example described how, starting from internal sequences of pristinamycin I synthase II, it is possible to synthesize oligonucleotides.

The internal sequences of the peptide synthase which is responsible for the incorporation of threonine and aminobutyric acid residues into the peptide chain of pristinamycin IA were deduced by microsequencing as described in Example 5.1.2. after trypsin hydrolysis and purification of the fragments obtained on a Vydac C18 column.

Sequences internal to the protein
pristinamycin I synthase II

```
(See residues 49 to 61 on SEQ ID NO. 27)
1         5         10
L A A F N D T A R P V P R
```

```
         1         5        10        15        20
         V P A A F V P L D A L P L T G N G V L D
```

(SEQ ID NO:36) From the underlined regions in these sequences, and in accordance with the degeneracy of the genetic-code specific to Streptomyces (see Example 8), the following mixtures of oligonucleotides were synthesized:

Mixture corresponding to the underlined portion of the sequence 1 internal to the protein pristinamycin I synthase II:

```
       5'                                      3'
         GCC GCC TTC AAC GAC ACC GCC CGC CC
          G   G               G   G   G
```

(SEQ ID NO:37) Mixture corresponding to the underlined portion of sequence 2 internal to the protein pristinamycin I synthase II:

```
       5'                                      3'
         TTC GTC CCC CTC GAC GCC CTC CCC CT
          G   G   G           G   G   G
```

(SEQ ID NO:38) 5.3.3. Labelling of the mixtures of synthetic oligonucleotides and Southern hybridization of cosmid PIBV3 DNA This example describes how oligonucleotides specific for a gene for the biosynthesis of pristinamycins I may be radioactively labelled and then hybridized with a membrance onto which cosmid pIBV3 DNA has been transferred.

Labelling of the oligonucleotides is carried out by transfer at the 5'- terminal position of the [γ-$^{32}$P]phosphate group of ATP with T4 polynucleotide kinase, as described in 5.1.3.

Approximately 500 ng of the mixture of oligonucleotides were labelled in this way with $^{32}$P, and were used for Southern hybridization of pIBV3 DNA digested with different enzymes. These hybridizations enabled it to be shown that a portion of the structural gene for pristinamycin I synthase II was carried by cosmid pIBV3, and enabled the region containing this gene to be identified. Souther blotting and hybridization were carried out as described in Example 5.1.4.

The hybridization results enabled it to be shown that cosmid pIBV3 possessed a 6.2-kb SphI fragment containing the sequence homologous to the probes synthesized in Example 5.3.2.

5.4. Demonstration of the presence of a portion of the structural gene for pristinamycin I synthase III (SnbD) on cosmid pIBV3

This example illustrates how it is possible to identify the presence of genes for the biosynthesis of pristinamycins I on a cosmid which has already been isolated (Example 5.1).

5.4.1. Identification of pristinamycin I synthase III involved in the incorporation of proline and p-dimethylaminophenylalanine residues into the peptide chain of pristinamycin IA This example illustrates how the protein responsible for the incorporation of proline and p-dimethylaminophenylalanine residues into the peptide chain of pristinamycin IA may be purified to homogeneity from S. pristinaespiralis SP92.

5.4.1.A. Assay of partial activities of pristinamycin I synthase III

This example illustrates the assay of activities of the biosynthesis pathway of pristinamycin IA which have never before been described and which possess the noteworthy property of being expressed only during the period of production of pristinamycins. The activities in question are partial activities of the peptide synthase responsible for the incorporation of proline and para-dimethylaminophenylalanine residues into the peptide chain of pristinamycin IA (FIG. 11) in the presence of SAM, ATP and $MgCl_2$.

The proline:AMP ligase and p-dimethylaminophenylalanine:AMP ligase activities are measured in an enzymatic test of ATP-pyrophosphate exchange similar to that described in 5.2.1.A. for 3-hydroxypicolinic acid:AMP ligase.

The aminoacylation reactions of the enzyme with proline and p-dimethylaminophenylalanine make it possible to differentiate the peptide synthase from other enzymes which may perform a ATP-pyrophosphate exchange, and in particular aminoacyl-tRNA synthases. The same applies to the N-methylation of the α-amino function of p-dimethylaminophenylalanine acylated on the enzyme. The latter test characteristic of N-methylation is hence the one which was used in this example.

The enzyme fractions to be assayed (0.2 to 2 units) are incubated for 15 min at 27° C. in a total volume of 250 μl of pH 6.8 50 mM bis-tris propane buffer, 1 mM DTT, 10% v/v glycerol in the presence of 1 μCi of [methyl-$^3$H]-SAM (15 Ci/mmol), paradimethylamino-L-phenylalanine (1 mM), ATP (2 mM) and $MgCl_2$ (5 mM).

The reaction is stopped by adding 150 μl of 25% trichloroacetic acid solution. The precipitated proteins are collected on a microfilter and washed with 3 times 400 μl of 7% trichloroacetic acid, before being eluted with twice 400 μl of N sodium hydroxide into a counting vial containing 1 ml N HCl and 12 ml of scintillation cocktail (Beckmann Readygel). The amount of radioactivity contained in this vial is measured with a scintillation counter (PACKARD Minaxi TriCarb 4000). It represents the amount of N-methylated paradimethylaminophenylalanine bound covalently to the desired peptide synthase.

The unit of enzymatic activity is defined as the amount of enzyme needed to bind 1 picomole of N-methylated p-dimethylaminophenylalanine covalently in 15 min under the conditions described above.

5.4.1.B. Purification of pristinamycin I synthase III

This experiment illustrates how an enzyme of S. pristinaespiralis SP92 participating in the biosynthesis pathway of pristinamycin IA may be purified.

Using the assay described above in Example 5.4.1.A, purification of the peptide synthase responsible for the incorporation of proline and paradimethylaminophenylalanine residues into the peptide chain of pristinamycin IA is carried out as described below, taking care to work at 4° C. and to store the active fractions at −70° C.

250 g of a centrifugation pellet, washed with 0.1M phosphate buffer pH 7.2, 1 mM PMSF, 5 mM EDTA, 5 mM EDTA, 0.5M KCl, 10% v/v glycerol, of an S. pristinaespiralis SP92 culture harvested at the beginning of the pristinamycin production phase are taken up with 750 ml of pH 8.0 100 mM Tris-HCl buffer containing 4 mM DTE, 5 mM benzamidine, 0.2 mM Pefabloc, 1 mM EDTA, 1 mM EGTA, 2 mg/l leupeptin, 2 mg/l STI, 2 mg/l aprotinin, 1 mg/l E-64, 20% v/v glycerol. The suspension thereby obtained is ground using a French Press adjusted to a pressure of 5000 psi, and then centrifuged at 50,00 g for 1 h. The crude extract thereby collected is fractionated by ammonium sulphate precipitation. The protein fraction coming out at between 0 and 35% ammonium sulphate saturation is redissolved in the disruption buffer and desalted on a column of Sephadex G 25 Fine equilibrated and eluted in this same buffer. The proteins thus prepared are injected in pH 8.0 100 mM Tris-HCl buffer, 4 mM DTE, 2 mM benzamidine, 2 mg/l leupeptin, 1 mg/l E-64, 20% v/v glycerol onto a column (200 ml) of Q Sepharose Fast Flow, and are then eluted with a linear KCl gradient (0 to 0.6M). At outflow from the column, each fraction is treated with one-tenth of its volume of a solution of 2 mM Pefabloc, 5 mM EDTA, 5 mM EGTA, 5 mM benzamidine. The fractions containing the enzymatic activity (detected by means of the test described in Example 5.4.1.A) are pooled and precipitated with ammonium sulphate at 80% saturation. The proteins which have come out are redissolved in pH 6.8 50 mM bis-tris propane buffer, 1 mM benzamidien, 1 mM DTE, 0.2 mM Pefabloc, 1 mM EDTA, 1 mM EGTA, 2 mg/l leupeptin, 0.15M NaCl, 20% v/v glycerol, and injected in 5 4-ml aliquot portions onton a Superdex 200 Hi-Load 16/60 permeation column equilibrated and eluted in this same buffer. After assay, the active fractions are pooled and reconcentrated to 3 ml of Centriprep 30, then rediluted to 20 ml with pH 8.0 100 mM Tris-HCl buffer, 4 mM DTE, 1 mM benzamidine, 1 mM PMSF, 20% v/v glycerol and applied in two portions to a MonoQ HR 10/10 column equilibrated and eluted with a linear gradient from 0.4M KCl in this same buffer. The best fractions containing the desired activity are pooled and used as material for characterization of the activities of the enzyme and for its microsequencing.

After this step, the enzyme is pure and, in SDS-PAGE electrophoresis, its molecular weight is estimated at approximately 250,000. This band also contains all the radioactivity of the protein labelled by aminoacylation with tritiated SAM and paradimethylaminophenylalanine. In permeation on Superose 6 HR 10/30, the native molecular weight of the enzyme is estimated at 700,000.

At this stage, the enzyme is also capable of forming adenylates with proline; an aminoacylation reaction of the enzyme with tritiated proline is detected, and the maximal activity in the presence of 200 $\mu$Ci/ml of [5-$^3$H]-L-proline (34 Ci/mmol) is 2490 pmol/mg in 15 min.

TABLE

Purification of pristinamycin I synthase III

| Purification step | Vol. (ml) | Protein (mg) | Sp.Act.[a] (units/mg) | Yield (%) | Purification factor |
|---|---|---|---|---|---|
| Crude extract | 800 | 8100 | (4) | — | — |
| 35% A.S. | 200 | 4000 | (6) | — | — |
| Q Sepharose | 132 | 498 | 46 | 100 | 1 |
| Superdex 200 | 45 | 39.5 | 417 | 71 | 9 |
| MonoQ HR | 9 | 5.3 | 1070 | 25 | 23 |

[a]:The activity in the crude extract and after ammonium sulphate precipitation cannot be measured accurately.

The purification factor is calculated from the increase in specific activity of the fractions during the purification.

5.4.2. Production of oligonucleotides from the protein sequence

This example describes how, starting from internal sequences of pristinamycin I synthase III, it is possible to synthesize oligonucleotides.

An internal sequence of the peptide synthase responsible for the incorporation of proline and paradimethylaminophenylalanine residues into the peptide chain of pristinamycin IA was deduced by mirco-sequencing as described in Example 5.1.2. after cyanogen bromide treatment and purification of the fragments obtained on a Vydac C18 HPLC column.

Sequence internal to the protein pristinamycin I synthase III

```
1 (see residues 2 to 20 on SEQ ID No. 28)
1      5         10        15        20
P- V T P Y R A Y A L A H L A G - D D D
```

From the underlined region in this sequence, and in accordance with the degeneracy of the genetic code specific to Streptomyces (see Example 8), the following mixture of oligonucleotides was synthesized:

Mixture corresponding to the underlined portion of the sequence internal to the protein pristinamycin I synthase III:

```
5'                              3'     (SEQ ID NO:39)
 GTC ACC CCG TAC CGC GCC TAC
  G   G   C       G   G
```

5.4.3. Labelling of the mixtures of synthetic oligonucleotides and Southern hybridization of cosmid pIBV3 DNA This example describes how oligonucleotides specific for a gene for the biosynthesis of pristinamycins I may be radioactively labelled and then hybridized with a membrane onto which cosmid pIBV3 DNA has been transferred.

Labelling of the oligonucleotides is carried out by transfer at the 5'-terminal position of the [$\gamma$-$^{32}$P]phosphate group of ATP with T4 polynucleotide kinase, as described in 5.1.3.

Approximately 500 ng of the mixture of oligonucleotides were labelled in this way with $^{32}$P, and were used for Southern hybridization of pIBV3 DNA digested with difference enzymes. These hybridizations enabled it to be shown that a portion of the structural gene for pristinamycin I synthase III was carried by cosmid pIBV3, and enabled the region containing this gene to be identified. Southern blotting and hybridization were carried out as described in Example 5.1.4.

The hybridization results enabled it to be shown that cosmid pIBV3 possessed an 8.4-kb SphI fragment containing the sequence homologous to the proves synthesized in Example 5.4.2.

5.5. Demonstration of the presence of a portion of the structural gene for pristinamycin I synthase IV (snbE) on cosmid pIBV3

This example illustrates how it is possible to identify the presence of genes for the biosynthesis of pristinamycins I on a cosmid which has already been isolated (Example 5.1).

5.5.1. Identification of the peptide synthase (referred to as pristinamycin I synthase IV) responsible for the incorporation of the phenylglycine residue into the peptide chain of pristinamycin IA 5.5.1.A. Assay of enzymatic activities carried by the peptide synthase (pristinamycin I synthase IV) responsible for the incorporation of the phenylglycine residue into the peptide chain of pristinamycin IA This example illustrates the assay of an enzymatic activity of the biosynthesis pathway of pristinamycin IA which has not been described hitherto and which possesses the noteworthy property of being expressed only during the period of production of pristinamycins in the wild-type microorganism. The activity in question is that of the peptide synthase (pristinamycin I synthase IV) responsible for the incorporation of the L-phenylglycine residue into the peptide chain (FIG. 12) in the presence of ATP and MgCl$_2$. The phenylglycine:AMP ligase activity of pristinamycin I synthase IV is measured in an enzymatic test of ATP-pyrophosphate exchange similar to that described in 5.2.1.A. for 3-hydroxypicolinic acid:AMP ligase activity, in the presence of L-phenylglycine (1 mM) and KCl (50 mM) in the incubation buffer.

5.5.1.B. Purification of the peptide synthase responsible for the incorporation of the phenylglycine residue (pristinamycin I synthase IV) into the peptide chain of pristinamycin IA This example illustrates how an enzyme of *S. pristinaespiralis* SP92 participating in the biosynthesis pathway of pristinamycin IA may be purified. Using the assay described above in Example 5.5.1.A. The purification of pristinamycin I synthase IV is carried out as described below. All the operations are performed at 4° C. The fractions containing the activity are frozen immediately and stored at −70° C.

70 g of wet cells, harvested as described in Example 5.2.1.B., are resuspended in 250 ml of cell lysis buffer (100 mM Tris-HCl pH 8.0 containing 25% of glycerol, 4 mM DTE, 1 mM EGTA, 1 mM EDTA, 1 mM PMSF, 1 mg/l E-64, 2 mg/l STI, 2 mg/l $\alpha_2$-macroglobulin, 1 mg/l leupeptin, 2 mg/l aprotinin, 5 mM benzamidine, 0.6 mg/ml lysozyme. The solution thereby obtained is kept stirring at 4° C. for 1 h and then centrifuged at 50,000 g for 1 h. The supernatant is then injected in the cell lysis buffer onto a column of Sephadex G-25, and the excluded fraction (approximately 250 mg of protein injected in each chromatographic run) is injected onto a column of Mono Q HR 16/10 (Pharmacia) equilibrated with 100 mM Tris-HCl buffer pH 8.0, 4 mM DTE, 1 mM EGTA, 1 mM EDTA, 1 mg/l E-64, 2 mg/l STI, 20% glycerol. The proteins are eluted with a linear gradient of from 0 to 0.6M KCl and, at outflow from the column, each fraction is treated with one-tenth of its volume of a solution of 2 mM Pefabloc, 5 mM EGTA, 5 mM EDTA. The fractions containing the activity are pooled and then mixed with 1 volume of 100 mM Tris-HCl pH 8.0, 15% glycerol, 1 mM PMSF, 1 mM benzamidine, 4 mM DTT, 3.4M ammonium sulphate per 3 volumes of fraction. The solution is injected onto a column of Phenyl Superose HR 10/10 (on-fifth of the solution is injected at each chromatographic run), and the proteins are eluted with a decreasing linear gradient of from 0.9 to 0M ammonium sulphate. The fractions containing the activity are pooled. The solution is concentrated to 3500 $\mu$l in a Centriprep 30 and injected in two portions onto a Superdex 200 Hi-Load 16/60 column equilibrated and eluted with 50 mM bis-tris propane buffer pH 6.8 containing 20% of glycerol, 0.15M NaCl, 4 mM DTT, 1 mM PMSF, 1 mM benzamidine, 1 mM EDTA. The active fraction is diluted with 9 volumes of 50 mM bis-tris propane buffer pH 6.8 containing 25% of glycerol, 4 mM DTT, 1 mM PMSF, 1 mM benzamidine, and then injected onto a column of Mono Q HR 5/5 equilibrated in the same buffer. The desired activity is eluted with a linear gradient of from 0 to 0.4M KCl and concentrated to 630 $\mu$l in a Centricon-30. The desired protein is then purified by electrophoresis on 6% polyacrylamide gel after denaturation of the sample by heating for 10 min at 80° C. with an SDS/mercapto-ethanol mixture. After electrophoresis and staining of the gel with Coomassie blue, the gel band containing the protein is cut out and the protein is electroeluted from the gel in a Centrilutor.

Note: the bank corresponding to pristinamycin I synthase IV is identified by comparison with a tritiated (by covalent binding to tritiated phenylglycine; see description in Example 5.5.2.) pristinamycin I synthase IV standard.

After this step, the enzyme is pure in electrophoresis (SDS-PAGE). Its molecular weight is estimated at approximately 170,000.

5.5.2. Labelling of pristinamycin I synthase IV by thioesterification of radioactive phenylglycine on the enzyme After activation in the form of an adenylate through phenylglycine:AMP ligase activity, phenylglycine is transferred to a thiol group of the active site of the enzyme before being incorporated into the peptide chain during elongation (general process of biosynthesis of peptide antibiotics known by the name of "thiotemplate mechanism"). Generally speaking, radioactive labelling of the protein effecting the activation of amino acid may hence be performed by preparing the thioester derivative with a radioactive form of the amino acid.

As an example, the radioactive labelling of pristinamycin I synthase IV is accomplished by incubating 50 $\mu$g of the protein (active fraction emerging from the Mono Q HR 5/5 chromatography column; see above in Example 5.5.1.B.) for 1 hour at 27° C. with 100 $\mu$Ci of (RS)-2-phenyl[2-$^3$H] glycine (18 Ci/mmol; Amersham) in 70 $\mu$l of 50 mM bis-tris propane buffer pH 6.8 containing 20% of glycerol, 25 mM MgCl$_2$, 5 mM ATP, 0.15M NaCl, 4 mM DTT, 1 mM PMSF, 1 mM benzamidine, 1 mM EDTA. After denaturation (SDS alone without mercaptoethanol), the proteins are separated by electrophoresis (SDS-PAGE, 6% gel) and visualized with Coomassie blue. Analysis of the radioactivity profile by counting the protein bands as well as by autoradiography (Hyperfilm MP; fluorography after impregnation of the gel with Amersham Amplify) discloses a single radioactive band with a molecular weight of 170,000.

TABLE

Purification of pristinamycin I synthase IV

| Purification step | Protein (mg) | Sp.Act. (cpm/mg)$^a$ | Protein (mg) | Purification factor |
|---|---|---|---|---|
| Crude extract | 2200 | 3.6 | — | — |
| Mono Q 16/10 | 136 | 59 | 100 | 16 |
| Phenyl Superose | 32.6 | 175 | 72 | 49 |
| Superdex 200 | 3.1 | 870 | 34 | 240 |
| Mono Q 5/5 | 2.0 | 1000 | 25 | 280 |
| Electroelution SDS-PAGE | 0.1 | — | — | — | the specific activity cannot be measured accurately in the crude extract owing to the high level of non-phenylglycine-dependent ATP-pyrophosphate exchange. The specific activity value was calculated from the number of units present at emergence from the first chromatographic step expressed with reference to the amount of protein in the crude extract.

5.5.3. Other activities carried by pristinamycin I synthase IV

Purification of the peptide synthase responsible for the incorporation of phenylglycine, described in Example 5.5.2., led to a pure protein of molecular weight 170,000. This protein does not activate the other amino acids tested, especially pipecolic acid or 4-oxopipecolic acid. A second preparation of this protein, performed under the conditions described in 5.5.1.B. eliminating, however, the Phenyl Superose step, starting from another culture of *S. pristinaespiralis* SP92, the crude extract of which was prepared in a France Press as described in 5.4.1B, led to a protein which, at emergence from the Mono Q HR 5/5 step, was equivalent in purity to that obtained at the same step in the example described in 5.5.1.B, but possessed a molecular weight of approximately 250,000 in SDS-PAGE. This new preparation was competent for the activation and thioesterification of phenylglycine, but possessed, in addition, an ATP-pyrophosphate exchange activity with L-pipecolic acid (1 mM) in the exchange test similar to that described in 5.2.1.A. for 3-hydroxypicolinic acid. Moreover, it could be shown that the 170,000 protein does not possess ATP-pyrophosphate exchange activity with L-pipecolic acid even in preparations of the protein that are still very impure. It should be noted that *S. pristinaespiralis* SP92 naturally produces small amounts of a pristinamycin IA analogue having a pipecolic acid residue in place of 4-oxopipecolic acid. Hence this demonstrates that the peptide synthase responsible for the incorporation of phenylglycine (pristinamycin I synthase IV) also catalyses the incorporation of the preceding residue (probably pipecolic acid). The difference in molecular weight obtained for pristinamycin I synthase IV in the two preparations (170,000 and 250,000) is attributed to a phenomenon of partial proteolytic cleavage in the first case, leading to loss of the activity of activation of L-pipecolic acid.

5.5.4. Synthesis of oligonucleotides from the protein sequence

This example described how, starting from an internal sequence of pristinamycin I synthase IV, it is possible to set about testing for the corresponding gene using suitably chosen oligonucleotides.

An internal sequence of pristinamycin I synthase IV of 15 amino acids was identified after cyanogen bromide cleavage of the purified protein and purification of the fragments obtained on a Vydac C18 HPLC column.

Sequence internal to the protein pristinamycin I synthase IV

```
    (See residues 82 to 98 on SEQ ID No. 31)
1        5         10        15
V T V F L N N T R L I O N F R P R - F - GD
```

From the underlined region in this sequence, and in accordance with the degeneracy of the genetic code specific to Streptomyces (see Example 8), the following mixture of oligonucleotides was synthesized:

Mixture corresponding to the underlined portion of the internal sequence of the protein pristinamycin I synthase IV:

```
                                    (SEQ ID NO:40)
5'                               3'(SEQ ID
                                       NO:40)
    ACG CGC CTC ATC CAG AAC TTC CGC CC
        C   G   G                   G
            T                       T
```

5.5.5. Labelling of the mixtures of synthetic oligonucleotides and Southern hybridization of cosmid pIBV3 DNA This example described how oligonucleotides specific for a gene for the biosynthesis of pristinamycins I may be radioactively labelled and then hybridized with a membrane onto which cosmid pIBV3 DNA has been transferred.

Labelling of the oligonucleotides is carried out by transfer at the 5'-terminal position of the [γ-$^{32}$P]phosphate group of ATP with T4 polynucleotide kinase, as described in 5.1.3.

Approximately 500 ng of the mixture of oligonucleotides were labelled in this way with $^{32}$P, and were used for Southern hybridization of pIBV3 DNA digested with difference enzymes. These hybridizations enabled it to be shown that a portion of the structural gene for pristinamycin I synthase II was carried by cosmid pIBV3, and enabled the region containing this gene to be identified. Southern blotting and hybridization were carried out as described in Example 5.1.4.

The hybridization results enabled it to be shown that cosmid pIBV3 possessed a 6.6-kb SphI fragment containing the sequence homologous to the probes synthesized in Example 5.5.4.

5.6. Isolation of cosmid pIBV4 containing the structural gene for FMN reductase (snaC)

This example illustrates how it is possible to obtain a cosmid as constructed in Example 3 containing at least one gene for the biosynthesis of PII.

5.6.1. Identification of FMN reductase associated with pristinamycin IIA synthase This example illustrates how the protein responsible for reduction of FMN by NADH to form the FMNH$_2$ needed for the reaction catalysed by pristinamycin IIA synthase may be purified to homogeneity from *S. pristinaespiralis* SP92.

5.6.1.A. Assay of FMN reductase activity

This example illustrates the assay of an activity of the biosynthesis pathway of pristinamycin IIA which has never before been described and which possesses the noteworthy property of being expressed only during the period of production of pristinamycins. The enzyme in question is FMN reductase, also referred to as NADH:FMN oxidoreductase, which catalyses the reduction of FMN to FMNH$_2$ (FIG. 13) in the presence of NADH. FMN reductases catalysing the same reaction which are specific or otherwise for NADH or NADPH and associated with other biosynthesis pathways have been described elsewhere (Duane et a., 1975, Jablonski et al., 1977, Watanable et al., 1982).

Two assays are used to detect this activity:

The first is based on a coupling with the pristinamycin IIA synthase described in Example 5.1.1., and is used for the first steps of purification. The enzyme fractions to be assayed (0.002 to 0.005 units) are incubated for 1 hour at 27° C. in a total volume of 500 μl of 50 mM bis-tris propane buffer pH 6.8 containing NADH (500 μM), FMN (2 μM), pristinamycin IIB (20 μM) and 0.01 units of pristinamycin IIA synthase described in Example 5.1.1. The pristinamycin IIA formed is assayed by HPLC as described in Example 5.1.1.A.

The unit of enzymatic activity is defined as the amount of enzyme needed to synthesize 1 μmol of pristinamycin IIA per minute under the conditions described above.

The second assay is a spectrophotometric assay, and can be employed only with at least partially purified fractions. The enzyme fractions to be assayed (0.006 to 0.030 units) are incubated for 13 min at 27° C. in a total volume of 3 ml of 50 mM bis-tris propane buffer pH 6.8 containing NADH (500 μM) and FMN (2 μM). After 7 min of incubation, 6 reading of the optical density at 340 nm taken at 1-min intervals are performed against a reference curve without enzyme. The activity in μmol/min is calculated by dividing the slope of decrease per min in the optical density by a factor of 6.2 (optical density of 1 mol of NADH at 340 nm).

The unit of enzymatic activity is defined as the amount of enzyme needed to consume 1 μmol of NADH per minute under the conditions described above.

5.6.1.B. Purification of *S. pristinaespiralis* SP92 FMN reductase

This experiment illustrates how an enzyme of *S. pristinaespiralis* SP92 participating in the biosynthesis pathway of pristinamycin IIA may be purified.

Using the assays described above in Example 5.6.1.A., the purification of FMN reductase is carried out as described below, taking care to freeze and store the active fractions at −30° C. between successive steps if necessary.

500 g of a centrifugation pellet, washed with 0.1 M phosphate buffer pH 7.2 containing 10% v/v of glycerol, of an *S. pristinaespiralis* SP92 culture harvested at the beginning of the pristinamycin production phase are taken up with 1500 ml of 50 mM bis-tris propane buffer pH 6.8 containing 5 mM DTT, 10% v/v of glycerol and 0.2 mg/ml of lysozyme. The suspension thereby obtained is incubated for 45 min at 27° C. and then centrifuged at 50,000 g for 1 hour. The crude extract thereby collected is fractionated by ammonium sulphate precipitation. The protein fraction precipitating at between 40 and 75% saturation is desalted on a column of Sephadex G-25 Fine and then injected in pH 6.8 50 mM bis-tris propane buffer, 5 mM DTT, 10% v/v glycerol onto a column (300 ml) of Q Sepharose Fast Flow. The active proteins are not retained on the column, and they are desalted on a column of Sephadex G-25 Fine and then reinjected in pH 8.2 50 mM Tris-Hcl buffer, 5 mM DTT, 10% v/v glycerol onto a column (35 ml) of Q Sepharose Fast Flow and eluted with a linear KCl gradient (0 to 0.5 M). The fractions containing the enzymatic activity (detected by means of the first test described in Example 5.6.1.A) are pooled, desalted on a column of Sephadex G-25 Fine and then injected in pH 8.2 50 mM Tris-HCl buffer, 5 mM DTT, 10% v/v glycerol onto a MonoQ HR 10/10 column. The proteins retained are eluted directly by the same buffer to which 0.2 M KCl has been added. They are collected in a volume of 1 ml, which is immediately reinjected onto a column of Superdex 75 HR 10/30 eluted with pH 6.8 50 mM bis-tris propane buffer, 1 mM DTT, 10% v/v glycerol. The fractions containing the desired activity (detected from this step onwards by means of the spectrophotometric test as described in Example 5.6.1.A) are pooled and the total volume of the pool is made to 7 ml; these 7 ml are injected onto a column packed with 8 ml of FMN-agarose; the column is washed with pH 6.8 50 mM bis-tris propane buffer, 1 mM DTT, 10% v/v glycerol, and then eluted with the same buffer containing 10 μM FMN. The active fractions are pooled, desalted on PD-10 columns, injected in pH 8.2 50 mM Tris-HCl buffer, 5 mM DTT, 10% v/v glycerol onto a MonoQ HR 5/5 column and eluted with a linear KCl gradient (0 to 0.25 M).

After this step, the enzyme is pure. In SDS-PAGE electrophoresis, a single fairly broad band is seen, centred at a molecular weight estimated at 28,000, while in Bio-Sil SEC 125 gel permeation chromatography, this protein forms a symmetrical peak centred around a molecular weight of approximately 30,000.

For sequencing, the protein is desalted on a 25-cm Vydac C4 column eluted with a linear gradient of from 30 to 70% of acetonitrile in water containing 0.07% of trifluoroacetic acid.

TABLE

Purification of FMN reductase

| Purification steps | Vol. (ml) | Protein (mg) | Sp.Act.[a,b] (units/mg) | Yield (%) | Purification factor |
|---|---|---|---|---|---|
| Crude extract | 1620 | 5100 | 0.004[a] | 100 | 1 |
| 40–75% A.S. | 155 | 2930 | 0.005[a] | 68 | 1.2 |
| Q Seph. pH 6.8 | 357 | 180 | 0.058[a] | 49 | 14 |
| Q Seph. pH 8.2 | 153 | 15 | 0.36[a] | 25 | 85 |
| MonoQ HR 10/10 | 1.0 | 8.8 | 0.50[a] 4.4[b] | 19 | 120 |
| Superdex 75 | 1.5 | 3.1 | 7.4[b] | 12 | 200 |
| FMN-agarose | 7.5 | 0.28 | 96[b] | 14 | 2600 |
| MonoQ HR 5/5 | 3.0 | 0.29 | 68[b] | 11 | 1900 |
| Bio-Sil 125 | 7.5 | 0.18 | 106[b] | 10 | 2900 |

[a]: assay coupled to pristinamycin IIA synthase
[b]: spectrophotometric assay

The purification factor is calculated from the increase in specific activity of the fractions during the purification.

5.6.2. Production of oligonucleotides from the protein sequence

This example describes how, starting from NH$_2$-terminal and internal sequences of the protein FMN reductase, it is possible to synthesize oligonucleotides.

The NH$_2$-terminal sequence of FMN reductase was deduced by microsequencing as described in Example 5.1.2. About 30 residues were identified in this way.

(NH$_2$-Terminal) sequences beginning at the 4th and at the 11th residue were also found in the sample sequenced.)

Two sequences internal to FMN reductase, of 13 and 21 amino acids, were also identified after trypsin hydrolysis and purification of fragments obtained on a Vydac C18 column NH$_2$-Terminal sequence of the protein FMN reductase

```
(See residues 2 to 25 on SEQ ID No. 22)
1         5         10        15        20        25
T G A D D P A R P A V G P Q S F R D A M A Q L A S P V
```

Internal sequences of the protein FMN reductase:

```
(See residues 102 to 122 on SEQ ID No. 22)
1         5         10        15        20
F A G G E F A A W D G T G V P Y L P D A K
```

```
(See residues 149 to 161 on SEQ ID No. 22)
1         5         10
T G D P A K P P L L W Y R
```

From the underline regions in each of the sequences, and in accordance with the degeneracy of the genetic code specific to Streptomyces (see Example 8), the following mixtures of oligonucleotides were synthesized:

Mixture corresponding to the NH$_2$-terminal sequence of the protein FMN reductase:

```
5'                                    3' (SEQ ID NO:41)
TTC CGC GAC GCC ATG GCC CAG CTC GC
     G   G   G   G
```

Mixtures corresponding to the internal sequences of the protein FMN reductase:

```
5'                                              3'    (SEQ ID NO:42)
TTC GCC GGC GGC GAG TTC GCC GCC TGG GAC GGC ACC GG
     G   G   G           G   G               G

5'                                    3'    (SEQ ID NO:43)
GAC CCC GCC AAG CCC CCC CTG CTG TGG TAC CG
     G   G           G   G   C   C
```

5.6.3. Labelling of the mixtures of synthetic oligonucleotides and hybridization of the genomic DNA libraries of *S. pristinaespiralis* SP92.

This example describes how oligonucleotides specific for a gene for the biosynthesis of pristinamycins may be radioactively labelled and then hybridized with membranes onto which DNA of genomic libraries of *S. pristinaespiralis* has been transferred.

Labelling the oligonucleotides is carried out by transfer at the 5'-terminal position of the [γ-$^{32}$P]phosphate group of ATP with T4 polynucleotide kinase, as described in Example 5.1.3.

Approximately 2×500 ng of each mixture of oligonucleotides were labelled in this way with $^{32}$P and were used to hybridize each of the two libraries.

Hybridization of the membranes of each library was carried out as described in Example 5.1.3.

5.6.4. Isolation of cosmid pIBV4 and determination of the region containing the structural gene for FMN reductase (snaC)

Cosmid pIBV4 was isolated from a clone of the library produced in *E. coli* strain HB101 which hybridized with all three mixtures of oligonucleotides simultaneously.

This cosmid was purified as described in Example 2. It contains a genomic DNA insert of *S. pristinaespiralis* SP92 whose size was estimated at 48 kb. A map (FIG. 7) was established from digestions with different restriction enzymes, as described in 5.1.4.

Southern hybridizations of pIBV4 DNA, digested by means of different enzymes, with the mixtures of oligonucleotides enabled the region containing snaC, the structural gene for FMN reductase, to be identified. Southern blotting and hybridizations were carried out as described in Example 5.1.4.

The hybridization results enable it to be shown that cosmid pIBV4 possessed a 4-kb BamHI—BamHI fragment containing the sequences homologous to the probes synthesized in Example 5.6.3.

5.7 Demonstration of the presence of the structural gene for p-aminophenylalanine (phenyl-N)-methyltransferase on cosmid pIBV2

This example illustrates how it is possible, starting from a purified protein, to identify the corresponding structural gene from among the genes which have already been analysed and sequenced as described in Example 6.7 and 7.8 and which have also been expressed in *E. coli* as described in Example 11.

5.7.1. Identification and purification of the protein involved in the methylation of p-aminophenylalanine to p-dimethylaminophenylalanine This example illustrates how the protein responsible for the methylation of p-aminophenylalanine to p-dimethylaminophenylalanine [p-aminophenylalanine (phenyl-N)-methyltransferase] may be purified to homogeneity from *S. pristinaespiralis* strain SP92, and how it may also be obtained pure from a recombinant strain of *E. coli*.

5.7.1.A. Assay of the activity of methylation of p-aminophenylalanine to p-methylaminophenylalanine and of the activity of methylation of p-methylaminophenylalanine to p-dimethylaminophenylalanine This example illustrates the assay of two terminal activities of the biosynthesis of p-dimethylaminophenylalanine, a component of pristinamycin IA. These activities have never before been described, and possess the noteworthy property of being expressed only during the period of production of pristinamycins. They are the methylation of p-aminophenylalanine to p-methylaminophenylalanine (methylation 1) on the one hand, and the methylation of p-methylaminophenylalanine to p-dimethylaminophenylalanine (methylation 2), both of these activities utilizing SAM as a methyl group donor (FIG. 14).

The enzyme fractions to be assayed (1 to 20 units) are incubated for 30 min at 27° C. in a total volume of 200 μl of pH 6.8 50 mM bis-tris propane buffer containing SAM (200 μM) in which the methyl group is radioactively labelled with isotope 14 of the carbon atom (2 Ci/mol), in the presence of p-amino-L-phenylalanine (1 mM) for the assay of methylation 1 or of p-methylamino-L-phenylalanine (2.5 mM) for the assay of methylation 2.

The reaction is stopped by adding 16 μl of 37% hydrochloric acid and then 20 μl of sodium heptane sulphonate as a concentration of 240 g/l. After centrifugation, 150 μl of supernatant are injected into the HPLC system in the following gradient mode:

| - mobile phase: | eluent A = 1.2 g of sodium heptanesulphonate + 2.5 ml of glacial acetic acid + water (qs 1000 ml) |   |
|---|---|---|
|   | eluent B = 1.2 g of sodium heptanesulphonate + 2.5 ml of glacial acetic acid + 300 ml of acetonitrile + water (qs 1000 ml) |   |
|   | gradient: t(min) | % B |
|   | 0 | 30 |
|   | 16 | 30 |
|   | 17 | 100 |
|   | 20 | 100 |
|   | 21 | 30 |
|   | 25 | 30 |

- stationary phase: 150 × 4.6 mm Nucleosil 5 μm C18 column (Macherey-Nagel)

At outflow from the column, the substrates and products of the enzymatic reaction are quantified by absorption at 254 nm. This detection is coupled to an in-line radiochemical detection by means of a Berthold LB506 detector equipped with a type GT400-U4 solid scintillation cell. This enables the incorporation of radioactive methyl groups into the reaction products to be monitored specifically.

The unit of enzymatic activity for methylation 1 (for methylation 2) is defined as the amount of enzyme needed to incorporated 1 nmol of methyl groups into p-aminophenylalanine (into p-methylaminophenylalanine).

5.7.1.B. Purification from *S. pristinaespiralis* SP92 of the SAM-dependent N-methyltransferase catalyzing the methylation of p-aminophenylalanine to p-dimethylaminophenylalanine [p-aminophenylalanine (phenyl-N)-methyltransferase]

This experiment illustrates how an enzyme of *S. pristinaespiralis* SP92 participating in the biosynthesis pathway of pristinamycin IA may be purified.

Using the assay described above in Example 5.7.1.A, the purification of the SAM-dependent N-methyltransferase is carried out as described below, takin care to freeze and store the active fractions at −70° C. between successive steps if necessary.

240 g of a centrifugation pellet, washed with pH 7.2 100 mM phosphate buffer, 1 mM PMSF, 5 mM EDTA, 5 mM EGTA, 0.5 M KCl, 10 % v/v glycerol, of an *S. pristinaespiralis* SP92 culture harvested at the beginning of the pristinamycin production phase are taken up in 480 ml of pH 8.01 0.1 M Tris-HCl buffer containing 4 mM DTE, 5 mM benzamidine, 0.2 mM Pefablock, 100 μg/l E-64, 2 mg/l leupeptin, 1 mM EDTA, 1 mM EGTA, 2 mg/l STI, 2 mg/l aprotinin, 20% v/v glycerol and 2 mg/ml lysozyme, this buffer being maintained at +4° C. The suspension thereby obtained is stirred vigorously at 4 ° C. After 30 min of stirring, 0.2 mg/ml deoxyribonuclease I and 5 mM $MgCl_2$ are added. After 90 min of stirring, the extract is centrifuged for 1 hour at 50,000 g. The supernatant is divided into 3 fractions of approximately 180 ml. Each one is desalted by gel permeation on a 500 ml column of Sephadex G-25 Fine equilibrated at the natural flow rate in pH 6.8 20 mM bis-tris buffer containing 4 mM DTE, 5 mM benzamidine, 0.2 mM Pefabloc, 100 μg/l E-64, 2 mg/l leupeptin, 1 mM EDTA, 1 mM EGTA, 2 mg/l STI, 2 mg/l aprotinin, 20% v/v glycerol. The protein eluate is then chromatographed (400 mg of protein at each cycle) on a MonoQ HR 16/10 column at a flow rate of 6 ml/min with an increasing linear gradient of sodium chloride (0 to 0.3 M) in pH 6.8 20 mM bis-tris buffer containing 4 mM DTE, 2 mM benzamidine, 100 μg/l E-64, 2 mg/l leupeptin, 20% v/v glycerol. AT outflow from the column, the fractions are supplemented with 10% v/v of pH 6.8 20 mM bis-tris buffer containing 4 mM DTE, 30 mM benzamidine, 2 mM Pefabloc, 100 μg/l E-64, 2 mg/l leupeptin, 5 mM EDTA, 5 mM EGTA, 10 mg/l STI, 10 mg/l aprotinin, 20% v/v glycerol. Under these conditions, both methylation activities (1 and 2) are detected identically in the exclusion fractions and the first elution fractions. These fractions are pooled and concentrated by ultrafiltration on CentriPrep 10. This concentrate is made to 0.85 M ammonium sulphate and then chromatographed (20 to 80 mg at each cycle) on a Phenyl Superose HR 10/10 column at a flow rate of 1 ml/min with a decreasing linear gradient of ammonium sulphate (0.85 to 0 M) in pH 6.8 50 mM bis-tris buffer containing 4 mM DTE, 2 mM benzamidine, 100 μg/l E-64, 2 mg/l leupeptin, 1 mM EDTA, 1 EGTA, 10% v/v glycerol. At outflow from the column, the fractions are supplemented with 10% v/v of pH 6.8 50 mM bis-tris buffer containing 4 mM DTE, 30 mM benzamidine, 2 mM Pefabloc, 100 μg/l E-64, 2 mg/l leupeptin, 1 mM EDTA, 1 EGTA, 10% mg/l STI, 10 mg/l aprotinin, 10% v/v glycerol. Under these conditions, both methylation activities (1 and 2) are detected identically in the elution fractions corresponding to approximately 0.15 M ammonium sulphate. These fractions are pooled, concentrated by ultrafiltration on Centricon 10, desalted on PD-10 columns equilibrated in pH 8.2 (at 5° C.) 50 mM Tris buffer containing 4 mM DTE, 2 mM benzamidine, 100 μg/l 100 μg/l E-64, 2 mg/l leupeptin, 20% v/v glycerol, and then chromatographed (approximately 10 mg at each cycle) on a MonoQ HR 5/5 column equilibrated in the same buffer at a flow rate of 1 ml/min. Under these conditions, the two activities are not retained on the column. At outflow from the column, the exclusion fractions hence containing these two activities are supplements with 10% v/v of pH 8.2 50 mM Tris buffer containing 4 mM, DTE, 30 mM benzamidine, 2 Pefabloc, 100 μg/l E-64, 2 mg/l leupeptin, 1 mM EDTA, 1 mM EGTA, 20% v/v glycerol. These fractions are then concentrated by ultrafiltration on Centricon 10 and thereafter chromatographed on a 300×7.5 mm 10 μm TSK G2000 SW column equilibrated at a flow rate of 0.5 ml/min in pH 7.0 50 mM Hepes buffer containing 4 mM DTE, 0.2 mM Pefabloc, 1 mM EDTA, 1 mM EGTA, 10% v/v glycerol, 0.15 M sodium chloride. The two activities co-elute in this technique at a retention time corresponding to a molecular weight close to 30,000. After this step, a preponderant protein is visible in SDS-PAGE. It is located at around 32,000.

TABLE

Purification of the enzyme methylating p-aminophenylalanine to p-dimethylaminophenylalanine

| Purification Steps | Vol. (ml) | Protein (mg) | Sp.Act. (units[a]/mg) | Yield (%) | Purification factor |
|---|---|---|---|---|---|
| Crude extract | 510 | 1800 | 29 | — | — |
| G-25 Fine | 560 | 1560 | 34 | 102 | 1.17 |
| MonoQ HR 16/10 | 670 | 82 | 430 | 67 | 14.8 |
| Phenyl Superose | 10 | 3.48 | 6300 | 42 | 217 |
| MonoQ HR 5/5 | 7 | 0.88 | 17200 | 29 | 593 |
| TSK G2000 | 0.8 | 0.113 | 40300 | 8.7 | 1390 |

[a]This refers to units of enzymatic activity for methylation 1. At each step, the value of the units of enzymatic activity for methylation 2 was equal to 120% of that of the units for methylation 1.

The purification factor is calculated from the increase in specific activity of the fractions during the purification.

5.7.1.C. Purification from *E. coli* pVRC706 of the recombinant protein of *S. pristinaespiralis* SP92 displaying the SAM-dependent N-methyltransferase activity catalysing the methylation of p-aminophenylalanine to p-dimethylaminophenylalanine This experiment illustrates how an enzyme of *S. prisinaespiralis* SP92 participating in the biosynthesis pathway of pristinamycin IA and expressed in *E. coli* by cloning of the papM gene may be purified.

Using the assay described above in Example 5.7.1.A., we showed that crude extracts of the recombinant strain *E. coli*:pVRC706 display a strong activity for methylation 1 and for methylation 2, whereas in the control *E. coli* strain (pMTL23) neither of these two activities was detected. The purification of the SAM-dependent p-aminophenylalanine (phenyl-N)-methyltransferase catalysing the methylation of p-aminophenylalanine to p-dimethylaminophenylalanine was then carried out.

Under the same conditions as those described in Example 5.7.1.B., except for a chromatography step which was eliminated (step of purification on MonoQ HR 5/5), we purified to homogeneity a protein which possesses a molecular weight in chromatography on a TSK G2000 column and in SDS-PAGE identical to those possessed by the protein purified in Example 5.7.1.B.

TABLE

Purification of the enzyme methylating
p-aminophenylalanine to p-dimethylaminophenylalanine
from *E. coli* strain pVRC706

| Purification Steps | Vol. (ml) | Protein (mg) | Sp.Act. (units[a]/mg) | Yield (%) | Purification factor |
|---|---|---|---|---|---|
| Crude extract | 15 | 190 | 235 | — | — |
| G-25 Fine | 22 | 175 | 231 | 91 | 1 |
| MonoQ HR 16/10 | 24 | 13.4 | 2100 | 63 | 8.9 |
| Phenyl Superose | 3.0 | 0.39 | 35500 | 31 | 145 |
| TSK G2000 | 0.8 | 0.092 | 45200 | 9.3 | 192 |

[a]This refers to units of enzymatic activity for methylation 1. At each step, the value of the units of enzymatic activity for methylation 2 was equal to 120% of that of the units for methylation 1.

The purification factor is calculated from the increase in specific activity of the fractions during the purification.

5.7.2. Identification of the structural gene for p-aminophenylalanine (phenyl-N)-methyltransferase The $NH_2$-terminal sequence of the 32,000 protein purified in Example 5.7.1.B was determined by microsequencing as described in Example 5.1.2. Ten residues were determined in this way:

TAAAPTLAQA

The $NH_2$-terminal sequence of the 32,000 protein purified in Example 5.7.1.C was determined by microsequencing as described in Example 5.1.2. Ten residues were determined in this way:

TAAAPTLAQA

In both cases the same residues are found, and this sequence corresponds exactly to the beginning of the protein sequence which is deduced from the sequence of the papM gene (see residues 2 to 11 on SEQ ID no. 25). The purified p-aminophenylalanine (phenyl-N)-methyltransferase is hence the protein PapM.

EXAMPLE 6

Subcloning of DNA fragments cloned into cosmids as prepared in Example 3 and containing the genes of interest This example illustrates how, starting from cosmids constructed as described in Example 3 and containing genes for the biosynthesis of pristinamycins II or pristinamycins I, it is possible to subclone DNA fragments containing these genes.

These subclonings were performed in order to be able to deduce subsequently the nucleic acid sequence of the genes identified, as well as to carry out the different construction presented in the examples which follow.

6.1 Isolation of the 5.5-kb EcoRI-BglII fragment containing the structural gene for 3-hydroxypicolinic acid:AMP ligase This example describes how, starting from cosmid pIBV2 containing the structural gene for 3-hydroxypicolinic acid:AMP ligase, it is possible to subclone a DNA fragment of smaller size containing this gene.

Approxmiately 10 µg of cosmid pIBV2 were cut successively with the restriction enzymes BglII and EcoRI (New England Biolabs) under the conditions recommended by the supplier. The restriction fragments thereby obtained were separated by electrophoresis on 0.8% agarose gel, and the 5.5-kb BglII-EcoRI fragment was isolated by electroelution as described in Maniatis et al. (1989).

Approximately 100 ng of pUC19 (Viera and Messing 1982) cut with BamHI and EcoRI were ligated with 200 ng of the 5.5-kb BglII-EcoRI fragment under the conditions described in Example 3.3.

After transformation of the strain TG1 and selection of the transformants of solid LB medium containing 150 µg/ml of ampicillin and 20 µg/ml of X-gal according to the technique described by Maniatis et al., (1989), a clone carrying the desired fragment was isolated. The recombinant plasmid was designated pVRC402. Its restriction map is presented in FIG. 15(A). It was shown by hybridization, in Example 5.2., that the 5.5-kb EcoRI-BglII fragment contains the structural gene for *S. pristinaespiralis* SP92 3-hydroxypicolinic acid:AMP ligase. Plasmid pVRC402 hence contains the structural gene for *S. pristinaespiralis* SP92 3-hydroxypicolinic acid:AMP ligase.

6.2. Isolation of a 4.6-kb BglII—BglII fragment from cosmid pIBV2

This example describes how, starting from cosmid pIBV2, it is possible to subclone a DNA fragment of smaller size for the purpose of identifying, in the regions adjacent to the structural gene for 3-hydroxypicolinic acid:AMP ligase, the presence of other genes involved in the biosynthesis of pristinamycins I.

The different cloning steps were carried out as described above.

Approximately 10 µg of cosmid pIVB2 were cut with BglII. The restriction fragments thereby obtained were separated by electrophoresis on 0.8% agarose gel, and the 4.6-kb BglII—BglII fragment was isolated by electroelution.

Approximately 100 ng of pUC19 cut with BamHI were ligated with 200 ng of the BglII—BglII fragment.

A clone carrying the desired fragment was isolated after transformation of the strain TG1 as described in Example 6.1. The recombinant plasmid was designated pVRC501. Its restriction map is presented in FIG. 15(B).

6.3. Isolation of the 6-kb BamHI—BamHI fragment containing the structural genes for the two subunits of pristinamycin IIA synthase This example describes how, starting from cosmid pIBV1, it is possible to subclone a DNA fragment of smaller size containing the structural genes for the two subunits of pristinamycin IIA synthase.

The different cloning steps were carried out as described above.

Approximately 10 µg of cosmid pIBV1 were cut with BamHI. The restriction fragments thereby obtained were separated by electrophoresis on 0.8% agarose gel, and the 6-kb BamHI fragment was isolated by electroelution.

Approximately 100 ng of pBKS⁻ (Stratagene Cloning Systems, La Jolla Calif.) cut with BamHI were ligated with 200 ng of the 6-kb BamHI fragment.

A clone carrying the desired fragment was isolated after transformation of the strain TG1. The recombinant plasmid was designated pXL2045. Its restriction map is presented in FIG. 16. It was shown by hybridization, in Example 5.1, that the 6-kb BamHI fragment contains the snaA and snaB genes coding for the two subunits of *S. pristinaespiralis* SP92 pristinamycin IIA synthase. Plasmid pXL2045 hence contains the snaA and snaB genes coding for the two subunits of *S. pristinaespiralis* SP92 pristinamycin IIA synthase.

6.4. Isolation of the 6.2-kb SphI fragment containing a portion of the structural gene for pristinamycin I synthase II This example describes how, starting from cosmid pIBV3, it is possible to subclone a DNA fragment of smaller size containing a portion of the structural gene of pristinamycin I synthase II.

The different cloning steps were carried out as described above.

Approximately 10 µg of cosmid pIBV3 were cut with SphI. The restriction fragments thereby obtained were separated on 0.8% agarose gel, and the 6.2-kb SphI fragment was isolated by the technique of the "Geneclean" kit marketed by the company Bio101-Ozyme.

Approximately 100 ng of pUC19 cut with SphI were ligated with 200 ng of the 6.2-kb SphI fragment.

A clone carrying the desired fragment was isolated after transformation of the strain TG1. The recombinant plasmid was designated pVRC1105. Its restriction map is presented in FIG. 17.

6.5. Isolation of the 8.4-kb SphI fragment containing a portion of the structural gene for pristinamycin I synthase III This example describes how, starting from cosmid pIBV3, it is possible to subclone a DNA fragment of smaller size containing a portion of the structural gene for pristinamycin I synthase III.

The different cloning steps were carried out as describe above.

Approximately 10 µg of cosmid pIBV3 were cut with SphI. The restriction fragments thereby obtained were separated on 0.8% agarose gel, and the 8.4-kb SphI fragment was isolated by the technique of the "Geneclean" kit marketed by the company Bio101-Oxyme.

Approximately 100 ng of pUC19 cut with SphI were ligated with 200 ng of the 8.4-kb SphI fragment.

A clone carrying the desired fragment was isolated after transformation of the strain TG1. The recombinant plasmid was designated pVRC1106. Its restriction map is represented in FIG. 18.

6.6. Isolation of a 6.6-kb SphI fragment containing a portion of the structural gene for pristinamycin I synthase IV This example describes how, starting from cosmid pIBV3, it is possible to subclone a DNA fragment of smaller size containing a portion of the structural gene for pristinamycin I synthase IV.

The different cloning steps were carried out as describe above.

Approximately 10 µg of cosmid pIBV3 were cut with SphI. The restriction fragments thereby obtained were separated on 0.8% agarose gel, and the 6.6-kb SphI fragment was isolated by the technique of the "Geneclean" kit marketed by the company Bio101-Oxyme.

Approximately 100 ng of pUC19 cut with SphI were ligated with 200 ng of the 6.6-kb SphI fragment.

A clone carrying the desired fragment was isolated after transformation of the strain TG1. The recombinant plasmid was designated pVRC1104. Its restriction map is presented in FIG. 19.

6.7 Isolation of the 17-kb HindIII—HindIII fragment containing cosmid pHC79 and carrying the genes located upstream of 3-hydroxypicolinic acid:AMP ligase (pristinamycin I synthase I)

This example describes how, started from cosmid pIBV2 containing the structural gene for 3-hydroxypicolinic acid:AMP ligase, it is possible to delete a large portion of this cosmid and retain only the portion located upstream of 3-hydroxypicolinic acid:AMP ligase.

Approximately 200 ng of cosmid pIBV2 were cut with the restriction enzyme HindIII. The enzyme was denatured for 30 min at 85° C. as recommended by the supplier. Cosmid pIBV2 digested in this way was precipitated with ethanol as described in Maniatis et al., (1989) and religated with itself in a volume of 50 µl.

After transformation of the strain TG1 and selection of the transformants on solid LB+150 µg/ml of ampicillin according to the technique described by Maniatis et al. (1989), a clone containing cosmid pHC79 and the portion located upstream of 3-hydroxypicolinic acid:AMP ligase (the whole corresponding to a size of approximately 17 kb) was isolated. The recombinant plasmid was designated pVRC900. Its restriction map is presented in FIG. 20.

6.8. Isolation of the 1.4-kb BamHI-SstI fragment originating from cosmid pIBV3

This example describes how, starting from cosmid pIBV3 containing the snaA gene coding for the large subunit of PIIA synthase, it is possible to subclone a DNA fragment located upstream in order to study and sequence it.

Approximately 10 µg of cosmid pIBV3 were cut successively with the restriction enzymes SstI and BamHI. The restriction fragments thereby obtained were separated on 0.8% agarose gel, and the 1.4-kb BamHI-SstI fragment was isolated by the technique of the "Geneclean" kit marketed by the company Bio101-Ozyme.

Approximately 100 ng of pDH5 (Hilleman et al. 1991) cut with BamHI and SstI were ligated with 200 ng of the BamHI-SstI fragment under the conditions described in Example 3.3.

After transformation of the strain TG1 and selection of the transformants of solid LB+150 µg/ml of ampicillin+X-gal according to the technique described by Maniatis et al. (1989), a clone carrying the desired fragment was isolated. The recombinant plasmid was designated pVRC1000. Its restriction map is represented in FIG. 21.

6.9. Isolation of the 4-kb BamHI—BamHI fragment containing the structural gene of FMN reductase This example describes how, starting from cosmid pIBV4 containing the structural gene for FMN reductase (snaC), it is possible to subclone a DNA fragment of smaller size containing this gene.

The different cloning steps were carried out as described above.

Approximately 10 µg of cosmid pIBV4 were cut with the restriction enzyme BamHI. The restriction fragments thereby obtained were separated on 0.8% agarose gel, and the 4-kb BamHI-BamHI fragment was isolated by electroelution.

Approximately 100 ng of pUC19 cut with BamHI were ligated with 200 ng of the 4-kb BamHI-BamHI fragment.

After transformation of *E. coli* strain DH5α (supE44 DlacU169 (f80lacZDM15) hsdR17 recA1 endA1 gyrA96 thi-1 relA1) (Hanahan, 1983) and selection of the transformants on solid LB+150 µg/ml of ampicillin +X-gal according to the technique described by Maniatis et al. (1989), a clone carrying the desired fragment was isolated. The recombinant plasmid was designated pVRC509. Its restriction map is presented in FIG. 22.

EXAMPLE 7

Sequence of the Isolated DNA fragments containing the genes for the biosynthesis of pristinamycins of *S. pristinaespiralis* SP92.

This example illustrates the sequencing of DNA fragments carrying, on the one hand genes involved in the biosynthesis of pristinamycins of the pristinamycin I family, and on the other hand genes involved in the biosynthesis of pristinamycins of the pristinamycin II family, of the *S. pristinaespiralis* strain.

7.1. Sequencing of a 5-kb BamHI-XhoI Fragment

This example illustrates how the nucleotide sequence of a fragment containing the snaA and snaB genes of *S. pristinaespiralis* SP92 may be obtained.

The BamHI-XhoI fragment is part of the 6-kb BamHI-BamHI Fragment which was cloned into phasmid pBKS⁻ to give plasmid pXL2045 described in Example 6.3. Subfragments of this 5-kb BamHI-XhoI insert were then obtained by enzymatic digestion and thereafter subcloned into phages M13mp18 or M13mp19 (Messing et al, 1981) in both orientations. The subcloning sites used are the following: EcoRI, PstI, PstI, NruI, EcoRI, NruI, NotI, SalI, SstI, XhoI, SalI and XhoI, and are shown in FIG. 16.

These different inserts were sequenced by the chain-termination reaction method, using as a synthetic primer the universal primer (Maniatis et al, 1989) or oligonucleotides which are synthesized (as is described in Example 5) and are complementary to a sequence of 20 nucleotides of the inert to be sequenced.

The overlap between these different inserts enabled the total nucleotide sequence to be established on both strands of the BamHI-XhoI fragment which comprises 5392 bp (SEQ ID no. 1).

7.2 Sequencing of a Region of 1870 bp of the 5.5-kb EcoRI-BGlII Fragment

This example illustrates how the nucleotide sequence of a fragment containing the snbA gene of *S. pristinaespiralis* SP92 may be obtained.

Figure 15A:
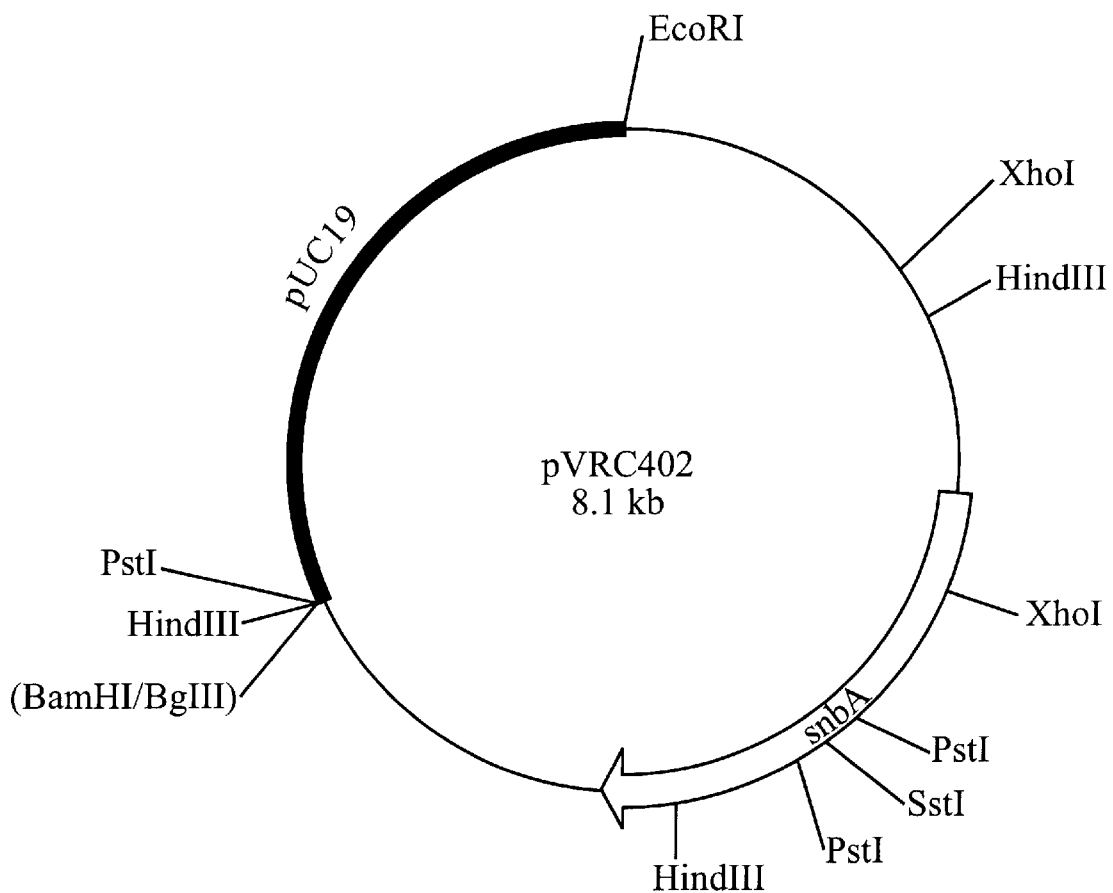

The region of 1870 bp sequenced is part of the 5.5-kb EcoRI-BGlII fragment which was cloned into plasmid pUC19 to give plasmid pVRC402 described in Example 6 (FIG. 15(A)). Subfragments of the 5.5-kb EcoRI-BglII insert were obtained by enzymatic cleavage and then subcloned into phages M13mp18 or M13mp19 in both orientations. The subcloning sites are BindIII, PstI and HindIII, and are shown in FIG. 15(A).

The overlap between these fragments enabled the total sequence of the Sau3A-Sau3A region, which comprises 1870 bp (SEQ ID no. 5), to be established.

7.3. Sequence of a Region of 1830 bp in the 4.6-kb BglII-BglII Fragment

This example illustrates how the nucleotide sequence of a fragment adjacent to that which contains the snbA gene of *S. pristinaespiralis* SP92 may be obtained.

Figure 15B:
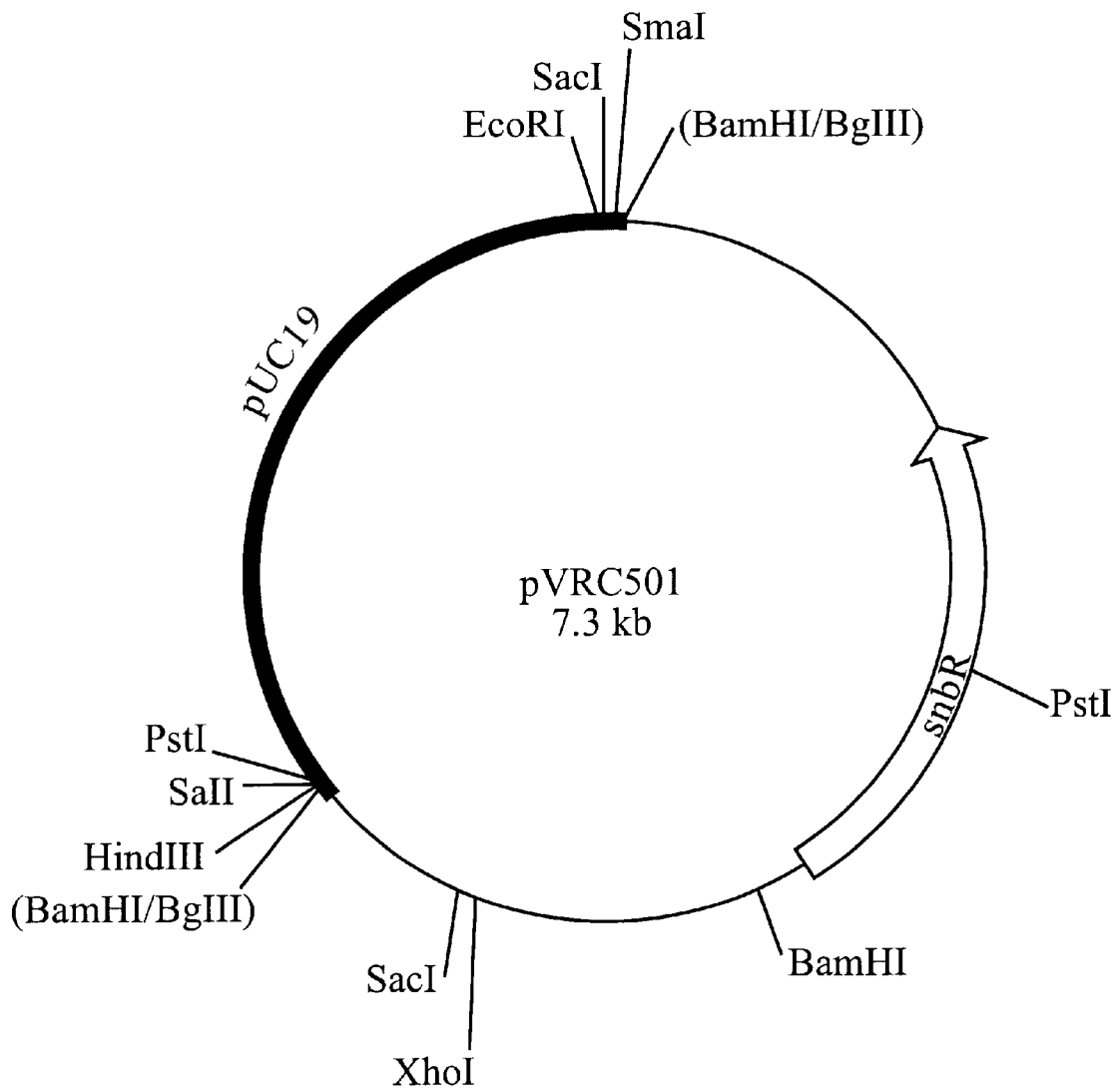

This sequence was deduced by subcloning the 1-kb BamHI-PstI and 2.1-kb Psti-EcoRI fragments (FIG. 15(B)) from pVRC501 (Example 6) into the vectors M13mp18 and M13mp19. The PstI site was traversed by subcloning a 423-bp Sau3A-Sau3A fragment overlapping this site, followed by sequencing. The sequence of 1830 bp thereby obtained is shown in (SEQ ID no. 6).

7.4. Sequencing of Two Regions of 227 bp and 247 bp of the 6.2-kb SphI Fragment This example illustrates how the nucleotide sequence of fragments containing a portion of the structural gene for pristinamycin I synthase II (snbC) of *S. pristinaespiralis* may be obtained.

The regions of 227 and 247 bp sequenced are parts of the 6.2-kb SphI fragment which was cloned into plasmid pUC19 to give plasmid pVRC1105 described in Example 6.4 (FIG. 17). Subfragments of the 6.2-kb SphI insert were obtained by enzymatic cleavage and then subcloned into phages M13mp18 or M13mp19 in both orientations. The subcloning sites are XhoI, PstI and BglII, and are shown in FIG. 17. The 227-bp PstI-BglII fragment was sequenced completely, and 247 bp were sequenced from the 900-bp XhoI fragment: these sequences are presented in SEQ ID nos. 11 and 12.

7.5 Sequencing of Two Regions of 192 bp and 474 bp of the 8.4-kb SphI Fragment This example illustrates how the nucleotide sequence of fragments containing portions of the structural gene for pristinamycin I synthase III (snbD) of *S. pristinaespiralis* may be obtained.

The regions of 192 and 474 bp sequenced are parts of the 8.4-kb SphI fragment which was cloned into plasmid pUC19 to give plasmid pVRC1106 described in Example 6.5 (FIG. 18). Subfragments of the 8.4-kb SphI insert were obtained by enzymatic cleavage and then subcloned into phages M13mp18 or M13mp19 in both orientations. The subcloning sites are XhoI, PstI, SphI and BglII, and are shown in FIG. 18.

The 192-bp BglII-SphI and 474-bp PstI-XhoI fragments were sequenced completely: these sequences are presented in SEQ ID nos. 13 and 14.

7.6 Sequencing of Two Regions of 485 bp and 291 bp of the 6.6-kb SphI Fragment This example illustrates how the nucleotide sequence of fragments containing portions of the structural gene for pristinamycin I synthase IV (snbE) of *S. pristinaespiralis* may be obtained.

The regions of 291 and 485 bp sequenced are parts of the 6.6-kb SphI fragment which was cloned into plasmid pUC19 to give plasmid pVRC1104 described in Example 6.6 (FIG. 19). Subfragments of the 6.6-kb SphI insert were obtained by enzymatic cleavage and then subcloned into phages M13mp18 or M13mp19 in both orientations. The subcloning sites are XhoI, PstI and SphI, and are shown in FIG. 19. The 485-bp XhoI-SphI fragment was sequenced completely, and 291 bp were sequenced from the 1500-bp PstI fragment: these sequences are presented in SEQ ID nos. 15 and 16.

7.7. Sequence of a Region of 645 bp in a 3.4-kb XhoI-XhoI Fragment Isolated from pVRC900

This example illustrates how the nucleotide sequence of a fragment located upstream of that which contains the snbA gene of *S. pristinaespiralis* may be obtained.

To deduce this sequence, the 3.4-kb XhoI-XhoI fragment was subcloned beforehand into the vector pUC18 from the vector pVRC900 described in 6.7. The different cloning steps were carried out as described in 6.1: plasmid pVRC900 was digested with the restriction enzyme XhoI, and the fragments thereby obtained were separated on 0.8% agarose gel. The 3.4-kb XhoI-XhoI fragment was purified by electroelution and was ligated with pUC18 cut with the restriction enzyme SalI. After transformation into TG1, a clone carrying the 3.4-kb XhoI-XhoI fragment was isolated. The recombinant plasmid was referred to as pVRC903. Its restriction map is presented in FIG. 23.

The 645-bp sequence was then deduced by subcloning the 1.4-kb PvuII-EcoRI and 0.9-kb PvuII-EcoRI fragments (FIG. 23) from pVRC903 described above into the vectors M13mp18 and M13mp19. To carry out these clonings, the vectors M13mp18 and m13mp19 were first digested with the restriction enzyme BamHI; The cohesive ends thereby liberated were filled in with the large fragment of DNA polymerase I (Klenow: New England Biolabs) according to the technique described by Maniatis et al. (1989) so as to generate blunt ends compatible with the ends liberated by PuvII digestion; the vectors were then digested with the restriction enzyme EcoRI. The PvuII site was traversed by subcloning a 2.2-kb PstI-PstI fragment, isolated from pVRC903, overlapping this site. The sequence of 645 bp thereby obtained is shown in SEQ ID no. 9.

7.8. Sequence of a Region of 1050 bp in a 4.1-kb PstI-PstI Fragment Isolated from pVRC900

This example illustrates how the nucleotide sequence of a fragment located upstream of that which contains the snbA gene of S. pristinaespiralls may be obtained.

To deduce this sequence, a 4.1-kb PstI-PstI fragment was subcloned beforehand into the vector pUC19 from the vector pVRC900 described in 6.7. The different cloning steps were carried out as described in 6.1. Plasmid pVRC900 was digested with restriction enzyme PstI, and the fragments thereby obtained were separated on 0.8% agarose gel. The 4.1-kb PstI-PstI fragment was purified by electroelution and was ligated with pUC19 cut with the restriction enzyme PstI. After transformation into TG1, a clone carrying the 4.1-kb PstI-PstI fragment was isolated. The recombinant plasmid was referred to as pVRC409. Its restriction map is presented in FIG. 24.

This sequence was then deduced by subcloning the 0.7-kb XhoI-XhoI and 1-kb XhoI-StuI fragments (FIG. 24) from pVRC409 described above into the vectors M13mp18 and M13mp19. The XhoI site internal to the sequence was traversed by double-strand sequencing from plasmid pVRC409. The sequence of 1050 bp thereby obtained is shown in SEQ ID no. 10.

7.9. Sequence of a Region of 640 bp in the 1.4-kb BamHi-SstI Fragment

This example illustrates how the nucleotide sequence of a fragment adjacent to that which contains the snaA and snaB genes of S. pristinaespiralis coding for the two subunits of PIIA synthase may be obtained.

This sequence was deduced by subcloning the 1.4-kb BamHI-SstI fragment (FIG. 21) from pVRC1000 (Example 6.8) into the vectors M13mp18 and M13mp19 (see Example 7.1). The sequence of 640 bp obtained is shown in SEQ ID no. 8.

7.10. Sequencing of the XhoI-KpnI Region of 694 bp Present in the 4-kb BamHI-BamHI Fragment This example illustrates how the nucleotide sequence of a fragment containing the snaC gene of S. pristinaespiralis may be obtained.

The region of 694 bp sequenced is part of the 4-kb BamHI-BamHI fragment which was cloned into plasmid pUC19 to give plasmid pVRC509 described in Example 6.9. A 694-bp XhoI-KpnI fragment, obtained by double digestion of plasmid pVRC509 with the restriction enzymes XhoI and KpnI and which hydridizes with the 3 oligonucleotide probes described in 5.6, was cloned into phages M13mp18 and M13mp19. The XhoI and KpnI subcloning sites are shown in FIG. 22.

The sequence of the 694-bp fragment thereby obtained is presented in SEQ ID no. 7.

EXAMPLE 8

Analysis of the Nucleotide Sequences by Determination of the Open Reading Frames This example illustrates how it is possible to determine the open reading frames present in the nucleotide sequences defined in Example 7, and to identify the genes involved in the biosynthesis of pristinamycins I and pristinamycin II of S. pristinaespiralis SP92 as well as the polypeptides encoded by these genes.

8.1. 5-kb BamHI-XhoI Fragment (pXL2045)

This example illustrates how it is possible to determine the open reading frames present within the 5-kb BamHI-XhoI fragment isolated above and sequenced as described in Examples 6 and 7.

We looked for the presence of open reading frames within the 5-kb BamHI-XhoI fragment utilizing the fact that Streptomyces DNA has a high percentage of G and C bases as well as a strong bias in the use of the codons of which the coding frames are composed (Bibb et al. 1984). The Staden and McLachlan (1982) method enables the probability of the coding frames to be calculated on the basis of the use of the codons of Streptomyces genes which are already sequenced and collated in a file containing 19673 codons obtained from the BISANCE data-processing server (Dessen et al. 1900).

This method enabled four highly probable open reading frames, which are shown in the following table, to be characterized within the 5-kb BamHI-XhoI fragment. They are designated frames 1 to 4 according to their position starting from the BamHI site. For each one, their length in bases, their position within the fragment (the BamHI site being located at position 1) and also the molecular weight in kDa of the corresponding protein are given. Frames 1, 3 and 4 are coded by the same strand and frame 2 by the complementary strand (FIG. 16).

| Frame number and gene name | Position | number of nucleotides | number of amino acids | MW in kDa of the protein encoded |
|---|---|---|---|---|
| 1 (snaA) | 48-1313 | 1266 | 422 | 46.5 |
| 2 | 2530–1328 | 1203 | 401 | — |
| 3 (snaB) | (inv) 2692–3522 | 831 | 277 | 29 |
| 4 (samS) | 3558–4763 | 1206 | 402 | 43 |

Frames 1 and 3 correspond respectively to the proteins SnaA (SEQ ID no. 17) and SnaB (SEQ ID no. 18) isolated above as described in Example 5 and for which the cloning of the gene is detailed in Example 6. In effect, the $NH_2$-terminal sequences of the products of ORFs 1 and 3 are identical to the $NH_2$-terminal sequences found for the proteins SnaA and SnaB, respectively, in Example 5.1.2, apart from the amino-terminal methionine which has been excized. Moreover, the molecular masses calculated from the sequences are comparable to the apparent molecular masses of the proteins SnaA and SnaB, estimated, respectively, in SDS-PAGE as described in Example 5.

Comparison of the product of open reading frame no. 4 with the protein sequences contained in the NBRF bank reveals a homology with various *S-adenosylmethionine* (or SAM) synthases, in particular of *E. coli* (Markham et al., (1984), of rat (Horikawa et al., 1989) and of *S. cerevisiae* (Thomas et al., 1988). The percentage homology values calculated over the whole of the sequence using Kanehisa's (1984) algorithm vary from 51.8 to 55.4%.

These sequence comparisons hence enable it to be demonstrated that the product of open reading frame no 4 is an SAM synthase involved in the biosynthesis of pristinamycins I or II. This gene was designated samS (SEQ ID no. 4)

The demonstration of the involvement of the samS gene in the biosynthesis of pristinamycins is confirmed by the construction of the SP92 mutant disrupted in this gene, as described in Example 9.2.

Comparison of the sequence of the product of open reading frame no. 2 with the protein sequences contained in the Genpro bank reveals that an internal portion of this protein is 36% homologous with an internal portion of the first open reading frame of the insertion sequence (IS891) of Anabaena (Bancroft and Wolk, 1989). This result suggests that open reading frame no. 2, designated ORF 401, belongs to an insertion sequence, and that there is hence an insertion sequence located between the snaA and snaB genes.

8.2. 1870-bp Sau3A-Sau3A fragment (pVRC4021)

This example illustrates how it is possible to determine open reading frames present within the 1870-bp Sau3A-Sau3A fragment isolated above and sequenced as described in Examples 6 and 7.

The search for open reading frames for the Sau3A-Sau3A fragment was performed as above. A single complete open reading frame could be demonstrated in this way. Its characteristics are as follows: this frame extends from position 109 to position 1858 of the Sau3A-Sau3A fragment, which corresponds to a frame of 1749 bases coding for a protein of 582 amino acids having a molecular mass of 61400 Da. This protein corresponds to the protein SnbA purified above as described in Example 5 and for which the cloning of the gene is detailed in Example 6. In effect, the $NH_2$-terminal sequence of the product of the ORF present on the Sau3A-Sau3A fragment is identical to the $NH_2$-terminal sequence found for the protein SnbA in Example 5.2. The molecular mass of 61400 Da calculated from the sequence is comparable to the apparent molecular mass of the protein SnbA, estimated at 67000 Da in SDS-PAGE and at 60000 Da by gel permeation as described in Example 5.2.1.B.

The snbA gene hence codes for the enzyme which catalyses the formation of the acyladenylate 3-hydroxypicolinyl-AMP from one molecule of 3-hydroxypicolinic acid and one molecule of ATP: 3-hydroxypicolinic acid:AMP ligase (SEQ ID no. 5).

8.3. 1830-bp fragment (pVRC501)

This example illustrates how it is possible to determine the open reading frames present within the 1830-bp fragment sequenced from the 3.1-kb BamHI-EcoRI fragment isolated above.

The search for open reading frames for the 1830-bp fragment was performed as above. A single complete open reading frame could be demonstrated in this way. Its characteristics are as follows: the probable beginning of this frame is located at position 103 and the end at position 1686 of the region of 1830 bp sequenced from the BamHI-EcoRI fragment, which corresponds to a protein of 528 amino acids having an approximate molecular weight of 54000.

Comparison of the sequence of this protein with the sequences contained in the Genepro bank reveals that it is homologous to proteins having a transport function for various metabolites, in particular for tetracycline in various microorganisms (Khan and Novic, 1983; Hoshino et al., 1985), actinorhodine (Fernandez-Moreno et al., 1991) and methylenomycin (Neal and Chater, 1987b) in *s. coelicolor*.

These data indicate that the product of the open reading frame contained in the 3.1-kb BamHI-EcoRI fragment is a transport protein enabling pristinamycins I (and possible pristinamycins II) to be exported out of the cell. This protein was designated SnbR (SEQ ID NO:21) and the corresponding gene snbR (SEQ ID no. 6).

Analysis of the hydrophobicity profile of the protein SnbR by the method of Kyte and Doolittle (1982) corroborates its membrane localization and hence its transport function.

8.4. 1050-bp fragment (pVRC409)

This example illustrates how it is possible to determine the open reading frames present within the 1050-bp fragment sequenced above from pVRC409 as described in Example 7.8.

The search for open reading frames for the 1050-bp fragment was performed as above. A single complete open reading frame could be demonstrated in this way. Its characteristics are as follows: this phase extends from position 84 to position 962 of the sequenced portion, which corresponds to a frame of 878 bases coding for a protein of 292 amino acids having a molecular mass of 32000 Da. This protein was referred to as protein PapM. It was, moreover, purified from *S. pristinaespiralis* strain SP92 as described in Example 5. The molecular mass of 32000 Da calculated from the sequence is identical to the apparent molecular mass of 32000 Da estimated on SDS-PAGE as described in Example 5. Moreover, the $NH_2$-terminal sequence of this protein, deduced as described in Example 5, corresponds well to the $NH_2$-terminal sequence of the protein PapM (SEQ ID NO:25) identified by analysis of the open reading frames of the sequence of 1050 bp (SEQ ID no. 10).

8.5. 220-bp and 247-bp fragments (pVRC1105)

This example illustrates how it is possible to determine the open reading frames present within the 227-bp and 247-bp fragments sequenced from pVRC1105 as described in Examples 6 and 7.

The search for open reading frames for these two fragments was performed as above. An incomplete reading frame could be demonstrated in both cases over the whole length of the fragment.

The sequence obtained from the open reading frame identified on the 247-bp fragment isolated from the 900-bp XhoI fragment contains one of the internal sequences of the protein SnbC purified as described in Example 5.

Comparison of the product of the open reading frames identified on the 227-bp and 247-bp fragments isolated from pVRC1105 with sequences of the Genpro bank reveals that they are homologous to peptide synthases. The one deduced from the 227-bp fragment displays 24.5% homology with *Acremonium chrysogenum* (α-aminoadipyl)cysteinylvaline synthetase (Gutierrez et al. 1991). The one deduced from the 247-bp fragment displays 34.9% homology with *Bacillus gramicidin* S synthase II (Hori et al. 1991) and 28% homology with *Acremonium chrysogenum* (α-aminoadipyl) cysteinylvaline synthetase (Gutierrez et al. 1991).

This confirms that cosmid pIBV3 isolated in Example 5.1 does indeed contain a portion of the structural gene for pristinamycin I synthase II described in Example 5.3, designated SnbC (SEQ ID no. 26 and 27).

8.6. 192-bp and 474-bp Fragments (pVRC1106)

This example illustrates how it is possible to determine the open reading frames present within the 192-bp and 474-bp fragments sequenced from pVRC1106 as described in Examples 6 and 7.

To search for open reading frames for these two fragments was performed as above. An incomplete reading frame could also be demonstrated on the 192-bp fragment isolated from pVRC1106. Its characteristics are as follows: this frame begins at position 29 of the portion sequenced in the direction of BglII. No stop codon was identified, indicating that this open frame is not terminated.

The sequence obtained from the open reading frame identified on the 192-bp BglII-SphI fragment contains the internal sequence of the protein SnbD purified as described in Example 5, which proves, in fact, to be the $NH_2$-terminal sequence of the protein.

An incomplete reading frame could be demonstrated over the whole length of the 474-bp XhoI-PstI fragment.

Comparison of the product of the open reading frame identified on the 474-bp fragment isolated from pVRC1106 with the sequences of the Genpro bank reveals that this protein fragment displays from 30 to 40% homology with peptide synthases, for example 39.4% with *Bacillus gramicidin* S synthase II (Hori et al. 1991) and and 34% with *Acremonium chrysogenum* (α-aminoadipyl)cysteinylvaline synthetase (Gutierrez et al. 1991).

This confirms that cosmid pIBV3 isolated in Example 5.1 does indeed contain a portion of the structural gene for pristinamycin I synthase III described in Example 5.4, designated SnbD (SEQ ID nos. 28 and 29).

8.7. 291-pb and 485-bp Fragments (pVRC1104)

This example illustrates how it is possible to determine the open reading frames present within the 291-bp and 485-bp fragments sequenced from pVRC1104 as described in Examples 6 and 7.

The search for open frames for these two fragments was performed as above. An incomplete reading frame could be demonstrated in both cases over the whole length of the fragment.

The sequence obtained from the open frame identified on the 291 fragment isolated from the 1450-bp PstI fragment contains the internal sequence of the protein SnbE purified as described in Example 5.

Comparison of the product of the open frame identified on the 485-bp XhoI-SphI fragment isolated from pVRC1104 with the sequences of the Genpro bank reveals that it is homologous to peptide synthases, for example 34.7% homologous with *Bacillus gramicidin* S synthase II (Hori et al. 1991) and and 36.2% with *Acremonium chrysogenum* (α-aminoadipyl)cysteinylvaline synthetase (Gutierrez et al. 1991).

This confirms that cosmid pIBV3 isolated in Example 5.1 does indeed contain a portion of the structural gene for pristinamycin I synthase IV described in Example 5.5, designated SnbE (SEQ ID 30 and 31).

8.8. 645-bp Fragment (pVRC903)

This example illustrates how it is possible to determine the open reading frames present within the 645-bp fragment sequenced above from plasmid pVRC903 as described in Example 6.7.

The search for open reading frames for the 645-bp fragment was performed as above. An incomplete open reading frame could be demonstrated in this way. Its characteristics are as follows: this frame affords two possibilities for initiation of translation, a GTG at position 61 and a GTG at position 70 of the sequenced portion (the ATG located at position 124 was not taken into account owing to the sequence homologies described later). Analysis of the probabilities of the presence of Shine-Dalgarno regions does not make it possible to distinguish which of these codons corresponds to the initiation. No stop codon was identified, which indicates that this open reading frame is not terminated. The gene identified in this way was referred to as papA, and the corresponding protein was referred to as protein PapA (SEQ ID no. 24).

Comparison of the product of the open reading frame identified in the 3,4-kb XhoI-XhoI fragment isolated from pVRC900 with sequences contained in the Genpro bank reveals that it is homologous to the II components of proteins of the p-aminobenzoate synthase and anthranilate synthase type, involved, respectively, in the synthesis of p-aminobenzoic acid (folic acid precursor) and in the synthesis of anthranilic acid (tryptophan precursor) of various microorganisms. It displays, in particular, a 48% homology with the protein TrpG of Azospirillum (Zimmer W., Aparicio C., and Elmerich c. Mol. Gen. Genet. (1991) 229:41–51) and a 47% homology with the protein PabA of *Klebsiella pneumoniae* (Kaplan J. B., Merkel W. K. and Nichols B. P. J. Mol. Biol. (1985) 183:327–340). The proteins TrpG and PabA carry the glutaminase activity involved in the transamination of chlorismic acid. The homologies demonstrated tend to show that the protein PapA might be involved as well in the activity of transamination of chlorismic acid. Chorismic acid is proposed as a precursor of p-dimethylaminophenylalanine, a component of pristinamycins I, by analogy with the synthesis of chloramphenicol, an antibiotic deduced by Streptomyces (Sharka B., Westlake D. W. S. and Vining L. C. (1970) Chem Zvesti 24, 66–72).

The role of the protein PapA will be shown subsequently (Example 9.3) by analysis of mutants of the strain SP92 in the papA gene.

8.9. 1.5-kb BamHI-SstI Fragment (PVRC1000)

This example illustrates how it is possible to determine the open reading frames present within the 1.5-kb BamHI-SstI fragment isolated above and sequenced as described in Examples 6.8 and 7.9.

The search for open reading frames for the sequenced region of 640 bp present in the 1.5-kb BamHI-SstI fragment was performed as described in Example 8.1. A single complete open reading frame could be demonstrated in this way. No initiation and no termination of translation could be demonstrated, which indicates that the sequenced region of 640 bp is probably internal to a much larger reading frame, designated snaD (SEQ ID no. 8).

Comparison of the protein sequence encoded by the region of 640 bp with the protein sequences contained in the Genpro and NBRF banks reveals that this protein is 20–25% homologous to an internal portion of peptide synthases such as *B. brevis* gramicidin synthase I (Hori et al. 1989), *B.*

*brevis* tyrocidin synthase I (Weckermann et al. 1988) and *Acremonium chrysogenum* ACV synthase (Gutierrez et al. (1991).

These data indicate that the protein partially encoded by the region of 640 bp is probably a peptide synthase involved in the biosynthesis of the peptide portion of pristinamycins II: in effect, all the peptide synthases involved in the biosynthesis of pristinamycins I have already been identified in other regions of the *S. pristinaespiralis* chromosome, as is described in Examples 5.2, 5.3, 5.4 and 5.5.

8.10. 694-bp Fragment (pVRC509)

This example illustrates how it is possible to determine the open reading frames present within the 694-bp fragment sequenced above from pVRC509 as described in Examples 6 and 7.

The search for open reading frames for the 694-bp fragment was performed as above. An incomplete open reading frame could be demonstrated in this way. Its characteristics are as follows: this frame begins at position 210 of the sequenced portion. No stop codon was identified, which indicates that this open frame is not terminated. Hence the molecular mass of the corresponding protein cannot be calculated and compared to the apparent molecular mass of 28,000 Da of the FMN reductase, estimated on SDS-PAGE as described in Example 5.6. On the other hand, the $NH_2$-terminal sequence of the protein identified in this way by analysis of the open reading frames of the sequence of 694-bp is identical to that $NH_2$-terminal sequence of the proteins SnaC purified as described in Example 5. Similarly, the two internal protein sequences of the FMN reductase described in 5.6 occur in the protein deduced from the sequenced portion. This confirms that the gene isolated from cosmid pIBV4 does indeed correspond to the protein FMN reductase described in Example 5.6, designated SnaC (SEQ ID no. 7).

A study of the DNA fragments of *S. pristinaespiralis* strain SP92 carried by cosmids pIBV1 to pIBV2 demonstrated the presence of several genes involved in the biosynthesis of pristinamycins II and pristinamycins I. The snaA, snaB and samS genes code for enzymes participating in the biosynthesis of pristinamycins II, pristinamycin IIA synthase and probable SAM synthase, and are grouped together physically on a large DNA fragment cloned into plasmid pIBV1. Similarly, the snbA, snbR, papA and papM genes—which code for proteins participating in the biosynthesis of pristinamycins I, 3-hydroxypicolinic acid:AMP ligase (SnbA), the protein SnbR probably responsible for the transport of pristinamycins I, the protein Papa involved in the biosynthesis of p-aminophenylalanine from chlorisimic acid, and p-aminophenylalanine (phenyl-N)-methyltransferase (PapM)—are grouped together on a large DNA fragment cloned into cosmid pIBV2. Similarly, the snaA and snaD genes on the one hand—which code for proteins participating in the biosynthesis of pristinamycins II, the protein SnaD probably being a peptide synthase—and the snbC, snbD and snbE genes on the other hand—which code for the 3 peptide synthases SnbC, SnbD and SnbE involved in the formation of the peptide chain of pristinamycin I from its 6 separate amino acids—are grouped together on a large DNA fragment cloned into cosmid pIVB3. These results confirm the hypothesis of the grouping together of the genes for the biosynthesis of pristinamycins II, and also of the genes for the biosynthesis of pristinamycins I, and afford the possibility of cloning the other genes involved in these biosyntheses, by chromosome walking, upstream and downstream of the regions studied.

Furthermore, it is possible by hybridization of the total DNA of the different strains producing streptogramins (see Table 1) with the snaA, snaB, snaC, snaD, samS, snbA, snbR, snbC, snbD, snbE, papA and papM genes, or with the genes identified by chromosome walking, or with fragments of these genes, to isolate the genes corresponding to the same functions in the other microorganisms producing streptogramins. This makes it possible, by the same approach as that envisaged for the pristinamycins, to isolate all the genes involved in the biosynthesis of the different streptogramins.

EXAMPLE 9

Genetic Study of DNA Fragments by Gene Disruption

This example illustrates how it is possible to demonstrate the involvement of genes in the biosynthesis of streptogramins by constructing strains derived from a producing strain and mutated in these genes by disruption, and by analysing the phenotype of such mutants. This example shows, furthermore, how to obtain strains that are left producing only one or other of the A and B components of streptogramins, or producing A and B components with ratios different from those observed with the strain SP92.

9.1. Construction of a Mutant of *S. pritinaespiralis* SP92 Disrupted in the snaA Gene This example illustrates how it is possible, by disruption of the snaA gene, to construct a strain of *S. pristinaespiralis* SP92 which no longer produces pristinamycin IIA and which produces, in contrast, pristinamycin IIB.

This mutant was constructed for the purpose of confirming the functionality of the protein SnA and of providing an intermediate of pristinamycin II production capable of being modified subsequently.

Its construction was carried out using a suicide vector capable of replicating in *E. coli* only but carrying a resistance marker which is expressed in Streptomyces. This vector, pDH5, was developed by Hillemann et al. (1991).

9.1.1. Construction of Plasmid pVRC505

This example illustrates how it is possible to construct a plasmid which does not replicate in *S. pristinaespiralis* SP92 and which may be used to disrupt the snaA gene by single homologous recombination.

Plasmid pVRC505 was constructed to produce the SP92 chromosomal mutant disrupted in the snaA gene from plasmid pXL2045 described in Example 6.3.

The 6-kb BamHI fragment, cloned into pXL2045 (FIG. 16), was cut with the restriction enzymes EcoRI and PstI. After separation of the fragments thereby generated by electrophoresis on 1% agarose gel, a 0.7-kb fragment containing the 5' end of the snaA gene was isolated and purified by Geneclean (Bio101, La Jolla, Calif.).

100 ng of vector pDH5 linearized by an EcoRI/PstI double digestion were ligated with 100 ng of the 0.7-kb fragment, as described in Example 3.3. A clone carrying the desired fragment was isolated after transformation of the strain TG1. The recombinant plasmid was designated pVRC505. Plasmid pVRC505 was prepared as described in Example 2.1. Its restriction map is presented in FIG. 25.

9.1.2. Isolation of the SP92 mutant disrupted in the snaA gene by homologous recombination This example illustrates how the mutant of *S. pristinaespiralis* SP92 disrupted in the snaA gene was constructed.

This mutant was isolated by transformation of the strain SP92 with the suicide plasmid pVRC505.

The preparation of the protoplasts and their transformation were carried out as described in D. Hopwood et al. (1985).

The strain SP92 was cultured in YEME medium, 34% sucrose, 5 mM $MgCl_2$, 0.25% glycine for 40 hours at 30° C. The mycelium was converted to protoplasts in the presence of lysozyme, and 5×1 μg of pVRC505 were used for the transformation (by the method employing PEG) of the protoplasts. Aster overnight regeneration of the protoplasts on R2YE medium (D. Hopwood et al. 1985), the recombinants were selected by overlaying 3 ml of SNA medium (D. Hopwood et al. 1985) containing 2.6 μg/ml of thiostrepton.

Of the 5 transformations carried out, 3 thiostrepton-resistant clones were isolated. This gives a recombinant efficiency of less than 1 per μg of DNA. These recombinants result from integration by single homologous recombination between the snaA gene carried by the chromosome of the strain SP92 and the 0.7-kb fragment of the suicide plasmid pVRC505. The small size of the fragment inserted into pVRC505, 0.7-kb, explains the low recombination efficiency.

The spores of the recombinants were isolated by plating out and growth on R2YE medium supplemented with 400 μg/ml of thiostrepton, and plated out again on the same medium to obtain isolated colonies.

In order to verify the position of integration of plasmid pVRC505, various Southern blots of the total DNA of several recombinant clones, which was digested with the appropriate restriction enzymes, were produced and hybridized with the vector pDH5 and the 0.7-kb fragment, used successively as probes after labelling by random priming (Random Primed DNA labeling kit, Boehringer Mannheim, France) with [α-$^{32}$P]-dCTP, as described in Maniatis et al. (1989). The hybridization results show the appearance in the genome of the recombinant clones of an additional EcoRI-PatI band, of the size of the vector pDH5 and which hybridizes with the latter, as well as of an additional EcoRI-EcoRI band which hybridizes with both the 2 probes. One of these mutants was designated SP92::pVRC505. This mutant corresponds well to the integration of plasmid pVRC505 in the snaA gene by single homologous recombination.

9.1.3. Production of pristinamycins by the mutant SP92::pVRC505

This example illustrates how it is determined that the mutant of *S. pristinaespiralis* SP92 disrupted in the snaA gene by integration of plasmid pVRC505 no longer produces pristinamycin IIA while continuing to produce pristinamycin IIB.

The mutant SP92::pVRC505, as well as the strain SP92 as control strain, were culture in liquid production medium. Fermentation was carried out as follows: 0.5 ml of a suspension of spores of the strains mentioned are added under sterile conditions to 40 ml of inoculum medium in a 300-ml Erlenmeyer. The inoculum medium consists of 10 g/l of corn steep, 15 g/l of sucrose, 10 g/l of $(NH_4)_2SO_4$, 1 g/l of $K_2HPO_4$, 3 g/l of NaCl, 0.2 g/l of $MgSO_4.7H_2O$ and 1.25 g/l of $CaCO_3$. The pH is adjusted to 6.9 with sodium hydroxide before the introduction of calcium carbonate. The Erlenmeyers are stirred for 44 hours at 27° C. on a rotary stirrer at a speed of 325 rpm. 2.5 ml of the above culture when 44 hours old are added under sterile conditions to 30 ml of production medium in a 300-ml Erlenmeyer. The production medium consists of 25 g/l of soya flour, 7.5 g/l of starch, 22.5 g/l of glucose, 3.5 g/l of feeding yeast, 0.5 g/l of zinc sulphate and 6 g/l of calcium carbonate. The pH is adjusted to 6.0 with hydrochloric acid before the introduction of calcium carbonate. The Erlenmeyers are stirred for 24, 28 and 32 hours at 27° C. At each time, 10 g of must are weighed into a smooth Erlenmeyer, and 20 ml of mobile phase composed of 62.5% of acetonitrile and 37.5% of 0.1 M $KH_2PO_4$ solution (adjusted to pH 3.0 with $H_3PO_4$), and which enables the pristinamycins to be extracted, are added to this. After stirring on a stirrer (325 rpm) for 20 min at room temperature, the whole is filtered through filter paper and the pristinamycins are assayed by HLPC as described in Example 5.1.1.A.

The results showed that, under the fermentation conditions implemented, the mutant SP92::pVRC505 produced an amount of pristinamycin I equivalent to that of the SP92 control, this being the case for all 3 times tested. In contrast, whereas the control produced approximately 70% of pristinamycin IIA and 30% of pristinamycin IIB at 24, 28 and 32 hours of fermentation, the mutant SP92::pVRC505 produced 100% of pristinamycin IIB for these same times, in amounts equivalent to the sum of pristinamycin IIA+ pristinamycin IIB produced by the strain SP92. Hence the mutant is indeed blocked in a step of biosynthesis of pristinamycin II which corresponds to the oxidation of the 2,3 bond of the D-proline of the intermediate pristinamycin IIB. This mutant hence accumulates pristinamycin IIB. This shows well the functional involvement of SnaA in the conversion of pristinamycin IIB to pristinamycin IIA.

This example shows that is is possible, starting from cloned genes for biosynthesis, to construct strains that are mutated in the steps of biosynthesis of pristinamycin. This was shown for pristinamycin II, but the same results may be obtained for pristinamycins I and, by extension, for the different components of streptogramins. Strains producing different intermediates may thus be obtained. These strains may be used to produce novel molecules by chemical, biochemical, enzymatic, and the like, modification(s) of the said intermediates. A block in an early step of the biosynthesis pathway of one or other of the components of streptogramins may also lead to mutated strains that are left producing only one or other of the components.

9.2. Construction of a mutant of *S. pristinaespiralis* SP92 disrupted in the samS gene This example illustrates how it is possible, by disruption of the samS gene, to construct a strain of *S. pristinaespiralis* SP92 which produces 35% less PIA and 10 times as much PIB (the chemical structures are shown in FIG. 2) relative to the wild-type SP92 strain. This mutant was constructed for the purpose of confirming the presumed SAM synthase function for the protein encoded by the samS gene, and for obtaining a strain that synthesizes more PIB than the wild-type SP92 strain.

9.2.1. Construction of plasmid pVRC702

From plasmid pXL2045 (described in Example 6.3), the 3.2-kb BamH1-EcoR1 fragment was isolated by enzymatic cleavage and purified after electrophoresis on 1% agarose gel by the Geneclean kit method (see Example 6.8). This fragment carries snaB gene as well as the samS gene (FIG. 16). This fragment is then cloned into a plasmid pUC18 in the following manner: 50 ng of pUC18 were linearized by double digestion using the enzymes EcoR1 and BamH1, and then ligated in the presence of T$ DNA ligase (Biolabs) with 300 ng of the 3.2-kb BamH1-EcoR1 fragment. After transformation of competent cells of *E. coli* strain TG1 with this ligation mixture, a recombinant clone possessing plasmid pUC18 with the 3.2-kb insert could be isolated, and this was designated pVRC701 (FIG. 26).

Plasmid pVRC702 is derived from plasmid pVRC701 by the introduction between the two Sst1 sites located in the middle of the samS gene (FIG. 27) of a cassette carrying the amR gene coding for resistance to amramycin and geniticin. To this end, a 2.2-kb BamH1—BamH1 fragment carrying the QamR cassette was first isolated by BamH1 digestion of plasmid pHP450amR (given by J. L. Pernodet, Laboratoire de Génétique d'Orsay) using the same technique as above. 200 ng of this fragment were then ligated with 50 ng of plasmid pUC1318 (Kay and McPherson, 1987) linearized with the enzyme BamH1, and this ligation mixture was introduced into competent E. coli TG1 cells. From the recombinant zone possessing plasmid pUC1318 containing the QamR cassette, 50 ng of a 2.2-kg Sst1—Sst1 fragment containing the QamR cassette could be reisolated by partial cleavage using the enzyme Sst1, and this fragment was ligated with 30 ng of plasmid PVRC701 cut with Sst1 (FIG. 26) to give, after transformation of competent E. coli TG1 cells, plasmid PVRC702, the structure odf which is detailed in FIG. 27.

Plasmid pVRC702 thereby obtained was prepared in large amounts according to the method described above in Example 2.1.

9.2.2. Construction of the strain having the samS::QamR chromosomal gene

This strain was obtained by transformation of S. pristinaespiralis protoplasts with 1 μg of the suicide plasmid pVRC702 which is incapable of replicating in a Streptomyces cell. The protocols for preparation of the protoplasts and for transformation are the same as above (Example 9.1). The only modifications made with respect to Example 10.1 relate to the selection antibiotic. In the present case, the recombinant protoplasts after regeneration for 18 hours at 30° C. on R2YE medium are selected in the presence of 50 μg/ml final of geniticin (Sigma Chemical Co.). Thus, an overlayer composed of 3 ml of SNA containing 383 μg/ml of geniticin is added to each dish of R2YE.

In this way, it was possible to isolate 500 geniticin-resistant recombinant clones, which may result either from an integration of plasmid pVRC702 into the chromosome following a single homologous recombination between chromosomal and plasmid samS genes (in the case of single crossing-over), or from an exchange between the chromosomal samS gene and the plasmid samS::QamR plasmid gene following a double homologous recombination event (in the case of double crossing-over). In these two cases in point, the QamR cassette becomes transferred onto the chromosome of the strain, and endows it with an amR resistance which is stable over generations.

The recombinant clones were isolated by plating out and growth on HT7 medium containing 50 μg/ml final of geniticin, and then analyzed by the colony hybridization technique. Hybridization of the clones with a first probe obtained as described in Example 9.1 from the 2.7-kb BamH1-EcoRI fragment originating from pVRC702 and corresponding to pUC18, as well as with a second probe corresponding to the 2.2-kb BamH1 fragment carrying the QamR cassette, enable the cases of single crossing-over (hybridizing with both probes) to be distinguished from the cases of double crossing-over (hybridizing only with the second probe). The 3 clones resulting from a double crossing-over thereby selected were purified by plating out and growth on YVD medium containing 50 mg/ml final of geniticin, and stocks of spores were obtained.

In order to verify the genomic structure of the 3 double recombinants, various Southern blots of the chromosomal DNA of these clones digested with the enzymes EcoRI and BamHI were produced and hybridized with the following three probes: the probe corresponding to the QamR cassette obtained from the 2.2-kb BamHI fragment of pVRC702, the probe corresponding to pUC18 obtained from the 2.7-kb BamHI-EcoRI fragment of pVRC701, and lastly a probe obtained from the 1.3-kb EcoRI-SstI fragment of pVRC701 carrying the snaB gene and the beginning of samS. These hybridizations enabled it to be verified that the three clones tested did indeed result from a double homologous recombination event permitting replacement of the intact chromosomal samS gene by the mutated samS gene interrupted by the QamR cassette.

One of these three mutant clones was designated SP92 samS::QamR.

9.2.3. Production of pristinamycins by the mutant strain samS::QamR

This example illustrates how it is determined that the mutant SP92 samS::QamR having the disrupted samS gene produces 35% less pristinamycin IA and 10-fold more pristinamycin IB than the wild-type SP92 strain.

The mutant SP92 samS::QamR as well as the control SP92 strain were cultured in liquid production medium, and their productions of pristinamycin II and pristinamycin I were assayed as described in Example 9.1.

The results showed that, under the fermentation conditions implemented, the mutant SP92 samS::QamR produces an amount of pristinamycins II equivalent to that of the SP92 control for all three times tested. In contrast, the mutant SP92 samS::QamR produces approximately 35% less pristinamycin IA and 10-fold pristinamycin IB than the control strain at all three times tested. The IB form of pristinamycins thus represents 20% of the collective total type I pristinamycins produced by the mutant SP92 samS::QamR, whereas the control strain synthesizes only of the order of 1% of PIB. The IB form of pristinamycins differs from the IA form in that the fifth residue is p-methylaminophenylalanine, instead of p-dimethylaminophenylalanine for pristinamycin IA. The fact that the mutant SP92 samS::QamR produces more pristinamycin IB and less pristinamycin IA shows that disruption of the samS gene causes a decrease in the degree of methylation of the fifth residue of pristinamycins I, and hence that the samS gene is probably involved in the biosynthesis of the methyl donor, SAM, that is to say that it codes for a SAM synthase.

9.3 Construction of a mutant of S. pristinaespiralis SP92 disrupted in the papA gene This example illustrates how it is possible, by disruption of the papA gene, to construct a strain of S. pristinaespiralis SP92 which no longer produces PI. This mutant is constructed for the purpose of confirming the functionality of the PapA protein. Its construction was carried out using the suicide vector pDH5 described in Example 9.1.

9.3.1. Construction of plasmid pVRC508

This example illustrates how it is possible to construct a plasmid which does not replicate in S. pristinaespiralis SP92 and which may be used to disrupt the papA gene by single homologous recombination.

Plasmid pVRC508 was constructed to produce the SP92 chromosomal mutant disrupted in the papA gene from plasmid pVRC903 described in Example 7.7.

In Example 7.7, the cloning of the 1.4-kb PvuII-EcoRI fragment into M13mp18 from plasmid pVRC903 for the purpose of sequencing the papA gene was described (this fragment corresponds to the 1.4-kb PvuII-XhoI fragment present in the vector pVRC900, FIG. 23).

This construction in M13mp18 was digested with the restriction enzyme HindIII and EcoRI. After separation of the vector M13mp18 and the 1.4-kb fragment containing a portion of the papA gene on 0.8% agarose gel, the latter fragment was isolated and purified by Geneclean (Bio101), La Jolla, Calif.). The localization of the fragment in the papA gene is presented in FIG. 23.

100 ng of vector pDH5 linearized by a double digestion with the restriction enzymes HindIII and EcoRI were ligated with 200 ng of the 1.4-kb fragment as described in Example 3.3. A clone carrying the desired fragment was isolated after transformation of the strain TG1. The recombinant plasmid was designated pVRC508. Plasmid pVRC508 was prepared as described in Example 2.1. Its restriction map is presented in FIG. 28.

9.3.2. Isolation of the SP92 mutant disrupted in the papA gene by homologous recombination This example illustrates how the mutant of *S. pristinaespiralis* SP92 disrupted in the papA gene was constructed. This mutant was isolated by transformation of the strain SP92 with the suicide plasmid pVRC508. The preparation of the protoplasts and their transformation were carried out as described in Example 9.1. After transformation of protoplasts of the strain SP92, the recombinants were selected by overlaying 3 ml of SNA medium containing 2.6 mg/ml of thiostrepton. Of the 5 transformations carried out with 5 times 1 μg of plasmid pVRC508, ten thiostrepton-resistant clones were isolated. This gives a recombinant efficiency of approximately 2 per μg of DNA. These recombinants result from integration by single homologous recombination between the papA gene carried by the chromosome of the strain SP92 and the 1.4-kb fragment of the suicide plasmid pVRC508.

The spores of the recombinants were isolated by plating out and growth on R2YE medium containing 400 μg/ml of thiostrepton, and plated out again on the same medium to obtain isolated colonies.

In order to verify the position of integration of plasmid pVRC508, various Southern blots of the total DNA of several recombinant clones, purified as described above, were produced and hybridized with the vector pDH5 and the 1.4-kb fragment, used successively as probes after labelling by random priming with [$\alpha$-$^{32}$P]dCTP as described in Maniatis et al. (1989). The hybridization results show the disappearance from the genome of the recombinant clones digested with the restriction enzyme EcoRI (site flanking the 1.4-kb fragment) of the 6.8-kb EcoRI band, and the appearance of two additional bands relative to the control SP92 strain, one of 2.4 kb hybridizing with the 1.4-kb fragment, and the other of 10.5 kb hybridizing both with pDH5 and with the 1.4-kb fragment. Digestion of the recombinant clones with the restriction enzyme PstI shows the appearance of two additional bands relative to the control SP92 strain, one of 1.0 kb hybridizing with the 1.4-kb fragment, and the other of 5.1 kb hybridizing both with pDH5 and with the 1.4-kb fragment. One of these mutants was designated SP92::pVRC508.

9.3.3. Production of pristinamycins by the mutant SP92:pVRC508

This example illustrates how it is determined that the mutant of *S. pristinaespiralis* SP92 disrupted in the papA gene by integration of plasmid pVRC508 no longer produces PI.

The mutant SP92::pVRC508, as well as the strain SP92 as control strain, were cultured in liquid production medium. The fermentation and also the assay of pristinamycins I and II were carried out as described in Example 9.1.

The results showed that, under the fermentation conditions implemented, whereas the control SP92 strain produced a standard amount of pristinamycins I, no trace of type I pristinamycins was detected in the fermentation must of the mutant SP92::pVRC508. Moreover, the production of pristinamycins II by the mutant SP92::pVRC508 is equivalent to that of the SP92 control. The mutant SP92::pVRC508 is left producing only pristinamycins II. These results show clearly that the papA gene codes for a protein involved in the biosynthesis of pristinamycins I.

To check the absence of polarity of the disruption carried out in the mutant SP92::pVRC508, the latter was fermented in the presence p-dimethylaminophenylalanine. The mutant SP92::pVRC508 was fermented as described above, with the addition, at 17 hours of fermentation, of 100 mg/l of p-dimethylaminophenylalanine. Under these conditions of complementation, the mutant SP92::pVRC508 produces an amount of pristinamycins I equivalent to that produced by the strain SP92. The production of pristinamycins II is equivalent in both strains. This enables us to conclude that the mutant SP92::pVRC508 does not produce pristinamycins I because it is indeed disrupted in a gene that participates in the biosynthesis of p-dimethylaminophenylalanine (the papA gene). Complementation of this mutant with p-dimethylaminophenylalanine restores its capacity to produce pristinamycins I, proving that the mutation has no polar effect on the synthesis of other pristinamycin I precursors or on the condensation of these precursors.

This example shows that it is possible, starting from cloned genes for biosynthesis, to construct strains that are mutated in the steps of biosynthesis of pristinamycins, and especially pristinamycins I. This example also shows that it is possible, by this approach, to construct strains of *S. pristinaespiralis* specifically producing pristinamycins II and, by extension, strains specifically producing pristinamycins I. This same approach could also be used for other strains of actinomycetes producing streptogramins.

9.4. Construction of mutant of *S. pristinaespiralis* SP92 distrupted in the snbA gene This example illustrates how it is possible, b disruption of the snbA gene, to construct a strain of *S. pristinaespiralis* SP92 which no longer produces pristinamycins I. This mutant was constructed for the purpose of confirming the functionality of the SnbA protein. Its construction was carried out using the suicide vector pDH5 described in Example 9.1.

9.4.1 Construction of plasmid pVRC404

This example illustrates how it is possible to construct a plasmid which no longer replicates in *S. pristinaespiralis* SP92 and which may be used to disrupt the snbA gene by single homologous recombination.

Plasmid pVRC404 was constructed from plasmid pVRC402 described in Example 6.2, to produce the SP92 chromosomal mutant disrupted in the snbA gene. Plasmid pVRC402 was digested with the restriction enzyme XhoI and HindIII. After separation of the fragments thereby generated by electrophoresis on 0.8% agarose gel, a 1170-bp fragment containing an internal portion of the snbA gene was isolated and purified by Geneclean (Bio101, La Jolla, Calif.). The localization of the fragment in the snbA gene is presented in FIG. 15A.

100 ng of vector pDH5 linearized by an SmaI digestion were ligated with 200 ng of the 1173-bp fragment as described in Example 3.3. A clone carrying the desired fragment was isolated after transformation of the strain TG1. The recombinant plasmid was designated pVRC404. Plasmid pVRC404 was prepared as described in Example 2.1. Its restriction map is presented in FIG. 29.

9.4.2. Isolation of the SP92 mutant disrupted in the snbA gene by homologous recombination p This example illustrates how the mutant of S. pristinaespiralis SP92 disrupted in the snbA gene was constructed.

This mutant was isolated by transformation of the strain SP92 with the suicide plasmid pVRC404. The preparation of the protoplasts and their transformation were carried out as described in Example 9.1. After transformation of protoplasts of the strain SP92, the recombinants were selected by overlaying 3 ml of SNA medium containing 2.6 mg/ml of thiostrepton. Of the 5 transformations carried out with 5 times 1 µg of plasmid pVRC404, about thirty thiostrepton-resistant clones were isolated. This gives a recombinant efficiency of approximately 5 per µg DNA. These recombinants result from integration by single homologous recombination between the snbA gene carried by the chromosome of strain SP92 and the 1170-bp fragment of the suicide plasmid pVRC404. The spores of the recombinants were isolated by plating out and growth on R2YE medium+400 mg/ml of thiostrepton, and plated out again on the same medium to obtain isolated colonies. In order to verify the position of integration of plasmid pVRC404, various Southern blots of the total DNA of several recombinant clones, purified as described above, were produced and hybridized with the vector pDH5 and the 1170-kb fragment, used successively as probes after labelling by random priming with [$\alpha$-$^{32}$P]dCTP as described in Maniatis et al. (1989). The hybridization results show the appearance in the genome of the recombinant clones digested with the restriction enzymes XhoI and HindIII of an additional 4.7-kb XhoI-HindIII band relative to the control SP92 strain (vector pDH5+1.17 kb), hybridizing both with pDH5 and with the 1170-bp fragment. Digestion of the recombinant clones with the restriction enzyme PflMI (sites flanking tbhe 1170-bp XhoI-HindIII fragment) shows the disappearance of the 3.1-kb pflMI—PflMI band and the appearance of a band at 8.8 kb hybridizing with both probes. These results indicate that the genomic structure of the clones analysed is indeed that expected after a homologous recombination event between pVRC404 and the chromosomal snbA gene. One of these mutants was designated SP92::pVRC404.

9.4.3. Production of pristinamycins by the mutant SP92::VRC404

This example illustrates how it is determined that the mutant of S. pristinaespiralis SP92 disrupted in the snbA gene by integration of plasmid pVRC404 no longer produces PI.

The mutant SP92::plasmid pVRC404, as well as the strains SP92 as control strain, were cultured in liquid production medium. The fermentation and also the assay of pristinamycins I and II were carried out as described in Example 9.1. The results showed that, under the fermentation conditions implemented, whereas the control SP92 strain produces a standard amount of pristinamycins I, no trace of pristinamycins I was detected in the fermentation must of the mutant SP92::plasmid pVRC404. Moreover, the production of pristinamycins II by the mutant SP92::plasmid pVRC404 is equivalent to that of the SP92 control. The mutant SP92::plasmid pVRC404 is left producing only pristinamycins II. This shows clearly that the snbA gene codes for a protein SnbA involved in the biosynthesis of pristinamycins I, as had been shown during the purification in Example 5.2.

This example shows, as in the preceding example, that it is possible, starting from cloned genes for biosynthesis, to construct strains that are mutated in the steps of biosynthesis of pristinamycins, and especially pristinamycins I. This example also shows that is possible, by this approach, to produce strains of S. pristinaespiralis specifically producing pristinamycins II and, by extension, strains specifically producing pristinamycins I, as described in the following example: 9.5. This same approach could also be used for other strains of actinomycetes producing streptogramins.

9.5. Construction of a mutant of S. pristinaespiralis SP92 disrupted in the snaD gene probably coding for a peptide synthase involved in the biosynthesis of pristinamycins II This example illustrates how it is possible, by disruption of the snaD gene probably coding for a peptide synthase involved in the biosynthesis of pristinamycins II, to construct a strain of S. pristinaespiralis SP92 which no longer produces pristinamycins II.

This mutant was constructed for the purpose of confirming the functionality of the snaD gene, and of obtaining a strain derived from SP92 left synthesizing only pristinamycins I.

Its construction was carried out using plasmid PVRC1000 described in Example 6.8, derived from the suicide vector pDH5, capable of replicating in E. coli only and carrying a resistance marker which is expressed in Streptomyces (see Example 9.1).

9.5.1 Construction of plasmid pVRC1000

This example illustrates how it is possible to construct a plasmid which does not replicate in S. pristinaespiralis SP92 and which may be used to disrupt the snaD gene by single homologous recombination. The construction of plasmid pVRC1000 carrying a portion of the snaD gene is described in Example 6.8.

9.5.2. Isolation of the SP92 mutant disrupted in the snaD gene by homologous recombination This example illustrates how the mutant of S. pristinaespiralis SP92 disrupted in the snaD gene was constructed. This mutant was isolated by transformation of the strain SP92 with the suicide plasmid pVRC1000. The preparation of the protoplasts and their transformation were carried out as described in Example 9.1. Of the 5 transformations carried out with 1 mg of pVRC1000, approximately 1500 thiostrepton-resistant clones were isolated. This give a recombinant efficiency of approximately 375 per µg of DNA. These recombinants result from integration by single homologous recombination between then snaD gene carried by the chromosome of the strain SP92 and the 1.5-kb BamHI-SstI fragment of the suicide plasmid pVRC1000. About twenty recombinants were subcultured on R2YE medium containing 400 µg/ml of thiostrepton, and the spores of these recombinants were isolated by plating out again and growth on R2YE medium containing 400 µg/ml of thiostrepton.

In order to verify the position of integration of plasmid pVRC1000, various Southern blots of the total DNA of 7 recombinant clones, purified as described above, were produced and hybridized with the vector pDH5 and the 1.5-kb BamHI-SatI fragment contained in PVRC1000, used successively as probes after labelling with [$\alpha$-$^{32}$ P]dCTP as described in Example 9.1. The hybridization results show the appearance in the genome of the 7 recombinant clones of a 13.8-kb EcoRI band and an approximately 17-kb BglII band hybridizing with both probes, as well as a 3.7-kb EcoRI band hybridizing with the 1.2-kb BamHI-StsI probe. One of these mutants was designated SP92::pVRC1000 and corresponds well to the integration of plasmid pVRC1000 in the snaD gene by single homologous recombination.

9.5.3. Production of pristinamycins by the mutatnt SP92::pVRC1000

This example illustrates how it is determined that the mutant of *S. pristinaespiralis* SP92 disrupted in the snaD gene by integration of plasmid pVRC1000 no longer produces pristinamycins II, but only pristinamycins I. The mutant SP92::pVRC1000, as well as the control SP92 strain, were cultured in liquid production medium, and their productions of pristinamycins II and I were assayed as described in Example 9.1.

The results showed that, under the fermentation conditions implemented and for all three times tested, the mutant SP92::pVRC1000 produces 0 mg/l of pristinamycins II and an amount of pristinamycins I equivalent to that of the SP92 control. Hence this mutant is indeed blocked in a step of biosynthesis of pristinamycins II, which shows that the snaD gene codes for an enzyme involved in the biosynthesis of pristinamycins II, and very probably for a peptide synthase.

This example shows, as in the preceding example; that it is possible, starting from cloned genes for biosynthesis, to construct strains that are mutated in the steps of biosynthesis of pristinamycins, and especially pristinamycins II. This example also shows that it is possible, by this approach, to produce strains of *S. pristinaespiralis* specifically producing pristinamycins I and, by extension, strains specifically producing pristinamycins II. This same approach could also be used for other strains of actinomycetes producing streptogramins.

EXAMPLE 10

Complementation of a non-producing mutant of the strain SP92

This example shows how it is possible to express genes for the biosynthesis of pristinamycins. This expression was implemented more especially for the snaA and snaB genes carried by cosmid pIBV1 in a mutant strain derived from SP92:SP120. This mutant does not produce pristinamycin IIA. It accumulates the last intermediate of the biosynthesis pathway of pristinamycin II: pristinamycin IIB.

10.1 Cloning of the snaA and snaB genes into the shuttle vector pIJ903

This example illustrates how a subfragment of cosmid pIVB1 containing the snaA and snaB genes was cloned into a vector capable of replicating both in *E. coli* and in Streptomyces.

The vector pIJ903 (Lydiate D. J. et al., 1985) is a low copy number (1 to 3 per cell) shuttle vector capable of replicating both in *E. coli* as a result of its origin of replication of pBR322, and in Streptomyces as a result of its origin of replication of SCP2*. The ampicillin resistance gene permits selection in *E. coli,* and the thiostrepton resistance gene permits selection in Streptomyces.

Cosmid pIBV1 was digested with the restriction enzyme SstI. A large 7.6-kb DNA fragment carrying the snaA and snaB genes was isolated by electrophoresis on 0.8% agarose gel and electroeluted. 500 ng of this fragment were ligated with 100 ng of the vector pUC1813 (Kay and McPherson, 1987) linearized with SstI. After transformation of *E. coli* strain DH5α (supE44 ΔlacU169 (f80lacZΔM15) hsdR17 recA1 endA1 gyrA96 thi-1 relA1), and selection of the transformants on solid LB containing 150 μg/ml of ampicillin and 20 μg/ml of X-gal, a clone carrying the 7.6-kb fragment was isolated. The plasmid was designated pVRC506. A preparation of this recombinant plasmid was carried out as described in Example 2.1.

Cloning into the vector pIJ903 was carried out at the HindIII site. Plasmid pVRC506 was cut with HindIII, and 7.6-kb fragment carrying the snaA and snaB genes was isolated by electrophoresis on 0.8% agarose gel and electroeluted. 500 ng of this fragment were ligated with 500 ng of the vector pIJ903 linearized with HindIII. After transformation of *E. coli* strain DH5α and selection of the transformants on solid LB containing 150 μg/ml of ampicillin, a clone carrying the 7.6-kb fragment was isolated. The plasmid was designated pVRC507. A preparation of this recombinant plasmid was carried out as described in Example 2.1. Its map is presented in FIG. 30.

10.2. Expression of the snaA and snaB genes in the mutant SP120

This example illustrated how it is possible to produce the proteins SnA and SnaB in *S. pristinaespiralis* SP92 by introducing a plasmid carrying the corresponding structural genes into this strain. Expression of the snaA and snaB genes was carried out after transformation of the mutant strain SP120 with 500 ng of plasmid pVRC507. Transformation of the protoplasts of SP120 and selection of the transformants with thiostrepton were carried out as described in Example 9.1.2.

Many transformants were obtained in this way, and 3 of them were chosen for the tests of production in a liquid medium. The strain SP120 carrying plasmid pIJ903 was chosen as control. The fermentations and also the extraction of the biosynthesis products were carried out as described in Example 9.1.3.

The results showed that, under the fermentation conditions implemented, whereas the control (SP120 carrying plasmid pIJ903) produced 100% of P IIB and 0% of P IIA at 24, 28 and 32 hours of fermentation, the 3 clones of the strain SP120 transformed with plasmid pVRC507 produced, for these same times, approximately 85 to 80% of pristinamycin IIB and 15 to 20% of pristinamycin IIA, the sum of which is equivalent in amount to the pristinamycin IIB production of the control strain (SP120 carrying plasmid pIJ903). The clones carrying pVRC507 were indeed partially complemented for the step of biosynthesis of pristinamycins II corresponding to the oxidation of the 2,3 bond of the D-proline of the intermediate pristinamycin IIB. This was confirmed by enzymatic assay of pristinamycin IIA synthase activity, as described in Example 5.5.1.A, for the strains SP120 carrying pVRC507 and SP120 carrying pIJ903. Whereas the control strain SP120 carrying pIJ903 displays no pristinamycin IIA synthase activity, the strain SP120 carrying pVCR507 displays PIIA synthase activity.

This example shows that it is possible to express genes for the biosynthesis of streptogramins. This expression was studied more especially for the genes coding for pristinamycin IIA synthase, but the other genes for the biosynthesis of pristinamycins II and pristinamycins I, as well as those involved in the biosynthesis of the components of the different streptogramins, may be expressed in this way. This expression may be carried out in mutant strains as is the case in Example 10, but also in producing strains in order to increase the levels of streptogramin production. The expression may be modified by cloning the genes into a vector having a different copy number (low or high) or into an integrative vector, by deregulation of these genes, by cloning these genes under a homologous or heterologous promoter (strong or specifically regulated promoter). Expression of the different genes for the biosynthesis of streptogramins may also be carried out in heterologous strains using appropriate expression vectors in order to produce hybrid antibiotics.

EXAMPLE 11

Expression of the papM Gene of S. pristinaespiralis in E. coli

This example illustrates how it is possible to express an S. pristinaespiralis gene in E. coli so as to be able to identify, purify and study the protein encoded by this gene.

11.1. Construction of Plasmid pVRC706

Expression of the papM gene in E. coli is obtained by placing this gene downstream of the promoter and ribosomes binding site of the lacZ gene of E. coli. The 1.7-kb MluI-StuI fragment was isolated from plasmid pVCR409 described in Example 7.8, and then cloned into plasmid pMT123 (Chambers et al. 1988) cut at the BamHI site subsequently filled in using the Klenow enzyme (Maniatis et al. 1989) and at the MluI site, to give plasmid pVRC706 shown in FIG. 31. Cloning at the MluI site enables an in-frame fusion to be obtained between the first 32 amino acids of β-galactosidase encoded by the lacZ gene of plasmid pMTL23 and the last eleven amino acids of the gene located immediately upstream of papM, thereby making it possible to preserve the translational coupling which appears to exist between the papM gene and this upstream gene in the light of the nucleotide sequence given in Example 7.8. Thus, the expression of the hybrid gene between lacZ and the gene upstream of papM and that of the papM gene is under the control of the expression signals of the lacZ gene.

11.2 Expression of E. coli Strain DH5a of the Product of the papM Gene

Plasmids pVRC706 and pMTL23 were introduced by transformation into E. coli strain DH5α, and the expression of their genes was studied under conditions where the promoter of lacZ gene is induced as already described (Maniatis et al. 1989). The E. coli strains carrying plasmid pVRC706 or the control plasmid pMTL23 were cultured in 500 ml of LB rich medium containing 100 mg/ml of ampicillin and 1 mM IPTG, permitting induction of the promoter of the lacZ gene. These cultures are sampled when they have reached an optical density at 600 nm in the region of 1, and the protein extracts are prepared as described below.

11.3 Assay of the Activity of the Product of the pamM Gene Expressed in E. coli The activity corresponding to the protein encoded by the papM gene is assayed on the two extracts prepared from E. coli cultures carrying plasmid pVRC706 or plasmid pMTL23 Example 5.7). It was shown that the extract prepared from the strain E. coli::pVRC706 catalyses the methylation of p-aminophenylalanine to p-dimethylaminophenylalanine with an activity of 235 unit/mg, whereas this activity is absent in the extracts of the control strain E. coli::pMTL23 (see Example 5.7.1.C). These results indicate that it is possible to express the papM gene of S. pristinaespiralis in E. coli, and that the corresponding protein is indeed the enzyme catalysing the methylation of p-aminophenylalanine to p-dimethylaminophenylalanine. This example shows that it is possible to express genes for the biosynthesis of streptogramins in heterologous strains (such as E. coli, but also in other microorganisms) using appropriate expression vectors in order to produce precursors of antibiotics or even natural or hybrid antibiotics.

EXAMPLE 12

Demonstration of the Homology of Genes Involved in the Biosynthesis of Streptogramins in Different Streptomyces This example illustrates how it is possible to demonstrate, by hybridization with total DNAs, the homology existing between different genes involved in the biosynthesis of streptogramins in different strains of Streptomyces producing streptogramins.

12.1. Extraction of Total DNA of Different Streptomyces Producing Streptogramins This example illustrates how the DNA of different strains producing streptogramins was purified. These strains of Streptomyces were chosen from those described in Table 1:

Streptomyces loidensis
Streptomyces olivaceus
Streptomyces ostreogriseus
Streptomyces virginiae A strain not producing streptogramins: Streptomyces hygroscopicus, was chosen as negative control.

The extractions of the different total DNAs were carried out from cultures in YEME medium, as described in Example 1.

12.2. Hybridization of Total DNAs of Strains Producing Streptogramins with DNA Fragments Containing Genes Involved in the Biosynthesis of Pristinamycins and Isolated from S. pristinaespiralis Strain SP92

This example illustrates how it is possible, starting from genes involved in the biosynthesis of pristinamycins and isolated from the strain SP92 as described in the preceding examples, to demonstrate homologous genes by hybridization of the total DNAs of strains producing streptogramins.

The DNA fragments used as a probe were:

The 3.9-kb XhoI-XhoI fragment isolated from pVRC1106 described in Example 6.5, the restriction map of which is presented in FIG. 18. This fragment contains a protein of the gene coding for pristinamycin I synthase II.

The 6-kb BamHI-BamHI fragment isolated from plasmid pXL2045 described in Example 6.3, the map of which is presented in FIG. 16. This fragment contains the structural genes for the two subunits of PIIA synthase.

The total DNAs of the four strains producing streptogramins, the strain S. hygroscopicus and also the strain SP92, were digested with the restriction enzymes BamHI and XhoI. The DNA fragments thereby obtained were separated on 0.7% agarose gel and the DNA was transferred onto a nylon membrane as described by Maniatis et al. (1989). Labelling of the 3.6-kb XhoI-XhoI and 6-kb BamHI-BamHI fragments was carried out by labelling by random priming as described in Example 9.1.2. Hybridization of the membranes was carried out in the presence of formamide at 42° C. as described in Maniatis et al. (1989). Washing of the membranes after hybridization was carried out at 50 and 60° C. in a solution containing SSC (Maniatis et al. 1989) diluted 10-fold and 0.1% SSC.

The following results are demonstrated by these hybridizations:

The strain S. hygroscopicus does not display and hybridization with the two probes used.

The total DNAs (digested with XhoI and BamHI) of the strains S. ostreogirseus, S. olivaceus, S. loidensis and S.

*virginiae* all display hybridization signals of intensity comparable to those observed on the total DNA of the strain SP92 with both probes used.

The total DNA (digested with XhoI and BamHI) of the strain *S. virginiae* displays signals with both probes used, but their intensity is weaker than that observed in SP92.

This example shows that different strains of Streptomyces producing streptogramins contain genes that hybridize with genes isolated in *S. pristinaespiralis* SP92 and which are involved in the biosynthesis of streptogramins, as presented in the preceding examples. These hybridizations thus demonstrate the homology existing between the genes involved in the biosynthesis of streptogramins of the strains SP92 and those involved in the biosynthesis of streptogramins of other strains producing streptogramins.

This example hence shows that it is possible, starting from genes isolated from SP92 and involved in the biosynthesis of streptogramins, to isolate by hybridization and cloning the homologous genes present in other strains producing streptogramins.

EXAMPLE 13

Study of the Physical Binding of the Different *S. pristinaespiralis* SP 92 Genes Involved in the Biosynthesis of Pristinamycins I and Pristinamycins II This example illustrates how it is possible to study the physical binding of the *S. pristinaespiralis* SP 92 genes involved in the biosynthesis of pristinamycins I and II. This study was carried out for the purpose of showing that all these genes are grouped together on the chromosome in a cluster, and that it is hence possible by chromosome walking from the genes already identified to isolate other genes involved in the biosynthesis of pristinamycins I and II. Such an approach mahy be envisaged for the genes involved in the biosynthesis of other streptogramins.

13.1 Restriction Enzymes Used for Pulsed-Field Electrophoresis

The *S. pristinaespiralis* SP92 genome is composed of 70% to 75% of nucleotides containing the basis G and C. To cut its genome into a small number of large fragments, we used which recognize a sequence rich in AT, such as AseI (AT/TAAT) and SspI (AAT/ATT) but also HindIII (A/AGCTT), EcoRI (G/AATTC), NdeI (CA/TATG) and ClaI (AT/CGAT).

13.2. *S. pristinaespiralis* Strains Used for Pulsed-Field Electrophoresis

We used the chromosomal DNA of several strains to study by pulsed-field electrophoresis the physical binding of the genes involved in the biosynthesis of pristinamycins I and pristinamycins II. We prepared inserts as described ibn Example 4.1 of the chromosomal DNA of *S. pristinaespiralis* strain SP92, and also of the chromosomal DNA of the strains derived from SP92 whose construction is described in Examples 9.1 and 9.4. These are the strain SP92::VRC505 in which the snaA gene has been disrupted by integration of plasmid pVRC505 (Example 9.1), and the strain SP92::pVRC404 in which the snbA gene has been disrupted by integration of plasmid pVRC404 (Example 9.4). The latter two strains were included in this study since they enabled the snaA and snbB genes to be positioned accurately on the chromosome map by exploiting the presence of sites which rarely cut chromosomal DNA, AseI, SspI, HindIII, EcoRI, NdeI and ClaI, in plasmids pVRC505 and pVRC404.

13.3. DNA Probes Used for Hybridization of the Fragments Isolated by Pulsed-Field Electrophoresis We used different DNA fragments to obtain radioactively labelled probes as is described in Example 9.1, which we hydridized with the fragments separated by pulsed-field electrophoresis after enzymatic cleavage of the chromosomal DNA inserts of the three strains presented above. The probes are as follows: the 3,2-kb EcoRI-BamHI fragment isolated from plasmid pVRC701 carrying the snaB and samS genes (see Example 9.2), the 1.5-kb BamH1-Sst1 fragment isolated from plasmid pVRC1000 carrying a portion of the snaD gene (see Example 6.8), the 1.1-kb XhoI-HindIII fragment isolated from plasmid pVRC402 carrying the snbA gene (see Example 6.1), the 2.4-kb Pst1-Pst1 fragment isolated from plasmid pVRC900 carrying papA gene (see Example 6.7) and the 1.5-kb XhoI-PstI fragment isolated from plasmid pVRC409 carrying the snaC gene (see Example 6.9).

13.4. Localization on the Chromosome of the Different Genes Involved in the Biosynthesis of Pristinamycins I and II and Study of their Physical Binding Hybridization of the chromosomal DNAs of *S. pristinaespiralis* strains SP92, SP92::pVRC404 and SP92::pVRC505, cut by single digestions and double digestions using the six enzymes mentioned above, with the different probes described above lead to the general map shown in FIG. 32: the position of major sites has been indicated, together with the position and direction of transcription of the genes involved in the biosynthesis of pristinamycins PI and PII. Thus, it is possible to calculate the distance separating the 3 chromosomal regions containing the genes identified, namely that of the snbA, snbR, papA and papM genes (cosmid PIBV2, Example 5.2), that of the snaA, snaB, samS, snaD, snbC, snbD and snbE genes (cosmids pIBV1 and 3, Example 5.1) and lastly that of the snaC gene (cosmid pIVB4, Example 5.6). For example, the distance between the snaA and snbA genes has been evaluated at approximately 160–170 kb. This shows that the genes already identified are all contained in a region covering only 200 kb of the chromosome of the *S. pristinaespiralis* strain, equivalent to less than 3% of the total length of the genome, which we have been able to estimate at 7500 kb by the pulsed-field electrophoresis technique.

These results show that the genes involved in the biosynthesis of pristinamycins I and II are grouped together on the chromosome in a cluster, and that it is hence possible by chromosome walking from the genes already identified to isolate other genes involved in the biosynthesis of pristinamycins I and pristinamycins II. More generally, it is possible, by chromosome walking from any gene involved in the biosynthesis of streptogramins, to identify the other genes involved in this biosynthesis.

TABLE 1

| MICROORGANISMS | ANTIBIOTICS |
|---|---|
| FUNGI | |
| Micromonosporea sp. | Vernamycins |

TABLE 1-continued

| MICROORGANISMS | ANTIBIOTICS |
| --- | --- |
| STREPTOMYCES | |
| S. albiorectus | Virginiamycins |
| S. conganesis (ATCC13528) | F1370 A, B |
| S. diastaticus | Plauracins, streptogramins |
| S. graminofasciens | Streptogramins |
| S. griseus (NRRL2426) | Viridogrisein (Etamycin) |
| S. griseaviridus | Griseoviridin |
| S. griseoviridus (FERMP3562) | Neoviridogriseins |
| S. lavendulae | Etamycins |
| S. loidensis (ATCC11415) | Vernamycins |
| S. mitakaensis (ATCC15297) | Mikamycins |
| S. olivaceus (ATCC12019) | Synergistins (PA114 A, B) |
| S. ostreogriseus (ATCC27455) | Ostreogrycins |
| S. pristinaespiralis (ATCC25486) | Pristinamycins |
| S. virginiae (ATCC13161) | Virgiuniamycins (Staphylomycins) |
| ACTINOMYCETES | |
| A. auranticolor (ATCC31011) | Plauracins |
| A. azureus (ATCC31157) | Plauracins |
| A. daghestanicus | Etamycin |
| A. philippinensis | A-2315 A, B, C |
| Actinioplanes sp. (ATCC33002) | A15104 |
| Actinoplanes sp. | A17002 A, B, C, F |
| Actinomadura flava | Madumycins |

Abbreviations Used

DNA: deoxyribonucleic acid
AMP: adenosine 5'-monophosphate
ATP: adenosine 5'-triphosphate
ETB: ethidium bromide
bis-tris: (bis[2-hydroxyethyl]iminotris[hydroxymethyl] methane)
bis-tris propane: (1,3-bis[tris(hydroxymethyl)methylamino] propane)
BSA: bovine serum albumin
HPLC: high performance liquid chromatography
OD: optical density
DTE: dithioerythritol
DTT: dithiothreitol
E64: trans-epoxysuccinyl-L-leucylamido-(4-guanidino) butane
EDTA: ethylenediaminetetraacetic acid
EGTA: ethylene glycol bis($\beta$-aminoethyl)tetraacetic acid
FMN: flavin mononucleotide
$FMNH_2$: reduced flavin mononucleotide
Hepes: (N-[2-hydroxyethyl]piperazin-N'-[2-ethanesulphonic acid])
IPTG: isopropyl $\beta$-D-thiogalactopyranoside
kDa: kilodalton
kb: kilobase
LB: Luria broth (rich growth medium for E. coli)
NAD: nicotinamide dinucleotide
NADH: reduced nicotinamide dinucleotide
PAGE: polyacrylamide gel electrophoresis
bp: base pair
PMSF: phenylmethylsulphonyl fluoride
PPi: pyrophosphate
rpm: revolutions per min
A.S.: ammonium sulphate
SAM: S-adenosylmethionine
SDS: sodium dodecyl sulphate
STI: soybean trypsin inhibitor
TE: buffer comprising 10 mM Tris-HCl, 1 mM EDTA, pH 7.5
Tris: 2-amino-2-hydroxymethyl-1,3-propanediol
UV: ultraviolet rays
Xgal: 5-bromo-4-chloro-3-indol b-D-galactoside
YEME: yeast extract-malt extract medium (rich growth medium for Streptomyces)
PEG: Polyethylene glycol
LMP: Low melting point
MW: Molecular weight

BIBLIOGRAPHY

Anzai H., Murakami T., Imai A., Satoh A. Nagaoka K. and Thompson C. J. (1987) *J. Bacteriol.,* 169: 3482–3488.

Bancroft I. and WolK C. P. (1989) *J. Bacteriol.,* 171: 5949–5954.

Bibb M. J., Findlay P. R. and Johnson M. W. (1984) *Gene,* 30: 157–166.

Birnboim H. C. and Doly J. (1979) *Nucleic Acids Res.,* 7: 1513–1523.

Blattner F. R., Williams B. G., Blechl A. E., Denniston-Thompson D., Faber H. E., Furlong L. A., Grunwald D. J., Keifer D. O., Moore D. D., Schumm J. W., Sheldon E. L. and Smithies O. (1977) *Science,* 196: 161–169.

Bolivar F. Rodriguez R. L., Greene P. J., Betlach M. C., Heynecker H. L., Boyer H. W., Crosa J. H. and Falkow S. (1977) *Gene,* 2: 95–113.

Boyer H. W. and Roulland-Dussoix D. (1969) *J. Mol. Biol.,* 41: 459.

Chater K. F. (1990) *Bio/Technology,* 8: 115–121.

Cocito C. G. (1979) *Microbiol. Rev.,* 43: 145–198.

Cocito C. G. (1983) *In Antibiotics,* 6: (Ed. F. E. Hahn), 296–332.

Dessen P. C., Fondrat C., Valencien C. et Mugnier C. (1990) *Comp. Appl. in Biosciences,* 6: 355–356.

Di Giambattista M., Chinali G. and Cocito C. G. (1989) *J. Antim. Chemother.,* 24: 485–507.

Fernandez-Moreno M. A., Caballero J. L., Hopwood D. A. and Malpartida F. (1991) *Cell,* 66: 769–780.

Gibson T. J. (1984) *Ph.D. thesis,* Cambridge University, England.

Hallam S. E., Malpartida F. and Hopwood D. A. (1988) *Gene,* 74: 305–320.

Hames H. D. and Higgins S. J. (1985) *IRL Press Ltd.,* Oxford, U.K.,

Hanahan D. (1983) *J. Mol. Biol.,* 166: 557

Hillemann D., Pülher A. and Wohlleben W. (1991) *Nucl. Acids Res.,* 19: 727–731.

Hohn B. and Collins J. F. (1980) *Gene,* 11: 291–298.

Hook J. D. and Vining L. C. (1973) *J.C.S. Chem. Comm.,* 185–186.

Hopwood D. A., Bibb M. J., Chater K. F., Keiser T., Bruton C. J., Kieser H. M., Lydiate D. J., Smith C. P., Ward J. M. and Scrempf H. (1985) *A laboratory manual.,* The John Innes Foundation, Norwich, England.

Hopwood D. A., Bibb M. J., Chater K. F., Janssen G. R., Malpartida F. and Smith C. (1986b) *In Regulation of gene expression—25 years on* (ed. I; A. Booth C; F. Higgins), 251–276.

Hopwood D. A., Malpartida F., Keiser H. M., Ikeda H., Duncan J., Fujii I., Rudd A. M., Floss H. G. and Omura S. (1985a) *Nature,* 314: 642–644.

Hopwood D. A., Malpartida F., Keiser H. M., Ikeda H. and Omura S. (1985b) *In Microbiology* (ed S. Silver). American Society for Microbiology, Washington D.C., 409–413.

Hopwood D. A., Malpartida F. and Chater K. F. (1986a) In Regulation of secondary metabolite formation. (eds. H. Kleinkauf, H. von Hohren, H. Dornauer G. Nesemann), 22–33.

Hoshino T., Ikeda T., Tomizuka N. and Furukawa K. (1985) *Gene,* 37: 131–138.

Hutchinson C. R., Borell C. W., Otten S. L., Stutzman-Engwall K. J. and Wang Y. (1989) *J. Med. Chem.,* 32: 929–937.

Ish-Horowitz D. and Burk J. F. (1981) *Nucleic Acids Res.,* 9: 2989–298.

Kanehisa M. I. (1984) *Nucleic Acids Res.,* 12: 203–215.

Kay R. and McPherson J. (1987) *Nucleic Acids Res.,* 15 (6): 2778.

Khan S. A. and Novick R. (1983) *Plasmid,* 10: 251–259.

Kingston D. G. I., Kolpak M. X., Lefevre W. and Borup-Grochtmann I. B. (1983) *J. Am. Chem. Soc.,* 105: 5106–5110.

Kyte J. and Doolittle R. (1982) *J. Biol. Mol.,* 157: 105–135.

Low B. (1968) *Proc. Nalt. Acad. Sci.,* 60: 160.

Lydiate D. J., Malpartida F. and Hopwood D. A. (1985) *Gene,* 35: 223–235.

Maniatis T., Fritsh E. F. and Sambrook J (1989) Molecular cloning: a labortory manual. Cold Spring Harbor, N.Y., Meinkoth J. and Wahl G. (1984) *Anal. Biochem.,* 138: 267–284.

Messing J., Crea R. and Seeburg P. H. (1981) *Nucleic Acids Res.,* 9: 309.

Neal R. J. and Chater K. F. (1987) *Gene,* 58: 229–241.

Ohnuki T., Imanaka T. and Aiba S. (1985) *J. Bacteriol.,* 164: 85–94.

Sawadogo M. and Van Dyke M. W. (1991) *Nucl. Acids Res.,* 19: 674.

Staad J. F., Elkins M. F. and Earhart C. F. (1989) *FEMS Microbial. Lett.,* 59: 15.

Staden R. and McLachlan A. D. (1982) *Nucleic Acids Res.,* 10: 141–156.

Videau D. (1982) *Path. Biol.,* 30: 529–534.

Chambers S. P., Prior S. E., Barstow D. A. and Minton N. P. (1988) Gene, 68:139

Gutierrez S., Diez B., Montenegro E. and Martin J. F. (1991) Journal of bacteriology, 173:2354–2365.

Hori K., Yamamoto Y., Minetoki T., Kurotsu T., Kanda M., Miura S., Okamura K., Kuruyama J. and Saito R. (1989) J. Biochem., 106: 639–645.

Horikawa S., Ishikawa M., Ozaka H. and Tsukada K. (1989) Eur. J. Biochem., 184: 497–501.

Kaplan J. Merkel W. and Nichols B. (1985) J. Mol. Biol., 183: 327–340.

Markham G. D., DeParasis J. and Gatmaitan J. (1984) *J. Biol Chem.,* 259: 14505–14507.

Sharka B., Westlake D. W. S. and Vining L. C. (1970) Chem. Zvesti, 24:66–72.

Thomas D., Rothstein R. Rosenberg N. and Surdin-Kerjan Y. (1988) Mol. Cell. Biol., 8:5132–5139.

Turgay K. et al (1992) Molecular Microbiology, 6(4):546.

Weckermann R., FŸrbab R. and Marahiel M. A. (1988) Nucl. Acids Res., 16:11841

Yanisch-Perron C., Vieira J. and Messing J. (1985) Gene, 33: 103–119.

Zimmer W., Aparicio C. and Elmerich C. (1991) Mol. Gen. Genet.,229:41–51.

Reed et al. J. Nat. Prod 49 (1986) 626

Molinero et al., J. Nat. Peod 52 (1989) 99

Reed et al. J. Org. Chem. 54 (1989) 1161

Watanabe et al., Mol. Cell. Biochem. 44(1982) 181

Jablonski et al., Biochemistry 16 (1977) 2832

Duane et al., Mol. Cell. Biochem. 6 (1975) 53.

---

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 5392 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iii) ANTI-SENSE: NO (vi) ORIGINAL SOURCE:
      (A) ORGANISM: S.pristinaespiralis (xi) SEQUENCE DESCRIPTION: SEQ ID NO: 1:

```
GGATCCTGGC GTCCGCCGTC AAGAACTGAA CCGAGGAGAC ACCCACCATG ACCGCACCCC    60
```

| | |
|---|---|
| GCCGGCGCAT CACCCTCGCC GGCATCATCG ACGGCCCCGG CGGCCATGTG GCCGCCTGGC | 120 |
| GCCACCCGGC GACCAAGGCG GACGCCCAGC TCGACTTCGA ATTCCACCGC GACAACGCCC | 180 |
| GCACCCTCGA ACGCGGCCTG TTCGACGCCG TGTTCATCGC GGACATCGTC GCCGTGTGGG | 240 |
| GCACCCGCCT GGACTCCCTG TGCCGCACCT CGCGCACCGA GCACTTCGAA CCGCTCACCC | 300 |
| TGCTCGCCGC CTACGCCGCG GTCACCGAGC ACATCGGCCT GTGCGCCACC GCCACCACCA | 360 |
| CGTACAACGA ACCGGCGCAC ATCGCCGCCC GCTTCGCCTC CCTCGACCAC CTCAGCGGCG | 420 |
| GCCGGGCCGG CTGGAACGTC GTCACCTCCG CCGCACCGTG GGAGTCCGCC AACTTCGGCT | 480 |
| TCCCCGAGCA CCTGGAGCAC GGCAAACGCT ACGAGCGGGC CGAGGAGTTC ATCGACGTCG | 540 |
| TCAAAAAACT GTGGGACAGC GACGGCCGCC CCGTCGACCA CCGCGGCACC CACTTCGAGG | 600 |
| CCCCCGGCCC GCTCGGGATC GCCCGCCCCC CGCAGGGCCG CCCCGTCATC ATCCAGGCCG | 660 |
| GCTCCTCGCC GGTGGGACGC GAGTTCGCCG CCCGGCACGC CGAGGTCATC TTCACCCGGC | 720 |
| ACAACCGGCT CTCCGACGCC CAGGACTTCT ACGGCGACCT CAAGGCACGC GTCGCCCGGC | 780 |
| ACGGCCGCGA CCCCGAGAAG GTCCTCGTGT GGCCGACCCT CGCGCCGATC GTCGCCGCCA | 840 |
| CCGACACCGA GGCGAAGCAG CGCCTGCAGG AACTGCAGGA CCTCACCCAC GACCATGTCG | 900 |
| CCCTGCGCAC CCTTCAGGAC CACCTCGGCG ACGTCGACCT GAGCGCGTAC CCGATCGACG | 960 |
| GGCCCGTCCC CGACATCCCG TACACCAACC AGTCCCAGTC GACGACCGAG CGGCTGATCG | 1020 |
| GCCTGGCCAG GCGCGAGAAC CTCAGCATCC GCGAGCTGGC CCTGCGGCTG ATGGGCGACA | 1080 |
| TCGTCGTCGG CACACCGGAG CAGCTCGCCG ACCACATGGA GAGCTGGTTC ACCGGCCGCG | 1140 |
| GCGCCGACGG CTTCAACATC GACTTCCCGT ACCTGCCGGG CTCCGCCGAC GACTTCGTCG | 1200 |
| ACCACGTGGT GCCCGAACTG CAGCGCCGCG GCCTGTACCG CTCGGGCTAC GAGGGCACCA | 1260 |
| CCCTGCGGGC CAACCTCGGC ATCGACGCCC CCGGAAGGC AGGTGCAGCG GCTTGACTTC | 1320 |
| CGTCCTAAAG GCGGGGGATT CCAGCGGTCG CCCGCTGGGG TTCCTGCTTC ACCGACGACC | 1380 |
| GCCCCGTCCG GGAGGACTCC CGTTGAGGTC TTATACCGTC TCCACAGGCC GACGCCGCCA | 1440 |
| GCCCGGCGGC CAGGATGTTG CGTGCCGCAT TCACGTCGCG GTCATGCACA GCGCCGCAGT | 1500 |
| CGCACGTCCA CTCCCGGACG TTCAGCGGCA GCTTCCCGCG GACCGTGCCG CAGGTTCCGC | 1560 |
| ACAGCTTGGA GCTGGGGAAC CAGCGGTCGA TCACGACGAG TTCGCGCCCA TACCAGGCGC | 1620 |
| ACTTGTACTC CAGCATGGAG CGCAGTTCCG TCCAGGCCGC GTCGGAGATG GCGCGCGCGA | 1680 |
| GCTTGCCGTT CTTCAGCAGG TTGCGGACGG TGAGGTCCTC GATCACGACC GTTTGGTTCT | 1740 |
| CACGGACGAG TCGAGTCGAC AGCTTGTGGA GGAAGTCGCA GCGCCGGTCG GTGATCCGGG | 1800 |
| CGTGGACGCG GGCGACCTTG CGGCGGGCTT TCTTCCGGTT CGCCGACCCC TTCGCCTTGC | 1860 |
| GCGACACGTC CCGCTGAGCC TTCGCGAGGC GGGCGCGGTC ACGGCGCTCG TGCTTGGGGT | 1920 |
| TGGTGATCTT CTCCCCGGTG ACAGGGTCA CCAGGGAGGT GATCCCGGCG TCATGCCGA | 1980 |
| CGGCCGCCGT GGTGGCGGGC GCGGGGGTGA TGGTGTCCTC GCACAGCAGG GACACGAACC | 2040 |
| AGCGGCCCGC ACGGTCGCGG GACACGGTCA CCGTCGTCGG CTCCGCCCCT TCGGGAAGGG | 2100 |
| GACGGGACCA GCGGATGTCC AGGGGCTCCG CGGTCTTCGC CAGCGTGAGC TGTCCGTTAC | 2160 |
| GCCACGTGAA GGCGCTGCGG GTGTACTCGG CCGACGCCCT GGACTTTTTC CGCGACTTGT | 2220 |
| ACCGCGGGTA CTTCGACCGC TTGGCGAAGA AGTTGGCGAA CGCCGTCTGC AAGTGCCGCA | 2280 |
| GCGCCTGCTG GAGCGGGACG GAGGACACCT CCGAGAGGAA GGCGAGTTCT TCGGTCTTCT | 2340 |
| TCCACTCCGT CAGCGCGGCG GACGACTGCA CGTAGGAGAC CCGGCGCTGC TCGCCGTACC | 2400 |
| AGGCTCGCGT GCGCCCCTCA AGCGCCTTGT TGTACACGAG GCGGACACAG CCGAACGTGC | 2460 |

-continued

```
GGGACAGCTC AGCCGCCTGC TCGTCCGTGG GATAAAAGCG GTACTTGAAA GCCCGCTTGA    2520

CCTGCTGCAT CACGCCTCAC ACGCTATCAG TTCCCGTGTG AGCGGCGGGT GTCTGCCGGT    2580

GGTTGCAGAC GCCGAACCGC CCTGGCGGCG ATTCGCCCAT CCCTGCCCTG CTCCGCAAGA    2640

GCTTCGTCTC CTCCCCGGTC TGAAGGCCGG GGTATCCACG AAGGAATTCT GATGACCGCG    2700

CCCATCCTCG TCGCCACCCT CGACACCCGC GGCCCCGCCG CCACCCTCGG CACGATCACC    2760

CGCGCCGTGC GGGCCGCGGA GGCCGCCGGA TTCGACGCCG TCCTGATCGA CGACCGGGCC    2820

GCCGCCGGCG TCCAGGGCCG GTTCGAGACG ACGACGCTGA CCGCCGCGCT GGCCGCCGTC    2880

ACCGAGCACA TCGGCCTGAT CACCGCCCCG CTCCCGGCCG ACCAGGCCCC CTACCACGTG    2940

TCCCGGATCA CCGCCTCGCT CGACCACCTC GCCCACGGCC GCACCGGCTG GCTCGCGAGC    3000

ACGGACACCA CCGACCCCGA GGGCCGCACC GGCGAACTCA TCGACGTCGT CCGCGGCCTG    3060

TGGGACAGCT TCGACGACGA CGCCTTCGTC CACGACCGCG CCGACGGCCT GTACTGGCGG    3120

CTGCCCGCCG TCCACCAACT CGACCACCAG GGCAGGCACT TCGACGTGGC CGGCCCCCTC    3180

AACGTCGCCC GCCCGCCGCA GGGCCACCCC GTCGTCGCCG TCACCGGCCC CGCCCTCGCC    3240

GCGGCCGCCG ACCTCGTCCT GCTCGACGAG GCGGCCGACG CCGCCTCGGT GAAGCAGCAG    3300

GCACCGCACG CCAAGATCCT CCTGCCGCTG CCCGGCCCGG CCGCCGAACT GCCCGCCGAC    3360

AGCCCCGCGG ACGGCTTCAC GGTGGCGCTC ACCGGCTCCG ACGACCCGGT CCTGGCCGCG    3420

CTCGCCGCCC GGCCCGGCCG CCCGGACCGC ACCGCGGCCA CCACCCTGCG CGAACGCCTG    3480

GGCCTGGCCC GCCCCGAGAG CCGCCACGCC CTCACCACCG CCTGACGACC CGTCCGCCCG    3540

CTGCTTCCTG GAGAGTCATG TCCCGTCGCC TGTTCACCTC GGAGTCCGTG ACCGAGGGCC    3600

ACCCCGACAA GATCGCCGAC CAGATCAGTG ACACCGTCCT CGACGCCCTG CTGCGCGAGG    3660

ACCCCGCCTC ACGCGTCGCG GTCGAGACCC TGATCACCAC CGGCCAGGTC CACATCGCCG    3720

GCGAGGTCAC CACCAAGGCG TACGCGCCCA TCGCCCAACT GGTCCGCGAC ACGATCCTGG    3780

CCATCGGCTA CGACTCGTCC GCCAAGGGCT TCGACGGCGC CTCCTGCGGC GTCTCCGTCT    3840

CCATCGGCGC GCAGTCCCCG GACATCGCCC AGGGCGTCGA CAGCGCCTAC GAGACCCGCG    3900

TCGAGGGCGA GGACGACGAG CTCGACCAGC AGGGCGCCGG CGACCAGGGC CTGATGTTCG    3960

GCTACGCCAC CGACGAGACC CCCTCGCTGA TGCCGCTGCC CATCGAGCTC GCCCACCGCC    4020

TCTCGCGCCG GCTCACCGAG GTCCGCAAGG ACGGCACCGT CCCCTACCTG CGCCCCGACG    4080

GCAAGACCCA GGTCACCATC GAGTACCAGG GCAGCCGCCC GGTGCGCCTG GACACCGTCG    4140

TCGTCTCCTC CCAGCACGCC GCCGACATCG ACCTCGGCTC CCTGCTCACC CCCGACATCC    4200

GCGAGCACGT CGTCGAGCAC GTCCTCGCCG CACTCGCCGA GGACGGCATC AAGCTCGAGA    4260

CGGACAACTA CCGCCTGCTG GTCAACCCGA CCGGCCGTTT CGAGATCGGC GGCCCGATGG    4320

GCGACGCCGG CCTGACCGGC CGCAAGATCA TCATCGACAC GTACGCGGC ATGGCCCGCC    4380

ACGGCGGTGG CGCGTTCTCC GGCAAGGACC CGTCCAAGGT CGACCGTTCC GCCGCGTACG    4440

CGATGCGCTG GGTCGCCAAG AACGTCGTCG CCGCGGGCCT CGCCTCCCGC TGCGAGGTCC    4500

AGGTCGCCTA CGCCATCGGC AAGGCCGAGC CGGTCGGCCT GTTCGTCGAG ACGTTCGGCA    4560

CCGGCACCGT CGCCCAGGAG CGCATCGAGA AGGCCATCAC CGAGGTCTTC GACCTGCGCC    4620

CCGCGGCCAT CATCCGCGAC CTCGACCTGC TGCGGCCCAT CTACGCCGCC ACCGCCGCCT    4680

ACGGCCACTT CGGCCGCGAA CTGCCCGACT TCACCTGGGA GCGGACCGAC CGCGCCCACC    4740

GGCTCAAGGC CGCGGCCGGT CTCTGAGCCG GCCGGACCTG TGAGGAGACC TGACGTGCGC    4800
```

-continued

```
ATCGCTGTCA CCGGTTCCAT CGCCACCGAC CATCTGATGG TCTTCCCCGG CCGGTTCGCG    4860

GATCAGCTGA TCCCCGACCA GCTCGCTCAT GTCTCGCTCT CCTTCCTGGT CGACGCACTC    4920

GAGGTGCGCC GGGGCGGAGT GGCGGACAAC GTCGCCTTCG GCCTCGGCGG CCTCGGCCTC    4980

ACCCCCCAGC TGGTCGGCGC CGTGGGCAGC GACTTCGCCG AGTACGAGGT CTGGCTCAAG    5040

GAACACGGCG TCGACACCGG CCCCGTCCTG GTCTCCACCG AGCGGCAGAC CGCCCGGTTC    5100

ATGTGCATCA CCGACCAGGA CTCCAACCAG ATCGCCTCCT TCTACGCGGG CGCCATGCAA    5160

GAGGCCCGCG ACATCGACCT GTGGCACCTG ACCACCGGCA GCGTCCGCCC CGACCTCGTC    5220

CTGGTCTGCC CGAACGACCC GGCGGCGATG CTGCGCCACA CGGGGAGTGC CGCGAAACTG    5280

GGCCTGCCGT TCGCCGCCGA CCCCTCCCAG CAGCTCGCCC GCCTGGAGGG AGGGAGGTAC    5340

GCGAACTCGG TCGACGGGGC CCGTTGGTTT TTCACCAACG AAGTACGAGG CC            5392
```

(2) INFORMATION FOR SEQ ID NO: 2:

(i) SEQUENCE CHARACTERISTICS:
        (A) LENGTH: 1268 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 1..1268

(xi) SEQUENCE DESCRIPTION: SEQ ID NO: 2:

```
ATG ACC GCA CCC CGC CGG CGC ATC ACC CTC GCC GGC ATC ATC GAC GGC        48
Met Thr Ala Pro Arg Arg Arg Ile Thr Leu Ala Gly Ile Ile Asp Gly
  1               5                  10                  15

CCC GGC GGC CAT GTG GCC GCC TGG CGC CAC CCG GCG ACC AAG GCG GAC        96
Pro Gly Gly His Val Ala Ala Trp Arg His Pro Ala Thr Lys Ala Asp
             20                  25                  30

GCC CAG CTC GAC TTC GAA TTC CAC CGC GAC AAC GCC CGC ACC CTC GAA       144
Ala Gln Leu Asp Phe Glu Phe His Arg Asp Asn Ala Arg Thr Leu Glu
         35                  40                  45

CGC GGC CTG TTC GAC GCC GTG TTC ATC GCG GAC ATC GTC GCC GTG TGG       192
Arg Gly Leu Phe Asp Ala Val Phe Ile Ala Asp Ile Val Ala Val Trp
     50                  55                  60

GGC ACC CGC CTG GAC TCC CTG TGC CGC ACC TCG CGC ACC GAG CAC TTC       240
Gly Thr Arg Leu Asp Ser Leu Cys Arg Thr Ser Arg Thr Glu His Phe
 65                  70                  75                  80

GAA CCG CTC ACC CTG CTC GCC GCC TAC GCC GCG GTC ACC GAG CAC ATC       288
Glu Pro Leu Thr Leu Leu Ala Ala Tyr Ala Ala Val Thr Glu His Ile
                 85                  90                  95

GGC CTG TGC GCC ACC GCC ACC ACC ACG TAC AAC GAA CCG GCG CAC ATC       336
Gly Leu Cys Ala Thr Ala Thr Thr Thr Tyr Asn Glu Pro Ala His Ile
            100                 105                 110

GCC GCC CGC TTC GCC TCC CTC GAC CAC CTC AGC GGC GGC CGG GCC GGC       384
Ala Ala Arg Phe Ala Ser Leu Asp His Leu Ser Gly Gly Arg Ala Gly
        115                 120                 125

TGG AAC GTC GTC ACC TCC GCC GCA CCG TGG GAG TCC GCC AAC TTC GGC       432
Trp Asn Val Val Thr Ser Ala Ala Pro Trp Glu Ser Ala Asn Phe Gly
    130                 135                 140
```

```
TTC CCC GAG CAC CTG GAG CAC GGC AAA CGC TAC GAG CGG GCC GAG GAG        480
Phe Pro Glu His Leu Glu His Gly Lys Arg Tyr Glu Arg Ala Glu Glu
145                 150                 155                 160

TTC ATC GAC GTC GTC AAA AAA CTG TGG GAC AGC GAC GGC CGC CCC GTC        528
Phe Ile Asp Val Val Lys Lys Leu Trp Asp Ser Asp Gly Arg Pro Val
                165                 170                 175

GAC CAC CGC GGC ACC CAC TTC GAG GCC CCC GGC CCG CTC GGG ATC GCC        576
Asp His Arg Gly Thr His Phe Glu Ala Pro Gly Pro Leu Gly Ile Ala
            180                 185                 190

CGC CCC CCG CAG GGC CGC CCC GTC ATC ATC CAG GCC GGC TCC TCG CCG        624
Arg Pro Pro Gln Gly Arg Pro Val Ile Ile Gln Ala Gly Ser Ser Pro
        195                 200                 205

GTG GGA CGC GAG TTC GCC GCC CGG CAC GCC GAG GTC ATC TTC ACC CGG        672
Val Gly Arg Glu Phe Ala Ala Arg His Ala Glu Val Ile Phe Thr Arg
    210                 215                 220

CAC AAC CGG CTC TCC GAC GCC CAG GAC TTC TAC GGC GAC CTC AAG GCA        720
His Asn Arg Leu Ser Asp Ala Gln Asp Phe Tyr Gly Asp Leu Lys Ala
225                 230                 235                 240

CGC GTC GCC CGG CAC GGC CGC GAC CCC GAG AAG GTC CTC GTG TGG CCG        768
Arg Val Ala Arg His Gly Arg Asp Pro Glu Lys Val Leu Val Trp Pro
                245                 250                 255

ACC CTC GCG CCG ATC GTC GCC GCC ACC GAC ACC GAG GCG AAG CAG CGC        816
Thr Leu Ala Pro Ile Val Ala Ala Thr Asp Thr Glu Ala Lys Gln Arg
            260                 265                 270

CTG CAG GAA CTG CAG GAC CTC ACC CAC GAC CAT GTC GCC CTG CGC ACC        864
Leu Gln Glu Leu Gln Asp Leu Thr His Asp His Val Ala Leu Arg Thr
        275                 280                 285

CTT CAG GAC CAC CTC GGC GAC GTC GAC CTG AGC GCG TAC CCG ATC GAC        912
Leu Gln Asp His Leu Gly Asp Val Asp Leu Ser Ala Tyr Pro Ile Asp
    290                 295                 300

GGG CCC GTC CCC GAC ATC CCG TAC ACC AAC CAG TCC CAG TCG ACG ACC        960
Gly Pro Val Pro Asp Ile Pro Tyr Thr Asn Gln Ser Gln Ser Thr Thr
305                 310                 315                 320

GAG CGG CTG ATC GGC CTG GCC AGG CGC GAG AAC CTC AGC ATC CGC GAG       1008
Glu Arg Leu Ile Gly Leu Ala Arg Arg Glu Asn Leu Ser Ile Arg Glu
                325                 330                 335

CTG GCC CTG CGG CTG ATG GGC GAC ATC GTC GTC GGC ACA CCG GAG CAG       1056
Leu Ala Leu Arg Leu Met Gly Asp Ile Val Val Gly Thr Pro Glu Gln
            340                 345                 350

CTC GCC GAC CAC ATG GAG AGC TGG TTC ACC GGC CGC GGC GCC GAC GGC       1104
Leu Ala Asp His Met Glu Ser Trp Phe Thr Gly Arg Gly Ala Asp Gly
        355                 360                 365

TTC AAC ATC GAC TTC CCG TAC CTG CCG GGC TCC GCC GAC GAC TTC GTC       1152
Phe Asn Ile Asp Phe Pro Tyr Leu Pro Gly Ser Ala Asp Asp Phe Val
    370                 375                 380

GAC CAC GTG GTG CCC GAA CTG CAG CGC CGC GGC CTG TAC CGC TCG GGC       1200
Asp His Val Val Pro Glu Leu Gln Arg Arg Gly Leu Tyr Arg Ser Gly
385                 390                 395                 400

TAC GAG GGC ACC ACC CTG CGG GCC AAC CTC GGC ATC GAC GCC CCC CGG       1248
Tyr Glu Gly Thr Thr Leu Arg Ala Asn Leu Gly Ile Asp Ala Pro Arg
                405                 410                 415

AAG GCA GGT GCA GCG GCT TG                                            1268
Lys Ala Gly Ala Ala Ala
            420
```

(2) INFORMATION FOR SEQ ID NO: 3:

(i) SEQUENCE CHARACTERISTICS:
        (A) LENGTH: 833 base pairs
        (B) TYPE: nucleic acid

```
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 1..833

(xi) SEQUENCE DESCRIPTION: SEQ ID NO: 3:

ATG ACC GCG CCC ATC CTC GTC GCC ACC CTC GAC ACC CGC GGC CCC GCC        48
Met Thr Ala Pro Ile Leu Val Ala Thr Leu Asp Thr Arg Gly Pro Ala
 1               5                  10                  15

GCC ACC CTC GGC ACG ATC ACC CGC GCC GTG CGG GCC GCG GAG GCC GCC        96
Ala Thr Leu Gly Thr Ile Thr Arg Ala Val Arg Ala Ala Glu Ala Ala
            20                  25                  30

GGA TTC GAC GCC GTC CTG ATC GAC GAC CGG GCC GCC GCC GGC GTC CAG       144
Gly Phe Asp Ala Val Leu Ile Asp Asp Arg Ala Ala Ala Gly Val Gln
        35                  40                  45

GGC CGG TTC GAG ACG ACG ACG CTG ACC GCC GCG CTG GCC GCC GTC ACC       192
Gly Arg Phe Glu Thr Thr Thr Leu Thr Ala Ala Leu Ala Ala Val Thr
 50                  55                  60

GAG CAC ATC GGC CTG ATC ACC GCC CCG CTC CCG GCC GAC CAG GCC CCC       240
Glu His Ile Gly Leu Ile Thr Ala Pro Leu Pro Ala Asp Gln Ala Pro
 65                  70                  75                  80

TAC CAC GTG TCC CGG ATC ACC GCC TCG CTC GAC CAC CTC GCC CAC GGC       288
Tyr His Val Ser Arg Ile Thr Ala Ser Leu Asp His Leu Ala His Gly
                85                  90                  95

CGC ACC GGC TGG CTC GCG AGC ACG GAC ACC ACC GAC CCC GAG GGC CGC       336
Arg Thr Gly Trp Leu Ala Ser Thr Asp Thr Thr Asp Pro Glu Gly Arg
            100                 105                 110

ACC GGC GAA CTC ATC GAC GTC GTC CGC GGC CTG TGG GAC AGC TTC GAC       384
Thr Gly Glu Leu Ile Asp Val Val Arg Gly Leu Trp Asp Ser Phe Asp
        115                 120                 125

GAC GAC GCC TTC GTC CAC GAC CGC GCC GAC GGC CTG TAC TGG CGG CTG       432
Asp Asp Ala Phe Val His Asp Arg Ala Asp Gly Leu Tyr Trp Arg Leu
130                 135                 140

CCC GCC GTC CAC CAA CTC GAC CAC CAG GGC AGG CAC TTC GAC GTG GCC       480
Pro Ala Val His Gln Leu Asp His Gln Gly Arg His Phe Asp Val Ala
145                 150                 155                 160

GGC CCC CTC AAC GTC GCC CGC CCG CCG CAG GGC CAC CCC GTC GTC GCC       528
Gly Pro Leu Asn Val Ala Arg Pro Pro Gln Gly His Pro Val Val Ala
                165                 170                 175

GTC ACC GGC CCC GCC CTC GCC GCG GCC GCC GAC CTC GTC CTG CTC GAC       576
Val Thr Gly Pro Ala Leu Ala Ala Ala Ala Asp Leu Val Leu Leu Asp
            180                 185                 190

GAG GCG GCC GAC GCC GCC TCG GTG AAG CAG CAG GCA CCG CAC GCC AAG       624
Glu Ala Ala Asp Ala Ala Ser Val Lys Gln Gln Ala Pro His Ala Lys
        195                 200                 205

ATC CTC CTG CCG CTG CCC GGC CCG GCC GCC GAA CTG CCC GCC GAC AGC       672
Ile Leu Leu Pro Leu Pro Gly Pro Ala Ala Glu Leu Pro Ala Asp Ser
210                 215                 220

CCC GCG GAC GGC TTC ACG GTG GCG CTC ACC GGC TCC GAC GAC CCG GTC       720
Pro Ala Asp Gly Phe Thr Val Ala Leu Thr Gly Ser Asp Asp Pro Val
225                 230                 235                 240

CTG GCC GCG CTC GCC GCC CGG CCC GGC CGC CCG GAC CGC ACC GCG GCC       768
Leu Ala Ala Leu Ala Ala Arg Pro Gly Arg Pro Asp Arg Thr Ala Ala
```

```
Leu Ala Ala Leu Ala Ala Arg Pro Gly Arg Pro Asp Arg Thr Ala Ala
            245                 250                 255

ACC ACC CTG CGC GAA CGC CTG GGC CTG GCC CGC CCC GAG AGC CGC CAC      816
Thr Thr Leu Arg Glu Arg Leu Gly Leu Ala Arg Pro Glu Ser Arg His
            260                 265                 270

GCC CTC ACC ACC GCC TG                                               833
Ala Leu Thr Thr Ala
            275
```

(2) INFORMATION FOR SEQ ID NO: 4:

(i) SEQUENCE CHARACTERISTICS:
        (A) LENGTH: 1208 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 1..1208

(xi) SEQUENCE DESCRIPTION: SEQ ID NO: 4:

```
ATG TCC CGT CGC CTG TTC ACC TCG GAG TCC GTG ACC GAG GGC CAC CCC       48
Met Ser Arg Arg Leu Phe Thr Ser Glu Ser Val Thr Glu Gly His Pro
  1               5                  10                  15

GAC AAG ATC GCC GAC CAG ATC AGT GAC ACC GTC CTC GAC GCC CTG CTG       96
Asp Lys Ile Ala Asp Gln Ile Ser Asp Thr Val Leu Asp Ala Leu Leu
             20                  25                  30

CGC GAG GAC CCC GCC TCA CGC GTC GCG GTC GAG ACC CTG ATC ACC ACC      144
Arg Glu Asp Pro Ala Ser Arg Val Ala Val Glu Thr Leu Ile Thr Thr
         35                  40                  45

GGC CAG GTC CAC ATC GCC GGC GAG GTC ACC ACC AAG GCG TAC GCG CCC      192
Gly Gln Val His Ile Ala Gly Glu Val Thr Thr Lys Ala Tyr Ala Pro
     50                  55                  60

ATC GCC CAA CTG GTC CGC GAC ACG ATC CTG GCC ATC GGC TAC GAC TCG      240
Ile Ala Gln Leu Val Arg Asp Thr Ile Leu Ala Ile Gly Tyr Asp Ser
 65                  70                  75                  80

TCC GCC AAG GGC TTC GAC GGC GCC TCC TGC GGC GTC TCC GTC TCC ATC      288
Ser Ala Lys Gly Phe Asp Gly Ala Ser Cys Gly Val Ser Val Ser Ile
                 85                  90                  95

GGC GCG CAG TCC CCG GAC ATC GCC CAG GGC GTC GAC AGC GCC TAC GAG      336
Gly Ala Gln Ser Pro Asp Ile Ala Gln Gly Val Asp Ser Ala Tyr Glu
            100                 105                 110

ACC CGC GTC GAG GGC GAG GAC GAC GAG CTC GAC CAG CAG GGC GCC GGC      384
Thr Arg Val Glu Gly Glu Asp Asp Glu Leu Asp Gln Gln Gly Ala Gly
        115                 120                 125

GAC CAG GGC CTG ATG TTC GGC TAC GCC ACC GAC GAG ACC CCC TCG CTG      432
Asp Gln Gly Leu Met Phe Gly Tyr Ala Thr Asp Glu Thr Pro Ser Leu
    130                 135                 140

ATG CCG CTG CCC ATC GAG CTC GCC CAC CGC CTC TCG CGC CGG CTC ACC      480
Met Pro Leu Pro Ile Glu Leu Ala His Arg Leu Ser Arg Arg Leu Thr
145                 150                 155                 160

GAG GTC CGC AAG GAC GGC ACC GTC CCC TAC CTG CGC CCC GAC GGC AAG      528
Glu Val Arg Lys Asp Gly Thr Val Pro Tyr Leu Arg Pro Asp Gly Lys
                165                 170                 175
```

```
ACC CAG GTC ACC ATC GAG TAC CAG GGC AGC CGC CCG GTG CGC CTG GAC      576
Thr Gln Val Thr Ile Glu Tyr Gln Gly Ser Arg Pro Val Arg Leu Asp
            180                 185                 190

ACC GTC GTC GTC TCC TCC CAG CAC GCC GCC GAC ATC GAC CTC GGC TCC      624
Thr Val Val Val Ser Ser Gln His Ala Ala Asp Ile Asp Leu Gly Ser
                195                 200                 205

CTG CTC ACC CCC GAC ATC CGC GAG CAC GTC GTC GAG CAC GTC CTC GCC      672
Leu Leu Thr Pro Asp Ile Arg Glu His Val Val Glu His Val Leu Ala
    210                 215                 220

GCA CTC GCC GAG GAC GGC ATC AAG CTC GAG ACG GAC AAC TAC CGC CTG      720
Ala Leu Ala Glu Asp Gly Ile Lys Leu Glu Thr Asp Asn Tyr Arg Leu
225                 230                 235                 240

CTG GTC AAC CCG ACC GGC CGT TTC GAG ATC GGC GGC CCG ATG GGC GAC      768
Leu Val Asn Pro Thr Gly Arg Phe Glu Ile Gly Gly Pro Met Gly Asp
                245                 250                 255

GCC GGC CTG ACC GGC CGC AAG ATC ATC ATC GAC ACG TAC GGC GGC ATG      816
Ala Gly Leu Thr Gly Arg Lys Ile Ile Ile Asp Thr Tyr Gly Gly Met
                260                 265                 270

GCC CGC CAC GGC GGT GGC GCG TTC TCC GGC AAG GAC CCG TCC AAG GTC      864
Ala Arg His Gly Gly Gly Ala Phe Ser Gly Lys Asp Pro Ser Lys Val
            275                 280                 285

GAC CGT TCC GCC GCG TAC GCG ATG CGC TGG GTC GCC AAG AAC GTC GTC      912
Asp Arg Ser Ala Ala Tyr Ala Met Arg Trp Val Ala Lys Asn Val Val
290                 295                 300

GCC GCG GGC CTC GCC TCC CGC TGC GAG GTC CAG GTC GCC TAC GCC ATC      960
Ala Ala Gly Leu Ala Ser Arg Cys Glu Val Gln Val Ala Tyr Ala Ile
305                 310                 315                 320

GGC AAG GCC GAG CCG GTC GGC CTG TTC GTC GAG ACG TTC GGC ACC GGC     1008
Gly Lys Ala Glu Pro Val Gly Leu Phe Val Glu Thr Phe Gly Thr Gly
                325                 330                 335

ACC GTC GCC CAG GAG CGC ATC GAG AAG GCC ATC ACC GAG GTC TTC GAC     1056
Thr Val Ala Gln Glu Arg Ile Glu Lys Ala Ile Thr Glu Val Phe Asp
            340                 345                 350

CTG CGC CCC GCG GCC ATC ATC CGC GAC CTC GAC CTG CTG CGG CCC ATC     1104
Leu Arg Pro Ala Ala Ile Ile Arg Asp Leu Asp Leu Leu Arg Pro Ile
                355                 360                 365

TAC GCC GCC ACC GCC GCC TAC GGC CAC TTC GGC CGC GAA CTG CCC GAC     1152
Tyr Ala Ala Thr Ala Ala Tyr Gly His Phe Gly Arg Glu Leu Pro Asp
    370                 375                 380

TTC ACC TGG GAG CGG ACC GAC CGC GCC CAC CGG CTC AAG GCC GCG GCC     1200
Phe Thr Trp Glu Arg Thr Asp Arg Ala His Arg Leu Lys Ala Ala Ala
385                 390                 395                 400

GGT CTC TG                                                           1208
Gly Leu
```

(2) INFORMATION FOR SEQ ID NO: 5:

(i) SEQUENCE CHARACTERISTICS:
        (A) LENGTH: 1879 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS (B) LOCATION: 110..1858

(xi) SEQUENCE DESCRIPTION: SEQ ID NO: 5:

```
GATCGGCTCC TGACGGAGCG GCGGCGCGCG GGCGCGGCGC ATCAGCGGCG TGTCAACGGC          60

GCTGCCGACA CTGGGCGCGA CGCGAGGACG AAGCCGGAAA GGACCAACG ATG CTG            115
                                                      Met Leu
                                                        1

GAC GGA TGC GTT CCC TGG CCC GAG GAT GTG GCC GCG AAG TAC CGG GCG          163
Asp Gly Cys Val Pro Trp Pro Glu Asp Val Ala Ala Lys Tyr Arg Ala
          5                  10                  15

GCC GGC TAC TGG CGG GGC GAG CCG CTG GGC ATG CTG CTG GGC CGC TGG          211
Ala Gly Tyr Trp Arg Gly Glu Pro Leu Gly Met Leu Leu Gly Arg Trp
     20                  25                  30

GCG GAG CAG TAC GGC GAG CGG GAG GCG CTG GTC GGC GCG GAC GGG TGC          259
Ala Glu Gln Tyr Gly Glu Arg Glu Ala Leu Val Gly Ala Asp Gly Cys
 35                  40                  45                  50

TCC CGT GTC ACC TAC CGT GCC CTG GAC CGC TGG TGC GAC CGG CTG GCG          307
Ser Arg Val Thr Tyr Arg Ala Leu Asp Arg Trp Cys Asp Arg Leu Ala
             55                  60                  65

GCG GGG TTC GCG GCG CGC GGG ATC GGC GCC GGC GAG CGG GTG CTG GTG          355
Ala Gly Phe Ala Ala Arg Gly Ile Gly Ala Gly Glu Arg Val Leu Val
         70                  75                  80

CAG CTG CCG AAC ACG CCC GAG TTC GTC GCG GTG TGC TTC GCG CTG TTC          403
Gln Leu Pro Asn Thr Pro Glu Phe Val Ala Val Cys Phe Ala Leu Phe
             85                  90                  95

CGT CTG GGC GCG CTG CCG GTG TTC GCG CTG CCC GCG CAC CGT GCC GCC          451
Arg Leu Gly Ala Leu Pro Val Phe Ala Leu Pro Ala His Arg Ala Ala
100                 105                 110

GAG GTG GGG CAC CTG CTC GAG CTG TCC GGC GCC GTC GCC CAC ATC CTG          499
Glu Val Gly His Leu Leu Glu Leu Ser Gly Ala Val Ala His Ile Leu
115                 120                 125                 130

CCG GGC ACC GGC ACC GGC TAC GAC CAT GTC GCG GCG GCC GTG GAG GCC          547
Pro Gly Thr Gly Thr Gly Tyr Asp His Val Ala Ala Ala Val Glu Ala
                135                 140                 145

CGT GCC CGC CGT GCC CGC CCG GTG CAG GTG TTC GTG GCG GGC GAG GCG          595
Arg Ala Arg Arg Ala Arg Pro Val Gln Val Phe Val Ala Gly Glu Ala
            150                 155                 160

CCC GCG GTG CTG CCC GAG GGG TTC ACC GCG CTG GCC GAC GTG GAC GGC          643
Pro Ala Val Leu Pro Glu Gly Phe Thr Ala Leu Ala Asp Val Asp Gly
        165                 170                 175

GAC CCG GTG GCG CCG GCG GAC GTG GAC GCC TTC CGA CGT GGC GTC TTC          691
Asp Pro Val Ala Pro Ala Asp Val Asp Ala Phe Arg Arg Gly Val Phe
    180                 185                 190

CTG CTG TCC GGG GGG ACG ACC GCG CTG CCG AAG CTG ATC CCG CGC ACC          739
Leu Leu Ser Gly Gly Thr Thr Ala Leu Pro Lys Leu Ile Pro Arg Thr
195                 200                 205                 210

CAC GAC GAC TAC GCC TAC CAG TGC CGG GTC ACG GCC GGT ATC TGC GGC          787
His Asp Asp Tyr Ala Tyr Gln Cys Arg Val Thr Ala Gly Ile Cys Gly
                215                 220                 225

CTG GAC GCG GAC AGT GTC TAT CTG GCG GTG CTG CCG GCC GAG TTC AAC          835
Leu Asp Ala Asp Ser Val Tyr Leu Ala Val Leu Pro Ala Glu Phe Asn
            230                 235                 240

TTC CCC TTC GGC TGC CCG GGC ATC CTG GGC ACC CTG CAC GCC GGC GGG          883
Phe Pro Phe Gly Cys Pro Gly Ile Leu Gly Thr Leu His Ala Gly Gly
        245                 250                 255

CGG GTG GTG TTC GCG CTG TCA CCG CAG CCC GAG GAG TGC TTC GCG CTG          931
Arg Val Val Phe Ala Leu Ser Pro Gln Pro Glu Glu Cys Phe Ala Leu
    260                 265                 270

ATC GAA CGC GAA CAC GTC ACC TTC ACC TCC GTC ATC CCC ACG ATC GTG          979
Ile Glu Arg Glu His Val Thr Phe Thr Ser Val Ile Pro Thr Ile Val
```

```

Ile Glu Arg Glu His Val Thr Phe Thr Ser Val Ile Pro Thr Ile Val
275                 280                 285                 290

CAC CTG TGG CTG GCG GCC GCC GCA CAA GGC CAC GGC CGC GAC CTG GGC     1027
His Leu Trp Leu Ala Ala Ala Ala Gln Gly His Gly Arg Asp Leu Gly
                        295                 300                 305

AGC CTT CAG CTG CTG CAG GTC GGC AGC GCC AAA CTC CAC GAG GAG CTC     1075
Ser Leu Gln Leu Leu Gln Val Gly Ser Ala Lys Leu His Glu Glu Leu
            310                 315                 320

GCC GCC CGG ATC GGC CCC GAA CTG GGG GTG CGG CTG CAG CAG GTG TTC     1123
Ala Ala Arg Ile Gly Pro Glu Leu Gly Val Arg Leu Gln Gln Val Phe
        325                 330                 335

GGC ATG GCC GAG GGA CTG CTG ACC TTC ACC CGC GAC GAC GAC CCG GCG     1171
Gly Met Ala Glu Gly Leu Leu Thr Phe Thr Arg Asp Asp Asp Pro Ala
    340                 345                 350

GAC GTG GTG CTG CGC ACC CAG GGC CGG CCG GTG TCC GAG GCC GAC GAG     1219
Asp Val Val Leu Arg Thr Gln Gly Arg Pro Val Ser Glu Ala Asp Glu
355                 360                 365                 370

ATA CGC GTC GCC GAC CCC GAC GGC CGG CCC GTG CCC CGC GGT GAG ACC     1267
Ile Arg Val Ala Asp Pro Asp Gly Arg Pro Val Pro Arg Gly Glu Thr
                        375                 380                 385

GGT GAA CTG CTC ACC CGC GGC CCC TAC ACG CTG CGC GGC TAC TAC CGG     1315
Gly Glu Leu Leu Thr Arg Gly Pro Tyr Thr Leu Arg Gly Tyr Tyr Arg
            390                 395                 400

GCC CCC GAG CAC AAC GCC CGC GCG TTC ACC GAG GAC GGC TTC TAC CGC     1363
Ala Pro Glu His Asn Ala Arg Ala Phe Thr Glu Asp Gly Phe Tyr Arg
        405                 410                 415

AGC GGC GAT CTG GTG CGG CTC ACC GCC GAC GGG CAG TTG GTG GTG GAG     1411
Ser Gly Asp Leu Val Arg Leu Thr Ala Asp Gly Gln Leu Val Val Glu
    420                 425                 430

GGC AGG ATC AAG GAC GTC GTC ATC CGC GGC GGC GAC AAG GTC TCC GCG     1459
Gly Arg Ile Lys Asp Val Val Ile Arg Gly Gly Asp Lys Val Ser Ala
435                 440                 445                 450

ACC GAG GTC GAG GGC CAC CTG GGC GCC CAC CCC GAC GTC CAG CAG GCC     1507
Thr Glu Val Glu Gly His Leu Gly Ala His Pro Asp Val Gln Gln Ala
                        455                 460                 465

GCC GTC GTC GCC ATG CCC GAC CCG GTG TGG GGC GAG AAG GTC TGC GCC     1555
Ala Val Val Ala Met Pro Asp Pro Val Trp Gly Glu Lys Val Cys Ala
            470                 475                 480

TAC ATC GTG CCC GCA CCC GGC CGT CCC GCA CCG CCG ATG GCG GCG CTG     1603
Tyr Ile Val Pro Ala Pro Gly Arg Pro Ala Pro Pro Met Ala Ala Leu
        485                 490                 495

CGC CGG CTG CTG CGC GCG CGG GGA CTG GCC GAC TAC AAG CTT CCC GAC     1651
Arg Arg Leu Leu Arg Ala Arg Gly Leu Ala Asp Tyr Lys Leu Pro Asp
    500                 505                 510

CGG GTG GAG GTC GTC GAC GCG TTC CCG CTG ACC GGC CTC AAC AAG GTC     1699
Arg Val Glu Val Val Asp Ala Phe Pro Leu Thr Gly Leu Asn Lys Val
515                 520                 525                 530

GAC AAG AAG GCC CTG GCG GCC GAC ATC GCC GCC AAG ACC GCC CCC ACC     1747
Asp Lys Lys Ala Leu Ala Ala Asp Ile Ala Ala Lys Thr Ala Pro Thr
                        535                 540                 545

CGC CCC ACC ACC GCC GGC CAC GGC CCG ACC ACG GAC GGC GAT ACG GCC     1795
Arg Pro Thr Thr Ala Gly His Gly Pro Thr Thr Asp Gly Asp Thr Ala
            550                 555                 560

GGT GGG GGT GGG TCC GCG GGC GGG GTG ACG GCC GCC GGT GGC GGG CGG     1843
Gly Gly Gly Gly Ser Ala Gly Gly Val Thr Ala Ala Gly Gly Gly Arg
        565                 570                 575

GAG GAG GCG GCG TGAGCGGGCC CGGGCCCGAG GGCG                          1879
Glu Glu Ala Ala
    580
```

(2) INFORMATION FOR SEQ ID NO: 6:

(i) SEQUENCE CHARACTERISTICS:
        (A) LENGTH: 1833 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 103..1689

(xi) SEQUENCE DESCRIPTION: SEQ ID NO: 6:

```
GGATCCCCTC GCCCAGGGCC CTGGCGGGCC CGCCGGGCCG TGGGGGAGGT GCGGGGCCG          60

CGGGCCCCGG CACCGCACGA ACAGAACAAC CGCTCCGGGC CC ATG CGG ACT TCA           114
                                              Met Arg Thr Ser
                                                1

CGG TCC CAC GAC CAG CGG GCC CCT ACC CCC TGG AGA CAT CCC TTG CAC          162
Arg Ser His Asp Gln Arg Ala Pro Thr Pro Trp Arg His Pro Leu His
  5              10                  15                  20

AGC ACC CGG CCC GCG CCC GCG GCC GAC CGT GAC CCC AGG CGC TGG GTC          210
Ser Thr Arg Pro Ala Pro Ala Ala Asp Arg Asp Pro Arg Arg Trp Val
                25                  30                  35

ATC CTC GGC GTG ATC TGC CTG GCC CAA CTC GTC GTC CTG CTC GAC AAC          258
Ile Leu Gly Val Ile Cys Leu Ala Gln Leu Val Val Leu Leu Asp Asn
            40                  45                  50

ACC GTC CTC AAC GTC GCC ATC CCG GTG CTC ACC ACC GAC CTG GGC GCC          306
Thr Val Leu Asn Val Ala Ile Pro Val Leu Thr Thr Asp Leu Gly Ala
        55                  60                  65

AGC ACC GCC GAC ATC CAG TGG ATG ATC AAC GCC TAC GCG CTC GTG CAG          354
Ser Thr Ala Asp Ile Gln Trp Met Ile Asn Ala Tyr Ala Leu Val Gln
    70                  75                  80

TCC GGG CTG CTG CTC ACC GCG GGC AGC CTC GCG GAC CGC TAC GGC CGC          402
Ser Gly Leu Leu Leu Thr Ala Gly Ser Leu Ala Asp Arg Tyr Gly Arg
 85                  90                  95                 100

AAA CGG CTG CTG ATG CTC GGA CTG GTG CTC TTC GGC GCC GGG TCC GCC          450
Lys Arg Leu Leu Met Leu Gly Leu Val Leu Phe Gly Ala Gly Ser Ala
                105                 110                 115

TGG GCG GCC TTC GCC CAG GAC TCC GCC CAA CTC ATC GCC GCC CGG GCC          498
Trp Ala Ala Phe Ala Gln Asp Ser Ala Gln Leu Ile Ala Ala Arg Ala
            120                 125                 130

GGC ATG GGC GTG GGC GGG GCG CTG CTG GCG ACC ACC ACC CTC GCC GTC          546
Gly Met Gly Val Gly Gly Ala Leu Leu Ala Thr Thr Thr Leu Ala Val
        135                 140                 145

ATC ATG CAG GTC TTC GAC GAC GAC GAA CGC CCC CGG GCG ATC GGC CTG          594
Ile Met Gln Val Phe Asp Asp Asp Glu Arg Pro Arg Ala Ile Gly Leu
    150                 155                 160

TGG GGA GCG GCC AGC TCA CTG GGC TTC GCG GCC GGC CCG CTG CTC GGC          642
Trp Gly Ala Ala Ser Ser Leu Gly Phe Ala Ala Gly Pro Leu Leu Gly
165                 170                 175                 180

GGC GCC CTC CTC GAC CAC TTC TGG TGG GGC TCC ATC TTC CTG ATC AAC          690
Gly Ala Leu Leu Asp His Phe Trp Trp Gly Ser Ile Phe Leu Ile Asn
                185                 190                 195

CTG CCC GTC GCG CTG CTG GGC CTG CTG GCC GTC GCC CGC CTG GTG CCC          738
```

```
Leu Pro Val Ala Leu Leu Gly Leu Leu Ala Val Ala Arg Leu Val Pro
            200                 205                 210

GAG ACG AAG AAC CCC GAA GGC CGG CGC CCC GAC CTG CTC GGC GCC GTG         786
Glu Thr Lys Asn Pro Glu Gly Arg Arg Pro Asp Leu Leu Gly Ala Val
            215                 220                 225

CTC TCC ACC CTC GGC ATG GTC GGC GTC GTC TAC GCC ATC ATC TCC GGC         834
Leu Ser Thr Leu Gly Met Val Gly Val Val Tyr Ala Ile Ile Ser Gly
            230                 235                 240

CCC GAA CAC GGC TGG ACG GCC CCG CAG GTC CTC CTG CCG GCC GCC GTC         882
Pro Glu His Gly Trp Thr Ala Pro Gln Val Leu Leu Pro Ala Ala Val
245                 250                 255                 260

GCG GCC GCC GCG CTC ACC GCG TTC GTC CGC TGG GAA CTG CAC ACC CCC         930
Ala Ala Ala Ala Leu Thr Ala Phe Val Arg Trp Glu Leu His Thr Pro
                265                 270                 275

CAC CCC ATG CTC GAC ATG GGC TTC TTC ACC GAC CGG CGC TTC AAC GGG         978
His Pro Met Leu Asp Met Gly Phe Phe Thr Asp Arg Arg Phe Asn Gly
            280                 285                 290

CCG TCG CCG GCG GAG TGC TCG TCG TTC GGC ATG GCC GGC TCG CTC TTC        1026
Pro Ser Pro Ala Glu Cys Ser Ser Phe Gly Met Ala Gly Ser Leu Phe
            295                 300                 305

CTG CTC ACC CAG CAC CTC CAA CTC GTC CTC GGC TAC GAC GCC CTG CAG        1074
Leu Leu Thr Gln His Leu Gln Leu Val Leu Gly Tyr Asp Ala Leu Gln
            310                 315                 320

GCC GGC CTG CGC ACC GCG CCA CTG GCT TTG ACG ATC GTC GCC CTC AAC        1122
Ala Gly Leu Arg Thr Ala Pro Leu Ala Leu Thr Ile Val Ala Leu Asn
325                 330                 335                 340

CTG GCC GGC CTC GGC GCG AAA CTC CTC GCC GCG CTC GGC ACC GCC CGC        1170
Leu Ala Gly Leu Gly Ala Lys Leu Leu Ala Ala Leu Gly Thr Ala Arg
                345                 350                 355

AGC ATC GCC CTG GGC ATG ACA CTG CTG GCC GCC GGC CTC AGC GCG GTG        1218
Ser Ile Ala Leu Gly Met Thr Leu Leu Ala Ala Gly Leu Ser Ala Val
            360                 365                 370

GCC GTC GGC GGA TCG GGC CCC GAC GCC GGC TAC GGC GGC ATG CTC GCC        1266
Ala Val Gly Gly Ser Gly Pro Asp Ala Gly Tyr Gly Gly Met Leu Ala
            375                 380                 385

GGC CTG CTC CTC ATG GGC GCG GGC ATC GCA CTG GCC ATG CCC GCC ATG        1314
Gly Leu Leu Leu Met Gly Ala Gly Ile Ala Leu Ala Met Pro Ala Met
            390                 395                 400

GCC ACC GCC GTG ATG TCC TCC ATC CCG CCC GCC AAG GCC GGG GCC GGA        1362
Ala Thr Ala Val Met Ser Ser Ile Pro Pro Ala Lys Ala Gly Ala Gly
405                 410                 415                 420

GCG GGC GTG CAG GGC ACC CTG ACC GAG TTC GGC GGC GGA CTG GGA GTG        1410
Ala Gly Val Gln Gly Thr Leu Thr Glu Phe Gly Gly Gly Leu Gly Val
                425                 430                 435

GCG ATC CTC GGC GCC GTC CTC GGC TCC CGC TTC GCC TCC CAA CTG CCC        1458
Ala Ile Leu Gly Ala Val Leu Gly Ser Arg Phe Ala Ser Gln Leu Pro
            440                 445                 450

GCC GCC ATC ACC GGC ACC GGC TCC CTC GAC GAG GCA CTG CGC GAC GCC        1506
Ala Ala Ile Thr Gly Thr Gly Ser Leu Asp Glu Ala Leu Arg Asp Ala
            455                 460                 465

ACA CCC CAA CAG GCC GGG CAG GTC CAC GAC GCG TTC GCC GAC GCG GTG        1554
Thr Pro Gln Gln Ala Gly Gln Val His Asp Ala Phe Ala Asp Ala Val
            470                 475                 480

AAC ACC AGC CAA CTC ATC GGC GCC GCC GCC GTG TTC ACC GGC GGC CTG        1602
Asn Thr Ser Gln Leu Ile Gly Ala Ala Ala Val Phe Thr Gly Gly Leu
485                 490                 495                 500

CTC GCC GCG CTG CTG CTG CAC CGC GCC GAC CGC AAG GCC GCC CCC CAG        1650
Leu Ala Ala Leu Leu Leu His Arg Ala Asp Arg Lys Ala Ala Pro Gln
                505                 510                 515
```

```
CCC ACC GCC CCC ACC CCC GAA CCC ACC ACC ACC GCC TGACCCCCGG    1696
Pro Thr Ala Pro Thr Pro Glu Pro Thr Thr Thr Ala
        520                 525

CCCGCCGGGC ACCACACAAC CCACGGCCCC ACCCCTGCGG CTCCCCACCG GGACCCACAG    1756

GGGCGGGGCC GTGCCGCTGC CCTGCCCACA CACACAGCCC CCACACACAC AGCCCCCGCA    1816

CGGCCGACAG CGCCGGG    1833
```

(2) INFORMATION FOR SEQ ID NO: 7:

(i) SEQUENCE CHARACTERISTICS:
        (A) LENGTH: 695 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 212..695
        (D) OTHER INFORMATION: /product= "Gene SnaC"

(xi) SEQUENCE DESCRIPTION: SEQ ID NO: 7:

```
CTCGAGCCGC GCCCCCAGGT GCTGGTGTCG CTCGCCGTGG AGAAGGGCGC CGACGGCACC    60

GCGCCGCCGG ACCGGCTGCT GATCCACGAC GGCTTCCCCT GGGGCCGCGC CGCCCCGCGC   120

GAAGCGGAGC TGCCCACCGG GCACCGCGCC CTGCCGGCCC TGGCCGGCGC CGCCCGCTGA   180

GGCGCGGCAA CCACCAACAG AAGGAGCCCC C GTG ACA GGA GCC GAC GAC CCG      232
                                  Val Thr Gly Ala Asp Asp Pro
                                   1               5

GCA AGG CCC GCG GTC GGC CCG CAG AGT TTC CGA GAC GCG ATG GCG CAG    280
Ala Arg Pro Ala Val Gly Pro Gln Ser Phe Arg Asp Ala Met Ala Gln
            10                  15                  20

CTG GCG TCG CCC GTC ACC GTC GTA ACC GTC CTC GAC GCG GCC GGA CGC    328
Leu Ala Ser Pro Val Thr Val Val Thr Val Leu Asp Ala Ala Gly Arg
 25                  30                  35

CGC CAC GGC TTC ACG GCC GGC TCG GTG GTC TCT GTG TCG CTG GAC CCG    376
Arg His Gly Phe Thr Ala Gly Ser Val Val Ser Val Ser Leu Asp Pro
 40                  45                  50                  55

CCG CTG GTG ATG GTC GGC ATC GCG CTC ACC TCC AGC TGC CAC ACG GCG    424
Pro Leu Val Met Val Gly Ile Ala Leu Thr Ser Ser Cys His Thr Ala
             60                  65                  70

ATG GCC GCC GCC GCC GAG TTC TGC GTC AGC ATC CTC GGC GAG GAC CAG    472
Met Ala Ala Ala Ala Glu Phe Cys Val Ser Ile Leu Gly Glu Asp Gln
             75                  80                  85

CGC GCC GTC GCG AAG CGG TGC GCG ACG CAC GGC GCC GAC CGG TTC GCG    520
Arg Ala Val Ala Lys Arg Cys Ala Thr His Gly Ala Asp Arg Phe Ala
         90                  95                 100

GGC GGC GAG TTC GCC GCC TGG GAC GGT ACG GGG GTG CCC TAC CTG CCG    568
Gly Gly Glu Phe Ala Ala Trp Asp Gly Thr Gly Val Pro Tyr Leu Pro
    105                 110                 115

GAC GCC AAG GTC GTC CTG CGC TGC CGC ACC ACG GAC GTG GTG CGC GCC    616
Asp Ala Lys Val Val Leu Arg Cys Arg Thr Thr Asp Val Val Arg Ala
120                 125                 130                 135

GGC GAC CAC GAC CTG GTG CTC GGC ACG CCC GTG GAG ATC CGC ACG GGC    664
Gly Asp His Asp Leu Val Leu Gly Thr Pro Val Glu Ile Arg Thr Gly
```

```
                     140              145              150
GAC CCG GCG AAG CCA CCC CTG CTG TGG TAC C                            695
Asp Pro Ala Lys Pro Pro Leu Leu Trp Tyr
            155              160
```

(2) INFORMATION FOR SEQ ID NO: 8:

(i) SEQUENCE CHARACTERISTICS:
        (A) LENGTH: 640 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 1..640
        (D) OTHER INFORMATION: /product= "gene SnaD"

(xi) SEQUENCE DESCRIPTION: SEQ ID NO: 8:

```
GCG ACC GCC CGG CTC ATC GGC CCG CTG CCG CGC CGG CTG GGC CTC CAG    48
Ala Thr Ala Arg Leu Ile Gly Pro Leu Pro Arg Arg Leu Gly Leu Gln
 1               5                  10                  15

GTG CAC CAG GTG ATG ACG GGC GCG TTC GCG CAG GCC CTC GCC CGC TGG    96
Val His Gln Val Met Thr Gly Ala Phe Ala Gln Ala Leu Ala Arg Trp
                20                  25                  30

CGG GGC AGC CGC GCC GTC ACC TTC GAC GTG GAG ACC CAC GGA CGG CAC   144
Arg Gly Ser Arg Ala Val Thr Phe Asp Val Glu Thr His Gly Arg His
            35                  40                  45

GGC CGC GAC GAA CTG TTC CGT ACC GTC GGC TGG TTC ACC TCC ATC CAC   192
Gly Arg Asp Glu Leu Phe Arg Thr Val Gly Trp Phe Thr Ser Ile His
     50                  55                  60

CCC GTC GTC CTG GGC GCG GAC CGC TCC GTG CAC CCC GAG CAG TAC CTC   240
Pro Val Val Leu Gly Ala Asp Arg Ser Val His Pro Glu Gln Tyr Leu
 65                  70                  75                  80

GCC CAG ATC GGC GCG GCG CTG ACC GCC GTA CCG GAC GGC GGC GTC GGC   288
Ala Gln Ile Gly Ala Ala Leu Thr Ala Ala Pro Asp Gly Gly Val Gly
                85                  90                  95

TTC GGC GCC TGC CGC GAG TTC TCC CCG GAC GCC GGG CTG CGC ACT CTG   336
Phe Gly Ala Cys Arg Glu Phe Ser Pro Asp Ala Gly Leu Arg Thr Leu
            100                 105                 110

CTG CGT GAC CTG CCG CCC GCC CTG GTG TGC TTC AAC TAC TAC GGT CAG   384
Leu Arg Asp Leu Pro Pro Ala Leu Val Cys Phe Asn Tyr Tyr Gly Gln
        115                 120                 125

GCC GAC CAG TTG AGC CCG AAC GGC GGT TTC CGT ATG TCG GGC CGT CCC   432
Ala Asp Gln Leu Ser Pro Asn Gly Gly Phe Arg Met Ser Gly Arg Pro
130                 135                 140

ATC CCG CGC GAG CAC TCC GCC CGC TGC GAG CGC GTC TAC GGC ATC GAG   480
Ile Pro Arg Glu His Ser Ala Arg Cys Glu Arg Val Tyr Gly Ile Glu
145                 150                 155                 160

GTG TAC GGC ATC GTC CAC GGC GGC CGC CTG CGC ATG GGC CTG ACC TGG   528
Val Tyr Gly Ile Val His Gly Gly Arg Leu Arg Met Gly Leu Thr Trp
                165                 170                 175

GTG CCG AGC CCG GCG GAC GGT GTG GAC GAG GCC GGC GTC GAC GCG CTC   576
Val Pro Ser Pro Ala Asp Gly Val Asp Glu Ala Gly Val Asp Ala Leu
            180                 185                 190
```

```
GTG GAG CAG ATG AGC TGG GTG CTG GCC ACG CTC GCG GGC GCC GAC CCG      624
Val Glu Gln Met Ser Trp Val Leu Ala Thr Leu Ala Gly Ala Asp Pro
        195                 200                 205

CAC GCC GTG ACC CCG G                                                640
His Ala Val Thr Pro
        210
```

(2) INFORMATION FOR SEQ ID NO: 9:

(i) SEQUENCE CHARACTERISTICS:
        (A) LENGTH: 645 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 61..645
        (D) OTHER INFORMATION: /product= "gene papA"

(xi) SEQUENCE DESCRIPTION: SEQ ID NO: 9:

```
GGCGTCAAGA ACCTGCCGCT GACCGTACGG CGCGGCTGAC ACAGACAAGG GGGCCACCTG      60

GTG CGC ACC GTG CGA ACC CTG CTG ATC GAC AAC TAC GAC TCG TTC ACC      108
Val Arg Thr Val Arg Thr Leu Leu Ile Asp Asn Tyr Asp Ser Phe Thr
  1               5                  10                  15

TAC AAC CTC TTC CAG ATG CTG GCC GAG GTG AAC GGC GCC GCT CCG CTC      156
Tyr Asn Leu Phe Gln Met Leu Ala Glu Val Asn Gly Ala Ala Pro Leu
                 20                  25                  30

GTC GTC CGC AAC GAC GAC ACC CGC ACC TGG CAG GCC CTG GCG CCG GGC      204
Val Val Arg Asn Asp Asp Thr Arg Thr Trp Gln Ala Leu Ala Pro Gly
             35                  40                  45

GAC TTC GAC AAC GTC GTC GTC TCA CCC GGC CCC GGC CAC CCC GCC ACC      252
Asp Phe Asp Asn Val Val Val Ser Pro Gly Pro Gly His Pro Ala Thr
         50                  55                  60

GAC ACC GAC CTG GGC CTC AGC CGC CGG GTG ATC ACC GAA TGG GAC CTG      300
Asp Thr Asp Leu Gly Leu Ser Arg Arg Val Ile Thr Glu Trp Asp Leu
 65                  70                  75                  80

CCG CTG CTC GGG GTG TGC CTG GGC CAC CAG GCC CTG TGC CTG CTC GCC      348
Pro Leu Leu Gly Val Cys Leu Gly His Gln Ala Leu Cys Leu Leu Ala
                 85                  90                  95

GGC GCC GCC GTC GTC CAC GCA CCC GAA CCC TTT CAC GGC CGC ACC AGC      396
Gly Ala Ala Val Val His Ala Pro Glu Pro Phe His Gly Arg Thr Ser
            100                 105                 110

GAC ATC CGC CAC GAC GGG CAG GGC CTG TTC GCG AAC ATC CCC TCC CCG      444
Asp Ile Arg His Asp Gly Gln Gly Leu Phe Ala Asn Ile Pro Ser Pro
        115                 120                 125

CTG ACC GTG GTC CGC TAC CAC TCG CTG ACC GTC CGG CAA CTG CCC GCC      492
Leu Thr Val Val Arg Tyr His Ser Leu Thr Val Arg Gln Leu Pro Ala
        130                 135                 140

GAC CTG CGC GCC ACC GCC CAC ACC GCC GAC GGG CAG CTG ATG GCC GTC      540
Asp Leu Arg Ala Thr Ala His Thr Ala Asp Gly Gln Leu Met Ala Val
145                 150                 155                 160

GCC CAC CGC CAC CTG CCC CGC TTC GGC GTG CAG TTC CAC CCC GAA TCG      588
Ala His Arg His Leu Pro Arg Phe Gly Val Gln Phe His Pro Glu Ser
                165                 170                 175
```

```
ATC AGC AGC GAA CAC GGC CAC CGG ATG CTC GCC AAC TTC CGC GAC CTG      636
Ile Ser Ser Glu His Gly His Arg Met Leu Ala Asn Phe Arg Asp Leu
        180                 185                 190

TCC CTG CGC                                                          645
Ser Leu Arg
        195
```

(2) INFORMATION FOR SEQ ID NO: 10:

(i) SEQUENCE CHARACTERISTICS:
        (A) LENGTH: 1052 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 84..962
        (D) OTHER INFORMATION: /product= "Gene PapM"

(xi) SEQUENCE DESCRIPTION: SEQ ID NO: 10:

```
CTCGAGGACG AGTGGATCGC CTCCGGCGGC GCCCCCGTCC CCACGCCCGT GCACGCGTCC      60

GCGTCCGCGC GGGGGGCCGT GTC GTG ACC GCC GCC GCA CCC ACC CTC GCC         110
                        Val Thr Ala Ala Ala Pro Thr Leu Ala
                         1               5

CAG GCG CTG GAC GAG GCC ACC GGG CAG CTG ACC GGC GCC GGG ATC ACC      158
Gln Ala Leu Asp Glu Ala Thr Gly Gln Leu Thr Gly Ala Gly Ile Thr
 10              15                  20                  25

GCC GAC GCC GCC CGG GCC GAC ACC CGG CTG CTG GCC GCC CAC GCC TGC      206
Ala Asp Ala Ala Arg Ala Asp Thr Arg Leu Leu Ala Ala His Ala Cys
                 30                  35                  40

CAG GTC GCC CCG GGG GAC CTC GAC ACC TGC CTG GCC GGC CCG GTG CCG      254
Gln Val Ala Pro Gly Asp Leu Asp Thr Cys Leu Ala Gly Pro Val Pro
             45                  50                  55

CCC CGG TTC TGG CAC TAC GTC CGG CGC CGT CTG ACC CGC GAA CCC GCC      302
Pro Arg Phe Trp His Tyr Val Arg Arg Arg Leu Thr Arg Glu Pro Ala
         60                  65                  70

GAA CGC ATC GTC GGC CAC GCC TAC TTC ATG GGC CAC CGC TTC GAC CTG      350
Glu Arg Ile Val Gly His Ala Tyr Phe Met Gly His Arg Phe Asp Leu
     75                  80                  85

GCC CCC GGC GTC TTC GTC CCC AAA CCC GAG ACC GAG GAG ATC ACC CGG      398
Ala Pro Gly Val Phe Val Pro Lys Pro Glu Thr Glu Glu Ile Thr Arg
 90                  95                 100                 105

GAC GCC ATC GCC CGC CTG GAG GCC CTC GTC CGC CGC GGC ACC ACC GCA      446
Asp Ala Ile Ala Arg Leu Glu Ala Leu Val Arg Arg Gly Thr Thr Ala
                110                 115                 120

CCC CTG GTC GTC GAC CTG TGC GCC GGA CCG GGC ACC ATG GCC GTC ACC      494
Pro Leu Val Val Asp Leu Cys Ala Gly Pro Gly Thr Met Ala Val Thr
            125                 130                 135

CTG GCC CGC CAC GTA CCG GCC GCC CGC GTC CTG GGC ATC GAA CTC TCC      542
Leu Ala Arg His Val Pro Ala Ala Arg Val Leu Gly Ile Glu Leu Ser
        140                 145                 150

CAG GCC GCC GCC CGC GCC GCC CGG CGC AAC GCC CGC GGC ACC GGC GCC      590
Gln Ala Ala Ala Arg Ala Ala Arg Arg Asn Ala Arg Gly Thr Gly Ala
    155                 160                 165
```

```
CGC ATC GTG CAG GGC GAC GCC CGC GAC GCC TTC CCC GAA CTG AGC GGC          638
Arg Ile Val Gln Gly Asp Ala Arg Asp Ala Phe Pro Glu Leu Ser Gly
170                 175                 180                 185

ACC GTC GAC CTC GTC GTC ACC AAC CCG CCC TAC ATC CCC ATC GGA CTG          686
Thr Val Asp Leu Val Val Thr Asn Pro Pro Tyr Ile Pro Ile Gly Leu
                190                 195                 200

CGC ACC TCC GCA CCC GAA GTG CTC GAG CAC GAC CCG CCG CTG GCC CTG          734
Arg Thr Ser Ala Pro Glu Val Leu Glu His Asp Pro Pro Leu Ala Leu
            205                 210                 215

TGG GCC GGG GAG GAG GGC CTC GGC ATG ATC CGC GCC ATG GAA CGC ACC          782
Trp Ala Gly Glu Glu Gly Leu Gly Met Ile Arg Ala Met Glu Arg Thr
        220                 225                 230

GCG GCC CGG CTG CTG GCC CCC GGC GGC GTC CTG CTC CTC GAA CAC GGC          830
Ala Ala Arg Leu Leu Ala Pro Gly Gly Val Leu Leu Leu Glu His Gly
    235                 240                 245

TCC TAC CAA CTC GCC TCC GTG CCC GCC CTG TTC CGC GCA ACC GGC CGC          878
Ser Tyr Gln Leu Ala Ser Val Pro Ala Leu Phe Arg Ala Thr Gly Arg
250                 255                 260                 265

TGG AGC CAC GCC TCG TCC CGT CCC ACC TGC AAC GAC GGC TGC CTG ACC          926
Trp Ser His Ala Ser Ser Arg Pro Thr Cys Asn Asp Gly Cys Leu Thr
                270                 275                 280

GCC GTA CGC AAC CAC ACC TGC GCA CCG CCC GCC TGACACGGCG TCACGGCACG        979
Ala Val Arg Asn His Thr Cys Ala Pro Pro Ala
                285                 290

GCCGGCCTGT CGGCAACGAC CCTACGCCAT TGACAAACCG ACCGTGCCGT TTTTTTAATG       1039

TCGGGGTGGC GGA                                                          1052

(2) INFORMATION FOR SEQ ID NO: 11:

(i) SEQUENCE CHARACTERISTICS:
        (A) LENGTH: 227 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 3..227
        (D) OTHER INFORMATION: /product= "Partie du gene SnbC"

(xi) SEQUENCE DESCRIPTION: SEQ ID NO: 11:

AG ATC TTC GAG CAC AAG ACC GTC GCC CAG CTC GCA CCC GTC GCC GAG           47
   Ile Phe Glu His Lys Thr Val Ala Gln Leu Ala Pro Val Ala Glu
   1               5                   10                  15

ACG CTC GCC GAC ACC ACC CGC GAG GAA CCC GCC GCC GTC GCC GCG ACC          95
Thr Leu Ala Asp Thr Thr Arg Glu Glu Pro Ala Ala Val Ala Ala Thr
                20                  25                  30

GGC GAC GTA CCG CTC ACC CCG ATC ATG CAC TGG CTG CGC GAA CGC GGC         143
Gly Asp Val Pro Leu Thr Pro Ile Met His Trp Leu Arg Glu Arg Gly
            35                  40                  45

GGC CCC GTC GAC GCG TTC AGC CAG ACG ATG GCC GTC ACC GTC CCC GCC         191
Gly Pro Val Asp Ala Phe Ser Gln Thr Met Ala Val Thr Val Pro Ala
        50                  55                  60

GGC CTG GAC CGG GAA CGG CTC GTG GCC GCC CTG CAG                         227
Gly Leu Asp Arg Glu Arg Leu Val Ala Ala Leu Gln
```

```
            65                  70                  75
```

(2) INFORMATION FOR SEQ ID NO: 12:

(i) SEQUENCE CHARACTERISTICS:
        (A) LENGTH: 247 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 1..247
        (D) OTHER INFORMATION: /product= "Partie du gene SnbC"

(xi) SEQUENCE DESCRIPTION: SEQ ID NO: 12:

```
CTC GAG TAC GAC ACC GCC CTG TAC GAG CGG GCC ACC GCC GAA GCC CTC          48
Leu Glu Tyr Asp Thr Ala Leu Tyr Glu Arg Ala Thr Ala Glu Ala Leu
 1               5                  10                  15

ACC GGC CGG CTG CTG CGG CTC CTC GAC GCC GTC GTC ACC GAC CCG CAG          96
Thr Gly Arg Leu Leu Arg Leu Leu Asp Ala Val Val Thr Asp Pro Gln
            20                  25                  30

GCG CCG GTC GGC TCC CAC GAC CTC CTC GAA GAG GCC GAA CAC GCC CGC         144
Ala Pro Val Gly Ser His Asp Leu Leu Glu Glu Ala Glu His Ala Arg
        35                  40                  45

CTG GCA GCC TTC AAC GAC ACC GCC CGG CCC GTG CCG CGA GCC GGC CTC         192
Leu Ala Ala Phe Asn Asp Thr Ala Arg Pro Val Pro Arg Ala Gly Leu
    50                  55                  60

GCC GAA CTC TTC ACC GCC CAG GCC CGC CGC ACC GCC GAT GCG GTC GCC         240
Ala Glu Leu Phe Thr Ala Gln Ala Arg Arg Thr Ala Asp Ala Val Ala
65                  70                  75                  80

GTC GTC G                                                               247
Val Val
```

(2) INFORMATION FOR SEQ ID NO: 13:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 3..192
        (D) OTHER INFORMATION: /product= "Partie du gene SnbD"

(xi) SEQUENCE DESCRIPTION: SEQ ID NO: 13:

```
GC ATG CCC CCC GTC ACC CCC TAC CGC GCC TAC CTG GCC CAC CTC GCC           47
   Met Pro Pro Val Thr Pro Tyr Arg Ala Tyr Leu Ala His Leu Ala
    1               5                  10                  15
```

```
GGC CGT GAC GAC GAC GCC GCC CGC GCC GCG TGG CGG ACC GCC CTC GCG        95
Gly Arg Asp Asp Asp Ala Ala Arg Ala Ala Trp Arg Thr Ala Leu Ala
             20                  25                  30

GAC CTG GAG GAG CCG AGC CTC GTC GCG GGC GCC GGA GCA GGC CGC GGC       143
Asp Leu Glu Glu Pro Ser Leu Val Ala Gly Ala Gly Ala Gly Arg Gly
             35                  40                  45

GCC GCC GAC GGC TCC GCC CTG CCC GGC CAG ATC CCC GGT TAC CGA GCT C     192
Ala Ala Asp Gly Ser Ala Leu Pro Gly Gln Ile Pro Gly Tyr Arg Ala
             50                  55                  60
```

(2) INFORMATION FOR SEQ ID NO: 14:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 1..474
        (D) OTHER INFORMATION: /product= "Partie du gene SnbD"

(xi) SEQUENCE DESCRIPTION: SEQ ID NO: 14:

```
CTG CAG GTC GAG GGC CGG CCC GCG CAC CTG GAA CTG CCC TGC GAC CAC        48
Leu Gln Val Glu Gly Arg Pro Ala His Leu Glu Leu Pro Cys Asp His
 1               5                  10                  15

CCC CGG CCC GCC GTC GCC ACC CAC CGC GGC GCC ACC GTG CCC TTC CAC        96
Pro Arg Pro Ala Val Ala Thr His Arg Gly Ala Thr Val Pro Phe His
             20                  25                  30

ATC GAC GCC GGC CTC CAC GAG AAG CTG ACC GCG CTC TCC AAG GCC TGC       144
Ile Asp Ala Gly Leu His Glu Lys Leu Thr Ala Leu Ser Lys Ala Cys
             35                  40                  45

GAC AGC AGC CTG TTC ATG GTG CTC CAG GCC GCG GTC GCC GCC CTG CTC       192
Asp Ser Ser Leu Phe Met Val Leu Gln Ala Ala Val Ala Ala Leu Leu
             50                  55                  60

ACC CGG CAC GGC GCC GGC ACC GAC ATC CCC GTC GGC AGC CCC GTC GCC       240
Thr Arg His Gly Ala Gly Thr Asp Ile Pro Val Gly Ser Pro Val Ala
 65              70                  75                  80

GGC CGC ACC GAC GAC GCC CTC GAC GAC CTG GTG GGC TTC TTC GTC AAC       288
Gly Arg Thr Asp Asp Ala Leu Asp Asp Leu Val Gly Phe Phe Val Asn
             85                  90                  95

ACC CTC GTC CTG CGC ACC GAC ACC TCC GGC GAC CCC ACC TTC CGC GAA       336
Thr Leu Val Leu Arg Thr Asp Thr Ser Gly Asp Pro Thr Phe Arg Glu
             100                 105                 110

CTC GTC GCA CGC GTG CGG CAG TTC GAC CTC GCC GCC TAC ACG CAC CAG       384
Leu Val Ala Arg Val Arg Gln Phe Asp Leu Ala Ala Tyr Thr His Gln
             115                 120                 125

GAC ATG CCG TTC GAA AAG CTC GTC GAA GAG GTC AAC CCC GAG CGC TCC       432
Asp Met Pro Phe Glu Lys Leu Val Glu Glu Val Asn Pro Glu Arg Ser
 130                 135                 140

CTG GCC CGC AAC CCG CTC TTC CAG GTC GTC CTG GCG CTG CAG               474
Leu Ala Arg Asn Pro Leu Phe Gln Val Val Leu Ala Leu Gln
 145                 150                 155
```

(2) INFORMATION FOR SEQ ID NO: 15:

(i) SEQUENCE CHARACTERISTICS:
        (A) LENGTH: 485 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 3..485
        (D) OTHER INFORMATION: /product= "Partie du gene SnbE"

(xi) SEQUENCE DESCRIPTION: SEQ ID NO: 15:

```
GC ATG CCG CGC TCC CTC GAC CTG TAC GTC GCA CTG CTC GCC GTC CTC        47
   Met Pro Arg Ser Leu Asp Leu Tyr Val Ala Leu Leu Ala Val Leu
   1               5                  10                  15

AAG ACC GGC GCC GCC TAC CTG CCC GTC GAC ATC TCC TAC CCG GCC GAA       95
Lys Thr Gly Ala Ala Tyr Leu Pro Val Asp Ile Ser Tyr Pro Ala Glu
                20                  25                  30

CGC ATC GCG TTC ATG ATC GAG GAC GCC CGC CCG GTG ACC GTC CTC GAC      143
Arg Ile Ala Phe Met Ile Glu Asp Ala Arg Pro Val Thr Val Leu Asp
            35                  40                  45

CGC CTG CCC GAC GAC CTG GGC GCC TAC CGG GAC ACC GAC CTC ACC GAC      191
Arg Leu Pro Asp Asp Leu Gly Ala Tyr Arg Asp Thr Asp Leu Thr Asp
        50                  55                  60

GCC GAC CGC ACG GCG CCG CTA CGG CCC GAA CAC CCG GCG TAC GTC ATC      239
Ala Asp Arg Thr Ala Pro Leu Arg Pro Glu His Pro Ala Tyr Val Ile
    65                  70                  75

CAC ACC TCC GGC TCC ACC GGC ACC CCC AAG GCC GTC GTC ATG CCC CAC      287
His Thr Ser Gly Ser Thr Gly Thr Pro Lys Ala Val Val Met Pro His
80                  85                  90                  95

GCC GGC CTG GTC AAC CTG CTG ACC TGG CAC GCC CGC CGC TTC CCC GGC      335
Ala Gly Leu Val Asn Leu Leu Thr Trp His Ala Arg Arg Phe Pro Gly
                100                 105                 110

GGC ACC GGG GTG CGC ACC GCC CAG TTC ACC GCC ATC GGC TTC GAC TTC      383
Gly Thr Gly Val Arg Thr Ala Gln Phe Thr Ala Ile Gly Phe Asp Phe
            115                 120                 125

TCG GTG CAG GAG ATC CTC TCC CCG CTC GTC ATG GGC AAG ACC CTC GCC      431
Ser Val Gln Glu Ile Leu Ser Pro Leu Val Met Gly Lys Thr Leu Ala
        130                 135                 140

GTG CCC TCG GAA GAG GTC CGC CAC AGC GCC GAA CTG CTG GCC GGC TGG      479
Val Pro Ser Glu Glu Val Arg His Ser Ala Glu Leu Leu Ala Gly Trp
    145                 150                 155

CTC GAG                                                               485
Leu Glu
160
```

(2) INFORMATION FOR SEQ ID NO: 16:

(i) SEQUENCE CHARACTERISTICS:
        (A) LENGTH: 291 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 1..291
        (D) OTHER INFORMATION: /product= "Partie du gene SnbE"

(xi) SEQUENCE DESCRIPTION: SEQ ID NO: 16:

| | | | | | | | | | | | | | | | |
|---|---|---|---|---|---|---|---|---|---|---|---|---|---|---|---|
| CTG | CAG | GCC | GAG | GGC | GCC | GAA | GTG | AGC | CTG | CTG | GCC | GTC | CTC | GAC | GGC | 48 |
| Leu | Gln | Ala | Glu | Gly | Ala | Glu | Val | Ser | Leu | Leu | Ala | Val | Leu | Asp | Gly | |
| 1 | | | | 5 | | | | | 10 | | | | | 15 | | |

| | | | | | | | | | | | | | | | |
|---|---|---|---|---|---|---|---|---|---|---|---|---|---|---|---|
| TAC | CCC | GAC | GCC | TAC | GAC | GGC | ACC | GAG | CAC | GAG | GTC | GGC | GAG | GAA | CAG | 96 |
| Tyr | Pro | Asp | Ala | Tyr | Asp | Gly | Thr | Glu | His | Glu | Val | Gly | Glu | Glu | Gln | |
| | | | 20 | | | | | 25 | | | | | 30 | | | |

| | | | | | | | | | | | | | | | |
|---|---|---|---|---|---|---|---|---|---|---|---|---|---|---|---|
| GTC | CTG | GCG | ATC | CTC | CTC | AAC | GCC | GCC | GGC | GTC | GAC | CGG | GCC | CAG | GCC | 144 |
| Val | Leu | Ala | Ile | Leu | Leu | Asn | Ala | Ala | Gly | Val | Asp | Arg | Ala | Gln | Ala | |
| | | | 35 | | | | | 40 | | | | | 45 | | | |

| | | | | | | | | | | | | | | | |
|---|---|---|---|---|---|---|---|---|---|---|---|---|---|---|---|
| TTC | GGC | GAC | GCC | CCC | CTC | CAA | CGG | GCC | GCC | GTG | CTC | GAG | AAG | CTG | CGC | 192 |
| Phe | Gly | Asp | Ala | Pro | Leu | Gln | Arg | Ala | Ala | Val | Leu | Glu | Lys | Leu | Arg | |
| | 50 | | | | | 55 | | | | | 60 | | | | | |

| | | | | | | | | | | | | | | | |
|---|---|---|---|---|---|---|---|---|---|---|---|---|---|---|---|
| GAC | AGC | GGC | AGC | GCC | CTG | GGC | AAC | CTC | GAC | GAC | GAC | GCG | GTC | GGC | CGC | 240 |
| Asp | Ser | Gly | Ser | Ala | Leu | Gly | Asn | Leu | Asp | Asp | Asp | Ala | Val | Gly | Arg | |
| 65 | | | | | 70 | | | | | 75 | | | | | 80 | |

| | | | | | | | | | | | | | | | |
|---|---|---|---|---|---|---|---|---|---|---|---|---|---|---|---|
| ATG | GTC | ACC | GTC | TTC | CTC | AAC | AAC | ACG | CGC | CTC | ATC | CAG | AAC | TTC | CGG | 288 |
| Met | Val | Thr | Val | Phe | Leu | Asn | Asn | Thr | Arg | Leu | Ile | Gln | Asn | Phe | Arg | |
| | | | | 85 | | | | | 90 | | | | | 95 | | |

CCC          291
Pro (2) INFORMATION FOR SEQ ID NO: 17:

(i) SEQUENCE CHARACTERISTICS:
        (A) LENGTH: 422 amino acids
        (B) TYPE: amino acid
        (C) STRANDEDNESS: single
        (D) TOPOLOGY: linear (xi) SEQUENCE DESCRIPTION: SEQ ID NO: 17:

Met Thr Ala Pro Arg Arg Arg Ile Thr Leu Ala Gly Ile Ile Asp Gly
 1               5                  10                  15

Pro Gly Gly His Val Ala Ala Trp Arg His Pro Ala Thr Lys Ala Asp
                20                  25                  30

Ala Gln Leu Asp Phe Glu Phe His Arg Asp Asn Ala Arg Thr Leu Glu
            35                  40                  45

Arg Gly Leu Phe Asp Ala Val Phe Ile Ala Asp Ile Val Ala Val Trp
    50                  55                  60

Gly Thr Arg Leu Asp Ser Leu Cys Arg Thr Ser Arg Thr Glu His Phe
65                  70                  75                  80

Glu Pro Leu Thr Leu Leu Ala Ala Tyr Ala Ala Val Thr Glu His Ile
                85                  90                  95

Gly Leu Cys Ala Thr Ala Thr Thr Tyr Asn Glu Pro Ala His Ile
            100                 105                 110

Ala Ala Arg Phe Ala Ser Leu Asp His Leu Ser Gly Gly Arg Ala Gly
            115                 120                 125

Trp Asn Val Val Thr Ser Ala Ala Pro Trp Glu Ser Ala Asn Phe Gly
    130                 135                 140

Phe Pro Glu His Leu Glu His Gly Lys Arg Tyr Glu Arg Ala Glu Glu

```
145                 150                 155                 160
Phe Ile Asp Val Val Lys Lys Leu Trp Asp Ser Asp Gly Arg Pro Val
                165                 170                 175

Asp His Arg Gly Thr His Phe Glu Ala Pro Gly Pro Leu Gly Ile Ala
            180                 185                 190

Arg Pro Pro Gln Gly Arg Pro Val Ile Ile Gln Ala Gly Ser Ser Pro
        195                 200                 205

Val Gly Arg Glu Phe Ala Ala Arg His Ala Glu Val Ile Phe Thr Arg
210                 215                 220

His Asn Arg Leu Ser Asp Ala Gln Asp Phe Tyr Gly Asp Leu Lys Ala
225                 230                 235                 240

Arg Val Ala Arg His Gly Arg Asp Pro Glu Lys Val Leu Val Trp Pro
                245                 250                 255

Thr Leu Ala Pro Ile Val Ala Ala Thr Asp Thr Glu Ala Lys Gln Arg
            260                 265                 270

Leu Gln Glu Leu Gln Asp Leu Thr His Asp His Val Ala Leu Arg Thr
        275                 280                 285

Leu Gln Asp His Leu Gly Asp Val Asp Leu Ser Ala Tyr Pro Ile Asp
290                 295                 300

Gly Pro Val Pro Asp Ile Pro Tyr Thr Asn Gln Ser Gln Ser Thr Thr
305                 310                 315                 320

Glu Arg Leu Ile Gly Leu Ala Arg Arg Glu Asn Leu Ser Ile Arg Glu
                325                 330                 335

Leu Ala Leu Arg Leu Met Gly Asp Ile Val Val Gly Thr Pro Glu Gln
            340                 345                 350

Leu Ala Asp His Met Glu Ser Trp Phe Thr Arg Gly Ala Asp Gly
        355                 360                 365

Phe Asn Ile Asp Phe Pro Tyr Leu Pro Gly Ser Ala Asp Asp Phe Val
370                 375                 380

Asp His Val Val Pro Glu Leu Gln Arg Arg Gly Leu Tyr Arg Ser Gly
385                 390                 395                 400

Tyr Glu Gly Thr Thr Leu Arg Ala Asn Leu Gly Ile Asp Ala Pro Arg
                405                 410                 415

Lys Ala Gly Ala Ala Ala
            420

(2) INFORMATION FOR SEQ ID NO: 18:

(i) SEQUENCE CHARACTERISTICS:
        (A) LENGTH: 277 amino acids
        (B) TYPE: amino acid
        (C) STRANDEDNESS: single
        (D) TOPOLOGY: linear (xi) SEQUENCE DESCRIPTION: SEQ ID NO: 18:

Met Thr Ala Pro Ile Leu Val Ala Thr Leu Asp Thr Arg Gly Pro Ala
1               5                   10                  15

Ala Thr Leu Gly Thr Ile Thr Arg Ala Val Arg Ala Ala Glu Ala Ala
            20                  25                  30

Gly Phe Asp Ala Val Leu Ile Asp Asp Arg Ala Ala Gly Val Gln
        35                  40                  45

Gly Arg Phe Glu Thr Thr Thr Leu Thr Ala Ala Leu Ala Val Thr
    50                  55                  60

Glu His Ile Gly Leu Ile Thr Ala Pro Leu Pro Ala Asp Gln Ala Pro
65                  70                  75                  80
```

```
Tyr His Val Ser Arg Ile Thr Ala Ser Leu Asp His Leu Ala His Gly
             85                  90                  95

Arg Thr Gly Trp Leu Ala Ser Thr Asp Thr Asp Pro Glu Gly Arg
            100                 105                 110

Thr Gly Glu Leu Ile Asp Val Val Arg Gly Leu Trp Asp Ser Phe Asp
            115                 120                 125

Asp Asp Ala Phe Val His Asp Arg Ala Asp Gly Leu Tyr Trp Arg Leu
130                 135                 140

Pro Ala Val His Gln Leu Asp His Gln Gly Arg His Phe Asp Val Ala
145                 150                 155                 160

Gly Pro Leu Asn Val Ala Arg Pro Pro Gln Gly His Pro Val Val Ala
                165                 170                 175

Val Thr Gly Pro Ala Leu Ala Ala Ala Asp Leu Val Leu Leu Asp
                180                 185                 190

Glu Ala Ala Asp Ala Ala Ser Val Lys Gln Gln Ala Pro His Ala Lys
            195                 200                 205

Ile Leu Leu Pro Leu Pro Gly Pro Ala Ala Glu Leu Pro Ala Asp Ser
            210                 215                 220

Pro Ala Asp Gly Phe Thr Val Ala Leu Thr Gly Ser Asp Asp Pro Val
225                 230                 235                 240

Leu Ala Ala Leu Ala Ala Arg Pro Gly Arg Pro Asp Arg Thr Ala Ala
                245                 250                 255

Thr Thr Leu Arg Glu Arg Leu Gly Leu Ala Arg Pro Glu Ser Arg His
                260                 265                 270

Ala Leu Thr Thr Ala
        275

(2) INFORMATION FOR SEQ ID NO: 19:

(i) SEQUENCE CHARACTERISTICS:
        (A) LENGTH: 402 amino acids
        (B) TYPE: amino acid
        (C) STRANDEDNESS: single
        (D) TOPOLOGY: linear (xi) SEQUENCE DESCRIPTION: SEQ ID NO: 19:

Met Ser Arg Arg Leu Phe Thr Ser Glu Ser Val Thr Glu Gly His Pro
  1               5                  10                  15

Asp Lys Ile Ala Asp Gln Ile Ser Asp Thr Val Leu Asp Ala Leu Leu
             20                  25                  30

Arg Glu Asp Pro Ala Ser Arg Val Ala Val Glu Thr Leu Ile Thr Thr
         35                  40                  45

Gly Gln Val His Ile Ala Gly Glu Val Thr Thr Lys Ala Tyr Ala Pro
     50                  55                  60

Ile Ala Gln Leu Val Arg Asp Thr Ile Leu Ala Ile Gly Tyr Asp Ser
65                  70                  75                  80

Ser Ala Lys Gly Phe Asp Gly Ala Ser Cys Gly Val Ser Val Ser Ile
             85                  90                  95

Gly Ala Gln Ser Pro Asp Ile Ala Gln Gly Val Asp Ser Ala Tyr Glu
            100                 105                 110

Thr Arg Val Glu Gly Glu Asp Glu Leu Asp Gln Gln Gly Ala Gly
            115                 120                 125

Asp Gln Gly Leu Met Phe Gly Tyr Ala Thr Asp Glu Thr Pro Ser Leu
130                 135                 140

Met Pro Leu Pro Ile Glu Leu Ala His Arg Leu Ser Arg Arg Leu Thr
145                 150                 155                 160
```

-continued

```
Glu Val Arg Lys Asp Gly Thr Val Pro Tyr Leu Arg Pro Asp Gly Lys
                165                 170                 175

Thr Gln Val Thr Ile Glu Tyr Gln Gly Ser Arg Pro Val Arg Leu Asp
            180                 185                 190

Thr Val Val Ser Ser Gln His Ala Ala Asp Ile Asp Leu Gly Ser
        195                 200                 205

Leu Leu Thr Pro Asp Ile Arg Glu His Val Val Glu His Val Leu Ala
    210                 215                 220

Ala Leu Ala Glu Asp Gly Ile Lys Leu Glu Thr Asp Asn Tyr Arg Leu
225                 230                 235                 240

Leu Val Asn Pro Thr Gly Arg Phe Glu Ile Gly Pro Met Gly Asp
                245                 250                 255

Ala Gly Leu Thr Gly Arg Lys Ile Ile Ile Asp Thr Tyr Gly Gly Met
                260                 265                 270

Ala Arg His Gly Gly Ala Phe Ser Gly Lys Asp Pro Ser Lys Val
            275                 280                 285

Asp Arg Ser Ala Ala Tyr Ala Met Arg Trp Val Ala Lys Asn Val Val
            290                 295                 300

Ala Ala Gly Leu Ala Ser Arg Cys Glu Val Gln Val Ala Tyr Ala Ile
305                 310                 315                 320

Gly Lys Ala Glu Pro Val Gly Leu Phe Val Glu Thr Phe Gly Thr Gly
                325                 330                 335

Thr Val Ala Gln Glu Arg Ile Glu Lys Ala Ile Thr Glu Val Phe Asp
            340                 345                 350

Leu Arg Pro Ala Ala Ile Ile Arg Asp Leu Asp Leu Leu Arg Pro Ile
        355                 360                 365

Tyr Ala Ala Thr Ala Ala Tyr Gly His Phe Gly Arg Glu Leu Pro Asp
370                 375                 380

Phe Thr Trp Glu Arg Thr Asp Arg Ala His Arg Leu Lys Ala Ala Ala
385                 390                 395                 400

Gly Leu (2) INFORMATION FOR SEQ ID NO: 20:

(i) SEQUENCE CHARACTERISTICS:
        (A) LENGTH: 582 amino acids
        (B) TYPE: amino acid
        (C) STRANDEDNESS: single
        (D) TOPOLOGY: linear (xi) SEQUENCE DESCRIPTION: SEQ ID NO: 20:

Met Leu
                                                          1

Asp Gly Cys Val Pro Trp Pro Glu Asp Val Ala Ala Lys Tyr Arg Ala
            5                   10                  15

Ala Gly Tyr Trp Arg Gly Glu Pro Leu Gly Met Leu Leu Gly Arg Trp
        20                  25                  30

Ala Glu Gln Tyr Gly Glu Arg Glu Ala Leu Val Gly Ala Asp Gly Cys
35                  40                  45                  50

Ser Arg Val Thr Tyr Arg Ala Leu Asp Arg Trp Cys Asp Arg Leu Ala
                55                  60                  65

Ala Gly Phe Ala Ala Arg Gly Ile Gly Ala Gly Glu Arg Val Leu Val
            70                  75                  80

Gln Leu Pro Asn Thr Pro Glu Phe Val Ala Val Cys Phe Ala Leu Phe
        85                  90                  95
```

```
Arg Leu Gly Ala Leu Pro Val Phe Ala Leu Pro Ala His Arg Ala Ala
    100                 105                 110

Glu Val Gly His Leu Leu Glu Leu Ser Gly Ala Val Ala His Ile Leu
115                 120                 125                 130

Pro Gly Thr Gly Thr Gly Tyr Asp His Val Ala Ala Val Glu Ala
                135                 140                 145

Arg Ala Arg Arg Ala Arg Pro Val Gln Val Phe Val Ala Gly Glu Ala
            150                 155                 160

Pro Ala Val Leu Pro Glu Gly Phe Thr Ala Leu Ala Asp Val Asp Gly
                165                 170                 175

Asp Pro Val Ala Pro Ala Asp Val Asp Ala Phe Arg Arg Gly Val Phe
            180                 185                 190

Leu Leu Ser Gly Gly Thr Thr Ala Leu Pro Lys Leu Ile Pro Arg Thr
195                 200                 205                 210

His Asp Asp Tyr Ala Tyr Gln Cys Arg Val Thr Ala Gly Ile Cys Gly
                215                 220                 225

Leu Asp Ala Asp Ser Val Tyr Leu Ala Val Leu Pro Ala Glu Phe Asn
            230                 235                 240

Phe Pro Phe Gly Cys Pro Gly Ile Leu Gly Thr Leu His Ala Gly Gly
                245                 250                 255

Arg Val Val Phe Ala Leu Ser Pro Gln Pro Glu Glu Cys Phe Ala Leu
260                 265                 270

Ile Glu Arg Glu His Val Thr Phe Thr Ser Val Ile Pro Thr Ile Val
275                 280                 285                 290

His Leu Trp Leu Ala Ala Ala Gln Gly His Gly Arg Asp Leu Gly
                295                 300                 305

Ser Leu Gln Leu Leu Gln Val Gly Ser Ala Lys Leu His Glu Glu Leu
                310                 315                 320

Ala Ala Arg Ile Gly Pro Glu Leu Gly Val Arg Leu Gln Gln Val Phe
            325                 330                 335

Gly Met Ala Glu Gly Leu Leu Thr Phe Thr Arg Asp Asp Pro Ala
    340                 345                 350

Asp Val Val Leu Arg Thr Gln Gly Arg Pro Val Ser Glu Ala Asp Glu
355                 360                 365                 370

Ile Arg Val Ala Asp Pro Asp Gly Arg Pro Val Pro Arg Gly Glu Thr
                375                 380                 385

Gly Glu Leu Leu Thr Arg Gly Pro Tyr Thr Leu Arg Gly Tyr Tyr Arg
            390                 395                 400

Ala Pro Glu His Asn Ala Arg Ala Phe Thr Glu Asp Gly Phe Tyr Arg
            405                 410                 415

Ser Gly Asp Leu Val Arg Leu Thr Ala Asp Gly Gln Leu Val Val Glu
            420                 425                 430

Gly Arg Ile Lys Asp Val Val Ile Arg Gly Gly Asp Lys Val Ser Ala
435                 440                 445                 450

Thr Glu Val Glu Gly His Leu Gly Ala His Pro Asp Val Gln Gln Ala
                455                 460                 465

Ala Val Val Ala Met Pro Asp Pro Val Trp Gly Glu Lys Val Cys Ala
            470                 475                 480

Tyr Ile Val Pro Ala Pro Gly Arg Pro Ala Pro Met Ala Ala Leu
            485                 490                 495

Arg Arg Leu Leu Arg Ala Arg Gly Leu Ala Asp Tyr Lys Leu Pro Asp
500                 505                 510
```

```
Arg Val Glu Val Val Asp Ala Phe Pro Leu Thr Gly Leu Asn Lys Val
515                 520                 525                 530

Asp Lys Lys Ala Leu Ala Ala Asp Ile Ala Ala Lys Thr Ala Pro Thr
                535                 540                 545

Arg Pro Thr Thr Ala Gly His Gly Pro Thr Thr Asp Gly Asp Thr Ala
            550                 555                 560

Gly Gly Gly Gly Ser Ala Gly Gly Val Thr Ala Ala Gly Gly Gly Arg
            565                 570                 575

Glu Glu Ala Ala
        580

(2) INFORMATION FOR SEQ ID NO: 21:

(i) SEQUENCE CHARACTERISTICS:
        (A) LENGTH: 528 amino acids
        (B) TYPE: amino acid
        (C) STRANDEDNESS: single
        (D) TOPOLOGY: linear (xi) SEQUENCE DESCRIPTION: SEQ ID NO: 21:

Met Arg Thr Ser
                                              1

Arg Ser His Asp Gln Arg Ala Pro Thr Pro Trp Arg His Pro Leu His
  5                  10                  15                  20

Ser Thr Arg Pro Ala Pro Ala Ala Asp Arg Asp Pro Arg Arg Trp Val
                 25                  30                  35

Ile Leu Gly Val Ile Cys Leu Ala Gln Leu Val Val Leu Leu Asp Asn
                 40                  45                  50

Thr Val Leu Asn Val Ala Ile Pro Val Leu Thr Thr Asp Leu Gly Ala
             55                  60                  65

Ser Thr Ala Asp Ile Gln Trp Met Ile Asn Ala Tyr Ala Leu Val Gln
         70                  75                  80

Ser Gly Leu Leu Leu Thr Ala Gly Ser Leu Ala Asp Arg Tyr Gly Arg
 85                  90                  95                 100

Lys Arg Leu Leu Met Leu Gly Leu Val Leu Phe Gly Ala Gly Ser Ala
                105                 110                 115

Trp Ala Ala Phe Ala Gln Asp Ser Ala Gln Leu Ile Ala Ala Arg Ala
                120                 125                 130

Gly Met Gly Val Gly Gly Ala Leu Leu Ala Thr Thr Thr Leu Ala Val
        135                 140                 145

Ile Met Gln Val Phe Asp Asp Asp Glu Arg Pro Arg Ala Ile Gly Leu
        150                 155                 160

Trp Gly Ala Ala Ser Ser Leu Gly Phe Ala Ala Gly Pro Leu Leu Gly
165                 170                 175                 180

Gly Ala Leu Leu Asp His Phe Trp Trp Gly Ser Ile Phe Leu Ile Asn
                185                 190                 195

Leu Pro Val Ala Leu Leu Gly Leu Leu Ala Val Ala Arg Leu Val Pro
                200                 205                 210

Glu Thr Lys Asn Pro Glu Gly Arg Arg Pro Asp Leu Leu Gly Ala Val
        215                 220                 225

Leu Ser Thr Leu Gly Met Val Gly Val Val Tyr Ala Ile Ile Ser Gly
        230                 235                 240

Pro Glu His Gly Trp Thr Ala Pro Gln Val Leu Leu Pro Ala Ala Val
245                 250                 255                 260

Ala Ala Ala Ala Leu Thr Ala Phe Val Arg Trp Glu Leu His Thr Pro
                265                 270                 275
```

```
His Pro Met Leu Asp Met Gly Phe Phe Thr Asp Arg Arg Phe Asn Gly
            280                 285                 290

Pro Ser Pro Ala Glu Cys Ser Ser Phe Gly Met Ala Gly Ser Leu Phe
            295                 300                 305

Leu Leu Thr Gln His Leu Gln Leu Val Leu Gly Tyr Asp Ala Leu Gln
            310                 315                 320

Ala Gly Leu Arg Thr Ala Pro Leu Ala Leu Thr Ile Val Ala Leu Asn
325                 330                 335                 340

Leu Ala Gly Leu Gly Ala Lys Leu Leu Ala Ala Leu Gly Thr Ala Arg
            345                 350                 355

Ser Ile Ala Leu Gly Met Thr Leu Leu Ala Ala Gly Leu Ser Ala Val
            360                 365                 370

Ala Val Gly Gly Ser Gly Pro Asp Ala Gly Tyr Gly Gly Met Leu Ala
            375                 380                 385

Gly Leu Leu Met Gly Ala Gly Ile Ala Leu Ala Met Pro Ala Met
390                 395                 400

Ala Thr Ala Val Met Ser Ser Ile Pro Pro Ala Lys Ala Gly Ala Gly
405                 410                 415                 420

Ala Gly Val Gln Gly Thr Leu Thr Glu Phe Gly Gly Leu Gly Val
            425                 430                 435

Ala Ile Leu Gly Ala Val Leu Gly Ser Arg Phe Ala Ser Gln Leu Pro
            440                 445                 450

Ala Ala Ile Thr Gly Thr Gly Ser Leu Asp Glu Ala Leu Arg Asp Ala
            455                 460                 465

Thr Pro Gln Gln Ala Gly Gln Val His Asp Ala Phe Ala Asp Ala Val
470                 475                 480

Asn Thr Ser Gln Leu Ile Gly Ala Ala Ala Val Phe Thr Gly Gly Leu
485                 490                 495                 500

Leu Ala Ala Leu Leu His Arg Ala Asp Arg Lys Ala Ala Pro Gln
            505                 510                 515

Pro Thr Ala Pro Thr Pro Glu Pro Thr Thr Thr Ala
            520                 525

(2) INFORMATION FOR SEQ ID NO: 22:

(i) SEQUENCE CHARACTERISTICS:
        (A) LENGTH: 161 amino acids
        (B) TYPE: amino acid
        (C) STRANDEDNESS: single
        (D) TOPOLOGY: linear (xi) SEQUENCE DESCRIPTION: SEQ ID NO: 22:

Val Thr Gly Ala Asp Asp Pro
                                     1                 5

Ala Arg Pro Ala Val Gly Pro Gln Ser Phe Arg Asp Ala Met Ala Gln
            10                  15                  20

Leu Ala Ser Pro Val Thr Val Thr Val Leu Asp Ala Ala Gly Arg
        25                  30                  35

Arg His Gly Phe Thr Ala Gly Ser Val Ser Val Ser Leu Asp Pro
40                  45                  50                  55

Pro Leu Val Met Val Gly Ile Ala Leu Thr Ser Ser Cys His Thr Ala
                60                  65                  70

Met Ala Ala Ala Glu Phe Cys Val Ser Ile Leu Gly Glu Asp Gln
        75                  80                  85

Arg Ala Val Ala Lys Arg Cys Ala Thr His Gly Ala Asp Arg Phe Ala
```

```
                    90                  95                 100
Gly Gly Glu Phe Ala Ala Trp Asp Gly Thr Gly Val Pro Tyr Leu Pro
    105                 110                115

Asp Ala Lys Val Val Leu Arg Cys Arg Thr Thr Asp Val Val Arg Ala
120                 125                 130                 135

Gly Asp His Asp Leu Val Leu Gly Thr Pro Val Glu Ile Arg Thr Gly
                140                 145                 150

Asp Pro Ala Lys Pro Pro Leu Leu Trp Tyr
                155                 160
```

(2) INFORMATION FOR SEQ ID NO: 23:

(i) SEQUENCE CHARACTERISTICS:
        (A) LENGTH: 213 amino acids
        (B) TYPE: amino acid
        (C) STRANDEDNESS: single
        (D) TOPOLOGY: linear (xi) SEQUENCE DESCRIPTION: SEQ ID NO: 23:

```
Ala Thr Ala Arg Leu Ile Gly Pro Leu Pro Arg Arg Leu Gly Leu Gln
 1               5                  10                  15

Val His Gln Val Met Thr Gly Ala Phe Ala Gln Ala Leu Ala Arg Trp
                20                  25                  30

Arg Gly Ser Arg Ala Val Thr Phe Asp Val Glu Thr His Gly Arg His
            35                  40                  45

Gly Arg Asp Glu Leu Phe Arg Thr Val Gly Trp Phe Thr Ser Ile His
        50                  55                  60

Pro Val Val Leu Gly Ala Asp Arg Ser Val His Pro Glu Gln Tyr Leu
65                  70                  75                  80

Ala Gln Ile Gly Ala Ala Leu Thr Ala Ala Pro Asp Gly Gly Val Gly
                85                  90                  95

Phe Gly Ala Cys Arg Glu Phe Ser Pro Asp Ala Gly Leu Arg Thr Leu
                100                 105                 110

Leu Arg Asp Leu Pro Pro Ala Leu Val Cys Phe Asn Tyr Tyr Gly Gln
            115                 120                 125

Ala Asp Gln Leu Ser Pro Asn Gly Gly Phe Arg Met Ser Gly Arg Pro
130                 135                 140

Ile Pro Arg Glu His Ser Ala Arg Cys Glu Arg Val Tyr Gly Ile Glu
145                 150                 155                 160

Val Tyr Gly Ile Val His Gly Gly Arg Leu Arg Met Gly Leu Thr Trp
                165                 170                 175

Val Pro Ser Pro Ala Asp Gly Val Asp Glu Ala Gly Val Asp Ala Leu
            180                 185                 190

Val Glu Gln Met Ser Trp Val Leu Ala Thr Leu Ala Gly Ala Asp Pro
        195                 200                 205

His Ala Val Thr Pro
        210
```

(2) INFORMATION FOR SEQ ID NO: 24:

(i) SEQUENCE CHARACTERISTICS:
        (A) LENGTH: 195 amino acids
        (B) TYPE: amino acid
        (C) STRANDEDNESS: single
        (D) TOPOLOGY: linear (xi) SEQUENCE DESCRIPTION: SEQ ID NO: 24:

Val Arg Thr Val Arg Thr Leu Leu Ile Asp Asn Tyr Asp Ser Phe Thr

```
          1               5                  10                 15
        Tyr Asn Leu Phe Gln Met Leu Ala Glu Val Asn Gly Ala Ala Pro Leu
                         20                 25                 30
        Val Val Arg Asn Asp Asp Thr Arg Thr Trp Gln Ala Leu Ala Pro Gly
                 35                 40                 45
        Asp Phe Asp Asn Val Val Val Ser Pro Gly Pro Gly His Pro Ala Thr
             50                 55                 60
        Asp Thr Asp Leu Gly Leu Ser Arg Arg Val Ile Thr Glu Trp Asp Leu
        65                 70                 75                 80
        Pro Leu Leu Gly Val Cys Leu Gly His Gln Ala Leu Cys Leu Leu Ala
                         85                 90                 95
        Gly Ala Ala Val Val His Ala Pro Glu Pro Phe His Gly Arg Thr Ser
                         100                105                110
        Asp Ile Arg His Asp Gly Gln Gly Leu Phe Ala Asn Ile Pro Ser Pro
                 115                120                125
        Leu Thr Val Val Arg Tyr His Ser Leu Thr Val Arg Gln Leu Pro Ala
        130                135                140
        Asp Leu Arg Ala Thr Ala His Thr Ala Asp Gly Gln Leu Met Ala Val
        145                150                155                160
        Ala His Arg His Leu Pro Arg Phe Gly Val Gln Phe His Pro Glu Ser
                         165                170                175
        Ile Ser Ser Glu His Gly His Arg Met Leu Ala Asn Phe Arg Asp Leu
                         180                185                190
        Ser Leu Arg
                195

(2) INFORMATION FOR SEQ ID NO: 25:

(i) SEQUENCE CHARACTERISTICS:
        (A) LENGTH: 292 amino acids
        (B) TYPE: amino acid
        (C) STRANDEDNESS: single
        (D) TOPOLOGY: linear (xi) SEQUENCE DESCRIPTION: SEQ ID NO: 25:

Val Thr Ala Ala Ala Pro Thr Leu Ala
                          1               5
        Gln Ala Leu Asp Glu Ala Thr Gly Gln Leu Thr Gly Ala Gly Ile Thr
        10                 15                 20                 25
        Ala Asp Ala Ala Arg Ala Asp Thr Arg Leu Leu Ala Ala His Ala Cys
                         30                 35                 40
        Gln Val Ala Pro Gly Asp Leu Asp Thr Cys Leu Ala Gly Pro Val Pro
                         45                 50                 55
        Pro Arg Phe Trp His Tyr Val Arg Arg Leu Thr Arg Glu Pro Ala
                 60                 65                 70
        Glu Arg Ile Val Gly His Ala Tyr Phe Met Gly His Arg Phe Asp Leu
                 75                 80                 85
        Ala Pro Gly Val Phe Val Pro Lys Pro Glu Thr Glu Ile Thr Arg
                 90                 95                 100                105
        Asp Ala Ile Ala Arg Leu Glu Ala Leu Val Arg Arg Gly Thr Thr Ala
                         110                115                120
        Pro Leu Val Val Asp Leu Cys Ala Gly Pro Gly Thr Met Ala Val Thr
                         125                130                135
        Leu Ala Arg His Val Pro Ala Ala Arg Val Leu Gly Ile Glu Leu Ser
                         140                145                150
```

```
Gln Ala Ala Ala Arg Ala Ala Arg Arg Asn Ala Arg Gly Thr Gly Ala
    155                 160                 165
Arg Ile Val Gln Gly Asp Ala Arg Asp Ala Phe Pro Glu Leu Ser Gly
170                 175                 180                 185
Thr Val Asp Leu Val Val Thr Asn Pro Pro Tyr Ile Pro Ile Gly Leu
                190                 195                 200
Arg Thr Ser Ala Pro Glu Val Leu Glu His Asp Pro Pro Leu Ala Leu
            205                 210                 215
Trp Ala Gly Glu Glu Gly Leu Gly Met Ile Arg Ala Met Glu Arg Thr
        220                 225                 230
Ala Ala Arg Leu Leu Ala Pro Gly Gly Val Leu Leu Leu Glu His Gly
    235                 240                 245
Ser Tyr Gln Leu Ala Ser Val Pro Ala Leu Phe Arg Ala Thr Gly Arg
250                 255                 260                 265
Trp Ser His Ala Ser Ser Arg Pro Thr Cys Asn Asp Gly Cys Leu Thr
                270                 275                 280
Ala Val Arg Asn His Thr Cys Ala Pro Pro Ala
            285                 290

(2) INFORMATION FOR SEQ ID NO: 26:

(i) SEQUENCE CHARACTERISTICS:
        (A) LENGTH: 75 amino acids
        (B) TYPE: amino acid
        (C) STRANDEDNESS: single
        (D) TOPOLOGY: linear (xi) SEQUENCE DESCRIPTION: SEQ ID NO: 26:

Ile Phe Glu His Lys Thr Val Ala Gln Leu Ala Pro Val Ala Glu
    1               5                   10                  15

Thr Leu Ala Asp Thr Thr Arg Glu Glu Pro Ala Ala Val Ala Ala Thr
                20                  25                  30

Gly Asp Val Pro Leu Thr Pro Ile Met His Trp Leu Arg Glu Arg Gly
            35                  40                  45

Gly Pro Val Asp Ala Phe Ser Gln Thr Met Ala Val Thr Val Pro Ala
        50                  55                  60

Gly Leu Asp Arg Glu Arg Leu Val Ala Ala Leu Gln
    65                  70                  75

(2) INFORMATION FOR SEQ ID NO: 27:

(i) SEQUENCE CHARACTERISTICS:
        (A) LENGTH: 82 amino acids
        (B) TYPE: amino acid
        (C) STRANDEDNESS: single
        (D) TOPOLOGY: linear (xi) SEQUENCE DESCRIPTION: SEQ ID NO: 27:

Leu Glu Tyr Asp Thr Ala Leu Tyr Glu Arg Ala Thr Ala Glu Ala Leu
1               5                   10                  15

Thr Gly Arg Leu Leu Arg Leu Leu Asp Ala Val Val Thr Asp Pro Gln
                20                  25                  30

Ala Pro Val Gly Ser His Asp Leu Leu Glu Glu Ala Glu His Ala Arg
            35                  40                  45

Leu Ala Ala Phe Asn Asp Thr Ala Arg Pro Val Pro Arg Ala Gly Leu
        50                  55                  60

Ala Glu Leu Phe Thr Ala Gln Ala Arg Arg Thr Ala Asp Ala Val Ala
65                  70                  75                  80
```

Val Val (2) INFORMATION FOR SEQ ID NO: 28:

(i) SEQUENCE CHARACTERISTICS:
        (A) LENGTH: 63 amino acids
        (B) TYPE: amino acid
        (C) STRANDEDNESS: single
        (D) TOPOLOGY: linear (xi) SEQUENCE DESCRIPTION: SEQ ID NO: 28:

Met Pro Pro Val Thr Pro Tyr Arg Ala Tyr Leu Ala His Leu Ala
1               5                   10                  15

Gly Arg Asp Asp Asp Ala Ala Arg Ala Ala Trp Arg Thr Ala Leu Ala
                20                  25                  30

Asp Leu Glu Glu Pro Ser Leu Val Ala Gly Ala Gly Ala Gly Arg Gly
            35                  40                  45

Ala Ala Asp Gly Ser Ala Leu Pro Gly Gln Ile Pro Gly Tyr Arg Ala
        50                  55                  60

(2) INFORMATION FOR SEQ ID NO: 29:

(i) SEQUENCE CHARACTERISTICS:
        (A) LENGTH: 158 amino acids
        (B) TYPE: amino acid
        (C) STRANDEDNESS: single
        (D) TOPOLOGY: linear (xi) SEQUENCE DESCRIPTION: SEQ ID NO: 29:

Leu Gln Val Glu Gly Arg Pro Ala His Leu Glu Leu Pro Cys Asp His
1               5                   10                  15

Pro Arg Pro Ala Val Ala Thr His Arg Gly Ala Thr Val Pro Phe His
                20                  25                  30

Ile Asp Ala Gly Leu His Glu Lys Leu Thr Ala Leu Ser Lys Ala Cys
            35                  40                  45

Asp Ser Ser Leu Phe Met Val Leu Gln Ala Ala Val Ala Ala Leu Leu
        50                  55                  60

Thr Arg His Gly Ala Gly Thr Asp Ile Pro Val Gly Ser Pro Val Ala
65              70                  75                  80

Gly Arg Thr Asp Asp Ala Leu Asp Leu Val Gly Phe Phe Val Asn
                85                  90                  95

Thr Leu Val Leu Arg Thr Asp Thr Ser Gly Asp Pro Thr Phe Arg Glu
            100                 105                 110

Leu Val Ala Arg Val Arg Gln Phe Asp Leu Ala Ala Tyr Thr His Gln
        115                 120                 125

Asp Met Pro Phe Glu Lys Leu Val Glu Glu Val Asn Pro Glu Arg Ser
    130                 135                 140

Leu Ala Arg Asn Pro Leu Phe Gln Val Val Leu Ala Leu Gln
145                 150                 155

(2) INFORMATION FOR SEQ ID NO: 30:

(i) SEQUENCE CHARACTERISTICS:
        (A) LENGTH: 161 amino acids
        (B) TYPE: amino acid
        (C) STRANDEDNESS: single
        (D) TOPOLOGY: linear (xi) SEQUENCE DESCRIPTION: SEQ ID NO: 30:

Met Pro Arg Ser Leu Asp Leu Tyr Val Ala Leu Leu Ala Val Leu
1               5                   10                  15

```
Lys Thr Gly Ala Ala Tyr Leu Pro Val Asp Ile Ser Tyr Pro Ala Glu
                20                  25                  30

Arg Ile Ala Phe Met Ile Glu Asp Ala Arg Pro Val Thr Val Leu Asp
                35                  40                  45

Arg Leu Pro Asp Asp Leu Gly Ala Tyr Arg Asp Thr Asp Leu Thr Asp
            50                  55                  60

Ala Asp Arg Thr Ala Pro Leu Arg Pro Glu His Pro Ala Tyr Val Ile
        65                  70                  75

His Thr Ser Gly Ser Thr Gly Thr Pro Lys Ala Val Val Met Pro His
80                  85                  90                  95

Ala Gly Leu Val Asn Leu Leu Thr Trp His Ala Arg Arg Phe Pro Gly
                100                 105                 110

Gly Thr Gly Val Arg Thr Ala Gln Phe Thr Ala Ile Gly Phe Asp Phe
                115                 120                 125

Ser Val Gln Glu Ile Leu Ser Pro Leu Val Met Gly Lys Thr Leu Ala
            130                 135                 140

Val Pro Ser Glu Glu Val Arg His Ser Ala Glu Leu Leu Ala Gly Trp
        145                 150                 155

Leu Glu
160

(2) INFORMATION FOR SEQ ID NO: 31:

(i) SEQUENCE CHARACTERISTICS:
        (A) LENGTH: 97 amino acids
        (B) TYPE: amino acid
        (C) STRANDEDNESS: single
        (D) TOPOLOGY: linear (xi) SEQUENCE DESCRIPTION: SEQ ID NO: 31:

Leu Gln Ala Glu Gly Ala Glu Val Ser Leu Leu Ala Val Leu Asp Gly
1               5                   10                  15

Tyr Pro Asp Ala Tyr Asp Gly Thr Glu His Glu Val Gly Glu Glu Gln
                20                  25                  30

Val Leu Ala Ile Leu Leu Asn Ala Ala Gly Val Asp Arg Ala Gln Ala
            35                  40                  45

Phe Gly Asp Ala Pro Leu Gln Arg Ala Ala Val Leu Glu Lys Leu Arg
        50                  55                  60

Asp Ser Gly Ser Ala Leu Gly Asn Leu Asp Asp Ala Val Gly Arg
65                  70                  75                  80

Met Val Thr Val Phe Leu Asn Asn Thr Arg Leu Ile Gln Asn Phe Arg
                85                  90                  95

Pro (2) INFORMATION FOR SEQ ID NO: 32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION:  SEQ ID NO: 32:

ATC GAY TTY CCN TAY CTS CCS GG                                      23

(2) INFORMATION FOR SEQ ID NO: 33:

(i) SEQUENCE CHARACTERISTICS:
```

(A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 33:

TTC GAC GAY GAY GCN TTC GTS CAY GAC                         27

(2) INFORMATION FOR SEQ ID NO: 34:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 34:

GTS CCS TGG CCS GAG GAC GTS GCS GCS AAG TAC             33

(2) INFORMATION FOR SEQ ID NO: 35:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO: 35:

GAG GTS GAG GGS CAC CTS GGS GCS CAC CCS GAC GTS CAG CAG GC       44

(2) INFORMATION FOR SEQ ID NO: 36:

(i) SEQUENCE CHARACTERISTICS:
            (A) LENGTH: 20 amino acids
            (B) TYPE: amino acid
            (C) STRANDEDNESS: single
            (D) TOPOLOGY: linear (xi) SEQUENCE DESCRIPTION: SEQ ID NO: 36:

Val Pro Ala Ala Phe Val Pro Leu Asp Ala Leu Pro Leu Thr Gly Asn
1               5                   10                  15

Gly Val Leu Asp
 20

(2) INFORMATION FOR SEQ ID NO: 37:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 37:

GCS GCS TTC AAC GAC ACS GCS CGS CC                          26

(2) INFORMATION FOR SEQ ID NO: 38:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 38:

TTC GTS CCS CTS GAC GCS CTS CCS CT                          26

```
(2) INFORMATION FOR SEQ ID NO: 39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 39:

GTS ACS CCS TAC CGS GCS TAC                                           21

(2) INFORMATION FOR SEQ ID NO: 40:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 40:

ACS CGB CTS ATC CAG AAC TTC CGB CC                                    26

(2) INFORMATION FOR SEQ ID NO: 41:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 41:

TTC CGS GAC GCS ATG GCS CAG CTS GC                                    26

(2) INFORMATION FOR SEQ ID NO: 42:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 42:

TTC GCS GGS GGS GAG TTC GCS GCS TGG GAC GGC ACC GG                    38

(2) INFORMATION FOR SEQ ID NO: 43:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 43:

GAC CCS GCS AAG CCS CCS CTS CTS TGG TAC CG                            32
```

What is claimed is:

1. A method for preparing cells blocked in a step of the biosynthesis pathway of streptogramins comprising:
   (a) specifically introducing a disabling mutation into at least one gene target in a microorganism that produces streptogramins, wherein said gene target is selected from genes that hybridize to snaA, snaB, snaC, snaD, papA, papM, samS, snbA, snbC, snbD, snbE, or snbR genes of *Streptomyces pristinaespiralis* in the presence of formamide at 42° C. with washes at 50° and 60° C., wherein said gene target encodes a polypeptide selected from the group of polypeptides consisting of SnaA, SnaB, SnaC, SnaD, PapA, PapM, SamS, SnbA, SnbC, SnbD, SnbE, and SnbR; and (b) selecting cells containing the mutated gene.

2. The method of claim 1, wherein said gene target is selected from the group consisting of snaA, snaB, snaC, snaD, papA, papM, samS, snbA, snbC, snbD, snbE, and snbR genes of *Streptomyces pristinaespiralis*.

3. The method of claim 1, wherein the mutation is introduced in vitro or in situ.

4. The method of claim 1, wherein the mutation comprises substitution or deletion of one or more bases in the gene target.

5. The method of claim 1, wherein the mutation comprises addition of one or more bases into the gene target.

6. The method of claim 1, wherein the mutation comprises suppression.

7. The method of claim 2, wherein the mutation is introduced in vitro or in situ.

8. The method of claim 2, wherein the mutation comprises substitution or deletion of one or more bases in the gene target.

9. The method of claim 2, wherein the mutation comprises addition of one or more bases into the gene target.

10. The method of claim 2, wherein the mutation comprises suppression.

11. An isolated mutant microorganism blocked in a step of the biosynthesis pathway of streptogramins, wherein the mutation has been introduced into the microorganism by:
 (a) specifically introducing a disabling mutation into at least one gene target in a microorganism that produces streptogramins, wherein said gene target is selected from genes that hybridize to snaA, snaB, snaC, snaD, papA, papM, samS, snbA, snbC, snbD, snbE, or snbR genes of *Streptomyces pristinaespiralis* in the presence of formamide at 42° C. with washes at 50° and 60° C., wherein said gene target encodes a polypeptide selected from the group of polypeptides consisting of SnaA, SnaB, SnaC, SnaD, PapA, PapM, SamS, SnbA, SnbC, SnbD, SnbE, and SnbR; and
 (b) selecting cells containing the mutated gene.

12. The mutant of claim 11, wherein said gene target is selected from the group consisting of snaA, snaB, snaC, snaD, papA, papM, samS, snbA, snbC, snbD, snbE, and snbR genes of *Streptomyces pristinaespiralis*.

13. The mutant of claim 11, wherein the mutation is introduced in vitro or in situ.

14. The mutant of claim 11, wherein the mutation comprises substitution or deletion of one or more bases in the gene target.

15. The mutant of claim 11, wherein the mutation comprises addition of one or more bases into the gene target.

16. The mutant of claim 11, wherein the mutation comprises suppression.

17. The mutant of claim 12, wherein the mutation is introduced in vitro or in situ.

18. The mutant of claim 12, wherein the mutation comprises substitution or deletion of one or more bases in the gene target.

19. The mutant of claim 12, wherein the mutation comprises addition of one or more bases into the gene target.

20. The mutant of claim 12, wherein the mutation comprises suppression.

* * * * *